United States Patent
Clelland et al.

(10) Patent No.: US 11,041,207 B2
(45) Date of Patent: Jun. 22, 2021

(54) METHOD FOR PREDICTING A SUBJECT'S RESPONSE TO VALPROIC ACID THERAPY

(71) Applicants: THE TRUSTEES OF COLUMBIA UNIVERSITY IN THE CITY OF NEW YORK, New York, NY (US); RESEARCH FOUNDATION FOR MENTAL HYGIENE, INC., Menands, NY (US)

(72) Inventors: Catherine L. Clelland, New York, NY (US); James D. Clelland, New York, NY (US)

(73) Assignees: THE TRUSTEES OF COLUMBIA UNIVERSITY IN THE CITY OF NEW YORK, New York, NY (US); RESEARCH FOUNDATION FOR MENTAL HYGIENE, INC., Menands, NY (US)

( * ) Notice: Subject to any disclaimer, the term of this patent is extended or adjusted under 35 U.S.C. 154(b) by 128 days.

(21) Appl. No.: 15/977,144

(22) Filed: May 11, 2018

(65) Prior Publication Data

US 2018/0275149 A1    Sep. 27, 2018

Related U.S. Application Data

(63) Continuation-in-part of application No. PCT/US2016/061654, filed on Nov. 11, 2016.

(60) Provisional application No. 62/255,145, filed on Nov. 13, 2015.

(51) Int. Cl.
| | |
|---|---|
| *C12Q 1/6883* | (2018.01) |
| *A61K 31/19* | (2006.01) |
| *A61K 31/198* | (2006.01) |
| *A61P 25/18* | (2006.01) |
| *G01N 33/68* | (2006.01) |

(52) U.S. Cl.
CPC ........... *C12Q 1/6883* (2013.01); *A61K 31/19* (2013.01); *A61K 31/198* (2013.01); *A61P 25/18* (2018.01); *G01N 33/6896* (2013.01); *C12Q 2600/106* (2013.01); *C12Q 2600/156* (2013.01); *G01N 2800/28* (2013.01); *G01N 2800/302* (2013.01); *G01N 2800/304* (2013.01); *G01N 2800/307* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2003/0100476 A1 | 5/2003 | Weinberger et al. | |
| 2004/0072156 A1* | 4/2004 | Nakamura | C12Q 1/6876 435/6.11 |
| 2006/0234223 A1 | 10/2006 | Darvasi et al. | |
| 2012/0195984 A1* | 8/2012 | Lombard | A23L 33/175 424/722 |

FOREIGN PATENT DOCUMENTS

| | | |
|---|---|---|
| EP | 2630489 B1 | 3/2017 |
| WO | 2013038200 A2 | 3/2013 |
| WO | 2013119326 A1 | 8/2013 |

OTHER PUBLICATIONS

Ahern, H. The Scientist. Jul. 1995. 9(15): 20-25.*
Rakvag et al Pain. 2005. 116: 73-78.*
De Koning et al Psychopharmacology. Jun. 12, 2015. 232: 3111-3122 (Year: 2015).*
Magnee et al (PLoS One. Oct. 5, 2011. 6(10): e25882 (Year: 2011).*
Lindenmayer JP, et al. Dimensions of psychosis in patients with bipolar mania as measured by the positive and negative syndrome scale. Psychopathology 2008; 41(4):264-70.
Luykx JJ, et al. D-amino acid aberrations in cerebrospinal fluid and plasma of smokers. Neuropsychopharmacology Sep. 2013; 38(10):2019-26.
Luykx JJ, et al. Genome-wide association study of NMDA receptor coagonists in human cerebrospinal fluid and plasma. Mol Psychiatry. 2015; doi: 10.1038/mp.2014.190.
Lyketsos CG, et al. (2011) Neuropsychiatric symptoms in Alzheimer's disease. Alzheimers Dement. 7(5):532-9.
Molina JA, et al. (1998) Cerebrospinal fluid levels of non-neurotransmitter amino acids in patients with Alzheimer's disease. J Neural Transm (Vienna); 105(2-3):279-86.
Nadler JV. Sodium-dependent proline uptake in the rat hippocampal formation: association with ipsilateral-commissural projections of CA3 pyramidal cells. J Neurochem 1987; 49:1155-60.
Negrón AE and Reichman WE. (2000) Risperidone in the treatment of patients with Alzheimer's disease with negative symptoms. Int Psychogeriatr. 12(4):527-36.
Nickolson VJ. "On" and "off" responses of K+-induced synaptosomal proline release: involvement of the sodium pump. J Neurochem 1982; 38:289-92.
Ojeda DA, et al. A novel cost-effective assay based on real-time PCR for COMT Val158Met genotyping. Biomarkers. Nov. 2014;19(7):567-70.
Orešič M, et al. Metabolome in schizophrenia and other psychotic disorders: a general population-based study. Genome Med 2011; 3(3):19.

(Continued)

*Primary Examiner* — Carla J Myers
(74) *Attorney, Agent, or Firm* — Bryan Cave Leighton Paisner LLP

(57) ABSTRACT

The present invention provides, inter alia, methods for treating or ameliorating the effects of a disorder, such as schizophrenia or bipolar disorder, by increasing or decreasing proline levels. Further provided are methods of predicting and monitoring the clinical response in a patient, and diagnostic systems for identifying a patient likely to benefit from proline modulation.

10 Claims, 8 Drawing Sheets
(7 of 8 Drawing Sheet(s) Filed in Color)

(56) References Cited

OTHER PUBLICATIONS

Paterlini M, et al. Transcriptional and behavioral interaction between 22q11.2 orthologs modulates schizophrenia-related phenotypes in mice. Nat Neurosci 2005; 8(11):1586-94.

Phang JM, et al. Disorders of proline and hydroxyproline metabolism, in Metabolic and molecular basis of inherited disease. New York, McGraw-Hill Press, 2001, pp. 1821-1838.

Pomara N, et al. Glutamate and other CSF amino acids in Alzheimer's disease. Am J Psychiatry Feb. 1992;149(2):251-4.

Raux G, et al. Involvement of hyperprolinemia in cognitive and psychiatric features of the 22q11 deletion syndrome. Hum Mol Genet 2007; 16(1):83-91.

Reichman WE, et al. (1996) Negative symptoms in Alzheimer's disease. Am J Psychiatry. 153(3):424-6.

Renick SE, et al. The mammalian brain high-affinity L-proline transporter is enriched preferentially in synaptic vesicles in a subpopulation of excitatory nerve terminals in rat forebrain. J Neurosci 1999; 19:21-33.

Scholl-Bürgi S, et al. The relation of cerebrospinal fluid and plasma glycine levels in propionic acidaemia, a 'ketotic hyperglycinaemia'. J Inherit Metab Dis Jun. 2008; 31(3):395-8.

Shifman S, et al. A highly significant association between a COMT haplotype and schizophrenia. Am J Hum Genet 2002; 71(6):1296-302.

Shifman S, et al. COMT: a common susceptibility gene in bipolar disorder and schizophrenia. Am J Med Genet B Neuropsychiatr Genet 2004; 128B(1):61-4.

Sonne SC and Brady KT. Bipolar Disorder and Alcoholism. NIAAA publication Nov. 2002; http://pubs.niaaa.nih.gov/publications/arh26-2/103-108.htm.

Starkstein SE and Pahissa J. (2014) Apathy following traumatic brain injury. Psychiatr Clin North Am. 37(1):103-12.

Stéfan A and Mathé JF; SOFMER group. (2016) What are the disruptive symptoms of behavioral disorders after traumatic brain injury? A systematic review leading to recommendations for good practices. Ann Phys Rehabil Med. Feb;59(1):5-17.

Tomiya M, et al. Alterations in serum amino acid concentrations in male and female schizophrenic patients. Clin Chim Acta 2007; 380(1-2):186-90.

Trushina E, et al. (2013) Identification of altered metabolic pathways in plasma and CSF in mild cognitive impairment and Alzheimer's disease using metabolomics. PLoS One. May 20;8(5):e63644. doi: 10.1371/journal.pone.0063644.

Tunbridge EM, et al. Catechol-o-methyltransferase, cognition, and psychosis: Val158Met and beyond. Biol Psychiatry 2006; 60:141-151.

Van Dam D, et al. (2016)Neuropsychiatric Disturbances in Alzheimer's Disease: What Have We Learned from Neuropathological Studies? Curr Alzheimer Res. 13(10):1145-64.

Vercelletto M, et al. (2002) Negative symptoms, depression and Alzheimer's disease. Int J Geriatr Psychiatry. 17(4):383-7.

Vorstman JA, et al. Proline affects brain function in 22q11DS children with the low activity COMT 158 allele. Neuropsychopharmacology 2009; 34(3):739-46.

Wu, G. Determination of proline by reversed-phase high-performance liquid chromatography with automated pre-column o-phthaldialdehyde derivatization. Journal of Chromatography A. vol. 641, Issue 1, 1993, pp. 168-175.

Wu AH, et al. Tea Intake, COMT Genotype, and Breast Cancer in Asian-American Women 1. Cancer Res. Nov. 1, 2003;63(21):7526-9.

Yoneda Y and Roberts E. A new synaptosomal biosynthetic pathway of proline from ornithine and its negative feedback inhibition by proline. Brain Res 1982; 239:479-88.

Zarchi O,—et al. Schizophrenia-like neurophysiological abnormalities in 22q11.2 deletion syndrome and their association to COMT and PRODH genotypes. J Psychiatr Res 2013; 47(11):1623-9.

Allen NC, et al. Systematic meta-analyses and field synopsis of genetic association studies in schizophrenia: the SzGene database. Nat Genet 2008; 40(7):827-34.

Arnould A, et al. (2015) Apathetic symptom presentations in patients with severe traumatic brain injury: Assessment, heterogeneity and relationships with psychosocial functioning and caregivers' burden. Brain Inj. 29(13-14):1597-603.

Baker KD and Skuse DH. Adolescents and young adults with 22q11 deletion syndrome: psychopathology in an at-risk group. Br J Psychiatry 2005; 186:115-20.

Baxter CF, et al. High proline levels in the brains of mice as related to specific learning deficits. Pharmacol Biochem Behav 1985; 22(6):1053-9.

Bender HU, et al. Functional consequences of PRODH missense mutations. Am J Hum Genet 2005; 76:409-20.

Benoit M, et al.; REAL-FR group. (2008) Apathy and depression in Alzheimer's disease are associated with functional deficit and psychotropic prescription. Int J Geriatr Psychiatry. 23(4):409-14.

Bilder RM, et al. The catechol-O-methyltransferase polymorphism: relations to the tonic-phasic dopamine hypothesis and neuropsychiatric phenotypes. Neuropsychopharmacology 2004; 29(11):1943-61.

Blanchard JJ, et al. Toward the next generation of negative symptom assessments: the collaboration to advance negative symptom assessment in schizophrenia. Schizophr Bull 2011; 37(2):291-9.

Brodaty H, et al. (2015) The course of neuropsychiatric symptoms in dementia: a 3-year longitudinal study. J Am Med Dir Assoc. 16(5):380-7.

Cattelani R, et al. (2008) Adverse effects of apathy and neurobehavioral deficits on the community integration of traumatic brain injury subjects. Eur J Phys Rehabil Med. Sep;44(3):245-51.

Chen J, et al. Functional analysis of genetic variation in catechol-O-methyltransferase (COMT): effects on mRNA, protein, and enzyme activity in postmortem human brain. Am J Hum Genet 2004; 75(5):807-21.

Clelland CL, et al. Evidence for association of hyperprolinemia with schizophrenia and a measure of clinical outcome. Schizophr Res 2011; 131(1-3):139-45.

Clelland JD, et al. Vitamin D insufficiency and schizophrenia risk: evaluation of hyperprolinemia as a mediator of association. Schizophr Res. Jun. 2014;156(1):15-22.

Clelland CL, et al. Evidence that COMT genotype and proline interact on negative-symptom outcomes in schizophrenia and bipolar disorder. Transl Psychiatry. Sep. 13, 2016;6(9):e891.

Cohen SM, Nadler JV. Proline-induced inhibition of glutamate release in hippocampal area CA1. Brain Res 1997; 769:333-9.

Cohen SM and Nadler JV. Proline-induced potentiation of glutamate transmission. Brain Res 1997; 761:271-82.

Crabtree GW, et al. Cytosolic Accumulation of L-Proline Disrupts GABA-Ergic Transmission through GAD Blockade. Cell Rep Oct. 4, 2016;17(2):570-582.

De Jonghe JF, et al. (2003) Negative symptoms in Alzheimer's disease: a confirmatory factor analysis. Int J Geriatr Psychiatry;18(8):748-53.

Dingman W and Sporn MB. The penetration of proline and proline derivatives into brain. J Neurochem 1959; 4(2):148-53.

Drake RE and Mueser KT. Co-occurring alcohol use disorder and schizophrenia. Alcohol Research & Health 2002; 26(2): 99-102.

Drew LJ, et al. The 22q11.2 microdeletion: fifteen years of insights into the genetic and neural complexity of psychiatric disorders. Int J Dev Neurosci 2011; 29(3):259-81.

Efron ML. Familial hyperprolinemia. Report of a second case, associated with congenital renal malformations, hereditary hematuria and mild mental retardation, with demonstration of an enzyme defect. N Engl J Med 1965; 272:1243-54.

Fauth EB and Gibbons A. (2014) Which behavioral and psychological symptoms of dementia are the most problematic? Variability by prevalence, intensity, distress ratings, and associations with caregiver depressive symptoms. Int J Geriatr Psychiatry. 29(3):263-71.

Fernandez-Garcimartin H, et al. Is it possible to combine different psychotic symptom scales in bipolar disorder? Psychiatry Res 2014; 220(3):1090-3.

Fine SE, et al. Autism spectrum disorders and symptoms in children with molecularly confirmed 22q11.2 deletion syndrome. J Autism Dev Disord 2005; 35(4):461-70.

(56) References Cited

OTHER PUBLICATIONS

Forlenza OV, et al. (2017) Recent advances in the management of neuropsychiatric symptoms in dementia. Curr Opin Psychiatry. Mar. 2017;30(2):151-158.

Galynker I, et al. (1997) Methylphenidate treatment of negative symptoms in patients with dementia. J Neuropsychiatry Clin Neurosci. 9(2):231-9.

Galynker II, et al. (2000) Hypofrontality and negative symptoms in patients with dementia of Alzheimer type. Neuropsychiatry Neuropsychol Behav Neurol. 13(1):53-9.

Goghari VM and Sponheim SR. Differential association of the COMT Val158Met polymorphism with clinical phenotypes in schizophrenia and bipolar disorder. Schizophr Res 2008; 103(1-3):186-91.

Gogos JA, et al. The gene encoding proline dehydrogenase modulates sensorimotor gating in mice. Nat Genet 1999; 21(4):434-9.

Gothelf D, et al. Obsessive-compulsive disorder in patients with velocardiofacial (22q11 deletion) syndrome. Am J Med Genet B Neuropsychiatr Genet. 2004; 126B(1):99-105.

Grainger DJ and Aitken S. A microtitre format assay for proline in human serum or plasma. Clin Chim Acta. 2004; 343(1-2):1 13-8.

Guillot CR, et al. COMT Associations with Disordered Gambling and Drinking Measures. J Gambl Stud. Jun. 2015; 31(2): 513-524.

Hashimoto K, et al. Decreased serum levels of D-serine in patients with schizophrenia: evidence in support of the N-methyl-D-aspartate receptor hypofunction hypothesis of schizophrenia. Arch Gen Psychiatry Jun. 2003; 60(6):572-6.

Hwang TJ, et al. (2004) Mild cognitive impairment is associated with characteristic neuropsychiatric symptoms. Alzheimer Dis Assoc Disord. 18(1):17-21.

Inoue H, et al. Determination of total hydroxyproline and proline in human serum and urine by HPLC with fluorescence detection. Biol Pharm Bull. 1996;19(2):163-6.

Ismail Z, et al.; ISTAART Neuropsychiatric Symptoms Professional Interest Area. (2016) Neuropsychiatric symptoms as early manifestations of emergent dementia: Provisional diagnostic criteria for mild behavioral impairment. Alzheimers Dement. Feb;12(2):195-202.

Jacquet H, et al. Hyperprolinemia is a risk factor for schizoaffective disorder. Mol Psychiatry 2005; 10(5):479-85.

Jiménez-Jiménez FJ, et al. Neurotransmitter amino acids in cerebrospinal fluid of patients with Alzheimer's disease. J Neural Transm (Vienna) 1998; 105(2-3):269-77.

Joober R, et al. Catechol-O-methyltransferase Val-108/158-Met gene variants associated with performance on the Wisconsin Card Sorting Test. Arch Gen Psychiatry 2002; 59(7):662-3.

Kane J, et al. Clozapine for the treatment-resistant schizophrenic. A double-blind comparison with chlorpromazine. Arch Gen Psychiatry 1988; 45(9):789-96.

Karayiorgou M, et al. 22q11.2 microdeletions: linking DNA structural variation to brain dysfunction and schizophrenia. Nat Rev Neurosci 2010; 11:402-16.

Karttunen K, et al. (2011) Neuropsychiatric symptoms and quality of life in patients with very mild and mild Alzheimer's disease. Int J Geriatr Psychiatry. 26(5):473-82.

Lachman HM, et al. Human catechol-O-methyltransferase pharmacogenetics: description of a functional polymorphism and its potential application to neuropsychiatric disorders. Pharmacogenetics 1996;6(3):243-50.

Landes AM, et al. (2005) Prevalence of apathy, dysphoria, and depression in relation to dementia severity in Alzheimer's disease. J Neuropsychiatry Clin Neurosci. 17(3):342-9.

Le Boucher J, et al. Amino acid determination in biological fluids by automated ion-exchange chromatography: performance of Hitachi L-8500A. Clin Chem. 1997; 43(8 Pt 1 ):1421-8.

Lechowski L, et al. (2009) Persistent apathy in Alzheimer's disease as an independent factor of rapid functional decline: the REAL longitudinal cohort study. Int J Geriatr Psychiatry. 24(4):341-6.

Leoutsakos JM, et al. (2015) Latent Classes of Neuropsychiatric Symptoms in NACC Controls and Conversion to Mild Cognitive Impairment or Dementia. J Alzheimers Dis. 48(2):483-93. doi: 10.3233/JAD-150421.

Lewis DA, et al. Dopamine transporter immunoreactivity in monkey cerebral cortex: regional, laminar, and ultrastructural localization. J Comp Neurol 2001; 432(1):119-36.

Liang S, et al. Determination of proline in human serum by a robust LC-MS/MS method: application to identification of human metabolites as candidate biomarkers for esophageal cancer early detection and risk stratification. Biomed. Chromatogr. 2015, 29: 570-577.

\* cited by examiner

METHOD FOR PREDICTING A SUBJECT'S RESPONSE TO VALPROIC ACID THERAPY

CROSS-REFERENCE TO RELATED APPLICATIONS

The present application is a continuation in part of PCT international application No. PCT/US2016/061654, filed Nov. 11, 2016, which claims priority to U.S. Provisional Patent Application No. 62/255,145 filed on Nov. 13, 2015. The entire contents of the aforementioned application is incorporated by reference as if recited in full herein.

GOVERNMENT FUNDING

This invention was made with government support under grants R21MH0706019, R21MH082331, R01MH100219, UL1TR000038, and KL2RR024157 from the National Institutes of Health. The government has certain rights in the invention.

FIELD OF THE INVENTION

The present invention provides, inter alia, methods for treating or ameliorating the effects of a disorder, such as schizophrenia or bipolar disorder, in a subject. Methods and diagnostic systems for identifying subjects with such a disorder, and for predicting clinical response to treatments of such disorders, are also provided herein.

BACKGROUND OF THE INVENTION

Negative symptoms, including avolition, blunted affect and social withdrawal, are amongst the most persistent and debilitating in schizophrenia, and are largely unaddressed by current medications (Blanchard et al., 2011). Negative symptoms, which are present across psychiatric disorders (Lindenmayer et al., 2008; Fernandez-Garcimartin et al., 2014), contribute significantly to the huge personal and economic costs of severe psychiatric illness and other disorders.

Proline is a precursor of the neurotransmitter glutamate and may function as a central nervous system (CNS) neuromodulator (Phang et al., 2001; and references therein). Peripheral hyperprolinemia, which reflects CNS proline elevation (Dingman and Sporn, 1959; Efron, 1965; Baxter et al., 1985; Gogos et al., 1999; Paterlini et al., 2005; Luykx et al., 2015), has been associated with psychiatric disorders including schizophrenia (Tomiya et al., 2007; Clelland et al., 2011; Orešič et al., 2011). The proline dehydrogenase gene (PRODH) encodes proline oxidase (PDX), the enzyme that catalyzes the first step in proline catabolism. The direct consequences of elevated proline for neurotransmission have been demonstrated by work on the hyperprolinemic Prodh null model (Gogos et al., 1999; Paterlini et al., 2005). In the presence of PDX deficiency and elevated proline (peripheral and CNS), the mouse exhibits altered glutamate and dopamine (DA) signaling, including an enhancement of glutamatergic synaptic transmission, prefrontal DA transmission, and functional hyper-DA responses (Paterlini et al., 2005).

PRODH maps to chromosome 22q11, a region associated with the highest known genetic risk for schizophrenia, aside from that shared by monozygotic twins. In addition, this location is also associated with the hemizygous microdeletion found in 22q11 deletion syndrome (22q11DS), and there is an increased risk of schizophrenia as well as other psychotic, mood-, obsessive compulsive-, and autism spectrum disorders in 22q11DS patients (Karayiorgou et al., 2010; Baker and Skuse, 2005; Fine et al., 2005; Gothelf et al., 2004). Approximately 37-50% of 22q11DS patients have significant elevation of fasting plasma proline, and proline levels inversely correlate with intelligence quotient in 22q11DS (Raux et al., 2007).

The catechol-O-methyltransferase gene (COMT) encodes the eponymous enzyme that methylates and inactivates catecholamines including DA, and also maps to 22q11, distal to PRODH. The COMTVal$^{158}$Met functional polymorphism (substitution of valine (Val) to methionine (Met) at residue 158), has been studied with regards to DA neurotransmission because Val/Val homozygotes have prefrontal cortex (PFC) enzyme activity approximately 40% higher than Met/Met homozygotes and are considered to have concomitant lower PFC DA levels (Lachman et al., 1996; Chen et al., 2004). It has thus been suggested that the Val$^{158}$Met polymorphism modulates cognitive functioning (Bilder et al., 2004; and references therein). Whilst COMT has been associated with psychotic and mood disorders including schizophrenia and bipolar disorder (Shifman et al., 2002; Shifman et al., 2004), results have been inconsistent (Allen et al., 2008).

A CNS functional interaction between COMT and PRODH has been proposed by Paterlini et al. (2005), who suggested that significant cortical Comt upregulation in the Prodh null mouse represents a compensatory response to increased PFC DA transmission, arising as a consequence of PRODH deficiency enhancing glutamatergic synaptic transmission. In addition, high levels of plasma proline in 22q11DS with the low activity Met allele have been associated with psychosis with positive symptoms (Raux et al., 2007), and significantly decreased smooth pursuit eye movement (SPEM) (Vorstman et al., 2009).

Recent reports have shown significantly elevated fasting peripheral proline in schizophrenia patients versus healthy controls (Clelland et al., 2011). Given the finding of increased COMT expression in the Prodh null mouse (Paterlini et al., 2005), and the significant interaction between proline and COMT genotype on psychosis risk in 22q11DS patients (Raux et al., 2007), this data suggests that COMT genotype and proline levels could be employed for treatment decisions for schizophrenia and other psychiatric disorders.

SUMMARY OF THE INVENTION

The present invention provides a method for predicting the clinical response of a subject with a disorder to a proline modulator comprising:

a) obtaining a biological sample from the subject;

b) determining the identity of the allele(s) of the Val$^{158}$Met locus associated with the COMT gene in the sample;

wherein the presence of Val/Val is indicative of a subject who will benefit from an agent that increases proline levels, and wherein the presence of at least one Met allele is indicative of a subject who will benefit from an agent that decreases proline levels; and c) administering, if appropriate based on the results of step b), an effective amount of a proline modulator to the subject to achieve an appropriate clinical response.

The present invention also provides a method for monitoring the treatment of a subject in need thereof, the method comprising:
 a) obtaining a biological sample from the subject;
 b) determining the genotype for the allele(s) of the COMT gene at amino acid position 158 in the biological sample;
 c) determining the subject's proline level; and
 d) modifying the course of treatment, if necessary, including administering a different proline modulator to the subject, or stopping or omitting treatment with a proline modulator, based upon the presence or absence of a Val$^{158}$Met polymorphism in the COMT gene, and/or an increase or decrease in the subject's proline level.

The present invention also provides a diagnostic system for identifying a subject with a disorder who will benefit from an agent that increases or decreases proline levels comprising:
 a) obtaining a biological sample from the subject; and
 b) determining the identity of alleles of the Val$^{158}$Met locus associated with the COMT gene in the sample;
 wherein the presence of Val/Val is indicative of a subject who will benefit from an agent that increases proline levels and wherein the presence of at least one Met allele is indicative of a subject who will benefit from an agent that decreases proline levels. Kits comprising the diagnostic systems of the present invention packaged together with instructions for use are also provided.

The present invention also provides a method for predicting the clinical response of a subject with a disorder to a proline modulator comprising:
 a) determining the identity of the allele(s) of the Val$^{158}$Met locus associated with the COMT gene using a biological sample of the subject;
 wherein the presence of Val/Val at the locus is indicative of a subject who will benefit from an agent that increases proline levels, and wherein the presence of at least one Met allele at the locus is indicative of a subject who will benefit from an agent that decreases proline levels; and
 b) administering, if appropriate based on the results of step (a), an effective amount of a proline modulator to the subject to achieve a clinically appropriate response.

The present invention also provides a method for monitoring the treatment of a subject with a disorder, the method comprising:
 a) determining the genotype for the allele(s) of the COMT gene at amino acid position 158 in a biological sample of the subject;
 b) determining the proline level of the subject; and
 c) modifying the course of treatment of the subject, if necessary, including administering a different proline modulator to the subject or stopping or omitting treatment with a proline modulator, based upon the presence or absence of a Val$^{158}$Met polymorphism in the COMT gene.

The present invention also provides a diagnostic system for identifying a subject with a disorder who will benefit from treatment with an agent that increases or decreases proline levels comprising:
 determining the identity of the allele(s) of the Val$^{158}$Met locus associated with the COMT gene using a biological sample from the subject;
 wherein the presence of Val/Val at the locus is indicative of a subject who will benefit from an agent that increases proline levels and wherein the presence of at least one Met allele at the locus is indicative of a subject who will benefit from an agent that decreases proline levels.

The present invention also provides a method for treating or ameliorating the effects of a disorder in a subject in need thereof comprising:
 a) obtaining a biological sample from the subject;
 b) determining, in the biological sample, the presence or absence of a Val$^{158}$Met polymorphism in the COMT gene; and
 c) administering to the subject, if appropriate based on the results of step (b), an effective amount of an agent that increases proline levels if the subject is determined from step (b) to have a Val/Val genotype at codon 158; or
 d) administering to the subject, if appropriate based on the results of step (b), an effective amount of an agent that decreases proline levels if the subject is determined from step (b) to have a Val/Met or Met/Met genotype at codon 158.

The present invention also provides a method for treating or ameliorating the effects of a disorder in a subject in need thereof comprising:
 a) determining, using a biological sample of the subject, the presence or absence of a Val$^{158}$Met polymorphism in the COMT gene of the subject; and
 b) administering to the subject, if clinically appropriate, an effective amount of an agent that increases proline levels if the subject is determined from step (a) to have a Val/Val genotype at codon 158; or
 c) administering to the subject, if clinically appropriate, an effective amount of an agent that decreases proline levels if the subject is determined from step (a) to have a Val/Met or Met/Met genotype at codon 158.

The present invention also provides a method for eradicating or reducing a negative symptom experienced by a subject who suffers from a disorder comprising:
 d) obtaining a biological sample from the subject;
 e) determining, in the biological sample, the presence or absence of a Val$^{158}$Met polymorphism in the COMT gene; and
 f) administering to the subject, if clinically appropriate, an effective amount of an agent that increases proline levels if the subject is determined from step (b) to have a Val/Val genotype at codon 158; or
 g) administering to the subject, if clinically appropriate, an effective amount of an agent that decreases proline levels if the subject is determined from step (b) to have at least one Met allele at codon 158; or
 h) modifying the course of treatment of the subject, if clinically appropriate, including stopping or omitting treatment with a proline modulator, based upon the presence or absence of a Val$^{158}$Met polymorphism in the COMT gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
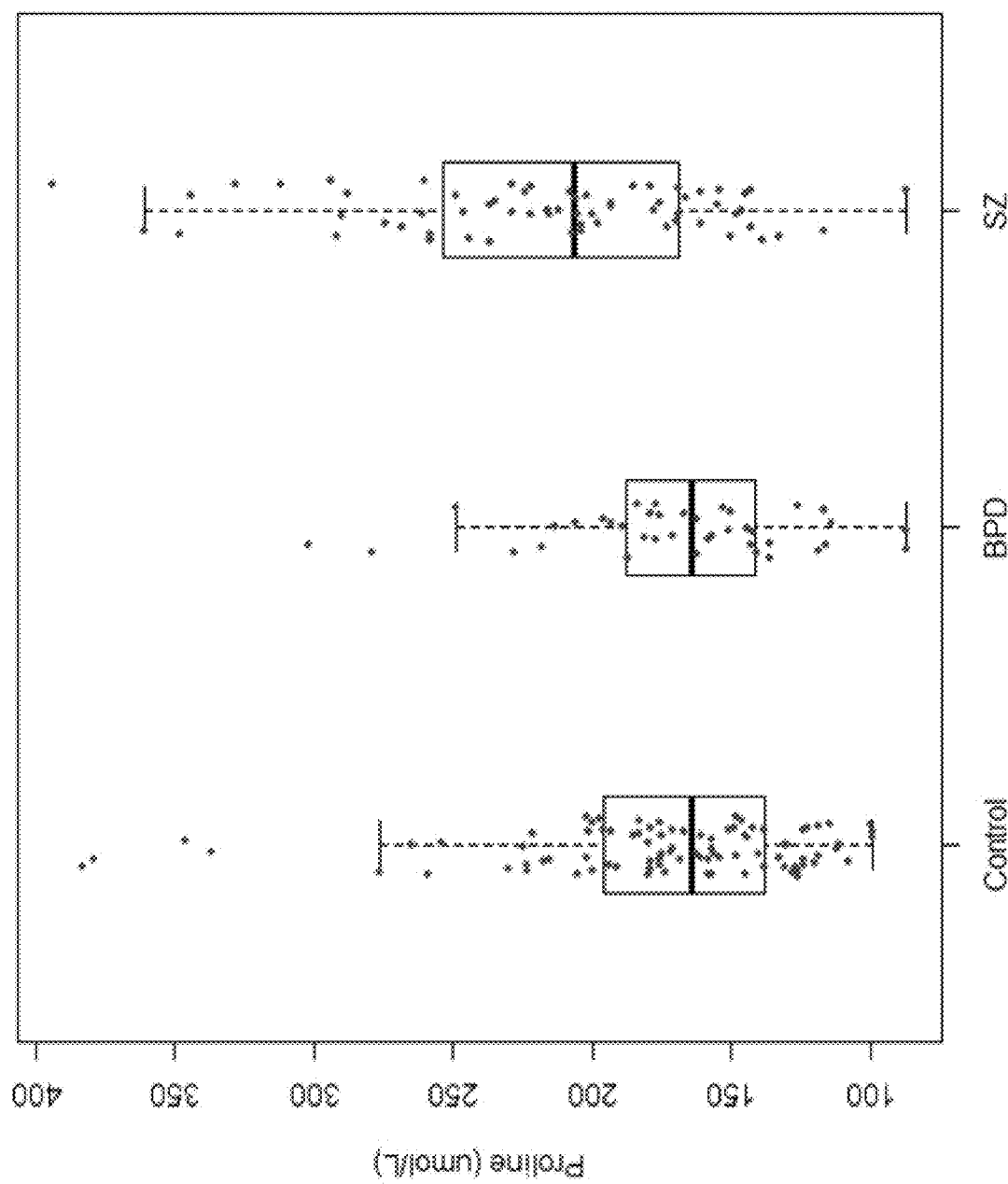
FIG. 1 shows a boxplot of fasting plasma proline levels plotted for controls (174.28±55.97, n=90), bipolar disorder patients (168.75±45.50, n=40) and schizophrenia patients (215.84±63.00, n=64). Red jittered points represent individual data. The horizontal line within each box represents the group mean (mean±SD reported). The box indicates the interquartile range (IQR). The whiskers extend to the most extreme data point which is 1.5 times the IQR. While hyperprolinemia was present in 26.6% of schizophrenia (SZ) patients (17/64), the proportion of bipolar disorder (BPD) patients exhibiting peripheral hyperprolinemia (3/37; 7.5%) was not significantly different to controls (5/85; 5.6%) (Fisher's exact p=0.70).

One embodiment of the present invention is a method for predicting the clinical response of a subject with a disorder to a proline modulator comprising:
  a) obtaining a biological sample from the subject;
  b) determining the identity of the allele(s) of the Val$^{158}$Met locus associated with the COMT gene in the sample;
  wherein the presence of Val/Val is indicative of a subject who will benefit from an agent that increases proline levels, and wherein the presence of at least one Met allele is indicative of a subject who will benefit from an agent that decreases proline levels; and
  c) administering, if appropriate based on the results of step b), an effective amount of a proline modulator to the subject to achieve an appropriate clinical response.

As used herein, the term "disorder" broadly refers to a syndrome, condition, chronic illness or a particular disease. For example, the disorder may be a psychiatric disorder. In the present invention, a "psychiatric disorder" is one of a number of disorders that affect mood, thinking, and behavior. Thus, as used herein, "psychiatric disorder" includes but is not limited to: schizophrenia, bipolar disorder, schizoaffective disorders, schizophreniform disorders, schizotypal and schizoid personality disorders, delusional disorders, 22q11.2 deletion syndrome, mood disorders, anxiety disorders, substance use disorders, and personality disorders.

Other non-limiting examples of disorders according to the present invention include: schizophrenia, bipolar disorder, schizophrenia spectrum and other psychotic disorders, 22q11.2 deletion syndrome, depressive disorders, mood disorders, Alzheimer's disease, substance use disorders, addictive disorders, alcohol use disorder (AUD), anxiety disorders, obsessive-compulsive disorders, traumatic brain injury (TBI), and trauma and stressor-related disorders. In a preferred embodiment, the disorder is e.g., schizophrenia, bipolar disorder, alcohol use disorder (AUD) or traumatic brain injury (TBI).

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment. The term "clinical response" as used herein means a reduction of the severity or number of symptoms or characteristics of a disorder, during or following treatment.

In some aspects of this and other embodiments, the subject is a mammal. Preferably, the mammal is selected from the group consisting of humans, primates, farm animals, and domestic animals. More preferably, the mammal is a human.

As used herein, a "biological sample" means a biological specimen, which may be a bodily fluid or a tissue. Biological samples include, for example, whole blood, serum, plasma, cerebro-spinal fluid, leukocytes or leukocyte subtype cells (e.g. neutrophils, basophils, and eosinophils, lymphocytes, monocytes, macrophages), fibroblast sample, olfactory neuron sample, and tissues from the central nervous system, such as the cortex and hippocampus. Examples of preferred biological samples include, e.g., a blood sample, a biopsy sample, a plasma sample, a saliva sample, a tissue sample, a serum sample, a tear sample, a sweat sample, a skin sample, a cell sample, a hair sample, an excretion sample, a waste sample, a bodily fluid sample, a nail sample, a cheek swab, a cheek cell sample, or a mucous sample.

There is one single gene for COMT, which codes for both soluble COMT (S-COMT) and membrane-bound COMT (MB-COMT) using two separate promoters. The nucleic acid sequence for the human COMT gene is set forth in GenBank Accession Number Z26491 (see, e.g., SEQ ID NO: 1). Human S-COMT contains 221 amino acids (see, e.g., SEQ ID NO: 2), and the molecular mass is 24.4 kDa. Human MB-COMT (see, e.g., SEQ ID NO: 3) contains 50 additional amino acids, of which 20 are hydrophobic membrane anchors. The remainder of the MB-COMT molecule is suspended on the cytoplasmic side of the intracellular membranes. The corresponding molecular mass is 30.0 kDa.

A single nucleotide polymorphism (SNP) in the COMT gene causes a trimodal distribution of low, intermediate, and high activity. That polymorphism is caused by autosomal codominant alleles and leads to 3- to 4-fold differences in COMT activity. It has been shown that the molecular basis for this variation in activity is due to a transition of guanine to adenine at codon 158 of the COMT gene that results in a substitution of valine (Val) by methionine (Met) at position 158 in MB-COMT (SEQ ID NO: 3) or the corresponding amino acid 108 in S-COMT (SEQ ID NO: 2). The SNP polymorphism is referred to interchangeably herein as "rs4680" or "G158A" or "Val$^{158}$Met". In subjects with 22q11.2 deletion syndrome (22q11DS), there is only one allele which determines COMT activity.

Exemplary methods which may be used for the determination/identification of the COMT genotype or Val$^{158}$Met polymorphism in the present invention are disclosed, for example, in US2003/0100476, which is incorporated herein by reference. Further examples of such methods include, but are not limited to, PCR-based restriction fragment length polymorphism analysis using the restriction enzyme αIII, allele specific hybridization, use of a primer in a polymerase chain reaction (PCR), such as, for example, anchor PCR or RACE PCR or in a ligase chain reaction (LCR), identification of alterations in restriction enzyme cleavage patterns, sequencing reactions, analysis of the protection from cleavage agents (such as, for example, nuclease, hydroxylamine or osmium tetroxide and with piperidine), recognition of mismatched base pairs in double strand DNA by specific enzymes, alterations in electrophoretic mobility, analysis of the movement of polymorphic fragments in polyacrylamide gels containing gradients of denaturant (denaturing gradient gel electrophoresis, DGGE), selective oligonucleotide hybridization (for example using a specialized exonuclease-resistance nucleotide), selective amplification depending on selective PCR or selective primer extension, oligonucleotide ligation assays, expansion methods using dideoxynucleotides derivatives, and Genetic Bit Analysis (GBA™). The detection of a variant in the COMT protein sequence can also be determined by methods such as in situ detection using an antibody specific to a variant sequence, immunoassays such as, for example, EIA or ELISA, immunofluorescence and the like. A preferred method for determining a COMT genotype is disclosed in Example 1.

As set forth above, the determination/identification of the COMT genotype or mutation in the COMT protein of a subject may be carried out by methods known to the skilled artisan. Such methods may be carried out, e.g., on a biological sample obtained from the subject, such as for example, a blood sample or a sample obtained after a biopsy has been carried out on the subject. Furthermore, any cell type or tissue may be utilized in the detection procedures described above. In a preferred embodiment, a bodily fluid, e.g., blood, is obtained from the subject to determine the presence of the allelic variant of a polymorphic region, such as the region including the Val$^{158}$Met, in the COMT gene. A bodily fluid, e.g., blood, can be obtained by known techniques (e.g., venipuncture). Alternatively, nucleic acid tests can be performed on dry samples (e.g., skin).

As used herein, "an agent that increases or decreases proline levels" is used interchangeably with the phrase "proline modulator" and means any drug or other composition that increases or decreases the plasma proline levels in a subject. Such proline modulators may be administered to a subject in partly or fully deuterated forms, or containing other stable, medically appropriate isotopes such as, e.g., $^{13}$C. Non-limiting examples of agents that increase proline levels include valproic acid (VPA, 2-propylpentanoic acid), divalproex sodium, valproate (2-propylpentanoate), sodium valproate, magnesium valproate, lactic acid, miR-23b, miR-23a/b, (L or D)-proline, (L or D)-arginine, (L or D)-glutamine, (L or D)-ornithine, (L or D)-glutamic acid, (L or D)-glutamate, poly(L or D)-proline, poly(L or D)-glutamine, poly(L or D)-ornithine, poly(L or D)-glutamate, poly(L or D)-arginine, analogs of any of the foregoing, and combinations thereof, including mixed polypeptides of (L or D)-proline, (L or D)-glutamine, (L or D)-ornithine, (L or D)-arginine, (L or D)-glutamic acid, or (L or D)-glutamate. As used herein, an "analog" of an agent means a chemical compound that is structurally and functionally similar to the agent. In the present invention, combinations of such agents and/or their analogs is also contemplated.

Non-limiting examples of agents that decrease proline levels include, e.g., activators of PRODH or activators of peroxisomal proliferator-activated receptor gamma (PPARy). As used herein, "activators" when used with respect to PRODH or PPARy, means a drug or other composition that can increase the function or expression of PRODH or PPARy. In the present invention, a proline modulator that decreases proline levels in a subject includes, e.g., vitamin $D_1$, vitamin $D_2$, vitamin $D_3$, vitamin $D_4$, vitamin $D_5$, Calcitriol, curcumin, one or more thiazolidinedione compounds, colchicine, Etanercept (Amgen/Pfizer), S26948 (Sigma-Aldrich), INT131 (InteKrin), phentoin, analogs of any of the foregoing, and combinations thereof.

In the present invention, a "proline modulator" also includes any molecule, enzyme, or treatment that affects circulating proline levels. For example, Table 51 (Supplemental Content), which is incorporated by reference herein in its entirety, identifies molecules that up- or down-regulate expression of genes regulating proline synthesis, transport, or metabolism. All such molecules are "proline modulators" of the present invention. The products of these genes influence circulating proline levels. These genes may also be targeted using known gene editing tools including, for example, CRISPR/Cas9 based systems, TALENs, etc., and thus are also considered "proline modulators" of the present invention. Table 1 contains a list of genes that are up- or down-regulated by valproate compounds, including VPA, valproate sodium salt and divalproate salt. These genes may provide targets for new treatments to modulate proline.

In the present invention, each embodiment optionally includes determining a proline level in the subject. Based on the determined proline level, if appropriate, the subject's treatment protocol may be adjusted. For example, by modifying the course of treatment, if necessary, including administering a different proline modulator to the subject, or stopping or omitting treatment with a proline modulator.

TABLE 1

Genes regulated by VPA, valproate sodium salt or divalproate sodium salt

Up-regulated genes

| | | | | | |
|---|---|---|---|---|---|
| ABAT | FOS | EHHADH | EGR1 | Acot1 | THRSP |
| Cyp4a14 | DBP | PDK4 | CA3 | TUBB2B | CYP1A1 |
| NR1D2 | DPP8 | AKR1D1 | ANGPTL4 | ELOVL4 | AIG1 |
| KIF5C | RETSAT | ELOVL6 | FZD5 | PEX11A | TIMP3 |
| CPT1A | RRAGD | CKB | VNN1 | SPP1 | SAP30 |
| DLX5 | SLC22A8 | LYZ | GCFC2 | MAPT | HSD17B2 |
| ZFP37 | CLIC6 | FMO2 | PPAP2C | CTSH | CYP51A1 |
| SLC34A2 | CD36 | RGN | TUBB2A | H1F0 | GRPR |
| CYP4A11 | UBR2 | AKR1C3 | Plscr2 | EGLN3 | NGFRAP1 |
| PFN2 | GPC3 | PENK | USP2 | ARMCX2 | CEP104 |
| BCL6 | LRP11 | GABRB1 | IL1B | TNRC18 | HLA-DQB1 |
| SERPINE1 | MT2A | PGM2L1 | HMGCS1 | ATP8B3 | EDNRA |
| GUCY1B3 | Prl2c2 | TNFRSF9 | FAM5C | GJB5 | KRT23 |
| L1TD1 | RSPO4 | LOC284379 | S100A8 | PODXL | Retnla |
| AKR1C3 | FETUB | CYP2S1 | UGT2B10 | BCMO1 | SERPINB2 |
| PRR15L | DIO2 | CEACAM19 | GJB3 | GPX2 | PPBP |
| SLC17A6 | GATA4 | MGARP | FAM163A | UPP1 | MMP10 |
| CD7 | EPGN | ACPP | LRRC2 | ATP13A4 | BST1 |
| TMPRSS11BNL | GPR115 | WFDC12 | MUC5B | HDC | KRT8 |
| C4orf26 | GRIK2 | KRT18 | DPPA4 | QRFPR | KCNA3 |
| LOC643037 | CRYAA | FGB | | | |

Down-regulated genes

| | | | | | |
|---|---|---|---|---|---|
| FAM111A | CDK1 | ALAS2 | ARNTL | TOLLIP | CCNA2 |
| DCXR | MX1 | SLC16A1 | C1orf210 | GPR37 | INMT |
| IGFBP3 | IL6 | NPAS2 | MFAP4 | CDKN1A | RRM2 |
| CHKA | ENPP2 | LOC100912446 | FBXW5 | CCNB2 | IRF7 |
| CDH17 | RBM8A | PC | ADAMTSL3 | MFAP4 | ITGA11 |
| C1QTNF3 | ASPN | DLK1 | PAPPA2 | CSPG4 | THBS4 |
| EGFL6 | COL8A1 | TSPAN18 | POSTN | Tlr13 | LYZ |
| FMOD | SOX10 | AFF3 | ITGBL1 | TNMD | NGFR |
| AW551984 | ELN | OGN | PTGDS | EPHA3 | NKD2 |
| COL14A1 | LPAR4 | PODN | LDB2 | TRIM66 | FAM180A |
| ADRA1B | Ccl9 | HR | MDGA1 | LPPR4 | SLC6A17 |
| PCSK9 | MSR1 | EDIL3 | SEMA3D | LAMA2 | LCP1 |
| CTSS | PTN | EMR1 | CHRDL1 | RSPO2 | |

As used herein, an "analog" of vitamin D means a chemical compound that is structurally and functionally similar to vitamin D, or (1,25-dihydroxyvitamin D3 [1,25 $(OH)_2D_3$]). Non-limiting examples of vitamin D and analogs thereof include ergocalciferol, cholecalciferol, 22-oxacalcitriol, paricalcitol, doxercalciferol, alfacalcidol, dihydrotachystero, pharmaceutically acceptable salts thereof, and combinations thereof.

As used herein, an "analog" of curcumin means a chemical compound that is structurally and functionally similar to curcumin, and curcuminoid species. Non-limiting examples of curcumin and analogs thereof include curcumin, curcuma oil, turmerone, demethoxycurcumin, bisdemethoxycurcumin, pharmaceutically acceptable salts thereof, and combinations thereof.

Non-limiting examples of thiazolidinedione compounds include troglitazone, rosiglitazone, roglitazone, ciglitazone, darglitazone, englitazone, hydroxypioglitazone, ketopioglitazone, pioglitazone, pioglitazone hydrochloride, ragaglitazar, naveglitazar, aleglitazar, rivoglitazone, netoglitazone, pharmaceutically acceptable salts thereof, analogs of any of the foregoing, and combinations thereof.

Non-limiting examples of pharmaceutically acceptable salts include, for example, acid salts formed from inorganic or organic acids. Such acid salts are non-toxic and include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, mesylate, benzoic, salicylic, sulfanilic, 2-acetoxybenzoic, fumaric, toluenesulfonic, methanesulfonic, ethane disulfonic, oxalic, and isethionic acid. Non-limiting examples of pharmaceutically acceptable base salts include, for example, aluminum, ammonium, calcium, copper, ferric, ferrous, lithium, magnesium, manganic, manganous, potassium, sodium, and zinc salts.

In some preferred embodiments, a pharmaceutically acceptable salt of valproate is sodium valproate. In other preferred embodiments, a pharmaceutically acceptable salt of valproate is magnesium valproate.

The terms "administering", "administration" and variants thereof (particularly "administering" an agent or modulator) as used herein means introducing an agent, e.g., proline modulator into the body of a subject, such as a human, in need of such treatment. In the present invention, however, administration of such a proline modulator or agent is "appropriate" only if such administration will reduce, alleviate, or eradicate at least one negative symptom as defined herein. In the present invention, based on the result of the COMT genotype analysis and/or a subject's proline levels, it may be that no treatment should be administered, that a prior treatment with a proline modulator should be reduced or discontinued, or that a different proline modulator be administered. The appropriateness of a particular treatment option is readily determined by a medical professional based on the COMT genotype analysis and/or proline determination as disclosed herein.

In the present invention, an "effective amount" or a "therapeutically effective amount" of a proline modulator, an agent, a compound, or a composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

A suitable, non-limiting example of a dosage of a proline modulator according to the present invention may be from about 1 ng/kg to about 5000 mg/kg. In general, however, doses employed for adult human treatment typically may be in the range of 0.0001 mg/kg/day to 0.0010 mg/kg/day, 0.0010 mg/kg/day to 0.010 mg/kg/day, 0.010 mg/kg/day to 0.10 mg/kg/day, 0.10 mg/kg/day to 1.0 mg/kg/day, 1.00 mg/kg/day to about 200 mg/kg/day, 200 mg/kg/day to about 5000 mg/kg/day. For example, the dosage may be about 1 mg/kg/day to about 100 mg/kg/day, such as, e.g., 2-10 mg/kg/day, 10-50 mg/kg/day, or 50-100 mg/kg/day. The dosage of the proline modulator also may be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, 2300 mg/kg, 2400 mg/kg, 2500 mg/kg, 2600 mg/kg, 2700 mg/kg, 2800 mg/kg, 2900 mg/kg, 3000 mg/kg, 3500 mg/kg, 4000 mg/kg, 5000 mg/kg.

With respect to proline modulators that are vitamin D and its analogs, the dosage of the proline modulator also may be denominated in International Units (IU) per day (IU/Day) and about 100 IU/day, 200 IU/day, 300 IU/day, 400 IU/day, 500 IU/day, 600 IU/day, 700 IU/day, 800 IU/day, 900 IU/day, 1000 IU/day, 1100 IU/day, 1200 IU/day, 1300 IU/day, 1400 IU/day, 1500 IU/day, 1600 IU/day, 1700 IU/day, 1800 IU/day, 1900 IU/day, 2000 IU/day, 2100 IU/day, 2200 IU/day, 2300 IU/day, 2400 IU/day, 2500 IU/day, 2600 IU/day, 2700 IU/day, 2800 IU/day, 2900 IU/day, 3000 IU/day, 3100 IU/day, 3200 IU/day, 3300 IU/day, 3400 IU/day, 3500 IU/day, 3600 IU/day, 3700 IU/day, 3800 IU/day, 3900 IU/day, 4000 IU/day, 4500 IU/day, 5000 IU/day, 5500 IU/day, 6000 IU/day, 6500 IU/day, 7000 IU/day, 7500 IU/day, 8000 IU/day, 9000 IU/day, 10,000 IU/day, 20,000 IU/day, 30,000 IU/day, 40,000 IU/day, 50,000 IU/day, 60,000 IU/day, 70,000 IU/day, 90,000 IU/day, 100,000 IU/day, 200,000 IU/day, 300,000 IU/day, 400,000 IU/day, 500,000 IU/day, 600,000 IU/day, 700,000 IU/day, 800,000 IU/day, 900,000 IU/day, 1,000,000 IU/day, 1,100,000 IU/day, 1,200,000 IU/day, 1,300,000 IU/day, 1,400,000 IU/day, or 1,500,000 IU/day. Preferably, the dosage of the vitamin D species and analogs range between about 1,000-1,500,000 IU administered on a periodic basis of dosing per day or per week or per month.

The effective dose of the proline modulator may be administered as two, three, four, five, six or more sub-doses, administered separately at appropriate intervals throughout the day.

The proline modulators, agents and compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the proline modulators, agents and compositions of the present invention may be administered in conjunction with other treatments. Each proline modulator, agent and composition of the present invention may be encapsulated or otherwise protected against gastric or other secretions, if desired.

Another embodiment of the present invention is a method for monitoring the treatment of a subject in need thereof, the method comprising:
 a) obtaining a biological sample from the subject;
 b) determining the genotype for the allele(s) of the COMT gene at amino acid position 158 in the biological sample;
 c) determining the subject's proline level; and
 d) modifying the course of treatment, if necessary, including administering a different proline modulator to the subject, or stopping or omitting treatment with a proline modulator, based upon the presence or absence of a Val$^{158}$Met polymorphism in the COMT gene, and/or an increase or decrease in the subject's proline level.

Assays for determining a subject's genotype for the allele(s) of the COMT gene have been disclosed previously herein. Assays for determining a subject's proline level are well-known in the art. See, e.g., Wu, 1993; Inoue et al., 1996; Le Boucher et al., 1997; and Grainger et al., 2004; Liang et al., 2015. Non-limiting examples of proline assays include high throughput (HTP) proline assay, liquid chromatography/mass spectrometry (LC-MS/MS), and automated ion-exchange chromatography. In addition, commercial services for such assays are also available from vendors such as ARUP Laboratories (Salt Lake City, Utah).

As used herein, "modifying the course of treatment" refers to any change in the subject's treatment type and/or dosage, including administering a different proline modulator to the subject, stopping or omitting treatment with a proline modulator, adding an additional proline modulator to the treatment, and increasing or decreasing the dosage of a proline modulator. For subjects homozygous for Val, when it is determined that a subject's proline levels are not optimal, a target overnight fasting proline range after treatment onset of greater than about 158 µM is desired. Other target proline ranges of the invention include, for example, between 150 µM to 700 µM or 150 µM to 550 µM. For subjects with at least one Met allele, when it is determined that a subject's proline levels are not optimal, a target overnight fasting proline range after treatment onset below about 258 µM, such as below 170 µM, is desired. Other target proline ranges of the invention include, for example, between 80 µM to 318 µM.

Another embodiment of the present invention is a diagnostic system for identifying a subject with a disorder who will benefit from an agent that increases or decreases proline levels, comprising:
 a) obtaining a biological sample from the subject;
 b) determining the identity of alleles of the Val$^{158}$Met locus associated with the COMT gene in the sample;
 wherein the presence of Val/Val is indicative of a subject who will benefit from an agent that increases proline levels and wherein the presence of at least one Met allele is indicative of a subject who will benefit from an agent that decreases proline levels.

In one aspect of the present invention, the diagnostic system may be used to assess prodromal subjects prior to onset of, e.g., psychotic symptoms, and to determine possible treatment protocols based on COMT and/or proline status.

One aspect of this embodiment may further comprise c) administering, to the subject who will benefit from an agent that increases proline levels, a composition that is selected from the group consisting of valproic acid (VPA), divalproex sodium, valproate, sodium valproate, magnesium valproate, lactic acid, miR-23b, miR-23a/b, (L or D)-proline, (L or D)-arginine, (L or D)-glutamine, (L or D)-ornithine, (L or D)-glutamic acid, (L or D)-glutamate, poly(L or D)-proline, poly(L or D)-glutamine, poly(L or D)-ornithine, poly(L or D)-glutamate, poly(L or D)-arginine, analogs of any of the foregoing, and combinations thereof, including mixed polypeptides of (L or D)-proline, (L or D)-glutamine, (L or D)-ornithine, (L or D)-arginine, (L or D)-glutamic acid, or (L or D)-glutamate. Alternatively, another aspect of this embodiment may further comprise c) administering, to the subject who will benefit from an agent that decreases proline levels, a composition that is selected from the group consisting of vitamin D$_1$, vitamin D$_2$, vitamin D$_3$, vitamin D$_4$, vitamin D$_5$, Calcitriol, curcumin, one or more thiazolidinedione compounds, colchicine, Etanercept, S26948, INT131, phentoin, analogs of any of the foregoing, and combinations thereof. In this embodiment, the obtaining and determining steps are previously disclosed herein.

Another embodiment of the present invention is a kit comprising any of the diagnostic systems disclosed herein. Such kits are packaged together with instructions for its use. Such a kit may include, for example, one or more reagents for determination/identification of a COMT genotype or Val$^{158}$Met polymorphism, a collection device, and one or more containers. The kit may be used in determining how to regulate proline levels in a subject to effect reduction or eradication of one or more negative symptoms of the subject. Exemplary reagents include, but are not limited to, primers, probes, antibodies, enzymes, oligonucleotides, and immunoassays.

Another embodiment of the present invention is a method for predicting the clinical response of a subject with a disorder to a proline modulator comprising:
 a) determining the identity of the allele(s) of the Val$^{158}$Met locus associated with the COMT gene using a biological sample of the subject;
 wherein the presence of Val/Val at the locus is indicative of a subject who will benefit from an agent that increases proline levels, and wherein the presence of at least one Met allele at the locus is indicative of a subject who will benefit from an agent that decreases proline levels; and
 b) administering, if appropriate based on the results of step (a), an effective amount of a proline modulator to the subject to achieve a clinically appropriate response.
The determining and administering steps as well as the proline modulators of this embodiment are as previously disclosed herein.

Another embodiment of the present invention is a method for monitoring the treatment of a subject with a disorder, the method comprising:
 a) determining the genotype for the allele(s) of the COMT gene at amino acid position 158 in a biological sample of the subject;
 b) determining the proline level of the subject; and
 c) modifying the course of treatment of the subject, if necessary, including administering a different proline modulator to the subject or stopping or omitting treatment with a proline modulator, based upon the presence or absence of a Val$^{158}$Met polymorphism in the COMT gene.

Another embodiment of the present invention is a diagnostic system for identifying a subject with a disorder who will benefit from treatment with an agent that increases or decreases proline levels comprising:
 determining the identity of the allele(s) of the Val$^{158}$Met locus associated with the COMT gene using a biological sample from the subject;

wherein the presence of Val/Val at the locus is indicative of a subject who will benefit from an agent that increases proline levels and wherein the presence of at least one Met allele at the locus is indicative of a subject who will benefit from an agent that decreases proline levels.

In the last two embodiments, the determining and modifying steps, if present, and the proline modulators, are as disclosed previously herein.

Another embodiment of the present invention is a method for treating or ameliorating the effects of a disorder in a subject in need thereof. The method includes:
a) obtaining a biological sample from the subject;
b) determining, in the biological sample, the presence or absence of a Val$^{158}$Met polymorphism in the COMT gene; and
c) administering to the subject, if appropriate based on the results of step (b), an effective amount of an agent that increases proline levels if the subject is determined from step (b) to have a Val/Val genotype at codon 158; or
d) administering to the subject, if appropriate based on the results of step (b), an effective amount of an agent that decreases proline levels if the subject is determined from step (b) to have a Val/Met or Met/Met genotype at codon 158.

In this embodiment, the obtaining, determining, and administering steps have been disclosed previously herein. As used herein, the terms "ameliorate", "ameliorating" and grammatical variations thereof mean to decrease the severity of the symptoms, particularly negative symptoms, of a disease in a subject, preferably a human. The polymorphism, disorders, biological samples, and agents for increasing or decreasing proline levels in this embodiment are as disclosed previously herein.

In one aspect of this embodiment, carrying out the method results in reducing or eradicating negative symptoms associated with the disorder. Examples of such negative symptoms include, but are not limited to, flat or blunted affect, social withdrawal, apathy, diminished emotional expression, avolition, alogia, autonomic dysfunction, impairment of executive performances, inattention, and behavioral problems. Preferred examples of negative symptoms according to the present invention include diminished emotional expression, avolition, impaired social functioning, alogia, apathy, anhedonia, or combinations thereof.

In another aspect of this embodiment, numerous ways to assess negative symptoms in a subject are provided, including, e.g., a Scale for Negative Symptoms (SANS) score, a Brief Psychiatric Rating Scale (BPRS) negative symptom sub-scale score, a Positive and Negative Syndrome Scale (PANSS) negative symptom sub-scale score, a Brief Negative Symptom Scale (BNSS) score, clinical assessment interview for negative symptoms, negative assessment, or other measures of negative symptoms in the subject. Other methods for detecting negative symptoms known in the art may also be used. Such additional methods include, e.g., tests and assessments for physical, physiological, or behavioral markers, including neuroimaging, electroencephalogram (EEG), and neurophysiological tests such as mismatched negativity (MMN), P3a, P50, and P100 indices, pre-pulse inhibition (PPI), startle habituation, and antisaccade. In the present invention, however, the preferred method for assessing negative symptoms is the SANS score as disclosed in more detail in the Examples and Figures.

Another embodiment of the present invention is a method for treating or ameliorating the effects of a disorder in a subject in need thereof comprising:
a) determining, using a biological sample of the subject, the presence or absence of a Val$^{158}$Met polymorphism in the COMT gene of the subject; and
b) administering to the subject, if clinically appropriate, an effective amount of an agent that increases proline levels if the subject is determined from step a) to have a Val/Val genotype at codon 158; or
c) administering to the subject, if clinically appropriate, an effective amount of an agent that decreases proline levels if the subject is determined from step a) to have a Val/Met or Met/Met genotype at codon 158.

In this embodiment, the determining and administering steps, and the agents, are as disclosed previously herein.

Yet another embodiment of the present invention is a method for eradicating or reducing a negative symptom experienced by a subject who suffers from a disorder comprising:
a) obtaining a biological sample from the subject;
b) determining, in the biological sample, the presence or absence of a Val$^{158}$Met polymorphism in the COMT gene; and
c) administering to the subject, if clinically appropriate, an effective amount of an agent that increases proline levels if the subject is determined from step b) to have a Val/Val genotype at codon 158; or
d) administering to the subject, if clinically appropriate, an effective amount of an agent that decreases proline levels if the subject is determined from step b) to have at least one Met allele at codon 158.

In this embodiment, the negative symptoms are as described previously. Furthermore, the obtaining, determining, and, if appropriate, administering steps in this embodiment have been described previously.

Below are a set of genes and variants which (individually and/or in various combinations and/or groups) may modify interaction(s) of proline and/or (glutamate, GABA, glycine, L- and/or D-serine, D-cycloserine, and molecules listed above) with COMT. They include proline and dopamine metabolism and transporter genes.

COMT genotypes and/or gene-associated variants including the Val$^{158}$Met polymorphism and/or rs6270 and/or rs6269 and/or rs4633 and/or rs4818 and/or rs6267 and/or rs5031015 and/or rs4986871 and/or rs4680 (including either allele and/or sequence alternative for COMT Uniprot variant Ids: VAR_013925 and/or VAR_013926 and/or VAR_020274 and/or VAR_020275 and/or VAR_005139 (both alleles (Val and/or Met)) and/or VSP_018778.

PRODH variants including the rs450046 and/or rs372055 and/or rs2904552 and/or rs137852934 and/or rs4819756 and/or rs193919334 and/or rs2008720 and/or rs2904551 and/or rs3970559 and/or rs1807467 and/or rs2870983 and/or rs3970555 and/or rs2238731 and/or rs2870984 and/or (including either allele alternative for PRODH Uniprot Variant ids: VAR_029566 and/or VAR_029568 and/or VAR_029569 and/or VAR_029570 and/or VAR_029571 and/or VAR_029572 and/or VAR_029573 and/or VAR_029575 and/or VAR_029577 and/or VAR_029567 and/or VAR_029569 and/or VAR_029571 and/or VAR_029574 and/or VAR_029575 and/or VAR_029577.

SLC6A7 variants and associated variants including rs1468564, and/or rs13153971 and/or rs3776083.

SLC6A20 variants and associated variants including rs17279437 and/or rs2271615 and/or rs6770261 and/or rs758386 and/or rs4327428.

SLC6A15 variants and associated variants including rs1545843 and/or rs12424429 and/or rs3782369 and/or rs1031681.

SLC6A18 variants and associated variants including rs34469326 and/or rs7728667 and/or rs7705355 and/or rs113861454 and/or rs4073918 and/or rs147278493 and/or rs12522796 and/or rs4975623 and/or rs4975625 and/or rs7447815 and/or rs7728646.

PEPD variants and associated variants including rs121917721 and/or rs121917724 and/or rs121917723 and/or rs17570 and/or rs121917722 and/or rs121917725 and/or rs267606944 and/or rs267606943 and/or rs757386104 and/or rs797045185 and/or rs794728007 and/or rs747700126 and/or rs794728008 and/or rs3786897 and/or rs4805885 and/or rs731839 and/or rs8182584 and/or rs889140 and/or (including either allele alternative for Prolidase PEPD Uniprot Variant ids:VAR_011614 and/or VAR_004404 and/or VAR_011615 and/or VAR_004405 and/or VAR_004406).

MAOA variants and associated variants including rs77698881 and/or rs587777457 and/or rs1799835 and/or rs1800466 and/or rs1137070 and/or rs1465107 and/or rs2072743 and/or rs2235186 and/or rs2283725 and/or rs3027400 and/or rs3027407 and/or rs3027409 and/or rs5906883 and/or rs5906957 and/or rs5953210 and/or rs6323 and/or rs6609257 and/or rs72554632 and/or rs796065311 and/or rs796065312 and/or rs909525 and/or rs979606 and/or (including either allele and/or sequence alternative for MAOA Uniprot Variant and associated variant ids VAR_036545 and/or id VSP_045173).

MAOB variants and associated variants including rs10521432 and/or rs1799836 and/or rs2283729 and/or rs3027415 and/or rs6651806 and/or (including either allele and/or sequence alternative for MAOB Uniprot Variant and associated variant ids VSP_057047 and/or VSP_057048 and/or VSP_057049).

GAD1 variants and associated variants including rs121918345 and/or rs45566933 and/or rs769403 and/or rs769402 and/or rs1049736 and/or rs11542313 and/or rs12185692 and/or rs2058725 and/or rs2241165 and/or rs3749034 and/or rs3762555 and/or rs3791850 and/or rs3791851 and/or rs3791878 and/or rs3828275 and/or rs769390 and/or rs769391 and/or rs769404 and/or rs769407.

GAD2 variants and associated variants including rs8190591 and/or rs8190600 and/or rs2839672 and/or rs2839673 and/or rs8190671 and/or rs2839678 and/or rs8190730 and/or rs1805398 and/or rs185649317 and/or rs2236418 and/or rs8190590 and/or rs8190748 and/or rs992990.

Additional Definitions

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Imino acids such as, e.g., proline, are also within the scope of "amino acid" as used here. An "amino acid mimetic" means a chemical compound that has a structure that is different from the general chemical structure of an amino acid, but that functions similarly to a naturally occurring amino acid.

As used herein, the terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

EXAMPLES

The following examples are provided to further illustrate certain aspects of the present invention. These examples are illustrative only and are not intended to limit the scope of the invention in any way.

Example 1

Materials and Methods
Participants:

Male and female, African American, Caucasian and Hispanic patients, aged 18-65, were recruited from Bellevue Hospital Center (BHC). A diagnosis of schizophrenia or bipolar disorder was confirmed using the Structured Clinical Interview for DSM IV Disorders (SCID). After description of the study to subjects, written informed consent was obtained in accordance with IRB regulations.

For schizophrenia inpatients, recruitment was cross-sectional and independent of their duration of hospitalization. Psychiatric symptoms were measured using the Scale for the Assessment of Negative Symptoms (SANS), the Scale for the Assessment of Positive Symptoms (SAPS), and the Brief Psychiatric Rating Scale (BPRS). Proline levels of a subset of the schizophrenia patients, those who did not receive treatment with VPA or divalproex, were reported previously (Clelland et al., 2011).

Bipolar patients were recruited upon presentation at the BHC Comprehensive Emergency Psychiatric Program. Psychiatric symptoms in bipolar disorder patients were measured at an admission visit (visit 1), using the BPRS. At a follow-up inpatient ward visit (visit 2), fasting bloods were collected plus a repeat BPRS assessment performed. Additionally, as shown in FIG. 1, an association with elevated proline in bipolar disorder patients was tested. It was found that patients did not have fasting proline levels different to controls, consistent with previous findings (Jacquet et al., 2005).

Determination of Fasting Plasma Levels:

Fasting morning blood draws were performed and proline measured in μmoles/liter as reported (Clelland et al., 2011).

Genotyping:

DNA was extracted from blood using the Puregene Blood Core Kit (Qiagen Inc) and the COMT fragment containing the Val$^{158}$Met polymorphism amplified using the 5'-3' primers: ACTGTGGCTACTCAGCTGTG (SEQ ID No: 4) and CCTTTTTCCAGGTCTGACAA (SEQ ID NO: 5). A step-down PCR was employed with an initial denaturation of 94° C.:15 minutes, then 12 cycles of 94° C.:30 seconds, 58° C.:45 seconds and 72° C.:30 seconds, followed by 31 cycles of 94° C.:30 seconds, 50° C.:45 seconds and 72° C.:30 seconds, with a final 72° C.:7 minute extension. Restriction enzyme NlaIII recognizes and cleaves the amplicon into Val (114 bp) or Met (96 bp) fragments, visualized following electrophoreses. To confirm genotyping accuracy, 25% of samples were repeat assayed.

Statistical Analysis:

Group differences were assessed using ANOVA, Kruskal-Wallis and Mann-Whitney tests (following skewness and kurtosis normality tests), $\chi^2$ or Fisher exact tests. Means±standard deviations (SD) were reported, plus Bonferroni adjusted p-values where appropriate. Genotype distributions were tested for Hardy-Weinberg equilibrium (HWE) using a $\chi^2$ or exact test.

Linear regression was employed to test for an interaction between fasting plasma proline and COMT on symptoms in schizophrenia, modelling the relationships of these variables on outcomes of total SANS, SAPS and BPRS scores. Based upon the schizophrenia sample result, the primary outcome for bipolar patients was assessed using the BPRS negative symptom subscale (Kane et al., 1988), and percent reduction in negative symptoms calculated. Positive symptom subscale of the BPRS (Id.) and total BPRS scores were also investigated. When outliers in the data or leverage points were identified, a robust regression procedure was employed using an MM estimator to minimize data-point effects (SASv9.3).

Significant models were investigated further: To assess utility in adjusting the dependent variable, demographic and clinical covariates were entered into a bivariate regression and terms found to have p-values of <0.10 carried forward to a multivariate model. Gender was a covariate in all models, to adjust for previously reported proline gender differences (Jacquet et al., 2005; Tomiya et al., 2007; Clelland et al., 2011). Model fit and selection was determined using the Wald test, testing the null hypothesis that non-significant (p>0.05) covariate parameters were simultaneously equal to zero in full and subsequent reduced models. Statistical analysis was performed in SASv9.3, Stata ICv12, with graphs plotted in GGplot2v1.0.1 in Rv3.1.2.

Example 2

Results

COMT Genotype Modifies the Relationship Between Proline and Negative Symptoms of Schizophrenia:

The schizophrenia sample consisted of 95 patients. Although recruitment was not targeted by COMT genotype, patients were well matched on demographic characteristics and medication use across genotypes (Table 2).

In the entire sample, fasting plasma proline was not significantly different across genotypes (range 87 μM to 502 μM). There were also no differences in BPRS total or negative symptoms (SANS total score), however positive symptoms were significantly different: Met/Met patients had lower SAPS scores than Val/Met (Mann-Whitney z=2.52, adjusted p=0.035) or Val/Val patients (z=2.92, adjusted p=0.001), as previously reported (Goghari & Sponheim, 2008). 100% accuracy was achieved from confirmatory re-genotyping and a sample of 90 control subjects were in HWE for COMT Val$^{158}$Met (p>0.05, data not shown). However, COMT distributions of the schizophrenia patients deviated from HWE ($\chi^2$=8.08, df=1, p<0.05). Although deviations for this polymorphism in schizophrenia have been reported (Joober et al., 2002), this finding may represent substructure due to mixed ethnicity: when stratified by ethnicity, all groups were in HWE (p>0.05).

TABLE 2

Demographic and Clinical Characteristics of Schizophrenic Patients (SZ), n = 95

| Characteristic | Met/Met n = 21 | Val/Met n = 32 | Val/Val n = 42 | Prob$^a$ |
|---|---|---|---|---|
| Gender, n (row %) | | | | 0.288 |
| Female | 11 (23.4) | 19 (40.4) | 17 (36.2) | |
| Males | 10 (20.8) | 13 (27.1) | 25 (52.1) | |

TABLE 2-continued

Demographic and Clinical Characteristics of Schizophrenic Patients (SZ), n = 95

|  | Met/Met n = 21 | Val/Met n = 32 | Val/Val n = 42 | Prob[a] |
|---|---|---|---|---|
| Ethnicity, n (row %) |  |  |  | 0.096 |
| African American | 5 (13.5) | 10 (27.0) | 22 (59.5) |  |
| Caucasian | 10 (35.7) | 10 (35.7) | 8 (28.6) |  |
| Hispanic | 6 (20.0) | 12 (40.0) | 12 (40.0) |  |
| Age (years), mean ± SD | 40.9 ± 10.9 | 39.1 ± 11.5 | 39.9 ± 11.6 | 0.820 |
| Smoking Status[b], n (row %) |  |  |  | 0.389 |
| Current or Previous | 15 (24.6) | 24 (39.3) | 22 (36.1) |  |
| Never Smoked | 6 (20.7) | 8 (27.6) | 15 (51.7) |  |
| History of Alcoholism, n (%) |  |  |  | 0.426 |
| Neither | 17 (23.6) | 27 (37.5) | 28 (38.9) |  |
| Abuse | 1 (10.0) | 2 (20.0) | 7 (70.0) |  |
| Dependence | 3 (23.1) | 3 (23.1) | 7 (53.8) |  |
| Education[c] | 3.6 ± 1.9 | 3.1 ± 1.0 | 3.4 ± 1.5 | 0.859 |
| Age at First Hospitalization[d], mean ± SD | 23.5 ± 8.0 | 25 ± 6.5 | 23.7 ± 7.5 | 0.465 |
| Hospital Duration (days)[e], mean ± SD | 19.1 ± 17.1 | 21.9 ± 23.4 | 20.0 ± 19.6 | 0.998 |
| Fasting Plasma Proline, umol/L | 219.9 ± 91.6 | 240.5 ± 68.6 | 246.4 ± 91.1 | 0.391 |
| Symptoms |  |  |  |  |
| BPRS[f] Total Symptoms, mean ± SD | 32 ± 8.5 | 33.6 ± 7.1 | 33.6 ± 8.4 | 0.500 |
| SAPS[g] Total Symptoms, mean ± SD | 10.3 ± 8.3 | 15.8 ± 9.6 | 18.2 ± 10.1 | 0.006* |
| SANS[h] Total Symptoms, mean ± SD | 24 ± 16.8 | 21.8 ± 13.1 | 17.5 ± 13.9 | 0.127 |
| Neuroleptic Medications |  |  |  |  |
| Neuroleptic Type, n (row %) |  |  |  | 0.348 |
| Typical only | 5 (27.8) | 3 (16.7) | 10 (55.6) |  |
| Atypical only | 13 (22.4) | 19 (32.8) | 26 (44.8) |  |
| Both | 3 (16.7) | 9 (50.0) | 6 (33.3) |  |
| None | 0 | 1 (100) | 0 |  |
| Daily CPZE dose[i], mean ± SD | 490.6 ± 234.0 | 571.1 ± 418.1 | 526.8 ± 281.0 | 0.981 |
| Mood Stabilizing Medications |  |  |  |  |
| Total Number Administered, n (row %) |  |  |  | 0.786 |
| 0 | 15 (26.3) | 19 (33.3) | 23 (40.4) |  |
| 1 | 6 (16.7) | 12 (33.3) | 18 (50.0) |  |
| 2 | 0 | 1 (50) | 1 (50) |  |
| VPA Treatment, n (row %) |  |  |  | 0.327 |
| Yes | 4 (12.9) | 11 (35.5) | 16 (51.6) |  |
| No | 17 (26.6) | 21 (32.8) | 26 (40.6) |  |
| Other Medications |  |  |  |  |
| Benzodiazapines, yes: n (row %) | 4 (21.0) | 8 (42.1) | 7 (36.8) | 0.641 |
| Antidepressants, yes: n (row %) | 1 (9.1) | 5 (45.4) | 5 (45.4) | 0.596 |

[a]*= significant p-value when comparing characteristic across three COMT genotypes, calculated by one-way ANOVA, Kruskal-Wallis, or Fisher exact tests.
[b]n = 90, five subjects not reported.
[c]Recorded as a continuous variable from the SCID (range 2-8). n = 93, two subjects not reported.
[d]n = 60 for whom this characteristic could be obtained.
[e]Days in hospital prior to fasting blood draw.
[f]Brief Psychiatric Rating Scale.
[g]Schedule for Assessment of Positive Symptoms.
[h]Schedule for Assessment of Negative Symptoms.
[i]Chlorpromazine (CPZ) equivalent dose, n = 94 as one subject's NL had no CPZ equivalent.

Figure 2A:
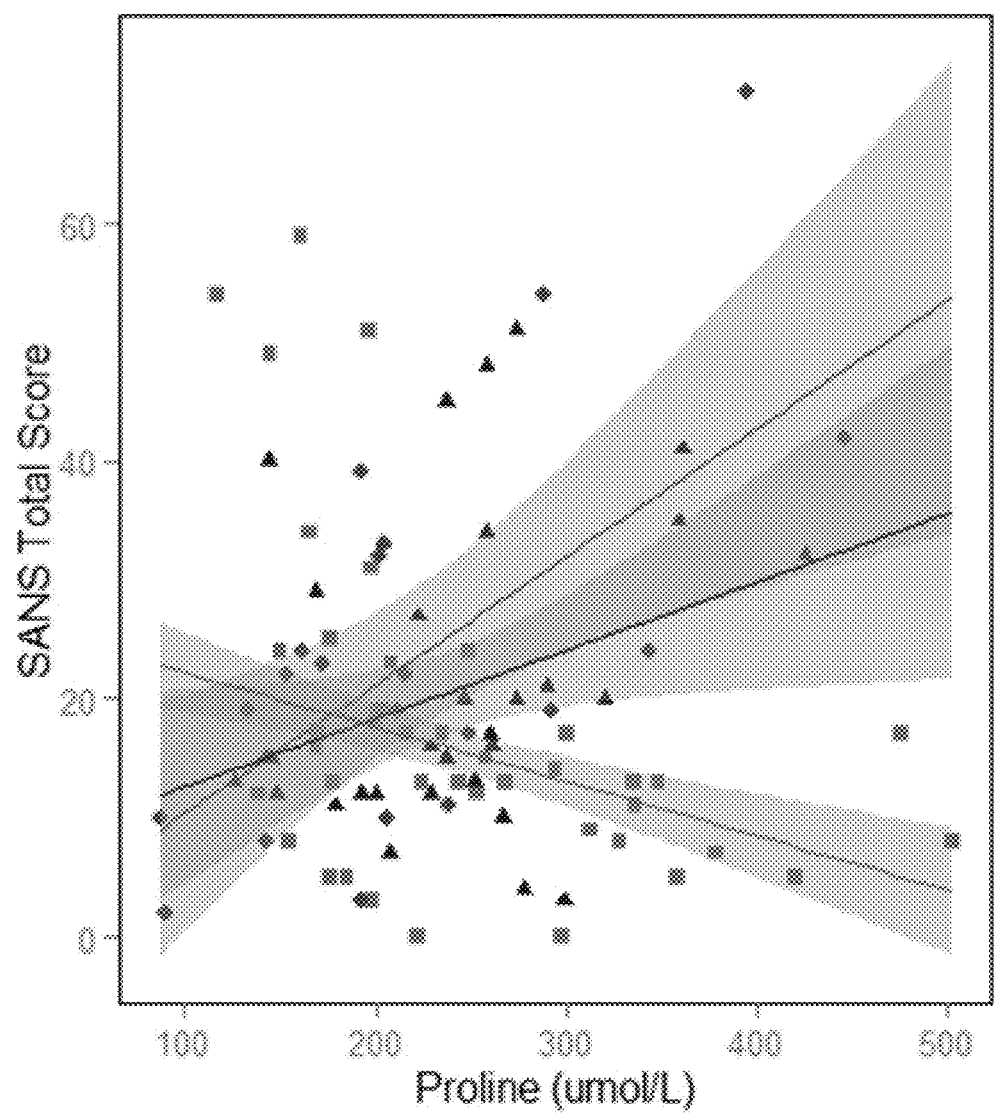
FIG. 2A shows a scatterplot graph of the relationship between proline and negative symptoms as measured using the Scale for the Assessment of Negative Symptoms (SANS), plotted for patients with the Met/Met (n=21, red diamonds), Val/Met (n=32, blue triangles) and Val/Val (n=42, green squares) COMT genotypes. Lines represent the predicted values from the regression model for each genotype, with 95% confidence intervals. There was a significant positive relationship between proline and SANS score in Met/Met and Val/Met patients, with high proline levels being associated with high SANS scores. Conversely there existed a significant negative relationship in Val/Val patients, with high proline associated with lower levels of negative symptoms.
Figure 2B:
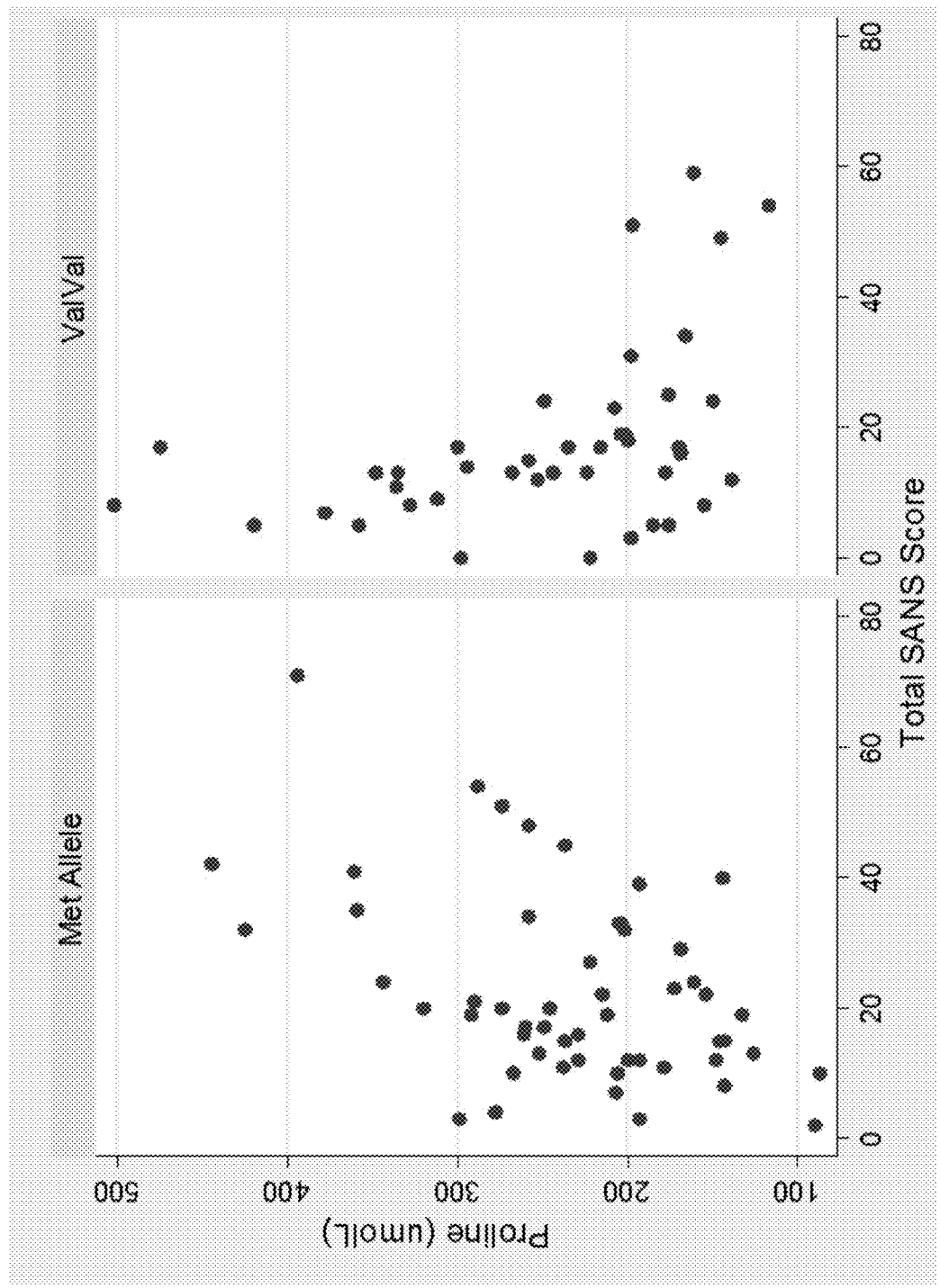
FIG. 2B shows scatterplot graphs of the relationship between proline and total negative symptoms, as assessed using the SANS, by COMT genotype (Met allele (left panel) or Val/Val (right panel)). There was a significant positive relationship between total SANS score and proline in schizophrenia patients with the Met allele (spearman's rho=0.36, p=0.009, n=53), while conversely there was a significant negative relationship between total SANS score and proline in Val/Val schizophrenia patients (spearman's rho=−0.47, p=0.0019, n=42).

Testing the primary hypothesis of effect modification, a significant interaction was observed between COMT genotype and proline on negative symptoms in schizophrenia patients (n=95, interaction β coefficient=0.082, p<0.0001). As shown in FIGS. 2A and 2B, for patients with both the Met/Met or Val/Met genotypes, high proline was associated with high SANS scores, while conversely high proline in Val/Val patients was associated with lower levels of negative symptoms. Stratifying by COMT (Met allele carrier or Val/Val), for Met carriers, every 100 μM increase in proline (approximately 1SD from the mean proline level) was associated with a SANS total score increase of over 8 points (β coefficient=0.084, p=0.001). Conversely, for Val/Val patients, every 100 μM increase in proline decreased SANS total scores by nearly 7 points (β=−0.067, p=0.003). Thus at proline levels only approximately 1 SD above the group means, Met carriers with a fasting plasma proline of 332 μM had a predicated SANS score of 30, while Val/Val patients with proline of 346 μM had a predicted score of only 10.

Possible confounds on this relationship were assessed (see Table 3). While there was no relationship between SANS score and either medication type, neuroleptic dose (summarized as daily chlorpromazine equivalents), or the number of days in hospital prior to blood draw and symptom assessment, covariate analysis showed that ethnicity and alcohol use were predictors of SANS score (p<0.1, Table 3), and along with gender were taken forward to a multivariate model (Table 4). Model fit was determined with the final model retaining genotype, proline, alcohol use, and the highly significant COMT-proline interaction (p<0.0001). The significant interaction also remained in a stratified analysis following removal of patients reporting alcohol abuse/dependence (p<0.001, n=72). Interestingly, there was no interaction of COMT genotype on the relationship between fasting peripheral proline and positive symptoms (interaction β=−0.005, p=0.64), or total symptoms (interaction β=−0.23, p=0.097), suggesting specificity of the relationship to negative symptoms.

TABLE 3

Bivariate Association Between Schizophrenia Patient Demographic and Clinical Characteristics, with Total SANS Score, n = 95

| Characteristic | β (95% CI) | Prob |
|---|---|---|
| Gender[a] | −1.697 (−7.609, 4.215) | 0.570 |
| Ethnicity[b] | | |
| African American v Caucasian | 6.059 (−1.026, 13.143) | 0.093* |
| African American v Hispanic | 7.028 (0.079, 13.977) | 0.047* |
| Age | 0.024 (−0.239, 0.287) | 0.857 |
| Education[c] | 0.389 (−1.660, 2.438) | 0.707 |
| Alcohol Dependence/abuse[b] | | |
| None v Abuse | −0.236 (−9.775, 9.303) | 0.961 |
| None v Dependence | −9.505 (−18.023, −0.987) | 0.029* |
| Smoking Status[d] | −0.882 (−4.112, 2.349) | 0.589 |
| Hospital Duration[e] | 0.026 (−0.121, 0.172) | 0.729 |
| Daily CPZE dose[f] | 0.004 (−0.005, 0.014) | 0.353 |

TABLE 3-continued

Bivariate Association Between Schizophrenia Patient Demographic and Clinical Characteristics, with Total SANS Score, n = 95

| Characteristic | β (95% CI) | Prob |
|---|---|---|
| Neuroleptic (NL) Type[b,g] | | |
| Atypical v Typical | 2.082 (−5.763, 9.930) | 0.599 |
| Atypical v both | −1.584 (−9.430, 6.261) | 0.689 |
| Total Number of NLs Administered[h] | −2.961 (−10.614, 4.692) | 0.444 |
| Total Number of Mood Stabilizers Administered[i] | 1.320 (−4.886, 7.526) | 0.674 |
| VPA Treatment[j] | −0.578 (−7.157, 6.001) | 0.862 |
| Benzodiazepines | −3.342 (−10.713, 4.028) | 0.370 |

[a]Binary variable: Male v female.
[b]For categorical analysis the reference category is the first level listed for each variable.
[c]Recorded as a continuous variable from the SCID (range 2-8)
[d]Binary variable: Never v current or previous smokers, n = 90 as four subjects did not report smoking status.
[e]Days in hospital prior to fasting blood draw and symptoms assessment.
[f]Chlorpromazine (CPZ) equivalent dose, n = 93 as one subject's NL had no CPZ equivalent, and one subjects did not receive a NL.
[g]n = 94, as one subject did not receive a NL.
[h]Binary variable: one v two, n = 92 (as one subject did not receive a NL, and only two subjects were administered >2 different NLs).
[i]Binary variable: no versus yes, n = 92 (as three subjects had not received <48 hours of VPA treatment).
[j]Binary variable: none versus one, n = 93 (as only two subjects were administered >1 mood stabilizers).

TABLE 4

Prediction of Negative Symptoms from Proline Level and COMT in Psychiatric Patients

| | β Coefficient | SE | Test statistic[a] | Prob | Wald test |
|---|---|---|---|---|---|
| Schizophrenia Models (DV = Total SANS Score, n = 95) | | | | | |
| Full Model[b] | | | | | |
| Proline | −0.1050 | 0.0333 | 9.94 | 0.0016* | |
| COMT (ValVal, ValMet, MetMet) | −13.0179 | 4.2452 | 9.40 | 0.0022* | |
| Interaction (Proline = COMT) | 0.0744 | 0.0169 | 19.48 | <.0001* | |
| Alcohol Use | | | | | |
| Alcohol Abuse v None | −4.2178 | 4.2706 | 0.98 | 0.3233 | |
| Alcohol Dependence v None | −9.0807 | 3.5632 | 6.49 | 0.0108* | |
| Gender | −1.0466 | 2.3795 | 0.19 | 0.6600 | |
| Ethnicity | | | | | |
| African-American v Caucasian | 3.0258 | 3.0258 | 1.14 | 0.2866 | |
| African-American v Hispanic | 4.6703 | 2.8214 | 2.74 | 0.0979 | p = 0.517[c] |
| Final Model[b] | | | | | |
| Proline | −0.0804 | 0.0321 | 6.28 | 0.0122* | |
| COMT (ValVal, ValMet, MetMet) | −9.6576 | 4.0300 | 5.74 | 0.0166* | |
| Interaction (Proline × COMT) | 0.0651 | 0.0161 | 16.39 | <.0001* | |
| Alcohol Use | | | | | |
| Alcohol Abuse v None | −5.1234 | 3.9854 | 1.65 | 0.1986 | |
| Alcohol Dependence v None | −9.7478 | 3.3526 | 8.45 | 0.0036* | p = 0.020[d] |
| Bipolar Disorder Models (DV = % Change in BPRS Negative Symptoms Scale, n = 43) | | | | | |
| Full Model | | | | | |
| Proline | 0.0012 | 0.0006 | 2.09 | 0.044* | |
| COMT (Met/Met v ValVal) | 0.4281 | 0.1650 | 2.60 | 0.014* | |
| Interaction (Proline × COMT) | −0.0017 | 0.0007 | −2.42 | 0.022* | |
| Gender | 0.1960 | 0.0656 | 2.99 | 0.005* | |
| Ethnicity | | | | | |
| African-American v Caucasian | 0.0186 | 0.0839 | 0.22 | 0.826 | |
| African-American v Hispanic | −0.1528 | 0.1052 | −1.45 | 0.156 | |
| Duration (days) between Assessments | 0.0049 | 0.0070 | 0.69 | 0.492 | |

TABLE 4-continued

Prediction of Negative Symptoms from Proline Level and COMT in Psychiatric Patients

|  | β Coefficient | SE | Test statistic[a] | Prob | Wald test |
|---|---|---|---|---|---|
| Neuroleptic Type |  |  |  |  |  |
| Atypical Neuroleptic v None | −0.0802 | 0.0818 | −0.98 | 0.334 |  |
| Typical Neuroleptic v None | −0.1401 | 0.2087 | −0.67 | 0.507 |  |
| Both v None | −0.1531 | 0.1184 | −1.29 | 0.206 |  |
| Benzodiazepines | −0.0840 | 0.0714 | −1.18 | 0.249 | p = 0.056[e] |
| Final Model |  |  |  |  |  |
| Proline | 0.0016 | 0.0006 | 2.55 | 0.015* |  |
| COMT (Met/Met v ValVal) | 0.5029 | 0.1766 | 2.85 | 0.007* |  |
| Interaction (Proline × COMT) | −0.0021 | 0.0007 | −2.83 | 0.007* |  |
| Gender | 0.1856 | 0.0656 | 2.83 | 0.007* | p = 0.0074[f] |

[a]$\chi^2$ (Schizophrenia models using Robust linear regression) or t (Bipolar models using linear regression)
[b]Robust regression, MM Estimation Method (28).
[c]Robust Wald tests canonical linear hypothesis that combined effect of non-significant covariates (Gender and Ethnicity) is zero.
[d]Robust Wald tests hypothesis that covariate effect (Alcohol use) is zero.
[e]Wald tests canonical linear hypothesis that combined effect of non-significant covariates (Ethnicity, Duration, Neuroleptic Type and use of Benzodiazepines) is zero.
[f]Wald tests hypothesis that covariate effect (Gender) is zero.

Example 3

Figure 3:
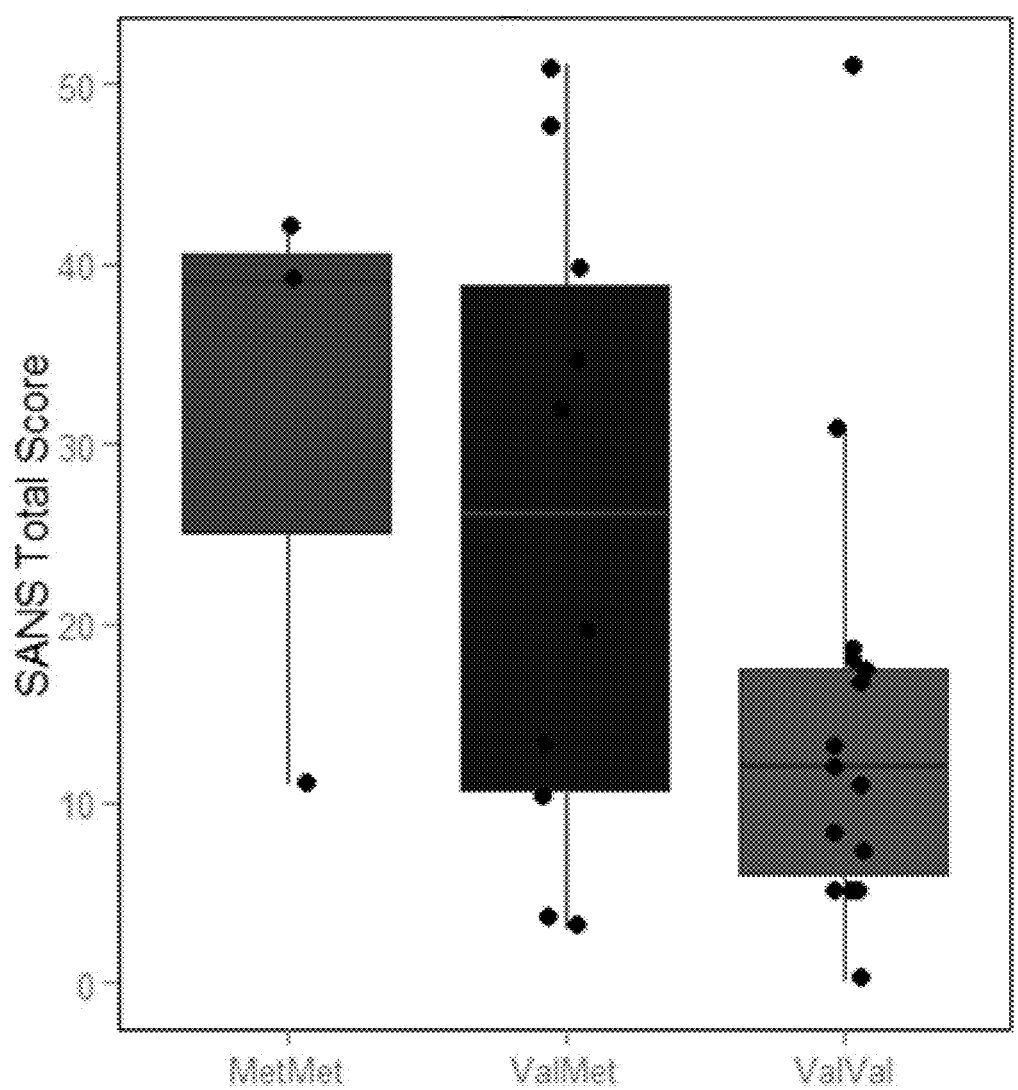
FIG. 3 shows a boxplot illustrating that negative symptoms, as assessed by the total SANS score, were significantly lower in VPA treated patients with the COMT Val/Val genotype (mean=14.6±12.67, n=15, green), as compared to pooled Met/Met (mean=30.67±17.1, n=3, red) and Val/Met (mean=25.6±17.93, n=10, blue) genotypes (F(1,26)=4.63, p=0.0408). Subjects were included if they had received 48 hours or more of VPA treatment, within 48 hours of the study visit (n=28, three subjects were dropped because they had less than 48 hours of VPA treatment). Black jittered points represent individual data. The horizontal line within each box represents the group median. The box indicates the IQR. The whiskers extend to the most extreme data point which is 1.5 times the IQR.

Valproate Treated COMT Val/Val Schizophrenia Patients have Significantly Lower Negative Symptoms than Met Allele Carriers:

An effect of VPA on plasma proline has been reported (Jacquet et al., 2005) and VPA-treated schizophrenia patients in the current study had significantly higher proline (mean=299.29±94.76, n=28) than those who did not receive VPA (mean=215.84±63, n=64) (z=−3.97, p=0.0001). Considering the finding of an interaction between COMT and proline on negative symptoms, the hypothesis was that VPA treated Val/Val patients would respond differently to the concomitant high levels of proline, with respect to their negative symptoms, as compared to Met carriers. As shown in FIG. 3, VPA-treated Val/Val schizophrenia patients had significantly lower SANS total scores, averaging twelve points lower than Val/Met and Met/Met patients (β=−12.17, p=0.041, n=28). This result remained significant after adjusting for the dose of VPA administered in the 48 hours prior to the blood draw (p=0.043).

Example 4

COMT Genotype Modifies the Relationship Between Proline and Negative Symptom Change in in Bipolar Disorder:

The hypothesis that COMT genotype modifies the relationship between proline and negative symptoms across psychiatric illnesses was explored, employing a second patient sample: 43 subjects with bipolar disorder who had completed a BPRS assessment upon admission to the psychiatric ER (visit 1) plus a second BPRS assessment and fasting blood draw during their follow-up visit (mean duration between assessments=9.5±4.6 days). Thus, for this sample the relationship between COMT and proline on the change in symptoms was calculated by the percent reduction in negative symptoms from admission to follow-up.

As for the schizophrenia cohort, recruitment of the bipolar sample was not targeted by COMT genotype, but subjects were matched on demographic characteristics (Table 5) and medication use at both study visits (Table 6). The distribution of COMT genotypes was in HWE ($\chi^2$=0.387, df=1, p>0.05). Due to the finding in schizophrenia that Met allele carriers have a similar response to high proline, and because of the smaller bipolar sample size, Met/Met and Val/Met bipolar groups were pooled for further analysis.

TABLE 5

Demographic and Clinical Characteristics of Bipolar Disorder Patients, n = 43

| Characteristic | Met/Met n = 5 | Val/Met n = 22 | Val/Val n = 16 | Prob[a] |
|---|---|---|---|---|
| Gender, n (row %) |  |  |  | 0.328 |
| Female | 1 (6.2) | 11 (68.8) | 4 (25.0) |  |
| Male | 4 (14.8) | 11 (40.7) | 12 (44.4) |  |
| Ethnicity, n (row %) |  |  |  | 0.450 |
| African American | 0 | 4 (57.1) | 3 (42.9) |  |
| Asian | 0 | 0 | 1 (100) |  |
| Caucasian | 3 (11.5) | 13 (50.0) | 10 (38.5) |  |
| Hispanic | 2 (22.2) | 5 (55.6) | 2 (22.2) |  |
| Age (years), mean ± SD | 34 ± 9.7 | 32.8 ± 8.4 | 33.2 ± 11.2 | 0.933 |
| Smoking Status[b], n (row %) |  |  |  | 1.000 |
| Current or Previous | 4 (13.3) | 15 (50.0) | 11 (36.7) |  |
| Never Smoked | 1 (8.3) | 6 (50.0) | 5 (41.7) |  |
| History of Alcoholism, n (row %) |  |  |  | 1.000 |
| Abuse | 1 (7.1) | 8 (57.1) | 5 (35.7) |  |

TABLE 5-continued

Demographic and Clinical Characteristics of Bipolar Disorder Patients, n = 43

| Characteristic | Met/Met n = 5 | Val/Met n = 22 | Val/Val n = 16 | Prob[a] |
|---|---|---|---|---|
| Dependence | 1 (12.5) | 4 (50.0) | 3 (37.5) | |
| Neither | 3 (14.3) | 10 (47.6) | 8 (38.1) | |
| Education[c], mean ± SD | 4.2 ± 2.0 | 3.8 ± 1.6 | 4.2 ± 2.0 | 0.709 |
| Fasting Plasma Proline[d], umol/L | 213.6 ± 72.7 | 205.5 ± 63.2 | 245.8 ± 123.4 | 0.669 |
| Age at Onset, mean ± SD | 25.8 ± 2.8 | 26.4 ± 8.3 | 24.1 ± 7.8 | 0.207 |
| Age at First Hospitalization, mean ± SD[a] | 26 ± 3.2 | 26.8 ± 9.3 | 22.9 ± 7.4 | 0.112 |
| Days between Symptom Assessments, mean ± SD | 10.2 ± 6.2 | 9.4 ± 3.7 | 9.5 ± 5.1 | 0.382 |

[a]P-value values when comparing Met allele carriers to Val/Val patients, calculated by Satterthwaite t-test, Mann-Whitney, Chi-Square or Fisher exact test.
[b]n = 42, one subject not reported.
[c]Recorded as a continuous variable from the SCID (range 2-8).
[d]Sampled at visit 2.

TABLE 6

Clinical Characteristics of Bipolar Disorder Patients, n = 43

| | Admission (Visit 1) | | | | Follow-up (Visit 2) | | | |
|---|---|---|---|---|---|---|---|---|
| Characteristic | Met/Met n = 5 | Val/Met n = 22 | Val/Val n = 16 | Prob[a] | MetMet n = 5 | Val/Met n = 22 | ValVal n = 16 | Prob[a] |
| Brief Psychiatric Rating Scale[b] | | | | | | | | |
| Total Symptoms, mean ± SD | 42 ± 7.3 | 36.3 ± 5.9 | 36.4 ± 4.7 | 0.592 | 34.8 ± 8.8 | 25.9 ± 5.8 | 27.4 ± 5.2 | 0.772 |
| Negative Symptoms[c], mean ± SD | 9.0 ± 5.1 | 6.3 ± 2.2 | 6.2 ± 1.7 | 0.872 | 6.0 ± 1.4 | 5.6 ± 0.9 | 5.6 ± 1.0 | 0.711 |
| Positive Symptoms[d], mean ± SD | 24.6 ± 5.0 | 18.7 ± 6.2 | 18.2 ± 6.2 | 0.457 | 18.4 ± 5.3 | 12.4 ± 4.8 | 13.7 ± 4.2 | 0.553 |
| Psychosis[e]: yes, n (row %) | 4 (13.3) | 14 (46.7) | 12 (40) | 0.735 | | | | |
| Neuroleptic (NL) Medications | | | | | | | | |
| NL Type, n (row %) | | | | 1.000 | | | | 0.745 |
| Typical only | 2 (22.2) | 4 (44.4) | 3 (33.3) | | 0 | 0 | 1 (100) | |
| Atypical only | 1 (12.5) | 4 (50.0) | 3 (37.5) | | 3 (9.7) | 17 (54.8) | 11 (35.5) | |
| Both | 0 | 3 (75) | 1 (25) | | 2 (40.0) | 1 (20.0) | 2 (40.0) | |
| None | 2 (9.1) | 11 (50.0) | 9 (40.9) | | 0 | 4 (66.7) | 2 (33.3) | |
| Daily CPZE dose[f], mean ± SD | 282.3 ± 202.1 | 284.1 ± 109.7 | 239.2 ± 81.5 | 0.403 | 566.7 ± 372.1 | 344.4 ± 162.6 | 362.3 ± 202.6 | 0.863 |
| Total number of NLs, n (row %) | | | | 0.906 | | | | 0.731 |
| 0 | 2 (9.1) | 11 (50) | 9 (40.9) | | 0 | 4 (66.7) | 2 (33.3) | |
| 1 | 3 (17.6) | 8 (47.1) | 6 (35.3) | | 2 (7.1) | 16 (57.1) | 10 (35.7) | |
| 2 | 0 | 3 (75.0) | 1 (25.0) | | 3 (37.5) | 2 (25) | 3 (37.5) | |
| Mood Stabilizing Medications | | | | | | | | |
| Total number of mood stabilizers, n (row %) | | | | 0.282 | | | | 0.785 |
| 0 | 5 (12.5) | 19 (47.5) | 16 (40.0) | | 0 | 1 (100) | 0 | |
| 1 | 0 | 3 (100) | 0 | | 3 (8.3) | 20 (55.6) | 13 (36.1) | |
| 2 | 0 | 0 | 0 | | 2 (33.3) | 1 (16.7) | 3 (50) | |
| VPA: yes, n (row %) | 0 | 1 (100) | 0 | 1.000 | 2 (9.5) | 11 (52.4) | 8 (38.1) | 1.000 |

TABLE 6-continued

Clinical Characteristics of Bipolar Disorder Patients, n = 43

| | Admission (Visit 1) | | | | Follow-up (Visit 2) | | | |
|---|---|---|---|---|---|---|---|---|
| Characteristic | Met/Met n = 5 | Val/Met n = 22 | Val/Val n = 16 | Prob[a] | MetMet n = 5 | Val/Met n = 22 | ValVal n = 16 | Prob[a] |
| Other Medications | | | | | | | | |
| Benzodiazepines: yes, n (row %) | 3 (15.8) | 10 (52.6) | 6 (31.6) | 0.542 | 4 (22.2) | 4 (22.2) | 10 (55.6) | 0.055 |
| Antidepressants: yes, n (row %) | 0 | 2 (66.7) | 1 (33.3) | 1.000 | 1 (5.6) | 7 (38.9) | 10 (55.6) | 0.055 |

[a]P-value values when comparing M allele carriers to ValVal patients, calculated by Satterthwaite t-test, Mann-Whitney, Chi-Square or Fisher exact test.
[b]BPRS = Brief Psychiatric Rating Scale.
[c]Negative Symptoms (BPRS items 3 + 13 + 14 + 16 + 18)
[d]Positive Symptoms (BPRS items 4 + 7 + 8 + 10 + 11 + 12 + 15 + 17)
[e]Psychosis determined as current or previous psychotic illness at admission only.
[f]Chlorpromazine (CPZ) equivalent dose.

Figure 4:
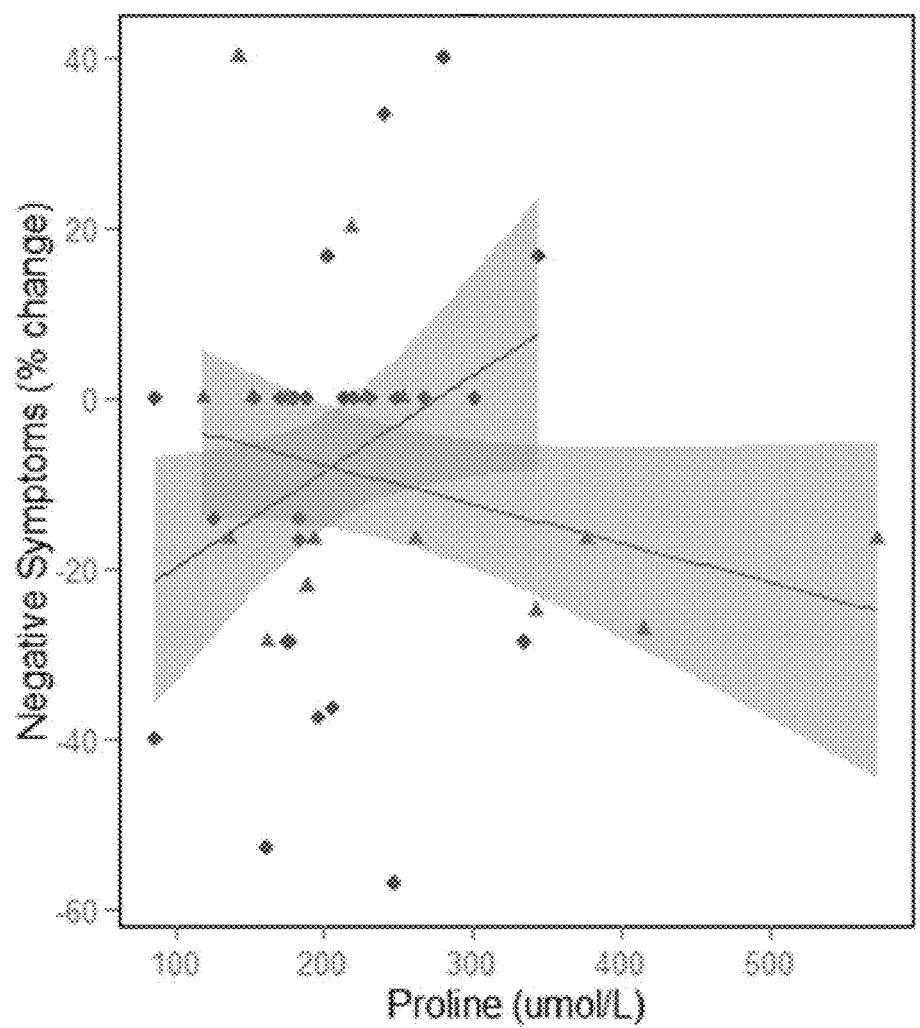
FIG. 4 is a graph showing the relationship between proline and percent change in negative symptoms, plotted for patients with the COMT Met allele (n=27, purple diamonds) and Val/Val genotype (n=16, green triangles). Lines represent the predicted values from the regression model. As proline rose, Val/Val patients exhibited a greater negative percent change in symptoms, thus their symptoms decreased. Conversely, there existed a positive relationship between change in symptoms and proline in Met allele carriers: those with high proline had less of a decrease of negative symptoms. Negative symptoms were evaluated using the following items from the Brief Rating Psychiatric Scale (BPRS): item 3 (emotional withdrawal), 13 (motor retardation), 14 (uncooperativeness), 16 (blunted affect) and 18 (disorientation). Percent change in symptoms was calculated using the following formula: ((negative symptoms at visit 2−negative symptoms at visit 1)/negative symptoms at visit 1)×100%.

A significant interaction was observed between COMT and fasting peripheral proline on the percent change in negative symptoms (n=43, interaction β coefficient=−0.0017, p=0.04). As shown in FIG. 4, high proline was associated with a greater reduction of negative symptoms for Val/Val bipolar patients but conversely, Met carrier patients with high proline levels had, in general, either no change or a positive change in negative symptoms, suggesting a worsening of symptoms over time. Again, possible confounds were assessed (Table 7). Regarding medication, while there was no relationship between the percent change in negative symptoms and mood stabilizer use or neuroleptic dose, covariate analysis indicated that neuroleptic type and benzodiazepine use, plus the duration between visits, were predictors of the change in negative symptoms, as were the demographic characteristics of ethnicity and gender (p<0.1, Table 7). These covariates were taken forward to multivariate models (Table 4). Sequential Wald Tests were performed, determining goodness-of-fit, with the proline-COMT interaction remaining significant after adjustment for gender in the final model (interaction β coefficient=−0.0021, p=0.0007).

Figure 5:
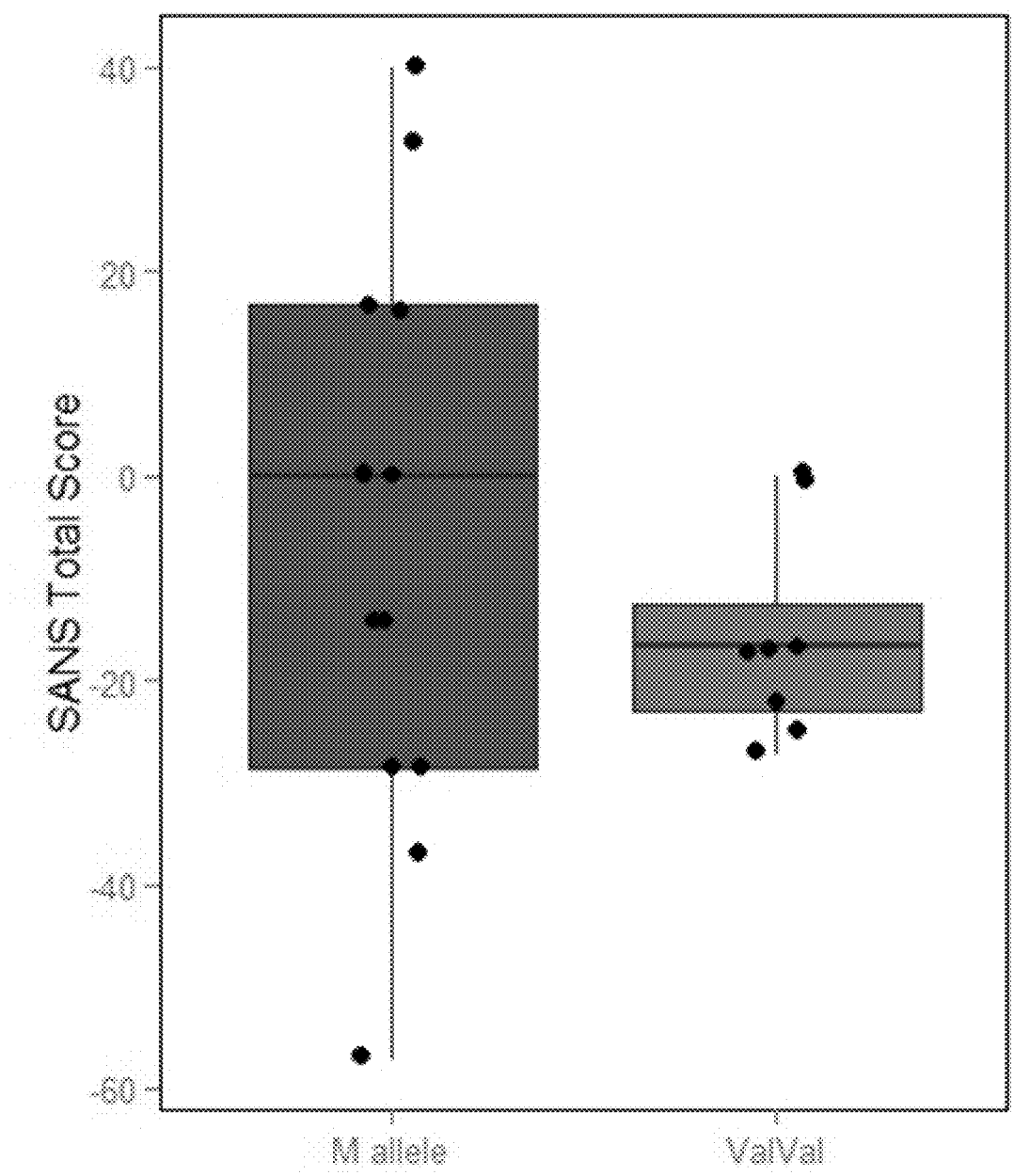
FIG. 5 is a graph showing the percent change in negative symptoms in bipolar disorder patients treated with VPA, by COMT genotype. Val/Val VPA treated bipolar patients had a greater overall percent reduction in negative symptoms (mean=−0.156±0.10, n=8) as compared to Met carrier patients (mean=−0.056±0.28, n=13). However, this result did not reach statistical significance (Mann-Whitney z=0.95, p=0.34), likely due to the variability observed in the Met patients as well as the small sample size. Black jittered points represent individual data. The horizontal line within each box represents the group median. The box indicates the IQR. The whiskers extend to the most extreme data point which is 1.5 times the IQR. The percent change in symptoms was calculated as: ((total negative symptoms subscale at visit 2−total negative subscale at visit 1)/(total negative subscale at visit 1))×100%.

As found with the schizophrenia sample, bipolar VPA-treated patients had significantly higher fasting plasma proline than those who did not receive VPA (FIG. 5). However, while Val/Val treated patients had a greater overall reduction in negative symptoms compared to Met carriers, this result did not reach significance, possibly due to the variability observed and the small sample (FIG. 5). There was no significant effect modification of COMT on the relationship between proline and percent change in positive symptoms (interaction β=0.0005, p=0.950), or percent change in total BPRS scores (interaction β=−0.0009, p=0.153), again suggesting specificity of the relationship between COMT and proline to negative symptoms.

TABLE 7

Bivariate Association Between Bipolar Disorder Patient Demographic and Clinical Characteristics, with Percent Change in Negative Symptoms, n = 43

| Characteristic (at Visit 2) | β (95% CI) | Prob[a] |
|---|---|---|
| Gender[b] | 1.359 (0.003, 0.268) | 0.045* |
| Ethnicity[c] | | |
| African American v Caucasian[d] | −0.048 (−0.022, 0.121) | 0.566 |
| African American v Hispanic | −0.272 (−0.473, −0.071) | 0.009* |
| Age | 0.003 (−0.004, 0.010) | 0.369 |
| Education[e] | 0.013 (−0.026, 0.051) | 0.513 |
| Alcohol Dependence/abuse[b] | | |
| None v Abuse | −0.020 (−0.174, 0.133) | 0.790 |
| None v Dependence | −0.055 (−0.240, 0.130) | 0.554 |
| Smoking Status[f] | −0.104 (−0.045, 0.253) | 0.165 |
| Duration (days) between symptom assessments | 0.013 (−0.002, 0.028) | 0.082* |
| Daily CPZE dose[g] | −0.000 (−0.000, 0.000) | 0.607 |
| Neuroleptic (NL) Type[b] | | |
| None v Atypical | −0.091 (−0.285, 0.103) | 0.348 |
| None v Typical | −0.006 (−0.476, 0.465) | 0.981 |
| None v both | −0.230 (−0.494, 0.033) | 0.085* |
| Total Number of NLs Administered[h] | −0.074 (−0.192, 0.043) | 0.209 |
| Total Number of Mood Stabilizers Administered[i] | −0.050 (−0.154, 0.054) | 0.338 |
| VPA Treatment | −0.013 (−0.148, 0.122) | 0.845 |
| Benzodiazepines | −0.120 (−0.251, 0.011) | 0.072* |
| Antidepressants | 0.004 (−0.133, 0.140) | 0.958 |

[a]*Taken forward into multivariate model.
[b]Binary variable: Male v female.
[c]For categorical analysis the reference category is the first level listed for each variable.
[d]Includes n = 1 Asian subject. Parameter estimates did not change following the removal of this subject, and so they were included in all final models.
[e]Recorded as a continuous variable from the SCID (range 2-8).
[f]Binary variable: Never v current or previous smokers, n = 42 (as one subject did not report smoking status).
[g]Chlorpromazine (CPZ) equivalent dose, n = 37 (as six subjects did not receive a NL).
[h]Continuous variable with three levels (none, one or two), n = 42 (as only subject was administered >two NLs).
[i]Binary variable: one v two, n = 42 (as one subject did not receive a mood stabilizer).

Example 5

Discussion

The data presented herein demonstrate that fasting peripheral proline and COMT Val[158]Met genotype predict negative symptom severity across psychiatric diagnoses. Specifically, evidence is presented that in schizophrenia patients with the Val/Val genotype (encoding the high activity COMT enzyme), high proline was associated with lower levels of negative symptoms. As proline rose across the Val/Val patient sample, negative symptoms decreased. Conversely, Met allele carriers displayed the opposite relationship, exhibiting significantly more negative symptoms as proline levels rose. Over the range of fasting proline in the schizophrenia sample (87-502 µM), this represents a significant and clinically relevant difference in negative symptoms between COMT genotype groups.

VPA upregulates circulating proline (Jacquet et al., 2005) and VPA-treated schizophrenia Val/Val patients had significantly less negative symptoms than VPA-treated Met allele patients, likely due to the impact of VPA on proline level. Interestingly, the relationship between proline, COMT and negative symptoms was consistent across the entire schizophrenia sample, whether subjects received VPA or not, suggesting that the source of circulating proline is less important than the actual level in predicting symptoms. This data has implications for treatment decisions, because proline-modulating medications such as VPA, which is very commonly used to treat bipolar disorder and also schizophrenia, may have differential benefits on negative symptoms and conversely, detrimental effects, based upon the Val[158]Met genotype.

In a second sample, the interaction between COMT and proline on negative symptom change was explored in patients with bipolar disorder (using the BPRS negative symptom subscale). Supporting the earlier schizophrenia finding, a significant interaction was observed between proline and COMT: high proline was associated with improvement of negative symptoms in homozygous Val/Val bipolar patients, while high proline in Met allele carriers was associated with less improvement or an increase in negative symptom severity. This finding was not confounded by medication use, the duration of time between assessments, or demographic characteristics of the bipolar sample. Interestingly, the bipolar patients did not have proline levels significantly higher than controls, suggesting that proline may impact negative symptoms and their severity, but not bipolar disorder risk.

The present disclosure is believed to be the first to document that proline and COMT interact to predict negative symptom outcomes in psychiatric and other disorders. The finding of a detrimental effect of high proline in combination with the COMT Met allele on schizophrenia and bipolar disorder negative symptoms, is in part supported by studies of 22q11DS patients, who have an increased risk of psychosis (albeit exhibiting positive symptoms (Raux et al., 2007)) plus a neurophysiological visual sensory deficit (Vorstman et al., 2009), when carrying the Met allele in the presence of high proline.

This finding that high proline is protective in Val/Val patients with schizophrenia and bipolar disorder is novel and significant. Intriguingly, Zarchi et al. (2013), reported the protective effect of a PRODH variant (the Tryptophan (Trp) allele of the Arg[185]Trp polymorphism) on a neurophysiological measure (MMN) in COMT Val 22q11DS patients. Since the Trp allele exhibits decreased PDX activity in vitro (Bender et al., 2005), Zarchi et al., discussed either an opposite effect of this allele in vivo, or alternatively that the Arg[185]Trp polymorphism is in linkage disequilibrium with another functional SNP; in each circumstance likely resulting in increased PDX activity and low peripheral proline. The data disclosed herein suggests the opposite to that interpretation: that high proline is actually protective in hemizygous 22q11DS patients with the Val genotype, with regards to MMN.

Putative CNS roles of proline have been described both in terms of its potential as a neurotransmitter, suggested by its uptake into and direct synthesis within synaptosomes and its release at the synapse after K+ induced depolarization (Phang et al., 2001; Nickolson, 1982; Yoneda and Roberts, 1982; Nadler, 1987), as well as a neuromodulator of neurotransmitter systems, suggested by the presence of high-affinity proline transporters in glutamatergic neurons (Phang et al., 2001; Renick et al., 1999; Cohen and Nadler, 1997a; Cohen and Nadler, 1997b), and the enhancements of glutamatergic and prefrontal DA transmission in the presence of Prodh deficiency and elevated proline (Paterlini et al., 2005). Although the mechanism by which proline elevation may impact neurotransmission requires further investigation, it is apparent from the Prodh null model (Gogos et al., 1999; Paterlini et al., 2005) and the human hyperprolinemias (Phang et al., 2001) that elevated proline can be detrimental in the CNS. In schizophrenia and bipolar disorder, carrying the Met allele may further accentuate proline's toxicity. In this model, enhanced DA-transmission in the PFC as a result of excess proline is exacerbated by low COMT activity and concomitant higher prefrontal DA availability, ultimately resulting in a frontal hyperdopaminergic state that mimics that of the Prodh null mouse (Paterlini et al., 2005; and as reviewed in Drew et al., 2011).

A hyperdopaminergic model influencing negative symptom severity is somewhat counterintuitive, given that negative symptoms are generally considered to arise from deficient mesocortical DA stimulation. However, COMT is involved in maintaining PFC cognitive stability (Bilder et al., 2004; Turnbridge et al., 2006), and in situations of high cortical DA concentrations and $D_1$ receptor stimulation (likely present in Met/Met and to a lesser degree Val/Met psychiatric patients), enhanced cognitive stability of neuronal network activation has been theorized by Bilder et al. (2004) to result in a cognitive rigidity that may increase the likelihood of negative symptoms. Thus, the Met allele may be less effective in alleviating the increased dopaminergic tone in schizophrenia and bipolar disorder patients with elevated proline, significantly impacting negative symptoms or at least the persistence of negative symptoms and their improvement after treatment.

Conversely, as disclosed herein, proline elevation beneficially influences negative symptom severity in Val/Val patients. In a COMT Val homozygous state, high enzymatic activity in the PFC would likely reduce prefrontal DA, limiting $D_1$ receptor-mediated excitation (Bilder et al., 2004; Turnbridge et al., 2006). Speculatively, proline elevation may increase prefrontal DA signaling, through interference with glutamatergic pathways (Paterlini et al., 2005), reducing vulnerability to a prefrontal hypodopaminergic state in Val/Val patients (Bilder et al., 2004). Taken together these models suggest that negative symptoms are significantly impacted in conditions of both hyper- or hypo-DA activity.

Interestingly, no relationship was found between COMT and proline on positive symptoms. Positive symptoms are considered to arise from hyperactive subcortical mesolimbic projections, and the current finding is consistent with the action of proline in murine cortical but not striatal DA potentiation (Paterlini et al., 2005). Additionally, DA transporters are relatively sparse in the PFC (Lewis et al., 2001), and the removal of DA there may be more impacted by COMT activity and the interaction with proline, as compared to subcortical regions.

Some study limitations exist: in the schizophrenia sample, proline was measured and symptoms assessed cross-sectionally. Thus the findings may be confounded by enrollment differences across genotypes. However, negative symptoms were not significantly different between genotypes, there was no significant main effect of COMT on negative symptoms, and the length of hospitalization prior to symptom assessment had no relationship with negative symptoms, suggesting that the cross-sectional nature of the study did not confound the results. Additionally, while the bipolar study allowed investigation of symptom change, the bipolar sample size was smaller and negative symptoms assessed using only a subscale of the BPRS. Further research would therefore benefit from a longitudinal approach, investigating the interaction between proline and COMT on the change in negative symptoms assessed via the SANS, in a large sample of both schizophrenia and bipolar disorder patients.

Nonetheless, there are currently no medications approved for the treatment of negative symptoms in psychiatric illness, which are associated with poor functional outcomes and quality of life, are highly persistent, and are a great burden for caregivers (Blanchard et al., 2011). The finding of a beneficial effect on negative symptoms of high proline in Val/Val patients suggests that personalization of treatments based upon a patient's COMT genotype, for the purpose of up- or down-regulating proline level, holds promise as a pharmacogenomics approach to intervene and target this unaddressed symptom domain.

Example 6

Figure 6:
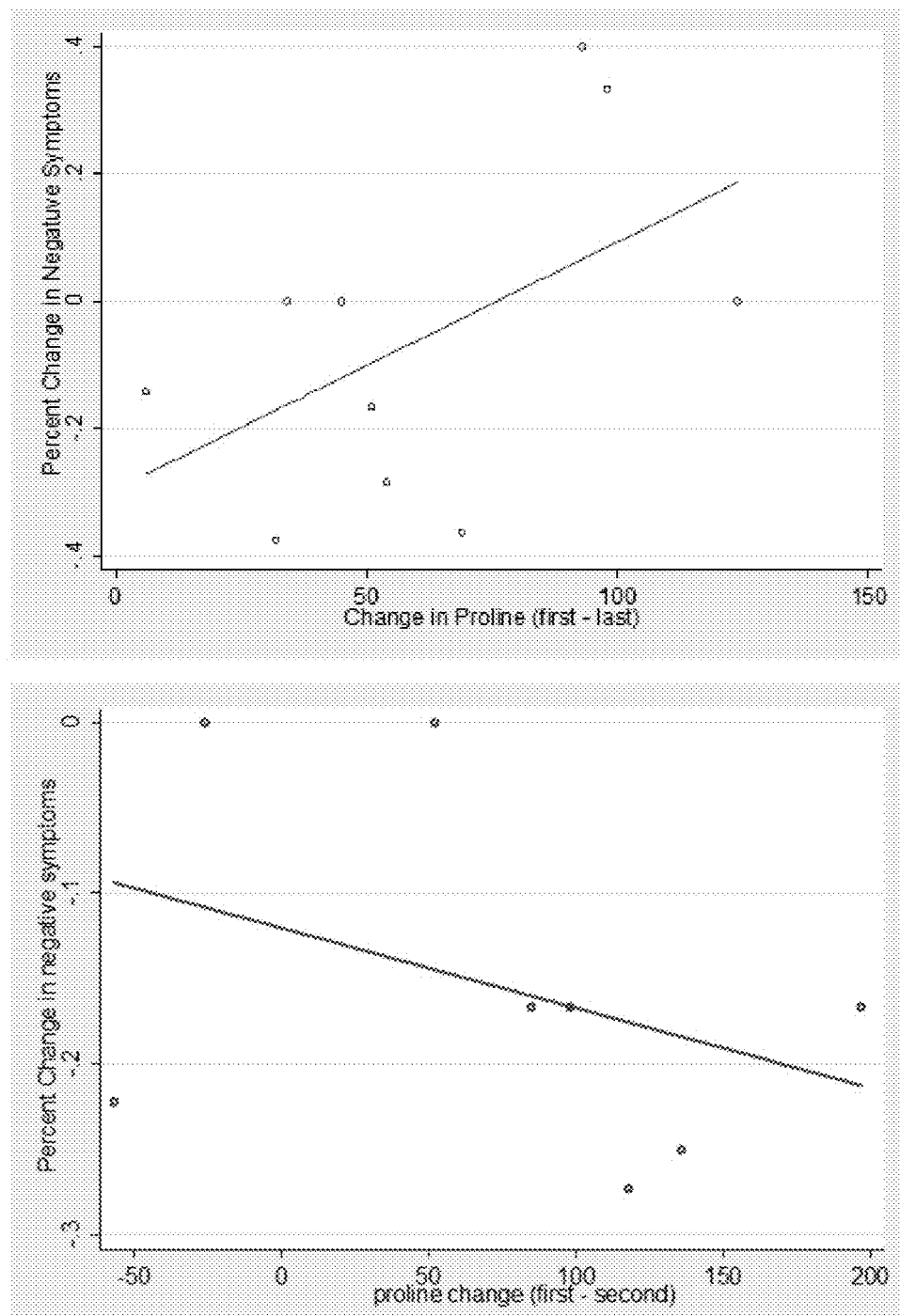
FIG. 6 shows scatterplot graphs of the direct relationship between the change in proline level (pre- to post-medication) and the change in negative symptoms. The top panel shows ten bipolar disorder Met allele carriers (Met/Met or Val/Met) that had a strong positive relationship between the change in proline and the percent change in negative symptoms: as proline increased, a positive change was observed in negative symptoms, suggesting a worsening of symptoms over time, although this result did not reach significance (p=0.19), likely due to the small sample size. The bottom panel shows that Val/Val patients treated with valproate (n=8) had a negative relationship between the change in proline and symptoms (spearman's rho=−0.4), although this result again did not reach significance likely due to the small sample size (p=0.3).

Relationship Between Change in Proline and Negative Symptoms:

Preliminary data also suggests that a change in proline level is directly related to change in negative symptoms. Specifically, twelve bipolar disorder patients had a pre- and post-medication fasting blood draw (with proline measured), plus pre- and post-assessment. Of these, ten were Met allele carriers (Met/Met or Val/Met). Findings suggest that high proline is associated with no improvement or a worsening of symptoms in the presence of high proline. Thus, it was expected that for these subjects, an increase in proline would be related to a worsening of symptoms. Testing this hypothesis, a strong positive relationship was found between the change in proline and the percent change in negative symptoms (see FIG. 6). As proline increased (change in proline was calculated as the post medication proline level–premedication proline level, and for all ten subjects proline increased), a positive change was observed in negative symptoms, suggesting a worsening of symptoms over time (spearman's rho=0.45), although this result did not reach significance (p=0.19), likely due to the small sample size.

Only two subjects were Val/Val homozygotes with both pre- and post-medication values. Interestingly, one subject whose proline went down (from 167 µM to 119 µM) had no change in negative symptoms. However, the other subject, whose proline went up (from 206 µM to 332 µM), had a corresponding decrease in negative symptoms (from a score of 8 to 6). Again, this supports the hypothesis that high proline is good for Val/Val homozygotes.

However, valproate increases peripheral proline, so it can be assumed that all Val/Val patients treated with Valproate (n=8) had an increase in peripheral proline between blood draws (regardless of whether the blood draw at visit one was fasting). Therefore, using this subsample, there was seen a negative relationship between the change in proline and symptoms (spearman's rho=−0.4), although this result again did not reach significance likely due to the small sample size (p=0.3).

Example 7

Proline and COMT in Other Disorders:

Pomara et al. (1992) showed elevated cerebrospinal fluid (CSF) proline level in Alzheimers disease (AD). Patients with AD are also known to display negative symptoms. Treatment to modulate proline levels based upon COMT Val$^{158}$Met genotype would be beneficial to control those symptoms in AD.

Ethanol increases circulating proline levels, and comorbid alcohol use disorder is the most common comorbidity in schizophrenia (Drake and Mueser, 2002), and is also common in bipolar disorder (Sonne and Brady, 2002). Up- or down-regulation of proline level may exacerbate negative symptoms or conversely improve them, depending on COMT genotype. Alcohol use may be a form of self-medication that could be replaced by other proline modulation methods/treatments. Recently, differential effects were found of alcohol abuse or dependence frequency based on genotype (COMT Val/Val subjects were 2.4 times more likely to report alcohol abuse and/or dependence than Met allele patients, p=0.09, unpublished).

Susceptibility to alcohol abuse and/or dependence may be related to differential effects on mood and/or pleasure-ability based upon proline level and COMT genotype. Treatments to alter proline level based on COMT genotype may be useful for the treatment of alcohol use disorders and potentially for gambling disorders (Guillot et al., 2015).

Example 8

Proline and COMT in Alcohol Use Disorder (AUD):

Comorbidity of Alcohol Use Disorder (AUD) with schizophrenia (SZ) is highly prevalent at over 33% of SZ patients. Comorbidity is associated with particularly unfavorable outcomes including raising mortality risk and treatment non-adherence. Of particular relevance, some SZ patients have reported a decrease of symptoms, including negative symptoms, following alcohol ingestion. This is important because the negative symptoms of SZ (loss of motivation, flattening of emotional responses, decreased speech and activity, and social withdrawal), are disabling and persistent, and significantly contribute to the immense personal and economic costs of SZ. No medications are FDA-approved for treatment of negative symptoms in SZ.

Proline is a precursor of the neurotransmitter glutamate and may function as a CNS neuromodulator. Elevated proline stimulates dopamine signaling in murine models. Catechol-O-methyltransferase (COMT) catalyzes deactivation of neurotransmitters including dopamine. In our recent, replicated, study we found that fasting plasma proline levels (which reflect CNS levels) and the COMT Val158Met functional polymorphism (high/low enzyme activity) significantly interact, predicting negative symptom outcomes in patients with severe psychiatric illness. Specifically, in Val/Val patients, high proline is protective with low negative symptom severity or a greater negative symptom reduction over time. Conversely, COMT Met carriers demonstrated the opposite: significantly more negative symptoms or less symptom improvement as proline increased.

Alcohol ingestion upregulates circulating proline, in those with a current or past AUD, and thus we hypothesized that comorbid patients self-medicate with alcohol to relieve their negative symptoms; predicting more frequent comorbid AUD in Val/Val SZ patients. In a preliminary study we indeed found a strong trend as compared to Met allele carriers for whom alcohol-induced proline elevation would be detrimental (p=0.06, 2-tailed). This finding is important because sodium valproate (VPA), prescribed to ~35% of SZ inpatients, is also a strong up-regulator of proline levels. We found a strong trend towards significance for an interaction between VPA treatment and AUD on cross-sectional proline levels (interaction p=0.050); with VPA vastly boosting proline levels in Val/Val patients with AUD, but not significantly in VPA-treated patients without an AUD (data not shown). We propose personalized VPA treatment or treatment with proline or modulators that increase proline levels, for negative symptoms in comorbid AUD and neuropsychiatric disorders including schizophrenia patients who carry the Val/Val genotype, to relieve negative symptoms and assist in maintaining abstinence.

Example 9

Proline and COMT in Alzheimer's Disease (AD)/Traumatic Brain Injury (TBI):

Neuropsychiatric symptoms such as apathy are frequently described in patients with Alzheimer's disease (AD), as well as those who have sustained a traumatic brain injury (TBI). In fact, reports have suggested that close to one half of all AD and TBI patients' exhibit apathy (Brodaty et al. 2015; Karttunen et al. 2011; Hwang et al. 2004; Lyketsos et al. 2011), which is characterized by the loss of motivation to participate in activities, social withdrawal, and emotional indifference and these symptoms often present in incipient AD (including MCI) (Leoutsakos et al. 2015; Van Dam et al. 2016) or within the first year after brain injury (Stefan et al. 2016). Apathy and related symptoms contribute substantially to the huge personal and economic costs for individuals living with AD and TBI: Apathy can disrupt patients' participation in family life and social integration, and can lead to more intensive utilization of health care services (Arnould et al. 2015; Cattelani et al. 2008). Furthermore, apathy in AD is associated with a rapid course of functional and cognitive decline (Benoit et al. 2008; Lechowski et al. 2009; Landes et al. 2005; Leoutsakos et al. 2015), and in TBI patients, negatively impacts rehabilitation (Starkstein et al. 2014). Of relevance, substantial caregiver burden and distress have been significantly associated with the presence and severity of apathy (Karttunen et al. 2011; Lyketsos et al. 2011; Starkstein et al. 2014; Arnould et al. 2015; Fauth et al. 2014).

Apathy is a "negative" neuropsychiatric symptom. Although commonly considered a major symptom domain of psychiatric illness, the full spectrum of negative symptoms can also present in patients with dementia (Reichman et al. 1996; Galynker et al. 1997; Negron et al. 2000; Galynker et al. 2000; Vercelletto et al. 2002; de Jonghe et al. 2003) and constitutes an independent behavioral dimension that is not an outcome of depression and/or cognitive status (Reichman et al. 1996; Galynker et al. 1997; de Jonghe et al. 2003).

Intriguingly, it has been suggested that targeting of these symptoms in AD may extend the time to conversion from MCI (Ismail et al. 2016) and possibly positively alter the trajectory of the disease process (Forlenza et al. 2017). However, there are no approved treatments for negative symptoms in AD or TBI, and thus there is clearly a need for new research into interventions that target neuropsychiatric symptoms of AD and TBI, in particular negative symptoms, to improve the quality of life for individuals living with TBI and AD, and also to alleviate the burden on their caregivers.

There is evidence of increased CNS and peripheral proline levels in patients with AD (Pomara et al. 1992; Molina et al. 1998; Trushina et al. 2013). We propose and will investigate that the proline x COMT interaction and its impact on negative symptoms, either beneficial or detrimental, as previously observed in psychiatric disorders, is generalizable across neuropsychiatric diseases including AD and TBI.

Example 10

Figure 7:
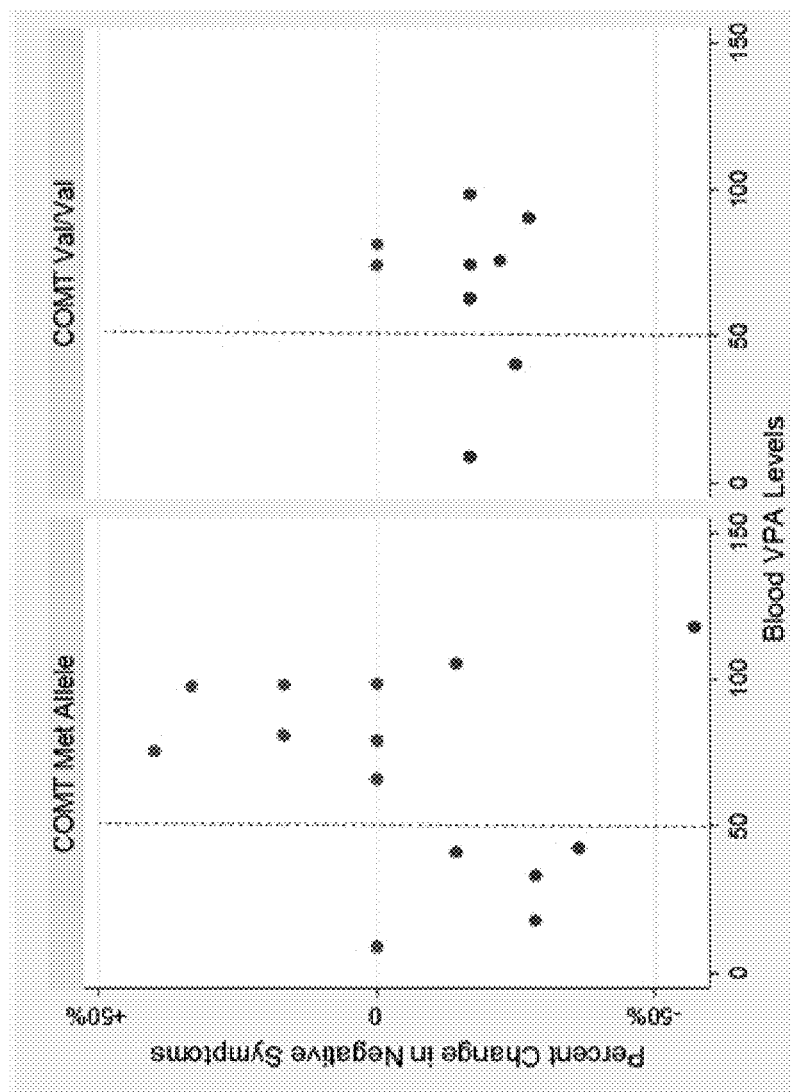
FIG. 7 is a scatterplot graph showing the relationship between blood VPA level (in μg/ml) and percent change in negative symptoms. The left panel shows nine Met allele carriers, only two of whom showed improvement in negative symptoms after treatment onset. The right panel shows seven Val/Val patients, five of whom improved after VPA treatment. The difference between genotypes did not reach significance (p=0.07), likely due to the small sample size.

Relationship Between Negative Symptoms and VPA Level:

The relationship between blood levels of VPA and negative symptoms was investigated by COMT genotype. It was hypothesized that those with the Met allele and high levels of blood VPA would have a lower % negative symptom change, i.e. a positive % change, indicating increased negative symptoms, due to exacerbation by increased proline level. Conversely, Val/Val patients would be expected to have a greater % decrease in negative symptoms as levels of VPA rose. As hypothesized, and as shown in FIG. 7, negative symptoms generally either increased or did not change after treatment onset (red points) for Met allele carriers as VPA levels rose, as compared to Val/Val patients. A blood level of 50 µg/ml of VPA is considered the lower end of the therapeutic range: of the Met allele carriers within this range, only 2 out of 9 showed improvement in negative symptoms, as opposed to 5 out of 7 Val/Val patients (p=0.07).

Example 11

Proline may function as a neuromodulator via stimulation or alteration of neuronal glutamate and/or GABA signaling, which may underlie its effect on negative and other neuropsychiatric symptoms (Clelland et al., 2016; Crabtree et al., 2016). Molecules that can modulate neuronal glutamate signaling including NMDA receptor and/or glutamatergic signaling functions, and have been considered and/or tested in clinical trials in psychiatric disorders include glycine, D-serine, D-cycloserine and bitopterin (Roche RG1678; RO-4917838), sarcosine, SSR103800, Org 25935 and betaine. These are thought to alter glutamate receptor activity or function either directly or indirectly via modulation of the concentration of glycine and/or function of the glycine binding site.

Considering that clinical studies of molecules also thought to influence glutamate signaling have had mixed results, an initial exploratory analysis was performed of fasting plasma glycine and l-serine and an interaction with COMT genotype on negative symptoms of schizophrenia. Plasma glycine concentrations reflect CNS levels (Jiménez-Jiménez et al., 1998; Scholl-Bürgi et al., 2008; Luykx et al., 2013) and CSF D-serine, which is derived from L-serine via serine racemase, is significantly correlated with plasma L-serine (Luykx et al., 2013; Hashimoto et al., 2003).

In a sample of schizophrenia patients (n=95), fasting plasma glycine and l-serine significantly predicted increased negative symptoms in those subjects with the COMT Val/Met or Met/Met genotypes (glycine r=0.48, p=0.0003, n=53; l-serine r=0.32, p=0.02, n=53), but not in Val/Val carriers (glycine r=−0.05, p=0.78, n=42; l-serine r=−0.12, p=0.46, n=42). Following on from this, in regression analysis any significant effect of glycine was tested for after adjusting for the potential confounding effect of proline. A significant effect of glycine on negative symptoms remained (p=0.013) with medium effect size (partial eta$^2$=0.116). As for proline, as glycine increased, so did negative symptoms in Met allele carrier patients.

In addition, analysis of valproate versus non-valproate-treated subjects indicated that valproate significantly upregulates fasting glycine levels (268 uM no valp n=64, 361 uM valp n=31, p=0.0007) and L-serine levels (103 uM no valp n=64, 117 uM valp n=31, p=0.004).

Given these findings of glycine and serine interactions with COMT, the interaction of COMT Val$^{158}$Met genotype with glycine on negative symptoms therefore also likely occurs when glycine modulators, including those listed above, are used in psychiatric and neuropsychiatric disorders.

As some of the molecules listed above have been extensively tested in clinical trials, reanalysis of the trial data and/or new trials accounting for COMT genotype when determining efficacy, may lead to evidence of therapeutic efficacy that has been previously undetected.

Trials of the molecules listed above for the treatment of psychiatric, neuropsychiatric, psychotic, mood and personality disorders, and symptoms thereof such as negative symptoms, should therefore be analyzed to account for the interaction of individuals' COMT Val$^{158}$Met genotype with glycine and (L- and/or D-) serine levels (and/or with potentially glutamate and/or GABA), with the expectation that COMT Val/Val genotype individuals will respond differently from Met allele carriers, and the failure of clinical trials to achieve efficacy may be due to patients not being chosen based on their COMT genotype (and thus whether they would benefit or be harmed by such treatment). In recent studies, we have identified that the proline modulator, LX6171, an SLC6A7 (PROT) transporter inhibitor, may be useful for treatment of COMT Val$^{158}$/Val, or for COMT Met$^{158}$Met or COMT Val$^{158}$Met carriers, and may act via increased synaptic proline and/or decreased gamma-aminobutyric acid (GABA) synthesis (data not shown).

TABLE S1

Molecules that regulate genes or gene products relevant to proline transport and metabolism.

A1. Molecules that upregulate PRODH:

| | | |
|---|---|---|
| gefitinib | harman | Dimethylformamide |
| Pyrilamine | Fluocinolone Acetonide | cephalonium |
| Phenacetin | Methylnitrosourea | Ketoconazole |
| dexibuprofen | Cortisone | Ceftriaxone |
| aristolochic acid I | Mycophenolic Acid | GW 501516 |
| Betamethasone | Rifabutin | Caffeine |
| Methotrexate | Fluphenazine | dihydroquinghaosu |
| piperaquine | Isotretinoin | Naproxen |
| leflunomide | bromodichloromethane | Itraconazole |
| Roxarsone | Dicumarol | fluvastatin |
| Hydrocortisone | diindolylmethane | cyclonite |
| Gliclazide | cerivastatin | Digoxin |
| Doxorubicin | Hexachlorophene | Ifosfamide |
| meloxicam | Melatonin | Malathion |
| Triiodothyronine | Sulfacetamide | Tacrolimus |
| Fluoxetine | Desoxycorticosterone | chloroxylenol |
| genipin | Trenbolone Acetate, (17beta)-isomer | phenacemide |
| erlotinib | Chlorpropamide | arsenic trioxide |
| decitabine | Terfenadine | Paraquat |
| Dantrolene | Cymarine | quelamycin |
| Maprotiline | 2,2-bis(bromomethyl)-1,3-propanediol | Ethamsylate |
| Dexamethasone | AICA ribonucleotide | methyl salicylate |
| Doxazosin | Methylprednisolone | loxoprofen |
| pipenzolate | Epirubicin | monobenzone |
| Valproic Acid | fluticasone | naphthalene |
| Ofloxacin | enrofloxacin | Hemicholinium 3 |
| Acrolein | 4-dichlorobenzene | 4,4'-diaminodiphenylmethane |
| depudecin | 1,3-dichlorobenzene | riddelliine |
| halofuginone | Ethyl Methanesulfonate | Clioquinol |
| p-Aminohippuric Acid | Antipyrine | N-benzyladenine |
| Oxprenolol | Diflunisal | Cyclosporine |
| Bithionol | loracarbef | ebastine |
| Chlorpyrifos | oxiconazole | Sulindac |
| Amoxapine | Oxyquinoline | Thioguanine |
| Pyrethrins | phenethyl isothiocyanate | Ultraviolet Rays |
| amprenavir | Cisapride | Bromisovalum |
| oxcarbazepine | Thioctic Acid | blebbistatin |
| trichlorofluoromethane | Methyldopa | Clemastine |
| Altretamine | Gold | Hydrochloric Acid |
| 9-(2-hydroxy-3-nonyl)adenine | torsemide | Etidronic Acid |
| Bisacodyl | Sulfisoxazole | Clobetasol |
| Erythromycin Ethylsuccinate | 1-Methyl-4-phenyl-1,2,3,6-tetrahydropyridine | Pimozide |
| Betahistine | Iproniazid | sodium arsenite |
| valdecoxib | oxybutynin | Promazine |
| letrozole | 4'-N-benzoylstaurosporine | Trichloroethylene |
| 4-octylphenol | naringin | Hydralazine |
| dibenzazepine | Gallamine Triethiodide | Flavoxate |
| Xylazine | Terazosin | Chlorpromazine |
| acetylleucine | Meclofenoxate | N-Methyl-3,4-methylenedioxyamphetamine |
| Acetazolamide | Calcium | Cephalexin |
| Saquinavir | Etoposide | Sulpiride |
| nabumetone | Luteolin | Metyrapone |
| Glipizide | Trimetazidine | Foscarnet |

TABLE S1-continued

Molecules that regulate genes or gene products relevant to proline transport and metabolism.

| | | |
|---|---|---|
| hexachlorobutadiene | adiphenine | lapatinib |
| n-hexanal | Trichlormethiazide | lamotrigine |
| benoxinate | 8-Bromo Cyclic Adenosine Monophosphate | Nitrazepam |
| Moxisylyte | N-(2-cyclohexyloxy-4-nitrophenyl)methanesulfonamide | fipexide |
| Y 27632 | Interleukins | Mianserin |
| Amiloride | Sulfadimethoxine | Amikacin |
| 1,1,1-trichloroethane | Lactic Acid | Rolipram |
| Tobramycin | oxaliplatin | Buspirone |
| Lithium Chloride | carbinoxamine | Cisplatin |
| gabapentin | Choline | Naphazoline |
| Cefuroxime | Flurbiprofen | anisindione |
| oxaprozin | Cholecalciferol | Dexfenfluramine |
| rescinnamine | Pivampicillin | Plicamycin |
| Dicyclomine | laudanosine | Antibodies, Monoclonal |
| trichostatin A | Daunorubicin | vesamicol |
| Ketoprofen | oxolamine | Captopril |
| Atovaquone | Fluorouracil | Furosemide |
| 2-amino-1-methyl-6-phenylimidazo(4,5-b)pyridine | Neomycin | carbetapentane |
| Isoflurophate | Prochlorperazine | Alprenolol |
| olanzapine | Oxymetazoline | Acarbose |
| Metaraminol | Levamisole | Trifluridine |
| oltipraz | arsenic acid | candesartan |
| Sulfamethoxazole | vorinostat | Metoclopramide |
| Prazosin | Dizocilpine Maleate | 2-(4-morpholinyl)-8-phenyl-4H-1-benzopyran-4-one |
| Metoprolol | Angiotensin-Converting Enzyme Inhibitors | imatinib |
| Phenelzine | Risperidone | Terbutaline |
| Harmaline | Fluspirilene | chelidonine |
| irinotecan | 6-thioguanosine | Imipramine |
| Vincristine | Atenolol | Haloperidol |
| 2,2'-Dipyridyl | Puromycin Aminonucleoside | Domperidone |
| Fenoprofen | Dobutamine | Norfloxacin |
| 3,3',4',5-tetrachlorosalicylanilide | Hydroxyurea | Diltiazem |
| Dichlorvos | Felodipine | N-Methylaspartate |
| Dyphylline | Zidovudine | sodium selenate |
| Clarithromycin | Nystatin | Azacitidine |
| Trihexyphenidyl | ONO 2235 | Aspirin |
| Busulfan | Nocodazole | Amlodipine |
| Nimodipine | 1-Methyl-3-isobutylxanthine | dasatinib |
| Nortriptyline | Losartan | Verapamil |
| Mebendazole | Loratadine | Baclofen |
| Piroxicam | Ionomycin | Zalcitabine |
| Flunarizine | Guanethidine | Deoxyglucose |
| Levodopa | 8-((4-chlorophenyl)thio)cyclic-3',5'-AMP | triptolide |
| Lorazepam | Sarin | Cyclophosphamide |
| Chlorambucil | Methyl Methanesulfonate | Ascorbic Acid |
| A2. Molecules that downregulate PRODH: | | |
| Aminosalicylic Acid | Ursodeoxycholic Acid | Miconazole |
| anastrozole | Clotrimazole | Nafenopin |
| Thioacetamide | Tinidazole | Salicylates |
| Spironolactone | rabeprazole | Hexachlorobenzene |
| Carbon Tetrachloride | bromfenac | Fenofibrate |
| Lovastatin | Praziquantel | Bezafibrate |
| pirinixic acid | Methapyrilene | Ethylestrenol |
| Fluconazole | Theobromine | Indomethacin |
| 7,8-Dihydro-7,8-dihydroxybenzo(a)pyrene 9,10-oxide | Isoniazid | Dipyrone |
| celecoxib | Stavudine | geraniol |
| Dimethylnitrosamine | Ketorolac | Simvastatin |
| Aminoglutethimide | pantoprazole | ferulic acid |
| Cyproterone Acetate | Stanozolol | Econazole |
| N-nitrosomorpholine | vinylidene chloride | Chloroform |
| Diethylstilbestrol | Ecdysterone | Mestranol |
| Benzbromarone | naftopidil | beta-Naphthoflavone |
| temafloxacin | atorvastatin | Ticlopidine |
| Aphidicolin | Ticrynafen | Piperonyl Butoxide |
| rosiglitazone | TO-901317 | Estriol |
| Proglumide | Cyproterone | Ibuprofen |
| bromobenzene | artemisinine | Ethinyl Estradiol |
| Chlormezanone | Gemfibrozil | Ajmaline |
| benziodarone | Diethylhexyl Phthalate | Diethylnitrosamine |
| Clonazepam | Clofibrate | beta-cyclodextrin-benzaldehyde |
| Pravastatin | Chloramphenicol | Phenobarbital |
| tranilast | Dehydroepiandrosterone | piclamilast |

TABLE S1-continued

Molecules that regulate genes or gene products relevant to proline transport and metabolism.

| | | |
|---|---|---|
| Bupropion | Pentobarbital | Fendiline |
| cetraxate | terbinafine | Danazol |
| Clonidine | Vinblastine | Ethylnitrosourea |
| carvedilol | pioglitazone | abacavir |
| Clofibric Acid | Cefixime | Shiga Toxin |
| Disulfiram | 2-Acetylaminofluorene | Carisoprodol |
| ipriflavone | Spectinomycin | irbesartan |
| perfluorooctanoic acid | Flutamide | methylformamide |
| lornoxicam | Mifepristone | bendazolic acid |
| ciprofibrate | Finasteride | Neostigmine |
| Methylcholanthrene | nimesulide | zileuton |
| Vitamin K 3 | 2-nitrofluorene | Metronidazole |
| amitraz | closantel | 4-nonylphenol |
| Oxytetracycline | penciclovir | Secobarbital |
| Cinnarizine | Ethambutol | Colchicine |
| salicylamide | zopiclone | desloratadine |
| Methyltestosterone | Tetrachlorodibenzodioxin | Granisetron |
| Safrole | trovafloxacin | 2-dichlorobenzene |
| Doxepin | Gonadotropins | eperisone |
| Carbamazepine | Roflumilast | N-methylolacrylamide |
| Azathioprine | hydrazine | Parathion |
| Ondansetron | Monocrotaline | Pyrogallol |
| Estradiol | balsalazide | Carmustine |
| phenothiazine | sparfloxacin | triadimefon |
| Clofazimine | 1-hydroxycholecalciferol | pristane |
| bortezomib | Mefloquine | Fonofos |
| Clomipramine | Tretinoin | systhane |
| coumarin | amineptin | naphthalenediimide |
| Acetaminophen | Enoxacin | Omeprazole |
| telmisartan | 4-(5-benzo(1,3)dioxol-5-yl-4-pyridin-2-yl-1H-imidazol-2-yl)benzamide | |
| | | Zimeldine |
| Isoproterenol | Benzalkonium Compounds | Dimercaprol |
| Bicuculline | tenofovir | tenidap |
| hydroxytamoxifen | norethindrone acetate | sulfathiazole |
| Erythromycin | Tolazamide | Galantamine |
| Minoxidil | Sertraline | Trimethadione |
| Dactinomycin | perfluorooctane sulfonic acid | Ethionine |
| Progesterone | Vanadates | venlafaxine |
| Tetracycline | rofecoxib | graveoline |
| tazobactam | lactacystin | Glycerol |
| Amitriptyline | Diclofenac | Griseofulvin |
| Naloxone | Caerulein | benoxaprofen |
| urapidil | Benzethonium | Megestrol |
| Floxuridine | quintozene | shikonin |
| Buthionine Sulfoximine | Prednisone | Lamivudine |
| Propylthiouracil | ranolazine | Protoveratrines |
| oxfendazole | Cefotetan | Aflatoxin B1 |
| Amantadine | Capsaicin | Megestrol Acetate |
| Todralazine | Amiodarone | ibufenac |
| sunitinib | Nifedipine | Norethindrone |
| meropenem | 1,10-phenanthroline | Ethionamide |
| Phenylephrine | compactin | Lasalocid |
| oxalylglycine | esmolol | lansoprazole |
| homatropine | Penicillamine | Lead |
| Nitroprusside | bambuterol | Bleomycin |
| Diphenhydramine | etofylline | Benzo(a)pyrene |
| Lomustine | methylparaben | Ouabain |
| etiracetam | idebenone | cilostazol |
| ochratoxin A | isoconazole | guanadrel |
| Nickel | 1-ethyl-2-benzimidazolinone | Rifampin |
| Raloxifene | Thiabendazole | Benzydamine |
| indole-3-carbinol | Hydroxyzine | Astemizole |
| Diazepam | Vitamin B 12 | Chitosan |
| Nisoldipine | Alprazolam | Aconitine |
| 4-hydroxytamoxifen | Oxazepam | Bacitracin |
| Dipyridamole | Citalopram | Atropine |
| efavirenz | Sotalol | Genistein |
| dironyl | Soman | U 0126 |
| deferiprone | pralidoxime | Propranolol |
| Camptothecin | Tolazoline | HI 6 |
| resveratrol | Cytarabine | Allopurinol |
| Quercetin | Clozapine | sildenafil |
| Labetalol | Albendazole | valsartan |
| Famotidine | Ciprofloxacin | Gentamicins |
| Tacrine | Amphetamine | Nadolol |
| Chlorpheniramine | Mitomycin | MRK 003 |
| Netilmicin | Paroxetine | Pregnenolone Carbonitrile |
| 6-bromoindirubin-3'-oxime | doxofylline | Azauridine |

TABLE S1-continued

Molecules that regulate genes or gene products relevant to proline transport and metabolism.

| | | |
|---|---|---|
| Paclitaxel | benzyloxycarbonylleucyl-leucyl-leucine aldehyde | NG-Nitroarginine Methyl Ester |
| N,N'-diphenyl-4-phenylenediamine | Calcitriol | Enalapril |
| SB 203580 | bisphenol A | Inosine Monophosphate |
| Perhexiline | cyanoginosin LR | gemcitabine |
| Kainic Acid | Pentylenetetrazole | 6-Mercaptopurine |
| Promethazine | | |
| B1. Molecules that upregulate COMT: | | |
| Sulbactam | 6-methoxy-2-naphthylacetic acid | Cefuroxime |
| Diazoxide | Stanozolol | Lead |
| 2,4-Dinitrophenol | tenidap | Norfloxacin |
| Cephalexin | rosiglitazone | pirinixic acid |
| Vanadates | Levobunolol | lorglumide |
| Metoprolol | Trimetazidine | oltipraz |
| Omeprazole | Methylcholanthrene | Quinpirole |
| chloroxylenol | Pyridoxine | tropisetron |
| Noscapine | Inosine Monophosphate | Nitroprusside |
| beta-Naphthoflavone | Clomipramine | Netilmicin |
| Fluphenazine | Itraconazole | bromodichloromethane |
| 4-dichlorobenzene | Benserazide | nabumetone |
| apramycin | Altretamine | butenafine |
| tomatidine | Econazole | Pemoline |
| NG-Nitroarginine Methyl Ester | Epirubicin | tazobactam |
| Diethylnitrosamine | etofenamate | Mitoxantrone |
| graveoline | betulinic acid | arsenic trioxide |
| Cortisone | Sotalol | Promethazine |
| temsirolimus | Dimethylformamide | Progesterone |
| sulfathiazole | beta-cyclodextrin-benzaldehyde | Galantamine |
| oxaliplatin | Trichloroethylene | vinorelbine |
| pentachlorobenzene | riddelliine | Ethacrynic Acid |
| Neomycin | Ethionine | valsartan |
| gefitinib | Terazosin | Mifepristone |
| Acarbose | bestatin | 1-Methyl-4-phenyl-1,2,3,6-tetrahydropyridine |
| Iproniazid | 3,3',4',5 tetrachlorosalicylanilide | Warfarin |
| Benzethonium | Chloroquine | Citalopram |
| Vitamin K 2 | gabapentin | Sulindac |
| Roxithromycin | oxfendazole | letrozole |
| Chitosan | N-Methyl-3,4-methylenedioxyamphetamine | Azithromycin |
| Clindamycin | Cytochalasin B | Sulfinpyrazone |
| pristane | Simazine | Cholecalciferol |
| Doxapram | erlotinib | Tetracycline |
| marimastat | Atropine | fenbufen |
| Tetrachlorodibenzodioxin | Flunarizine | Niacin |
| PK 11195 | Polychlorinated Biphenyls | Clonidine |
| homosalate | spiradoline | Phentolamine |
| Ethamsylate | Scopolamine Hydrobromide | Chlorambucil |
| 1,1,1-trichloroethane | asperflavin | zomepirac |
| Selenomethionine | N-(2-aminophenyl)-4-(N-(pyridin-3-ylmethoxycarbonyl)aminomethyl)benzamide | Benzo(a)pyrene |
| clebopride | Concanavalin A | Lovastatin |
| mebeverine | Doxorubicin | Lorazepam |
| Simvastatin | 6-bromoindirubin-3'-oxime | sorafenib |
| rofecoxib | U 0126 | celecoxib |
| SU 5402 | sildenafil | imatinib |
| anastrozole | 2-(4-morpholinyl)-8-phenyl-4H-1-benzopyran-4-one | adiphenine |
| methantheline | clemizole | olanzapine |
| fluvastatin | chelidonine | lansoprazole |
| ebastine | cyanoginosin LR | clopidogrel |
| bromfenac | alfuzosin | carvedilol |
| dihydroquinghaosu | idebenone | vitexin |
| fragment C, human serum albumin | closantel | cobaltous chloride |
| bromopride | ceforanide | ascorbate-2-phosphate |
| ciclopirox | 2,4-diaminotoluene | 9-(2-hydroxy-3-nonyl)adenine |
| cineole | tolfenamic acid | 6-thioguanosine |
| hexylcaine | pimethixene | 5-fluorouridine |
| triptolide | Cardiotoxins | Dichlororibofuranosylbenzimidazole |
| Antibodies, Monoclonal | Caerulein | Ionomycin |
| Streptomycin | Bleomycin | Chorionic Gonadotropin |
| Beclomethasone | Cyproterone Acetate | Chlormadinone Acetate |
| Finasteride | Colistin | Alpha-Amanitin |
| Rifampin | Amoxapine | Mianserin |
| Clozapine | Dactinomycin | Enoxacin |
| Ciprofloxacin | 1-Methyl-3-isobutylxanthine | Acyclovir |

TABLE S1-continued

Molecules that regulate genes or gene products relevant to proline transport and metabolism.

| | | |
|---|---|---|
| 8-Bromo Cyclic Adenosine Monophosphate | Allopurinol | Melatonin |
| Cytochalasin D | gamma-Tocopherol | alpha-Tocopherol |
| Vitamin E | Acenocoumarol | Astemizole |
| Diltiazem | Nitrazepam | Diazepam |
| Apazone | Cotinine | Kainic Acid |
| Fluorouracil | Risperidone | Zidovudine |
| Stavudine | Cytarabine | Chlorpheniramine |
| Nevirapine | Nicardipine | Trazodone |
| Amiodarone | Fluconazole | Clotrimazole |
| Nicotine | Pilocarpine | Lobeline |
| Reserpine | Vinblastine | Quinidine |
| Papaverine | Apomorphine | Dacarbazine |
| Acetazolamide | Thiethylperazine | Bithionol |
| Isoflurophate | Auranofin | Ethylnitrosourea |
| Dimethylnitrosamine | Erythromycin | Haloperidol |
| Ifosfamide | Cyclophosphamide | Chloroform |
| 7,8-Dihydro-7,8-dihydroxybenzo(a)pyrene 9,10-oxide | Naproxen | Demeclocycline |
| Loratadine | Amitriptyline | Losartan |
| Ketamine | Isoniazid | Ketoprofen |
| Ibuprofen | Fenoprofen | Diflunisal |
| Mefenamic Acid | Diethylcarbamazine | Aminocaproic Acids |
| Gemfibrozil | Clofibric Acid | Azoxymethane |
| Azauridine | Methapyrilene | Dobutamine |
| Amrinone | Guanethidine | Amoxicillin |
| Cefotaxime | Dibucaine | Sulpiride |
| Busulfan | Isoxsuprine | Bismuth |
| Calcium | | |

B2. Molecules that down regulate COMT:

| | | |
|---|---|---|
| Tin Fluorides | Tobramycin | Phenacetin |
| dexibuprofen | bendazolic acid | 3-hydroxyacetanilide |
| Cyclosporine | flubendazole | Acrolein |
| cephalonium | Fluoxetine | valdecoxib |
| Hesperidin | nimetazepam | Niacinamide |
| Diethylstilbestrol | ajmalicine | Trichlorfon |
| 2-nitrofluorene | clinafloxacin | Ethinyl Estradiol |
| methiazole | Gentamicins | Cyproheptadine |
| Chlorpropamide | Iornoxicam | Bezafibrate |
| Methoxsalen | 4-hydroxyestradiol-17 beta | Suprofen |
| Piperonyl Butoxide | norethindrone acetate | Clomiphene |
| Nizatidine | 4-acetylaminofluorene | DDT |
| Meptazinol | Trioxsalen | Carmustine |
| acidocin CH5, *Lactobacillus acidophilus* | Cymarine | Acetylmuramyl-Alanyl-Isoglutamine |
| Tiletamine | atorvastatin | salicylamide |
| cilostazol | vinylidene chloride | ferulic acid |
| Cyclizine | ifenprodil | hydroquinone |
| Dyphylline | Procarbazine | Ampicillin |
| Estriol | Propylthiouracil | Fursultiamin |
| Cloxacillin | fipronil | Theophylline |
| apicidin | Coumaphos | ONO 2235 |
| meloxicam | lomefloxacin | phosphonoacetamide |
| oxiconazole | fulvestrant | Podophyllotoxin |
| Acetaminophen | cinchonine | Aspirin |
| Atractyloside | penciclovir | Cinnarizine |
| Terfenadine | Ketorolac | Raloxifene |
| trichostatin A | Tretinoin | Natamycin |
| Mestranol | Estradiol | Nystatin |
| 2-chloropyrazine | Azathioprine | Flufenamic Acid |
| picrotoxinin | Aminosalicylic Acid | asiaticoside |
| daidzein | Tiapamil Hydrochloride | Valproic Acid |
| Diquat | Carboplatin | Tacrolimus |
| ranolazine | piperacetazine | Curcumin |
| pramoxine | Idoxuridine | Ethylestrenol |
| Todralazine | boldine | sparfloxacin |
| Cetylpyridinium | Nafenopin | abamectin |
| Canrenoate Potassium | Dantrolene | Cisapride |
| bisphenol A | Dihydroergocristine | Calcitriol |
| decitabine | Diethylhexyl Phthalate | Budesonide |
| 2-dichlorobenzene | Okadaic Acid | eperisone |
| Carbimazole | Genistein | Hymecromone |
| biphenylylacetic acid | Ampyrone | canadine |
| U 54494A | syrosingopine | tetrahydrotriamcinolone |
| blebbistatin | phenacemide | Hydralazine |
| Propranolol | Oxazepam | terbinafine |
| Pyrantel | Leucovorin | Mustard Gas |

TABLE S1-continued

Molecules that regulate genes or gene products relevant to proline transport and metabolism.

| | | |
|---|---|---|
| nimesulide | Acetohexamide | Propanil |
| pioglitazone | benfluorex | Pregnenolone |
| 1,2-dithiol-3-thione | Dinoprostone | Phenobarbital |
| Thioctic Acid | Propantheline | Protriptyline |
| Clofibrate | Cytokines | bis(tri-n-butyltin)oxide |
| Sulfaphenazole | Piribedil | hydrazine |
| Aztreonam | tosufloxacin | Oxymetazoline |
| 4-biphenylamine | Lomustine | 1-hydroxycholecalciferol |
| ubiquinol | Doxylamine | Levamisole |
| scriptaid | phenylhydrazine | hydroxyhydroquinone |
| Betamethasone | Pheniramine | Tolnaftate |
| 4-(5-benzo(1,3)dioxol-5-yl-4-pyridin-2-yl-1H-imidazol-2-yl)benzamide | direct black 3 | Dipyridamole |
| repaglinide | naphthalenediimide | rimexolone |
| Thiostrepton | Sulfamethazine | Timolol |
| Tacrine | acetovanillone | Trichloroepoxypropane |
| eticlopride | 8-aminohexylamino cAMP | Streptozocin |
| HC toxin | vorinostat | genipin |
| dibenzazepine | 4-methyl-N-(3-(4-methylimidazol-1-yl)-5-(trifluoromethyl)phenyl)-3-((4-pyridin-3-ylpyrimidin-2-yl)amino)benzamide | LBH589 |
| lapatinib | dasatinib | bevacizumab |
| CPG-oligonucleotide | bortezomib | 17-(allylamino)-17-demethoxygeldanamycin |
| Y 27632 | 1-ethyl-2-benzimidazolinone | azacyclonol |
| tenofovir | benzyloxycarbonylvalyl-alanyl-aspartyl fluoromethyl ketone | bexarotene |
| daboiatoxin | piclamilast | cerivastatin |
| telmisartan | irbesartan | colforsin |
| benzyloxycarbonylleucyl-leucyl-leucine aldehyde | zardaverine | zileuton |
| 2,3-dioxo-6-nitro-7-sulfamoylbenzo(f)quinoxaline | dorzolamide | resveratrol |
| 1,2-dilinolenoyl-3-(4-aminobutyryl)propane-1,2,3-triol | gemcitabine | aceclofenac |
| levocabastine | buparvaquone | leflunomide |
| vanoxerine | 1,3-dichlorobenzene | oxalylglycine |
| monorden | ozagrel | artemether |
| lysophosphatidic acid | bromobenzene | beta-glycerophosphoric acid |
| artemisinine | doxofylline | sulmazole |
| dexamisole | ochratoxin A | perfluorooctanoic acid |
| 2-methoxyestradiol | 4-O-methyl-12-O-tetradecanoylphorbol 13-acetate | ciprofibrate |
| sodium arsenite | 4-hydroxytamoxifen | 8-((4-chlorophenyl)thio)cyclic-3',5'-AMP |
| lycorine | dipivefrin | amitraz |
| tranilast | compactin | benoxaprofen |
| acadesine | halofuginone | diphenylpyraline |
| wortmannin | 4,4'-diaminodiphenylmethane | alginic acid |
| naringin | isoascorbic acid | benzothiazide |
| geldanamycin | Shiga Toxin | Cholera Toxin |
| BCG Vaccine | Ribavirin | Phytohemagglutinins |
| Antigen-Antibody Complex | Enalapril | Captopril |
| Phenylalanine | Palmitic Acid | Alprostadil |
| Deoxyglucose | Clobetasol | Dexamethasone |
| Danazol | Vecuronium Bromide | Dihydrotestosterone |
| Androsterone | Viomycin | Bacitracin |
| Clofazimine | Carbamazepine | Quinacrine |
| Oxolinic Acid | Clioquinol | Oxyquinoline |
| Amodiaquine | Thioguanine | Bucladesine |
| Vidarabine | Methotrexate | Saquinavir |
| Indomethacin | Dicumarol | Rotenone |
| Quercetin | Luteolin | Aflatoxin B1 |
| Nocodazole | Atrazine | Rolipram |
| Clemastine | Triprolidine | 2,2'-Dipyridyl |
| Nifedipine | Trihexyphenidyl | Aminoglutethimide |
| Cycloheximide | Paroxetine | Domperidone |
| Ketoconazole | Betazole | Miconazole |
| Pentylenetetrazole | Caffeine | Dextromethorphan |
| Vincristine | Ajmaline | Harmaline |
| Dihydroergotamine | Pergolide | Colchicine |
| Cam ptothecin | Fusaric Acid | Hydroxyurea |
| Allantoin | Dimethyl Sulfoxide | Hydrochlorothiazide |
| 6-Mercaptopurine | Triflupromazine | Thioridazine |
| Promazine | Perphenazine | Mesoridazine |
| Chlorpromazine | Acetylcysteine | Mitomycin |
| Diazinon | Dichlorvos | Pregnenolone Carbonitrile |
| Clarithromycin | Brefeldin A | Melphalan |
| Carbon Tetrachloride | Pravastatin | Vitamin K 3 |

TABLE S1-continued

Molecules that regulate genes or gene products relevant to proline transport and metabolism.

| | | |
|---|---|---|
| Plicamycin | Daunorubicin | Aclarubicin |
| Meclizine | Thapsigargin | Paclitaxel |
| Amantadine | Methyl Methanesulfonate | Phenelzine |
| Doxepin | Diclofenac | Dicyclomine |
| Puromycin | Ascorbic Acid | Dextropropoxyphene |
| Disulfiram | Mycophenolic Acid | Butyric Acid |
| Vigabatrin | Baclofen | Azacitidine |
| Ipratropium | Granisetron | Edrophonium |
| Gallamine Triethiodide | Benzalkonium Compounds | Aminophylline |
| Fluvoxamine | Verapamil | Mephentermine |
| Methamphetamine | Amphetamine | Methyldopa |
| Levodopa | Bromhexine | Furosemide |
| Ceftazidime | Cephaloridine | Cephalothin |
| Cefazolin | 2-Acetylaminofluorene | Nadolol |
| Metaproterenol | Midodrine | Isoproterenol |
| Epinephrine | Clenbuterol | Choline |
| Cisplatin | Lithium Carbonate | |
| C1. Molecules that upregulate PYCR1: | | |
| Ethionamide | halofuginone | coumarin |
| Asbestos | Hyaluronic Acid | methylformamide |
| Teriparatide | Phenylephrine | Carbon Tetrachloride |
| Mannitol | Ethambutol | 1,3-dichloro-2-propanol |
| artemisinine | clebopride | 4-(4-fluorophenyl)-2-(4-hydroxyphenyl)-5-(4-pyridyl)imidazole |
| Methimazole | Hypericum extract LI 160 | Carbimazole |
| Riluzole | bromobenzene | 6-bromoindirubin-3'-oxime |
| Methapyrilene | Chlormezanone | U 0126 |
| Trimethadione | Chloroform | Tunicamycin |
| Nafcillin | Cloxacillin | hydrazine |
| crotamiton | Ticlopidine | Procyclidine |
| ceforanide | estradiol 3-benzoate | 4-methyl-N-(3-(4-methylimidazol-1-yl)-5-(trifluoromethyl)phenyl)-3-((4-pyridin-3-ylpyrimidin-2-yl)amino)benzamide |
| Okadaic Acid | ascorbate-2-phosphate | GW 3965 |
| Azoxymethane | Estriol | Propylthiouracil |
| Trenbolone Acetate, (17beta)-isomer | 4-dichlorobenzene | Estradiol |
| Cymarine | 3-nitropropionic acid | Molindone |
| Tryptophan | Trichlormethiazide | Propoxycaine |
| graveoline | Glycocholic Acid | Mestranol |
| 4,5-dianilinophthalimide | N-(2-aminophenyl)-4-(N-(pyridin-3-ylmethoxycarbonyl)aminomethyl)benzamide | Thioctic Acid |
| Thiabendazole | Insulin | Clodronic Acid |
| 2-dichlorobenzene | Disulfiram | Cephapirin |
| Doxycycline | Carbamazepine | anastrozole |
| Acetaminophen | Cephalexin | Cyproterone Acetate |
| shogaol | Stavudine | 2,4-Dinitrophenol |
| Dihydrotestosterone | Carcinogens | Bromocriptine |
| iodoform | Thapsigargin | Danazol |
| Dimethylformamide | arcaine | vanoxerine |
| fosfosal | Thioacetamide | Canavanine |
| Piromidic Acid | pantoprazole | KCB-1 protein, recombinant |
| epidermal growth factor (1-45) | oltipraz | Omeprazole |
| diisopropyl methylphosphonate | Hydrogen Peroxide | Clonazepam |
| acetylleucine | Reserpine | Dapsone |
| Fluconazole | Ethinyl Estradiol | Sulfadimethoxine |
| Nalidixic Acid | Estrogens | Azacitidine |
| etofenamate | Erythromycin | Sulindac |
| epoxomicin | sulconazole | Methylene Chloride |
| Pipemidic Acid | Cefazolin | Bleomycin |
| Trimipramine | Ultraviolet Rays | tolfenamic acid |
| Spiperone | Todralazine | Phenobarbital |
| Allopurinol | Isoniazid | 1,2-dithiol-3-thione |
| oxaliplatin | Equilin | Orphenadrine |
| Amphotericin B | N-(2-cyclohexyloxy-4-nitrophenyl)methanesulfonamide | zaprinast |
| apicidin | BCG Vaccine | closantel |
| Roxithromycin | kavain | dironyl |
| tracazolate | Methyltestosterone | Ionomycin |
| Amanitins | Lasalocid | withaferin A |
| Pentolinium Tartrate | pristane | Hexachlorobenzene |
| oxolamine | Hydroflumethiazide | Hydroxyzine |
| Stanozolol | sodium nitrate | Triflupromazine |
| Oxyquinoline | Roflumilast | Thiethylperazine |
| Gossypol | phenothiazine | Fursultiamin |

TABLE S1-continued

Molecules that regulate genes or gene products relevant to proline transport and metabolism.

| | | |
|---|---|---|
| Muromonab-CD3 | Ibuprofen | Trimethoprim |
| cerivastatin | N-benzyladenine | Tetrachlorodibenzodioxin |
| X-Rays | Diazepam | Phenazopyridine |
| Cyproheptadine | Selegiline | salmeterol |
| bromperidol | Clioquinol | Pizotyline |
| Ketorolac | acetorphan | Cefaclor |
| verteporfin | Phenelzine | Khellin |
| (melle-4)cyclosporin | Nifedipine | Isoproterenol |
| Diethylstilbestrol | Vitamin E | Diquat |
| Prenylamine | Deoxyglucose | gibberellic acid |
| Cinnarizine | Azathioprine | Acetazolamide |
| Carmustine | butoconazole | Diclofenac |
| Domperidone | abamectin | Benzocaine |
| famprofazone | Particulate Matter | Progesterone |
| Gentamicins | Desoxycorticosterone | Monensin |
| Remoxipride | sodium arsenite | Benzethonium |
| Genistein | hydrastinine | Phenylalanine |
| Felodipine | Glycerol | Captopril |
| fulvestrant | Acetohexamide | nifuroxazide |
| hydroxyachillin | Tobramycin | bisphenol A |
| Astemizole | rituximab | Folic Acid |
| methylbenzethonium | enterotoxin B, staphylococcal | Hydrogel |
| Cyclosporine | Caerulein | Mesalamine |
| Naproxen | bicalutamide | fragment C, human serum albumin |
| tibolone | Antibodies, Monoclonal | LBH589 |
| phorbolol myristate acetate | Soman | Niclosamide |
| Tiapamil Hydrochloride | Clotrimazole | SC 514 |
| Mitomycin | Dactinomycin | Quercetin |
| Flecainide | Ketoconazole | N-nitrosomorpholine |
| sunitinib | Aminoglutethimide | irinotecan |
| Apomorphine | thymoglobulin | HC toxin |
| methyleugenol | Anti-Retroviral Agents | Dipyridamole |
| Berberine | mometasone furoate | Promethazine |
| ethotoin | 4-hydroxytamoxifen | HI 6 |
| Diazinon | Flutamide | 8-Bromo Cyclic Adenosine Monophosphate |
| beta-Naphthoflavone | Cardiotoxins | Piracetam |
| Dantrolene | Lithium | arsenic trioxide |
| Itraconazole | Ozone | scriptaid |
| N-Methylaspartate | methylatropine | Econazole |
| nimesulide | Diphenhydramine | acadesine |
| mono-(2-ethylhexyl)phthalate | vorinostat | Selenomethionine |
| Mebendazole | Choline | Iproniazid |
| Indomethacin | Dichlororibofuranosylbenzimidazole | Furosemide |
| Altretamine | bortezomib | Enoxacin |
| Citalopram | Sotalol | atorvastatin |
| Pregnenolone | Aspirin | valdecoxib |
| Carbonitrile | | |
| olanzapine | meloxicam | Clozapine |
| Risperidone | Perphenazine | Chlorpromazine |
| Amitriptyline | | |
| C2. Molecules that downregulate PYCR1: | | |
| 1-(5-Isoquinolinesulfonyl)-2-Methylpiperazine | Aphidicolin | Methylnitrosourea |
| monastrol | Aclarubicin | geldanamycin |
| mafosfamide | blebbistatin | Ornidazole |
| N-methylpyrrolidone | 4-(N-methyl-N-nitrosamino)-1-(3-pyridyl)-1-butanone | Dimethyl Sulfoxide |
| Disopyramide | Metaproterenol | gefitinib |
| sesamin | Immunoglobulin M | Lithium Carbonate |
| Mycophenolic Acid | Clofibric Acid | benziodarone |
| Idarubicin | enzastaurin | 2-(1H-indazol-4-yl)-6-(4-methanesulfonylpiperazin-1-ylmethyl)-4-morpholin-4-ylthieno(3,2-d)pyrimidine |
| edelfosine | Doxorubicin | Puromycin Aminonucleoside |
| bendazolic acid | Daunorubicin | Mycotoxins |
| Camptothecin | imatinib | MRK 003 |
| nickel sulfate | Synephrine | Etoposide |
| naringenin | Clofibrate | Coumaphos |
| Cycloheximide | Sirolimus | ethaverine |
| Gemfibrozil | trichostatin A | Idoxuridine |
| imiquimod | Cisplatin | Vincristine |
| Protriptyline | CEP 14083 | Paroxetine |
| decitabine | Benzbromarone | Potassium Dichromate |
| hydrastine | tetrahydrozoline | 17-(allylamino)-17- |

TABLE S1-continued

Molecules that regulate genes or gene products relevant to proline transport and metabolism.

| | | |
|---|---|---|
| Diethylhexyl Phthalate | Fonofos | demethoxygeldanamycin |
| Minocycline | Streptozocin | Dexamethasone |
| Dihydroergotamine | bamipine | pronethalol |
| Dilazep | Ethyl Methanesulfonate | perfluorooctane sulfonic acid |
| levocabastine | Santonin | eticlopride |
| Ceftriaxone | Sulfapyridine | CD 437 |
| cidofovir | 4-acetylaminofluorene | Gonadotropins |
| troglitazone | Hemin | wortmannin |
| zardaverine | Simvastatin | 1-Methyl-3-isobutylxanthine |
| Prazosin | sulforafan | Vinblastine |
| Mafenide | 2-(4-morpholinyl)-8-phenyl-4H-1-benzopyran-4-one | Fenofibrate |
| | | Curcumin |
| clinafloxacin | Benzo(a)pyrene | buparvaquone |
| cyanopindolol | Caffeine | Zimeldine |
| Fenoterol | everolimus | 2-Acetylaminofluorene |
| minaprine | pioglitazone | 1-ethyl-2-benzimidazolinone |
| Dichlorphenamide | methiazole | TO-901317 |
| 8-((4-chlorophenyl)thio)cyclic-3',5-AMP | Chitosan | 4-(5-benzo(1,3)dioxol-5-yl-4-pyridin-2-yl-1H-imidazol-2-yl)benzamide |
| Doxepin | alpha-Amino-3-hydroxy-5-methyl-4-isoxazolepropionic Acid | Tretinoin |
| Bezafibrate | colforsin | Phalloidine |
| Diltiazem | Deferoxamine | flubendazole |
| biphenylylacetic acid | Oxolinic Acid | SB 203580 |
| 3,3',5-triiodothyroacetic acid | carcinine | Luteinizing Hormone |
| Plicamycin | Phenylbutazone | lapatinib |
| 15-deoxy-delta(12, 14)-prostaglandin J2 | Enalapril | Allantoin |
| diloxanide furoate | Etidronic Acid | Metribolone |
| chelidonine | marimastat | Chorionic Gonadotropin |
| fenspiride | Valproic Acid | Clonidine |
| dibenzazepine | gabazine | Corticosterone |
| vinylidene chloride | Thioguanine | Ethionine |
| Isoetharine | Vidarabine | LPS 9 |
| letrozole | salsolidine | Betazole |
| Oxymetazoline | Ethylnitrosourea | Dextran Sulfate |
| linalool | NG-Nitroarginine Methyl Ester | Pyrantel |
| Zinc Oxide | Fusaric Acid | Tetradecanoylphorbol Acetate |
| Ranitidine | Dexfenfluramine | canadine |
| mycophenolate mofetil | rosiglitazone | AICA ribonucleotide |
| Metolazone | Tolazoline | Alprostadil |
| Oxazepam | Colchicine | Mefenamic Acid |
| dexchlorpheniramine | alginic acid | Sulpiride |
| Dinoprost | Acetylcysteine | systhane |
| Finasteride | vinorelbine | Fluphenazine |
| gemcitabine | erlotinib | Raloxifene |
| 1,2-dilinolenoyl-3-(4-aminobutyryl)propane-1,2,3-triol | bis(tri-n-butyltin)oxide | Pergolide |
| Ascorbic Acid | Monocrotaline | Papaverine |
| Imipramine | Trifluoperazine | Phenol |
| Metformin | benzyloxycarbonylleucyl-leucyl-leucine aldehyde | triadimefon |
| Rifampin | leflunomide | nimetazepam |
| Methyl Methanesulfonate | Dimethylnitrosamine | Ajmaline |
| Tetracycline | Cefuroxime | monorden |
| cobaltous chloride | Paraquat | Chlorambucil |
| naphthalan | Chlorpheniramine | Emetine |
| terbinafine | lansoprazole | Methotrexate |
| Nicotine | Cyclophosphamide | Diethylnitrosamine |
| Prochlorperazine | Haloperidol | Quinidine |
| Digoxin | Losartan | fluvastatin |
| Puromycin | Cytarabine | Paclitaxel |
| pirinixic acid | Tranylcypromine | dasatinib |
| resveratrol | carvedilol | Ribavirin |
| Calcitriol | Ofloxacin | Rolipram |
| Amiodarone | Thioridazine | Lovastatin |
| Fluoxetine | | |
| D1. Molecules that upregulate ALDH18A1: | | |
| halofuginone | bestatin | Tunicamycin |
| Ecdysterone | beta-cyclodextrin-benzaldehyde | Methapyrilene |
| Vanadates | Captopril | Dimethylnitrosamine |
| ONO 2235 | Azathioprine | Thapsigargin |
| Loratadine | acodazole | Biperiden |
| Stanozolol | 3-nitropropionic acid | Clodronic Acid |

TABLE S1-continued

Molecules that regulate genes or gene products relevant to proline transport and metabolism.

| | | |
|---|---|---|
| Naloxone | enterotoxin B, staphylococcal | rifapentine |
| 1,3-dichloro-2-propanol | sildenafil | Glycocholic Acid |
| Hypericum extract LI 160 | irbesartan | sulconazole |
| apicidin | Paroxetine | Lomustine |
| balsalazide | Cyclosporine | U 0126 |
| cetraxate | amineptin | Ethambutol |
| ascorbate-2-phosphate | Levodopa | Capsaicin |
| Calcium | 4,4'-diaminodiphenylmethane | Etodolac |
| Cardiotoxins | Carmustine | Allopurinol |
| Acetaminophen | Indinavir | SB 203580 |
| Piracetam | valdecoxib | Niridazole |
| Altretamine | lornoxicam | Ethylnitrosourea |
| Ethionamide | Diflunisal | 6-Mercaptopurine |
| Hyaluronic Acid | Busulfan | Doxepin |
| Fluphenazine | cyanoginosin LR | Salicylic Acid |
| Isoproterenol | Promazine | Clomipramine |
| Rifampin | Thioacetamide | tetrandrine |
| amprenavir | LG 268 | Ketoconazole |
| pristane | Ampicillin | Albendazole |
| Itraconazole | Triiodothyronine | Muromonab-CD3 |
| fulvestrant | nimesulide | meloxicam |
| telmisartan | Raloxifene | Bromisovalum |
| Terbutaline | Nitrofurazone | tracazolate |
| 6-bromoindirubin-3'-oxime | Bleomycin | vinylidene chloride |
| valsartan | geraniol | Progesterone |
| lacidipine | tropisetron | 4-(4-fluorophenyl)-2-(4-hydroxyphenyl)-5-(4-pyridyl)imidazole |
| Sulindac | enterotoxin I, staphylococcal | eperisone |
| Stavudine | estradiol 3-benzoate | testosterone 17 beta-cypionate |
| Thiorphan | Podophyllotoxin | Doxapram |
| ferulic acid | Ethinyl Estradiol | ovalicin |
| Pentobarbital | Ethionine | Tetracycline |
| Cyproterone Acetate | desloratadine | Vinblastine |
| olanzapine | lead acetate | Chloroform |
| Isotretinoin | artemisinine | pirenperone |
| Aspirin | Diethylstilbestrol | Diclofenac |
| N-(2-aminophenyl)-4-(N-(pyridin-3-ylmethoxycarbonyl)aminomethyl)benzamide | Estradiol | Mebendazole |
| Valproic Acid | pantoprazole | Ticrynafen |
| Isoflurophate | Lithium Carbonate | Labetalol |
| lansoprazole | Carbon Tetrachloride | Particulate Matter |
| 1-amino-2,4-dibromoanthraquinone | clorsulon | Pentylenetetrazole |
| Lead | tris(2,3-dibromopropyl)phosphate | Pregnenolone Carbonitrile |
| alginic acid | ciclopirox | Phenylephrine |
| Teriparatide | Glipizide | thymoglobulin |
| Folic Acid | Ozone | linezolid |
| Oxyquinoline | Clotrimazole | fazarabine |
| 8-Bromo Cyclic Adenosine Monophosphate | Serotonin | Caerulein |
| Neostigmine | Lithium | Proglumide |
| Morantel | Saquinavir | CpG ODN 2216 |
| Dipyrone | Tinidazole | Cisapride |
| Glycerol | Mannitol | Chlormadinone Acetate |
| Memantine | Minoxidil | Tetracaine |
| 1,5-naphthalenediamine | Monensin | nateglinide |
| bromodichloromethane | Phytohemagglutinins | Insulin |
| erlotinib | Trifluridine | zomepirac |
| Aminosalicylic Acid | Amitriptyline | Hydrogen Peroxide |
| 2,4-diaminotoluene | Triacetin | Mestranol |
| Ethanol | 4'-N-benzoylstaurosporine | ferric nitrilotriacetate |
| Nortriptyline | Thiamphenicol | Metformin |
| benzyloxycarbonylleucyl-leucyl-leucine aldehyde | Risperidone | Calcitriol |
| Pyrethrins | Melphalan | BCG Vaccine |
| R 848 | 4-acetylaminofluorene | bortezomib |
| Diphenhydramine | procyanidin | Soman |
| Tranexamic Acid | Atovaquone | Cyclophosphamide |
| Pempidine | Luteolin | Metaraminol |
| Indomethacin | HI 6 | Citric Acid |
| Omeprazole | anastrozole | Diethylnitrosamine |
| N-acetylsphingosine | Imipramine | Curcumin |
| Ritonavir | Lobeline | Ipratropium |
| Digitoxin | temsirolimus | Ionomyin |
| Metoprolol | flavopiridol | 1-Methyl-4-phenyl-1,2,3,6-tetrahydropyridine |

TABLE S1-continued

Molecules that regulate genes or gene products relevant to proline transport and metabolism.

| | | |
|---|---|---|
| Promethazine | Lamivudine | Streptomycin |
| Tubocurarine | Vitamin E | Nitrendipine |
| Riluzole | Glycine | 2,2'-Dipyridyl |
| Enalapril | Doxazosin | Aphidicolin |
| Amlodipine | Ketoprofen | benazepril |
| Hydrochlorothiazide | Vincristine | dexchlorpheniramine |
| Nisoldipine | Lisinopril | Alpha-Amanitin |
| doxofylline | Piroxicam | Dimenhydrinate |
| Amphetamine | Cimetidine | Naproxen |
| Ketorolac | Citalopram | tenidap |
| efavirenz | Sulpiride | 4-(5-benzo(1,3)dioxol-5-yl-4-pyridin-2-yl-1H-imidazol-2-yl)benzamide |
| candesartan | gemcitabine | ochratoxin A |
| Ribavirin | Deoxyglucose | Chitosan |
| Nevirapine | Miconazole | Nicotine |
| Hydroxyurea | Ticlopidine | Sarin |
| Nafenopin | Atropine | |

D2. Molecules that downregulate ALDH18A1:

| | | |
|---|---|---|
| neuropeptide Y (18-36) | Platelet Activating Factor | Chloroquine |
| sodium chromate(VI) | GW 501516 | Methylnitronitrosoguanidine |
| troglitazone | Natriuretic Peptide, C-Type | scriptaid |
| 1-hydroxycholecalciferol | amitraz | Perhexiline |
| Terfenadine | Amiodarone | hexachloroethane |
| Prostaglandins E | Gentian Violet | Rolipram |
| Zalcitabine | Vecuronium Bromide | HC toxin |
| Ethylestrenol | vinorelbine | AICA ribonucleotide |
| torsemide | sodium selenate | Mephentermine |
| 8-aminohexylamino cAMP | artemether | Idarubicin |
| Fluocinolone Acetonide | Thioguanine | Humic Substances |
| monastrol | trovafloxacin | insulin-like growth factor I (57-70) |
| Hexachlorophene | benoxaprofen | rofecoxib |
| rosiglitazone | Chlorpyrifos | Shiga Toxin |
| Methylnitrosourea | Fluoxetine | Cyclandelate |
| Etoposide | methyl salicylate | Tolazoline |
| Acrolein | Benzocaine | zardaverine |
| Roflumilast | parbendazole | Methyl Methanesulfonate |
| CPG-oligonucleotide | zopiclone | ibufenac |
| carvedilol | Methylcholanthrene | benzyloxycarbonylvalyl-alanyl-aspartyl fluoromethyl ketone |
| quintozene | 4-dichlorobenzene | Sulfadiazine |
| Clofibrate | Puromycin Aminonucleoside | hydrastine |
| Metronidazole | Menthol | beta-Naphthoflavone |
| Sirolimus | Dexfenfluramine | sodium arsenite |
| Cisplatin | Daunorubicin | 2-Acetylaminofluorene |
| Phenobarbital | Simvastatin | Camptothecin |
| Niacin | Tacrine | Sotalol |
| Nifedipine | nitrosobenzylmethylamine | Alprazolam |
| fenspiride | Immunoglobulin M | mafosfamide |
| Doxorubicin | Dichlorvos | Dihydrostreptomycin Sulfate |
| Clofazimine | Ceftazidime | Niacinamide |
| Emodin | naphthalan | clinafloxacin |
| naphthalenediimide | rabeprazole | Diazinon |
| Propantheline | Pergolide | 6-methoxy-2-naphthylacetic acid |
| Digoxin | Probenecid | Pimozide |
| Carboplatin | benfluorex | terbinafine |
| Tetrachlorodibenzodioxin | Ampyrone | Mafenide |
| tetrahydrozoline | Lindane | phosphonoacetamide |
| Maprotiline | Neomycin | infliximab |
| 2-methoxyestradiol | Finasteride | Dexamethasone |
| Methylene Chloride | Cycloheximide | 1-(5-Isoquinolinesulfonyl)-2-Methylpiperazine |
| Flavoxate | Hydralazine | Etidronic Acid |
| Poly I-C | Mercuric Chloride | zileuton |
| trichostatin A | DDT | Methotrexate |
| atorvastatin | Bismuth | oxcarbazepine |
| tosufloxacin | piclamilast | Vidarabine |
| Anti-Retroviral Agents | Benzo(a)pyrene | cerivastatin |
| cobaltous chloride | Propylthiouracil | Erythromycin |
| Hydrocortisone | Bepridil | Caffeine |
| Benserazide | LBH589 | Amikacin |
| Trifluoperazine | Harmaline | Fenofibrate |
| tranilast | chromium hexavalention | Aflatoxin B1 |
| gabapentin | lomefloxacin | fomepizole |
| Metoclopramide | Chlorpropamide | Phenol |
| Histidinol | Chlorpromazine | chelidonine |

TABLE S1-continued

Molecules that regulate genes or gene products relevant to proline transport and metabolism.

| | | |
|---|---|---|
| myricetin | Bezafibrate | letrozole |
| phenacemide | everolimus | edelfosine |
| Clonidine | imatinib | celecoxib |
| Pravastatin | Prochlorperazine | nifenazone |
| Granisetron | oxiconazole | Isoniazid |
| phorbolol myristate acetate | Suloctidil | Albuterol |
| Acetazolamide | Diethylhexyl Phthalate | Ethosuximide |
| Halothane | tenofovir | 1,2,3-trichloropropane |
| Metaproterenol | N-(2-cyclohexyloxy-4-nitrophenyl)methanesulfonamide | Fusaric Acid |
| beta-1,3-glucan | ipriflavone | Fluconazole |
| 2-(1H-indazol-4-yl)-6-(4-methanesulfonylpiperazin-1-ylmethyl)-4-morpholin-4-ylthieno(3,2-d)pyrimidine | Inosine Monophosphate | hydrazine |
| Betamethasone | isoconazole | Cyproheptadine |
| Gonadotropins | Sumatriptan | Dihydroergotamine |
| Furosemide | Fluspirilene | Ciprofloxacin |
| Azaguanine | Mifepristone | Clarithromycin |
| Gentamicins | arsenic trioxide | Dihydroergocristine |
| decitabine | Ultraviolet Rays | Genistein |
| Sertraline | Ethylene Glycol | Zinc Oxide |
| Sulfaphenazole | Rifabutin | 4-octylphenol |
| hydroquinone | Paclitaxel | Foscarnet |
| lingzhi | tazobactam | Bithionol |
| Furazolidone | calycanthine | Thioridazine |
| 2-(4-morpholinyl)-8-phenyl-4H-1-benzopyran-4-one | Iproniazid | Flutamide |
| diphenylpyraline | Chorionic Gonadotropin | 2-dichlorobenzene |
| 15-deoxy-delta(12, 14)-prostaglandin J2 | Dinoprost | hexachlorobutadiene |
| Clozapine | CEP 14083 | pioglitazone |
| betulinic acid | Fludrocortisone | Lovastatin |
| Pyridoxine | Sulfadoxine | Acetylcysteine |
| glycidol | isocorydine | blebbistatin |
| 1,3-dichlorobenzene | Clofibric Acid | X-Rays |
| 1-ethyl-2-benzimidazolinone | Troleandomycin | boldine |
| Tretinoin | Amoxapine | Pregnenolone |
| Tolazamide | Ethacrynic Acid | Coumaphos |
| 5-episisomicin | oxaliplatin | Cefadroxil |
| pyrvinium | Monocrotaline | Tramadol |
| harmol | Phenelzine | fluvastatin |
| ethotoin | Puromycin | Ergocalciferols |
| oltipraz | Penicillamine | acemetacin |
| dexibuprofen | Piperonyl Butoxide | Topotecan |
| Choline | PI103 | dorzolamide |
| Dantrolene | Norethindrone | Bromocriptine |
| Gossypol | bisphenol A | Alprostadil |
| Carbachol | repaglinide | Melatonin |
| Clonazepam | Quinacrine | Moxalactam |
| Domperidone | Bisacodyl | Prednisolone |
| phenethyl isothiocyanate | Butyric Acid | ebastine |
| Malathion | Azacitidine | Lorazepam |
| Ethyl Methanesulfonate | Nitric Oxide | 1-Methyl-3-isobutylxanthine |
| geldanamycin | Nimodipine | Colchicine |
| Fluvoxamine | Nystatin | monorden |
| Mitomycin | Atenolol | vorinostat |
| Chlorambucil | NG-Nitroarginine Methyl Ester | Metergoline |
| irinotecan | Netilmicin | gefitinib |
| 3-deazaneplanocin | Benperidol | Deferoxamine |
| Y 27632 | canadine | Losartan |
| Dizocilpine Maleate | Cytarabine | Haloperidol |
| Clemastine | resveratrol | dibenzazepine |
| Enoxacin | Rotenone | Amiloride |
| Prazosin | Terazosin | Quercetin |
| 17-(allylamino)-17-demethoxygeldanamycin | mono-(2-ethylhexyl)phthalate | Gemfibrozil |
| SU 5402 | Emetine | Flunarizine |
| Plicamycin | Vitamin K 3 | 4-hydroxy-2-nonenal |
| Nocodazole | Fenoprofen | Zidovudine |
| Ranitidine | Dicyclomine | Mycophenolic Acid |
| compactin | dasatinib | leflunomide |
| Econazole | Galantamine | Diazepam |
| lysophosphatidic acid | 8-((4-chlorophenyl)thio)cyclic-3',5'-AMP | Dactinomycin |
| Ofloxacin | Fluorouracil | Oxymetazoline |
| Papaverine | Ifosfamide | Amantadine |
| Disulfiram | Methyldopa | |

TABLE S1-continued

Molecules that regulate genes or gene products relevant to proline transport and metabolism.

E1. Molecules that upregulate OAT:

| | | |
|---|---|---|
| Forskolin | LBH589 | fipronil |
| sorafenib | riddelliine | Sirolimus |
| trichostatin A | decitabine | tetra(4-N-methylpyridyl)porphine |
| testosterone 17 beta-cypionate | Sodium Benzoate | Aphidicolin |
| Diquat | bevacizumab | ellipticine |
| Amitrole | benzimidazole | Ecdysterone |
| marimastat | Copper Sulfate | dasatinib |
| Sulpiride | Cantharidin | erlotinib |
| Meptazinol | 4,4'-diaminodiphenylmethane | Aclarubicin |
| Idoxuridine | Diethylhexyl Phthalate | Tolnaftate |
| sulforafan | 2-nitrofluorene | thermozymocidin |
| fludarabine | Theophylline | suxibuzone |
| Valproic Acid | beta-Naphthoflavone | HC toxin |
| Methylnitrosourea | 1-ethyl-2-benzimidazolinone | vorinostat |
| Molindone | Triiodothyronine | cidofovir |
| Pyrethrins | Fenoterol | Aflatoxins |
| butamben | diisopropyl methylphosphonate | Paraquat |
| Thapsigargin | Mannitol | geldanamycin |
| monastrol | Hycanthone | Pregnenolone Carbonitrile |
| Ofloxacin | Thiostrepton | bafilomycin A |
| tripterine | tenidap | 4-cyclododecyl-2,6-dimethylmorpholine acetate |
| senecionine | Vincristine | Benzalkonium Compounds |
| Methyldopa | zardaverine | Phenylmercuric Acetate |
| Papaverine | Isoniazid | Fenofibrate |
| sanguinarine | Haloperidol | Pregnenolone |
| Metribolone | 2-methoxyestradiol | phenethyl isothiocyanate |
| imatinib | Cam ptothecin | Ozone |
| blebbistatin | Gabexate | 4-nonylphenol |
| Amphetamine | Clodronic Acid | Methylprednisolone |
| VX | Cytokines | Dihydrotestosterone |
| Tretinoin | doxofylline | Thioctic Acid |
| Fenoprofen | oxaprozin | cerivastatin |
| Yellow Fever Vaccine | Hemin | N-methylpyrrolidone |
| Zidovudine | Etidronic Acid | tenofovir |
| Diflunisal | isoconazole | trilinolein |
| Methanol | Folic Acid | Clofibrate |
| nimesulide | Fluphenazine | Quercetin |
| Botulinum Toxins, Type A | Prostaglandins E | Acrolein |
| Cefuroxime | Chlorpheniramine | Tetanus Toxin |
| Ribavirin | bis(tri-n-butyltin)oxide | Methylcholanthrene |
| heliotrine | triptolide | ciclopirox |
| Bupropion | Clenbuterol | Dicyclomine |
| Strophanthidin | gefitinib | Hydrogen Peroxide |
| gedunin | Caffeine | Trenbolone Acetate, (17beta)-isomer |
| atorvastatin | romidepsin | Hydroxyurea |
| Flurbiprofen | Nevirapine | Moxisylyte |
| Cytochalasin B | pristane | bicalutamide |
| Cholera Toxin | Zalcitabine | gamma-Tocopherol |
| 8-Bromo Cyclic Adenosine Monophosphate | Anti-Retroviral Agents | Phenylbutazone |
| 8-((4-chlorophenyl)thio)cyclic-3',5-AMP | 1-(5-Isoquinolinesulfonyl)-2-Methylpiperazine | Corticosterone |
| thymoglobulin | Insulin | cathelicidin antimicrobial peptide |
| everolimus | BCG Vaccine | X-Rays |
| letrozole | Mycophenolic Acid | Doxepin |
| Enalapril | NG-Nitroarginine Methyl Ester | Dimethyl Sulfoxide |
| Metoprolol | Methotrexate | Furosemide |
| Enoxacin | alpha-Tocopherol | Cyclosporine |
| Phenylephrine | 4-methyl-N-(3-(4-methylimidazol-1-yl)-5-(trifluoromethyl)phenyl)-3-((4-pyridin-3-ylpyrimidin-2-yl)amino)benzamide | Deferoxamine |
| Rifampin | Vinblastine | Amitriptyline |
| Quinidine | oxybutynin | Dactinomycin |
| lysophosphatidic acid | Atropine | resveratrol |
| Terbutaline | Paroxetine | 17-(allylamino)-17-demethoxygeldanamycin |
| Losartan | Albendazole | Diphenhydramine |

TABLE S1-continued

Molecules that regulate genes or gene products relevant to proline transport and metabolism.

| | | |
|---|---|---|
| Fluoxetine | Fluorouracil | bisphenol A |
| acetopyrrothine | 1-Methyl-3-isobutylxanthine | Cytarabine |
| Vitamin K 3 | Paclitaxel | Benomyl |
| E2. Molecules that downregulate OAT | | |
| Thioacetamide | Ticlopidine | bendazolic acid |
| Dimethylnitrosamine | Hexachlorobenzene | methylformamide |
| Chlormezanone | coumarin | bromobenzene |
| Flutamide | Ethambutol | lornoxicam |
| Piperonyl Butoxide | Clonazepam | nitrosobenzylmethylamine |
| N-nitrosomorpholine | Propylthiouracil | Diethylnitrosamine |
| 1,3-dichloro-2-propanol | pantoprazole | Methimazole |
| Am inoglutethim ide | Hexamethonium | Carbamazepine |
| artemisinine | 1,2-dithiol-3-thione | oltipraz |
| Chloroform | Monocrotaline | 4-dichlorobenzene |
| Ethionamide | Stavudine | Asbestos |
| hydroxytamoxifen | Carbimazole | Phenobarbital |
| ochratoxin A | Pyrogallol | Disopyramide |
| Gemfibrozil | alachlor | Carbon Tetrachloride |
| 2-dichlorobenzene | Acetaminophen | Cinnarizine |
| Chloramphenicol | 2-Acetylaminofluorene | terbinafine |
| Naproxen | Colchicine | Lorazepam |
| gentamicin C | salicylamide | Econazole |
| estradiol 3-benzoate | Omeprazole | bambuterol |
| Phenacetin | garcinol | Gentian Violet |
| Okadaic Acid | Phenytoin | Clotrimazole |
| Testosterone | iodoform | Trimethadione |
| Citrinin | Hydroxyzine | nimetazepam |
| Polychlorinated Biphenyls | crotamiton | benziodarone |
| iturelix | Dehydroepiandrosterone | Mestranol |
| Methyltestosterone | Etodolac | Miconazole |
| Dantrolene | PI103 | Safrole |
| Estriol | Niclosamide | Ibuprofen |
| Malathion | Penicillamine | Calcium Chloride |
| Carmustine | Methapyrilene | lead tetraacetate |
| vanadyl sulfate | Benperidol | dexamisole |
| Procarbazine | hexachlorobutadiene | Benzbromarone |
| Methylene Chloride | Cymarine | ranolazine |
| Azathioprine | Chromium | Famotidine |
| Tryptophan | Lead | Ketanserin |
| Atovaquone | Phleomycins | Trypsin Inhibitor, Bowman-Birk Soybean |
| Amanitins | meloxicam | Sulfasalazine |
| Mifepristone | Salicylates | Dinoprostone |
| Sulindac | 5'-methylthioadenosine | Patulin |
| Danazol | Doxorubicin | Metolazone |
| pioglitazone | zileuton | Canavanine |
| Dizocilpine Maleate | Urethane | Tacrine |
| sodium chromate(VI) | Estradiol | Disulfiram |
| fosfosal | 4-(5-benzo(1,3)dioxol-5-yl-4-pyridin-2-yl-1H-imidazol-2-yl)benzamide | fenamiphos |
| Vancomycin | Dimethylformamide | Lomustine |
| Luteolin | Lasalocid | naphthalene |
| Diazepam | perfluorooctanoic acid | 2,4-Dinitrophenol |
| phenothiazine | Nitrazepam | acetovanillone |
| acadesine | Gentamicins | Diltiazem |
| Ketorolac | shikonin | Edrophonium |
| Isotretinoin | rabeprazole | Fursultiamin |
| Lidocaine | Fluocinolone Acetonide | Genistein |
| Minocycline | syrosingopine | GW 3965 |
| Thiabendazole | Ethinyl Estradiol | Itraconazole |
| Fluorometholone | 3-deazaneplanocin | Fluconazole |
| Diethylstilbestrol | Cyproterone Acetate | Promethazine |
| rosiglitazone | aristolochic acid 1 | Cisplatin |
| scriptaid | Ganciclovir | Emetine |
| Diclofenac | lingzhi | ferric nitrilotriacetate |
| Ethionine | Khellin | hydrazine |
| Canrenoate Potassium | Nystatin | 9-(2-hydroxy-3-nonyl)adenine |
| Tunicamycin | systhane | Caerulein |
| Phenylalanine | Calcium | Clofibric Acid |
| arsenic trioxide | Hemicholinium 3 | Ethylnitrosourea |
| sodium arsenite | Remoxipride | Oxazepam |
| Dexamethasone | Hydrocortisone | dirithromycin |
| homatropine | U 0126 | Clobetasol |
| triadimefon | Melphalan | Zimeldine |
| Antigen-Antibody Complex | Nitrofurazone | Ethanol |

TABLE S1-continued

Molecules that regulate genes or gene products relevant to proline transport and metabolism.

| | | |
|---|---|---|
| cephaelin | apratoxin A | Aspirin |
| arsenic acid | Betamethasone | furaltadon |
| flunixin | 1,3-dichlorobenzene | anastrozole |
| nifuroxazide | Lovastatin | Pivampicillin |
| Nifedipine | Tolazoline | Nocodazole |
| tropisetron | Orotic Acid | Simvastatin |
| Carcinogens | CpG ODN 2216 | isoxicam |
| naftopidil | leflunomide | Nicotine |
| Dihydroergotamine | acidocin CH5, *Lactobacillus acidophilus* | Bezafibrate |
| Serotonin | Allopurinol | Spironolactone |
| Piribedil | Glyburide | Clomiphene |
| temozolomide | Nordefrin | Niacinamide |
| Primidone | Lobeline | Ethylestrenol |
| Tetrachlorodibenzodioxin | Carnitine | 4-(4-fluorophenyl)-2-(4-hydroxyphenyl)-5-(4-pyridyl)imidazole |
| Trichloroethylene | Clonidine | sevoflurane |
| Immunoglobulin M | motexafin gadolinium | Pilocarpine |
| Deoxycholic Acid | dihydroquinghaosu | piperaquine |
| Amiodarone | Ajmaline | Amantadine |
| picrotoxinin | versipelostatin | Mephentermine |
| Calcitriol | tracazolate | gatifloxacin |
| nilutamide | securinine | Azaguanine |
| Ampicillin | Epitestosterone | Y 27632 |
| Nicergoline | Isoproterenol | 16-ketoestradiol |
| mycophenolate mofetil | Aminocaproic Acids | Epirubicin |
| fulvestrant | Immunoglobulins, Intravenous | Amphotericin B |
| Shiga Toxin | Pemoline | balsalazide |
| Chlortetracycline | Inosine Monophosphate | Pimozide |
| Betaxolol | MF59 oil emulsion | Nimodipine |
| enterotoxin B, staphylococcal | Nitrofurantoin | pirinixic acid |
| carvedilol | Methazolamide | Azacitidine |
| Indomethacin | Rotenone | Rolipram |
| Propranolol | Albuterol | Dichlorvos |
| Sotalol | enzastaurin | Nitric Oxide |
| N-Ac-CHAVC-NH2 | Tranylcypromine | Cyclophosphamide |
| Puromycin | mono-(2-ethylhexyl)phthalate | Neomycin |
| Plicamycin | phosphonoacetamide | Ascorbic Acid |
| bortezomib | rofecoxib | Mitomycin |
| Chlorpromazine | fluvastatin | Clindamycin |
| Palm itic Acid | Deoxyglucose | Kainic Acid |
| Alpha-Amanitin | Pergolide | Oxymetazoline |
| Vitamin E | Mebendazole | Ketoconazole |
| Ciprofloxacin | Clomipramine | isoascorbic acid |
| Ionomyin | Thioguanine | Cycloheximide |
| Methyl Methanesulfonate | | |

F1. Molecules that upregulate ALDH4A1:

| | | |
|---|---|---|
| Cyclopenthiazide | Sulfadimethoxine | Mephenesin |
| Tiletamine | Methotrimeprazine | Trimethoprim |
| tomatidine | Pilocarpine | citiolone |
| Bisoprolol | butacaine | Glycopyrrolate |
| Bufexamac | chloropyramine | pipenzolate |
| Meclizine | Zimeldine | acetylleucine |
| Albuterol | amylocaine | Methoxamine |
| bacampicillin | Etanidazole | Riluzole |
| Propranolol | zaprinast | telenzepine |
| Azathioprine | Cefixime | Buspirone |
| Bemegride | 4-acetylaminofluorene | Sulfisoxazole |
| ajmalicine | pelargonic acid | trimethobenzamide |
| naringin | sulfanilamide | Oxyquinoline |
| Dihydrostreptomycin Sulfate | triadimefon | Hydralazine |
| oxaliplatin | Norethindrone | Chlorpheniramine |
| Procaine | Aclarubicin | diflorasone diacetate |
| Felodipine | Tolmetin | Sulfacetamide |
| Amiloride | Bromocriptine | harman |
| Propidium | TO-901317 | benzothiazide |
| Propylthiouracil | Remoxipride | efavirenz |
| Cefazolin | tridihexethyl | Aristolochic Acids |
| Dipyrone | Moricizine | Dihydrotestosterone |
| 1-(2-cyano-3,12-dioxooleana-1,9-dien-28-oyl)imidazole | Etoposide | Pargyline |
| triptolide | diisopropyl methylphosphonate | Ethylnitrosourea |

TABLE S1-continued

Molecules that regulate genes or gene products relevant to proline transport and metabolism.

| | | |
|---|---|---|
| Hymecromone | Josamycin | Methylnitrosourea |
| clopidogrel | Heptaminol | Orphenadrine |
| Tobramycin | 4-(N-methyl-N-nitrosamino)-1-(3-pyridyl)-1-butanone | |
| eperisone | Moxisylyte | Nalidixic Acid |
| arcaine | Spironolactone | Ondansetron |
| fenhexamid | Doxorubicin | trichostatin A |
| Cyclopentolate | clidinium | monastrol |
| artemisinine | lorglumide | Hydrocortisone |
| troglitazone | 8-(3-Chlorostyryl)-1,3,7-trimethylxanthine | Forskolin |
| Cromolyn Sodium | Selenomethionine | geldanamycin |
| 4,4'-diaminodiphenylmethane | Glutamic Acid | 2-nitrofluorene |
| Guanfacine | vorinostat | Vecuronium Bromide |
| Ethambutol | Diethylnitrosamine | Streptozocin |
| Azaperone | diperodon | Mephenytoin |
| fomepizole | Lamivudine | Allantoin |
| Sulfasalazine | VX | Etilefrine |
| 1-Methyl-3-isobutylxanthine | Enalapril | oxolamine |
| Hydroxyzine | Dilazep | carbinoxamine |
| Glycocholic Acid | Sulfameter | Cisplatin |
| apicidin | ethotoin | clemizole |
| Levodopa | isopyrin | decitabine |
| Ticlopidine | salicylamide | Aminopyrine |
| chloroacetaldehyde | butenafine | enzastaurin |
| gefitinib | Acetaminophen | fenspiride |
| Kinetin | Clarithromycin | 2-Acetylaminofluorene |
| Cortisone | Thiabendazole | Practolol |
| Aflatoxin B1 | HC toxin | Nisoldipine |
| Thiethylperazine | Ketanserin | discretamine |
| tris(2,3-dibromopropyl)phosphate | Mianserin | 3-nitropropionic acid |
| | | Megestrol Acetate |
| Aflatoxins | Ultraviolet Rays | vinorelbine |
| pyrithyldione | pirenperone | Daunorubicin |
| LBH589 | lapatinib | asiaticoside |
| Methacholine Chloride | oxcarbazepine | Ipratropium |
| 8-((4-chlorophenyl)thio)cyclic-3',5-AMP | Etidronic Acid | Tin Fluorides |
| Sulfamethazine | rosiglitazone | 3,3',4',5-tetrachlorosalicylanilide |
| amitraz | romidepsin | ascorbate-2-phosphate |
| Corticosterone | Pyrazinamide | vinpocetine |
| Ethamsylate | Minocycline | Ketamine |
| Rolipram | Ronidazole | Curcumin |
| Pinacidil | Trichlormethiazide | Mitomycin |
| Luteolin | lomefloxacin | Dexamethasone |
| piclamilast | 1,3-dichlorobenzene | tranilast |
| Carboplatin | Glafenine | diphemanil methylsulfate |
| Sulfadiazine | Testosterone | Verapamil |
| velnacrine | Phorbol Esters | Zalcitabine |
| Zidovudine | butamben | Atrazine |
| Ciprofloxacin | Sumatriptan | Tacrine |
| fazarabine | Cytochalasin B | Carbimazole |
| Botulinum Toxins, Type A | Mustard Gas | Carbamazepine |
| Amphotericin B | Dipyridamole | Furosemide |
| lead tetraacetate | Mannitol | cefepime |
| Sorbitol | letrozole | Serotonin |
| Tolbutamide | Androsterone | abacavir |
| blebbistatin | Cisapride | Flunarizine |
| Ritodrine | Pentoxifylline | scriptaid |
| Camptothecin | Bupropion | picrotoxinin |
| delsoline | Hydroxyurea | 4-hydroxy-2-nonenal |
| Valproic Acid | Amoxapine | Metaraminol |
| Oxazepam | Theophylline | marimastat |
| Citric Acid | Podophyllotoxin | Altretamine |
| Mycophenolic Acid | candesartan | Paclitaxel |
| Fenoprofen | Gentamicins | Vincristine |
| versipelostatin | erlotinib | Nitric Oxide |
| Phenoxybenzamine | Prochlorperazine | 8-Bromo Cyclic Adenosine Monophosphate |
| Enoxacin | Chlortetracycline | Choline |
| Pregnenolone Carbonitrile | Phenobarbital | Chloramphenicol |
| Vitamin E | Clofibrate | Busulfan |
| sodium selenate | Methotrexate | Trifluoperazine |

TABLE S1-continued

Molecules that regulate genes or gene products relevant to proline transport and metabolism.

| | | |
|---|---|---|
| Physostigmine | Dimethyl Sulfoxide | benazepril |
| imatinib | Galantamine | Azauridine |
| Diflunisal | Fluorouracil | 4-(5-benzo(1,3)dioxol-5-yl-4-pyridin-2-yl-1H-imidazol-2-yl)benzamide |
| Phenylephrine | sodium arsenite | Aspirin |
| Neomycin | Iproniazid | Saquinavir |
| Melphalan | 1-Methyl-4-phenyl-1,2,3,6-tetrahydropyridine | dasatinib |
| Ascorbic Acid | Nocodazole | Soman |
| U 0126 | HI 6 | Captopril |
| Ionomyin | Chitosan | Digoxin |
| Dactinomycin | Cycloheximide | Amitrole |
| Nicotine | Chlorpyrifos | Dichlorvos |
| Cyclophosphamide | Azacitidine | |

F2. Molecules that downregulate ALDH4A1:

| | | |
|---|---|---|
| spiradoline | alfuzosin | Buthionine Sulfoximine |
| hydroxytamoxifen | Oxolinic Acid | Nialamide |
| tianeptine | am ineptin | homosalate |
| 9-(2-hydroxy-3-nonyl)adenine | Vinblastine | Lidoflazine |
| Gliclazide | althiazide | Isosorbide |
| Isotretinoin | sunitinib | enrofloxacin |
| telmisartan | Cefuroxime | doxofylline |
| Estradiol | Quinidine | Ursodeoxycholic Acid |
| piretanide | ubiquinol | daidzein |
| Aminosalicylic Acid | Colchicine | Genistein |
| fulvestrant | Imipramine | Probenecid |
| Amantadine | desloratadine | Pheniramine |
| Fluoxetine | Disopyramide | Ecdysterone |
| Simvastatin | Methylergonovine | ebselen |
| betulinic acid | repaglinide | Anti-Retroviral Agents |
| naringenin | Reserpine | nickel chloride |
| Lithocholic Acid | N-acetylsphingosine | bisphenol A |
| vinylidene chloride | valdecoxib | Tetracycline |
| beta-Naphthoflavone | Cinoxacin | bendazolic acid |
| Diclofenac | Cytochalasin D | Ethinyl Estradiol |
| venlafaxine | Lovastatin | Mestranol |
| moroxydine | Cephapirin | alachlor |
| Chloroquine | norethindrone acetate | Erythromycin |
| Sparteine | Labetalol | 2-dichlorobenzene |
| Clonidine | lacidipine | Indomethacin |
| Gold | Sulindac | Etodolac |
| Clemastine | 4-hydroxytamoxifen | Diethylstilbestrol |
| Ranitidine | Oxytetracycline | Zinc Sulfate |
| Natamycin | etofylline | isopropamide iodide |
| olanzapine | Estriol | triflusal |
| Canrenoate Potassium | Methapyrilene | Lobeline |
| Alprazolam | Pergolide | pioglitazone |
| Ethionamide | hydrastinine | Clozapine |
| Pravastatin | calycanthine | N-(2-cyclohexyloxy-4-nitrophenyl)methanesulfonamide |
| Sertraline | Naproxen | Digitoxin |
| Carbon Tetrachloride | estradiol 3-benzoate | bicalutamide |
| Roflumilast | suxibuzone | acetorphan |
| Viomycin | Dichlorphenamide | aluminum sulfate |
| Acetohexamide | carvedilol | Vincamine |
| Thioacetamide | Metoprolol | Raloxifene |
| Doxepin | Promethazine | geraniol |
| Niridazole | Nafenopin | Antigen-Antibody Complex |
| dexchlorpheniramine | Nitrendipine | Isoflurophate |
| Amitriptyline | Miconazole | Biotin |
| Betamethasone | Glycine | Phenelzine |
| Sotalol | Trihexyphenidyl | Tacrolimus |
| famciclovir | Isoniazid | 4-dichlorobenzene |
| Cimetidine | Bumetanide | Dinitrophenols |
| benziodarone | Paroxetine | Fluocinolone Acetonide |
| Dimethylformamide | sulfathiazole | Danazol |
| Rifampin | Phenindione | boldine |
| Pirenzepine | Fluphenazine | Naloxone |
| Ethionine | sorafenib | Pemoline |
| Amiodarone | Capsaicin | Disulfiram |
| motexafin gadolinium | Hydrogel | oxfendazole |
| Antimycin A | prochloraz | sildenafil |
| ipriflavone | Deoxycholic Acid | N-Methylscopolamine |
| gabapentin | dexibuprofen | Cyclosporine |
| Brefeldin A | Secobarbital | anastrozole |

TABLE S1-continued

Molecules that regulate genes or gene products relevant to proline transport and metabolism.

| | | |
|---|---|---|
| rabeprazole | Meclofenamic Acid | Diphenhydramine |
| oxybutynin | Phenytoin | atorvastatin |
| canadine | biphenylylacetic acid | Dobutamine |
| pantoprazole | Diltiazem | Risperidone |
| Astemizole | Methylcholanthrene | aceclofenac |
| genipin | Rotenone | idebenone |
| cobaltous chloride | Diazinon | titanium dioxide |
| Estrogens | deferiprone | alpha-Amino-3-hydroxy-5-methyl-4-isoxazolepropionic Acid |
| Sirolimus | Ifosfamide | 1,1,1-trichloroethane |
| halofuginone | pristane | Chloroform |
| sulforafan | Flutamide | phenylhydrazine |
| 5'-methylthioadenosine | lysophosphatidic acid | Ecdysone |
| quetiapine | Acyclovir | Finasteride |
| epoxomicin | Indapamide | Nalbuphine |
| Gemfibrozil | Azlocillin | beta-cyclodextrin-benzaldehyde |
| modafinil | rifapentine | 4-octylphenol |
| Nortriptyline | Ofloxacin | Dantrolene |
| efalizumab | Diethylhexyl Phthalate | Poly I-C |
| tazobactam | sparfloxacin | nimesulide |
| Citalopram | Phentolamine | 4-nonylphenol |
| Bacitracin | Tiapamil Hydrochloride | Nimodipine |
| Bezafibrate | Chlorpromazine | Metyrapone |
| benfluorex | Chlormadinone Acetate | Coumaphos |
| Potassium Dichromate | 6-Mercaptopurine | Clomipramine |
| leflunomide | Thioridazine | Chlorambucil |
| cyanoginosin LR | Thapsigargin | 2-(4-morpholinyl)-8-phenyl-4H-1-benzopyran-4-one |
| Clonazepam | meloxicam | 2-methoxyestradiol |
| cilostazol | Quinacrine | Ibuprofen |
| fluvastatin | phenethyl isothiocyanate | chlorcyclizine |
| Vanadates | lactacystin | Ketoconazole |
| Itraconazole | Econazole | Isoproterenol |
| Tocainide | benzamil | Floxuridine |
| Thioguanine | Tranexamic Acid | temsirolimus |
| Concanavalin A | Aminoglutethimide | Deoxyglucose |
| Clotrimazole | Terazosin | resveratrol |
| SB 203580 | Nadolol | cerivastatin |
| Fluconazole | Tinidazole | Promazine |
| Allopurinol | lansoprazole | Perhexiline |
| linezolid | Pentylenetetrazole | ONO 2235 |
| Deferoxamine | Loratadine | bortezomib |
| ferulic acid | Sulpiride | Tropicamide |
| Cytarabine | Baclofen | Nifedipine |
| acadesine | Fluvoxamine | Melatonin |
| Haloperidol | Methazolamide | Streptomycin |
| Omeprazole | Clindamycin | terbinafine |
| Terfenadine | Diazepam | Ramipril |
| Caffeine | Cinnarizine | Calcitriol |
| Quercetin | Granisetron | Phenylalanine |
| valsartan | Dicyclomine | Ketorolac |
| Lisinopril | Cyproheptadine | Nevirapine |
| Pyrogallol | Piroxicam | Stavudine |
| rofecoxib | benzyloxycarbonylleucyl-leucyl-leucine aldehyde | zileuton |
| gemcitabine | irinotecan | pirinixic acid |
| isoascorbic acid | Oxymetazoline | Papaverine |
| Acetazolamide | Hydrochlorothiazide | Lomustine |
| Carmustine | Clofibric Acid | Amphetamine |

G1. Molecules that upregulate SLC36A1:

| | | |
|---|---|---|
| pridinol | Talampicillin | N(1)-methyl-2-lysergic acid diethylamide |
| Piperacillin | sertaconazole | Theobromine |
| isopyrin | Sulfaquinoxaline | adrenosterone |
| iturelix | troglitazone | Salicylates |
| CpG ODN 2216 | Grape Seed Proanthocyanidins | pioglitazone |
| 4-hydroxy-2-nonenal | Insulin | tripterine |
| lenalidomide | Erythromycin Ethylsuccinate | Pentolinium Tartrate |
| Aclarubicin | SC 514 | cryptoxanthin |
| tridihexethyl | Cromolyn Sodium | Mycotoxins |
| Endotoxins | Glafenine | SB 203580 |
| Yellow Fever Vaccine | Vitamin E | withaferin A |
| Botulinum Toxins, Type A | lorglumide | flumequine |
| Propanil | rosiglitazone | Albuterol |

TABLE S1-continued

Molecules that regulate genes or gene products relevant to proline transport and metabolism.

| | | |
|---|---|---|
| CD 437 | Fluorometholone | 1,3-dichlorobenzene |
| MF59 oil emulsion | Inosine Monophosphate | Trimethoprim |
| Methoxamine | romidepsin | Didanosine |
| diphemanil methylsulfate | sodium chlorate | 15-deoxy-delta(12,14)-prostaglandin J2 |
| gefitinib | Trimeprazine | fazarabine |
| Valproic Acid | Tetrachloroethylene | 1,5-naphthalenediamine |
| decitabine | procyanidin | monobenzone |
| indole-3-carbinol | Mexiletine | direct black 3 |
| Biotin | Metribolone | mefexamide |
| trichostatin A | Quercetin | GW 3965 |
| 2-dichlorobenzene | 4-dichlorobenzene | alginic acid |
| Roxarsone | rilmenidine | Nefopam |
| Fludrocortisone | lapatinib | Dexamethasone |
| midecamycin | Hycanthone | Monocrotaline |
| caffeic acid | zaprinast | Dihydrotestosterone |
| blebbistatin | monastrol | enzastaurin |
| Calcitriol | pristane | vesamicol |
| geldanamycin | Pempidine | cyanopindolol |
| Trifluoperazine | Cytochalasin B | Lincomycin |
| fragment C, human serum albumin | LPS 9 | Thioridazine |
| Dimethylnitrosamine | Epirizole | Cefuroxime |
| Perhexiline | N-nitrosomorpholine | Octopamine |
| Dichlororibofuranosylbenzimidazole | Paclitaxel | Metoclopramide |
| Bleomycin | Acetylcysteine | Vincristine |
| ajmalicine | Gonadotropins | Simazine |
| Pipemidic Acid | homatropine | daboiatoxin |
| lomefloxacin | Rifabutin | Amiloride |
| Heparin | Chlorpromazine | celecoxib |
| homochlorocyclizine | quintozene | Lynestrenol |
| Carcinogens | Ascorbic Acid | Immunoglobulin M |
| Carbachol | Oxyquinoline | Doxepin |
| Malathion | vorinostat | Rolipram |
| kavain | Vitamin K 3 | 16-ketoestradiol |
| 4-amino-6-hydrazino-7-beta-D-ribofuranosyl-7H-pyrrolo(2,3-d)-pyrimidine-5-carboxamide | Apomorphine | Phenoxybenzamine |
| imatinib | Dinoprost | sapphyrin |
| benzyloxycarbonylleucyl-leucyl-leucine aldehyde | Doxorubicin | Disulfiram |
| sulfathiazole | triadimefon | LBH589 |
| Diltiazem | Hydroxyzine | Aztreonam |
| adalimumab | Benzo(a)pyrene | heliotrine |
| resveratrol | Methylnitrosourea | rituximab |
| Ethacrynic Acid | Propylthiouracil | Diazinon |
| fluticasone | Tetradecanoylphorbol Acetate | Methotrexate |
| Sulfasalazine | Clomipramine | fulvestrant |
| copolymer 1 | Piperonyl Butoxide | Levonorgestrel |
| 4-hydroxytamoxifen | bromodichloromethane | dasatinib |
| Acetaminophen | Tretinoin | Azathioprine |
| Hemin | Chorionic Gonadotropin | Labetalol |
| Fluoxetine | Nifedipine | Iproniazid |
| testosterone | 17 beta- | |
| Aflatoxin B1 | Phenacetin | cypionate |
| Ergocalciferols | HI 6 | Topotecan |
| irinotecan | Mycophenolic Acid | Methyl Methanesulfonate |
| colforsin | bortezomib | Hydrogen Peroxide |
| 4-(5-benzo(1,3)dioxol-5-yl-4-pyridin-2-yl-1H-imidazol-2-yl)benzamide | methylatropine | Nitric Oxide |
| pantoprazole | Pregnenolone Carbonitrile | Immunotoxins |
| sulforafan | Ethosuximide | Promazine |
| Methylene Chloride | Colchicine | Nortriptyline |
| Particulate Matter | Medroxyprogesterone Acetate | torsemide |
| rabeprazole | Risperidone | Nocodazole |
| Puromycin | ochratoxin A | Tacrine |
| Penicillamine | Enalapril | Atropine |
| Caffeine | Indomethacin | Camptothecin |
| fluvastatin | sodium arsenite | Diazepam |
| Fluorouracil | Clotrimazole | Amitriptyline |
| Azacitidine | | |

G2. Molecules that downregulate SLC36A1:

| | | |
|---|---|---|
| carbetapentane | Methoxsalen | lonidamine |
| Alpha-Amanitin | genipin | quinethazone |
| Betaxolol | clemizole | Bisoprolol |
| verteporfin | Prenylamine | Nafronyl |
| fenspiride | ciclopirox | ascorbate-2-phosphate |
| Indapamide | GW 501516 | Cholera Toxin |

TABLE S1-continued

Molecules that regulate genes or gene products relevant to proline transport and metabolism.

| | | |
|---|---|---|
| Dihydroergotamine | Methamphetamine | parbendazole |
| harmol | Trioxsalen | BCG Vaccine |
| Eugenol | Benserazide | Apigenin |
| moxonidine | Immunoglobulin G | naphthalene |
| enterotoxin I, staphylococcal | Bethanechol | Curcumin |
| Mesalamine | Famotidine | Growth Hormone |
| Santonin | mebhydroline | Cisapride |
| Coumarins | Platelet Activating Factor | Mannitol |
| Tetrachlorodibenzodioxin | 2-nitrofluorene | Ambroxol |
| Aflatoxins | Ganciclovir | hydroxyachillin |
| Ethambutol | MK 0591 | Tolmetin |
| flunixin | Acetohexamide | phthalylsulfathiazole |
| Thapsigargin | Tunicamycin | Sulfadimethoxine |
| rauwolscine-OHPC | lobelanidine | acidocin CH5, *Lactobacillus acidophilus* |
| infliximab | Glipizide | Concanavalin A |
| chelidonine | Clorgyline | Antigen-Antibody Complex |
| 2,2'-(hydroxynitrosohydrazono)bis-ethanamine | Practolol | Azoxymethane |
| Oxytocin | skimmianine | Ethisterone |
| shikonin | Minocycline | 1-Methyl-3-isobutylxanthine |
| Flutamide | Primaquine | Mafenide |
| Diethylhexyl Phthalate | Acepromazine | Cyclophosphamide |
| Harmine | Protoveratrines | solasodine |
| Dinoprostone | 17-(allylamino)-17-demethoxygeldanamycin | Prednisolone |
| Corticosterone | Ceftazidime | CPG-oligonucleotide |
| Palmitic Acid | Selenomethionine | Cholecalciferol |
| halofuginone | Beclomethasone | beta-cyclodextrin-benzaldehyde |
| amlexanox | trilinolein | amylocaine |
| Staurosporine | Deoxycholic Acid | Gemfibrozil |
| Atrazine | Isoniazid | sangivamycin |
| triptolide | Enterotoxins | Rifampin |
| titanium dioxide | ellipticine | AICA ribonucleotide |
| nifuroxazide | Estriol | Paroxetine |
| Dextran Sulfate | Pyrazinamide | Procainamide |
| Dilazep | Imipramine | TO-901317 |
| Clonidine | salsolidine | Estradiol |
| 6-azathymine | 4-acetylaminofluorene | Chlorprothixene |
| Niclosamide | Methyltestosterone | Ethanol |
| 8-Bromo Cyclic Adenosine Monophosphate | Propofol | Poly I-C |
| Immunoglobulins, | Intravenous Hydralazine | sanguinarine |
| Dextromethorphan | Piracetam | Acrolein |
| Cyclosporine | Vincamine | Lovastatin |
| Cycloheximide | ciprofibrate | Luteinizing Hormone |
| Penicillin G | vinclozolin | emtricitabine |
| bis(tri-n-butyltin)oxide | Benzbromarone | Folic Acid |
| bicalutamide | Pyrogens | Biculculline |
| Doxazosin | Deoxyglucose | docetaxel |
| R 848 | Phenobarbital | tenofovir |
| arsenic trioxide | Luteolin | Pentylenetetrazole |
| Mitoxantrone | Norfloxacin | poly ICLC |
| lead acetate | Diethylstilbestrol | cobaltous chloride |
| Hydroxyurea | fasudil | piclamilast |
| dibenzazepine | Sirolimus | X-Rays |
| 2-(4-morpholinyl)-8-phenyl-4H-1-benzopyran-4-one | enterotoxin B, staphylococcal | trovafloxacin |
| Cisplatin | Cytokines | Dinitrofluorobenzene |
| Cephalothin | quelamycin | Epitestosterone |
| Albendazole | Anti-Retroviral Agents | salicylamide |
| Niacinamide | Chlormadinone Acetate | Guanethidine |
| Amoxicillin | versipelostatin | Ionomyin |
| Metform in | Papaverine | mycophenolate mofetil |
| pirinixic acid | balsalazide | Bezafibrate |
| Trimethadione | Sulpiride | Haloperidol |
| Forskolin | Ticlopidine | Ultraviolet Rays |
| Tacrolimus | Methapyrilene | Chloroform |
| Nicotine | Procarbazine | Dactinomycin |
| Phytohemagglutinins | bisphenol A | erlotinib |
| nimesulide | Cytarabine | Carmustine |
| Naproxen | Diclofenac | Aspirin |
| Clofibrate | | |

H1. Molecules that upregulate SLC36A2:

| | | |
|---|---|---|
| Ascorbic Acid | Teriparatide | aluminum sulfate |
| Gonadotropins | Bismuth | Salicylates |
| acodazole | Enterotoxins | rosiglitazone |

TABLE S1-continued

Molecules that regulate genes or gene products relevant to proline transport and metabolism.

| | | |
|---|---|---|
| beta-Naphthoflavone | Tretinoin | Chorionic Gonadotropin |
| Azacitidine | Hyaluronic Acid | 4-(5-benzo(1,3)dioxol-5-yl-4-pyridin-2-yl-1H-imidazol-2-yl)benzamide |
| Cycloheximide | Metronidazole | bisphenol A |
| Heparin | MF59 oil emulsion | pioglitazone |
| Tetracycline | Phenobarbital | blebbistatin |
| Niacinamide | CPG-oligonucleotide | Trenbolone Acetate, (17beta)-isomer |
| 4-hydroxytamoxifen | Dimethylnitrosamine | Hemin |
| Insulin | Azoxymethane | imatinib |
| Quercetin | Doxorubicin | Immunotoxins |
| Clomipramine | Dinoprostone | Sulindac |
| gefitinib | Tetrachlorodibenzodioxin | Genistein |
| Indomethacin | Dactinomycin | bortezomib |
| Diethylstilbestrol | Methotrexate | Sirolimus |
| H2. Molecules that downregulate SLC36A2: | | |
| ubiquinol | BRL 37344 | Bleomycin |
| Trichloroepoxypropane | ranolazine | Nandrolone |
| chlorinated dibenzofurans | pristane | withaferin A |
| Berberine | lysophosphatidic acid | Ouabain |
| Melphalan | 1,5-naphthalenediamine | vanadium pentoxide |
| Ozone | quintozene | resveratrol |
| Chitosan | R 848 | Dinitrofluorobenzene |
| Anti-Retroviral Agents | Estradiol | dexibuprofen |
| sulforafan | Cytokines | enterotoxin B, staphylococcal |
| Megestrol Acetate | Isoproterenol | acidocin CH5, Lactobacillus acidophilus |
| Hydralazine | Antigen-Antibody Complex | Betamethasone |
| Growth Hormone | Vitamin E | Dexamethasone |
| Methylene Chloride | Fluoxetine | Estriol |
| Cyclophosphamide | Phenytoin | Captopril |
| Progesterone | Kainic Acid | Tetradecanoylphorbol Acetate |
| Calcitriol | Colchicine | Valproic Acid |
| Bezafibrate | Cisplatin | |
| I1. Molecules that upregulate SLC36A4: | | |
| Glutamic Acid | Phytohemagglutinins | Cymarine |
| daidzein | Brefeldin A | Caffeine |
| 2,2-bis(bromomethyl)-1,3-propanediol | Ergocalciferols | Patulin |
| Deferoxamine | Cefuroxime | 1-ethyl-2-benzimidazolinone |
| Dihydrotestosterone | Methylnitrosourea | Tretinoin |
| 8-Bromo Cyclic Adenosine Monophosphate | 25-hydroxycholesterol | Lithium |
| Ecdysone | bisphenol A | Eugenol |
| Medroxyprogesterone | Acetate R 848 | fragment C, human serum albumin |
| Genistein | Malathion | alpha-Tocopherol |
| Potassium Dichromate | N-Methylaspartate | infliximab |
| bafilomycin A | 6-bromoindirubin-3'-oxime | Estradiol |
| 4-biphenylamine | tenofovir | Dinoprostone |
| 2,2'-(hydroxynitrosohydrazono)bis-ethanamine | DDT | Enterotoxins |
| Diethylstilbestrol | benzyloxycarbonylleucyl-leucyl-leucine aldehyde | interferon alfa-2b |
| gamma-Tocopherol | cyanoginosin LR | Glycerol |
| Folic Acid | Azacitidine | vorinostat |
| sorafenib | procyanidin | Progesterone |
| Tunicamycin | Pregnenolone Carbonitrile | Cardiotoxins |
| Dexamethasone | Calcitriol | Nifedipine |
| Captopril | Piperonyl Butoxide | Plicamycin |
| Acetaminophen | indole-3-carbinol | Levonorgestrel |
| Vincristine | Cholecalciferol | Thapsigargin |
| Ranitidine | pristane | quintozene |
| Theophylline | triadimefon | Doxepin |
| Choline | 2-(4-morpholinyl)-8-phenyl-4H-1-benzopyran-4-one | Azoxymethane |
| Y 27632 | rosiglitazone | letrozole |
| Enalapril | Dactinomycin | Acetylcysteine |
| Cisplatin | Phosphorylcholine | cobaltous chloride |
| Aflatoxin B1 | Propylthiouracil | colforsin |
| Cadmium | Insulin | Ecdysterone |
| lead acetate | 4-hydroxytamoxifen | Paclitaxel |

TABLE S1-continued

Molecules that regulate genes or gene products relevant to proline transport and metabolism.

| | | |
|---|---|---|
| Promethazine | Chlorpromazine | Camptothecin |
| Ionomyin | Amitrole | Ethanol |
| Isoniazid | sodium arsenite | Pyrazinamide |
| Chlorambucil | Ultraviolet Rays | 4-(5-benzo(1,3)dioxol-5-yl-4-pyridin-2-yl-1H-imidazol-2-yl)benzamide |
| bortezomib | imatinib | gefitinib |
| Ethinyl Estradiol | Vitamin K 3 | Hydroxyurea |

I2. Molecules that downregulate SLC36A4:

| | | |
|---|---|---|
| chromium hexavalention | 3-deazaneplanocin | 1-(2-cyano-3,12-dioxooleana-1,9-dien-28-oyl) imidazole |
| Metformin | Inosine Monophosphate | Am 580 |
| cryptoxanthin | lapatinib | 1-(5-lsoquinolinesulfonyl)-2-Methylpiperazine |
| SC 514 | 4-cyclododecyl-2,6-dimethylmorpholine acetate | 4-dichlorobenzene |
| Histidinol | Aphidicolin | N-(2-aminophenyl)-4-(N-(pyridin-3-ylmethoxycarbonyl)aminomethyl)benzamide |
| trichostatin A | Hemin | blebbistatin |
| Sirolimus | Quercetin | N-nitrosomorpholine |
| Azithromycin | decitabine | Methylene Chloride |
| Cycloheximide | TO-901317 | Poly I-C |
| lactacystin | Polychlorinated Biphenyls | Benzo(a)pyrene |
| fulvestrant | romidepsin | Diethylhexyl Phthalate |
| bicalutamide | Dinitrofluorobenzene | enzastaurin |
| monastrol | fluticasone | salmeterol |
| Doxycycline | Bucladesine | 2-dichlorobenzene |
| Calcium | 2-(1H-indazol-4-yl)-6-(4-methanesulfonylpiperazin-1-ylmethyl)-4-morpholin-4-ylthieno(3,2-d)pyrimidine | Calcium Chloride |
| halofuginone | 4-acetylaminofluorene | CPG-oligonucleotide |
| geldanamycin | Cyproterone Acetate | Phenobarbital |
| withaferin A | Hydrogen Peroxide | Raloxifene |
| bexarotene | Dimethyl Sulfoxide | Curcumin |
| atorvastatin | Doxorubicin | erlotinib |
| dihydroquinghaosu | piperaquine | fasudil |
| sapphyrin | BCG Vaccine | acidocin CH5, *Lactobacillus acidophilus* |
| Antigen-Antibody Complex | Lactic Acid | Vitamin E |
| bromobenzene | troglitazone | Zinc Oxide |
| Tacrine | phorbolol myristate acetate | pioglitazone |
| Ribavirin | Papaverine | Bleomycin |
| LBH589 | X-Rays | Ascorbic Acid |
| Cyclosporine | Daunorubicin | bevacizumab |
| Pyrogens | beta-Naphthoflavone | Ozone |
| 1-Methyl-3-isobutylxanthine | gatifloxacin | Methimazole |
| 2-Acetylaminofluorene | peginterferon alfa-2a | Tetradecanoylphorbol Acetate |
| Etoposide | docetaxel | beta-glycerophosphoric acid |
| leflunomide | Indomethacin | Diclofenac |
| Formaldehyde | Cyclophosphamide | Methotrexate |
| Valproic Acid | | |

J1. Molecules that upregulate SLC6A20:

| | | |
|---|---|---|
| Sulfamerazine | sodium selenate | gefitinib |
| dibenzazepine | Hemin | N,N-dimethylarginine |
| aluminum sulfate | fingolimod | 7-aminocephalosporanic acid |
| 1-Methyl-4-phenyl-1,2,3,6-tetrahydropyridine | MRK 003 | everolimus |
| acodazole | SB 203580 | carbinoxamine |
| Curcumin | Pizotyline | Cephalexin |
| picrotoxinin | trichlorofluoromethane | Chlorhexidine |
| bis(tri-n-butyltin)oxide | Perhexiline | picotamide |
| Tetradecanoylphorbol Acetate | Particulate Matter | naphthalan |
| thioperamide | Fursultiamin | levocabastine |
| erlotinib | isocorydine | ochratoxin A |
| Cyclopenthiazide | SEW2871 | esculetin |
| Atractyloside | Dihydrostreptomycin Sulfate | lobelanidine |
| acetorphan | Vehicle Emissions | Naltrexone |
| Loxapine | medrysone | Pancuronium |

TABLE S1-continued

Molecules that regulate genes or gene products relevant to proline transport and metabolism.

| | | |
|---|---|---|
| Ultraviolet Rays | cyanoginosin LR | Dichlororibofuranosylbenzimidazole |
| N-(2-cyclohexyloxy-4-nitrophenyl)methanesulfonamide | Pentetic Acid | iodoform |
| Pheniramine | Indapamide | Meptazinol |
| Flutamide | Acebutolol | Edrophonium |
| Spiramycin | Etiocholanolone | Alprostadil |
| boldine | asiaticoside | Loperamide |
| Sulfamethazine | gibberellic acid | citiolone |
| vanoxerine | Cefotaxime | Bicuculline |
| pyrvinium | hesperetin | Isradipine |
| Tiapamil Hydrochloride | Suloctidil | Ganciclovir |
| Paraquat | Selegiline | Mesalamine |
| diphenidol | Clodronic Acid | decitabine |
| Dilazep | Bleomycin | Hexetidine |
| Meclofenoxate | clemizole | Paclitaxel |
| bicalutamide | Gabexate | Enterotoxins |
| Heparin | Am iloride | triptolide |
| Cytokines | Metribolone | enzastaurin |
| Tranylcypromine | Am 580 | enterotoxin B, staphylococcal |
| flunisolide | Carboplatin | Zinc Oxide |
| Methylnitrosourea | trichostatin A | pramoxine |
| Sirolimus | Phenelzine | Hydrogen Peroxide |
| Reserpine | Genistein | phosphonoacetamide |
| Primaquine | Dihydrotestosterone | Flurbiprofen |
| Clonidine | glimepiride | Carbimazole |
| Fenoprofen | Fluorouracil | Chlorambucil |
| Naproxen | Roxithromycin | Valproic Acid |
| Chloroquine | Probenecid | geldanamycin |
| Ergocalciferols | Cortisone | Phenobarbital |
| Acyclovir | Nitrofurantoin | Pyrogens |
| Calcium | Neomycin | Ifosfamide |
| R 848 | X-Rays | imatinib |
| gatifloxacin | resveratrol | Cyclosporine |
| Quercetin | Nifedipine | Ranitidine |
| Azithromycin | Benzo(a)pyrene | Doxorubicin |
| Diethylstilbestrol | Tretinoin | Methyl Methanesulfonate |
| Lactic Acid | Azacitidine | Methapyrilene |
| Acetaminophen | Cisplatin | |
| J2. Molecules that downregulate SLC6A20: | | |
| Go 6976 | Progesterone | Parathion |
| testosterone 17 beta-cypionate | Apomorphine | Fonofos |
| Alpha-Amanitin | Shiga Toxin | Grape Seed Proanthocyanidins |
| shikonin | Malathion | sulfanilamide |
| Fusaric Acid | polidocanol | Teriparatide |
| Doxylamine | tibolone | Ethylene Oxide |
| mefexamide | infliximab | quintozene |
| Arecoline | Dextran Sulfate | caffeic acid |
| Gonadotropins | Estradiol | acyline |
| gabapentin | Puromycin | chlorcyclizine |
| sodium arsenite | 3-deazaneplanocin | Hydrochloric Acid |
| estradiol 3-benzoate | Isoniazid | Folic Acid |
| nilutamide | Eugenol | imiquimod |
| Levodopa | Rifampin | Diethylhexyl Phthalate |
| Chorionic Gonadotropin | Epitestosterone | Deoxyglucose |
| Luteinizing Hormone | Cocaine | Zinc |
| rosiglitazone | Anti-Retroviral Agents | bromodichloromethane |
| Captopril | Azoxymethane | bisphenol A |
| Choline | Methylene Chloride | Tetrachlorodibenzodioxin |
| efavirenz | Deferoxamine | Cholecalciferol |
| bortezomib | vorinostat | Dexamethasone |
| Clomipramine | Lamivudine | Etoposide |
| Diclofenac | Fluoxetine | Metformin |
| K1. Molecules that upregulate SLC6A13: | | |
| sapphyrin | 1-(5-Isoquinolinesulfonyl)-2-Methylpiperazine | Furosemide |
| Diethylhexyl Phthalate | Chitosan | triptolide |
| Clofibrate | Ethyl Methanesulfonate | monastrol |
| Digitoxin | Isoflurane | Carteolol |
| phosphonoacetamide | Zinc Oxide | fosfosal |
| topiramate | Mexiletine | Carbarson |
| 2-nitrofluorene | flunisolide | tiaprofenic acid |
| sildenafil | Estradiol | Sulfameter |
| Proglumide | Cytokines | butenafine |

TABLE S1-continued

Molecules that regulate genes or gene products relevant to proline transport and metabolism.

| | | |
|---|---|---|
| deferiprone | hexachloroethane | Ethylene Glycol |
| Lidoflazine | sulforafan | cefepime |
| carcinine | Amiodarone | tenoxicam |
| prednicarbate | Meclofenamic Acid | Acetaminophen |
| lead tetraacetate | midecamycin | myricetin |
| Clarithromycin | Lithium Chloride | trovafloxacin |
| Propranolol | Amprolium | Simvastatin |
| shikonin | glycidol | ochratoxin A |
| scriptaid | sodium chlorate | Puromycin Aminonucleoside |
| VX | sulfathiazole | Talampicillin |
| Isoflurophate | Diclofenac | Auranofin |
| torsemide | bendazolic acid | Hymecromone |
| Busulfan | Deoxycholic Acid | sparfloxacin |
| phenylhydrazine | Vidarabine | Ibuprofen |
| Dichlororibofuranosylbenzimidazole | Lomustine | Clofibric Acid |
| Mianserin | troglitazone | picotamide |
| Pantothenic Acid | Quercetin | Penicillamine |
| Polychlorinated Biphenyls | Niacinamide | sodium nitrate |
| ponasterone A | Valproic Acid | Indomethacin |
| Fenofibrate | oltipraz | Meclofenoxate |
| benoxaprofen | Dexamethasone | erlotinib |
| Xylazine | Minoxidil | Finasteride |
| Sulfachlorpyridazine | Aspirin | diindolylmethane |
| amitraz | Chlorzoxazone | tropisetron |
| Doxorubicin | Captopril | Meptazinol |
| vinylidene chloride | benphothiamine | Azaguanine |
| Perhexiline | compactin | phenethyl isothiocyanate |
| Diquat | Mitomycin | Neomycin |
| zaleplon | trichostatin A | Testosterone |
| balsalazide | alitretinoin | hesperetin |
| Kinetin | Cycloheximide | rofecoxib |
| chloroxylenol | Lindane | Dimethylformamide |
| sesam in | Ciprofloxacin | Staurosporine |
| Vincristine | Cefixime | fluvastatin |
| aplidine | Oxyquinoline | Ticrynafen |
| Azacitidine | Spironolactone | venlafaxine |
| Sulfadoxine | Tocainide | Pregnenolone |
| ibufenac | graveoline | 1-hydroxycholecalciferol |
| Amlodipine | Carmustine | phenothiazine |
| Prednisolone | romidepsin | bromfenac |
| Procarbazine | Thiabendazole | CPG-oligonucleotide |
| tranilast | sodium selenate | Methyl Methanesulfonate |
| Aristolochic Acids | terbinafine | carbinoxamine |
| Digoxin | Gliclazide | Pivampicillin |
| leflunomide | oxcarbazepine | Gentamicins |
| Fenbendazole | rosiglitazone | decitabine |
| Methylcholanthrene | lead acetate | Megestrol Acetate |
| Chlorambucil | Pravastatin | homatropine |
| dioxybenzone | Betamethasone | 6-methoxy-2-naphthylacetic acid |
| Promethazine | Ritonavir | modafinil |
| dexibuprofen | Lovastatin | Kanamycin |
| Naproxen | Nevirapine | hydrastinine |
| Etoposide | Thioguanine | Triamterene |
| Cyproterone Acetate | Ofloxacin | 4-dichlorobenzene |
| Deferoxamine | nabumetone | sodium arsenite |
| R 848 | bisphenol A | sangivamycin |
| Epirubicin | Benzocaine | wortmannin |
| Netilmicin | Nitrofurantoin | 1,2,3-trichloropropane |
| Raloxifene | Cisplatin | BCG Vaccine |
| Canavanine | lamotrigine | hydroxyachillin |
| Antibodies, Monoclonal | Nitrofurazone | famciclovir |
| Mercuric Chloride | Triiodothyronine | Droperidol |
| irinotecan | Acetazolamide | Maprotiline |
| Tacrine | Thiostrepton | Lithium |
| cerivastatin | Tretinoin | Dibucaine |
| Domperidone | Rifabutin | Benzethonium |
| Camptothecin | Azoxymethane | Imipramine |
| Disopyramide | Pregnenolone Carbonitrile | Losartan |
| Ketoprofen | Methotrexate | Baclofen |
| SU 5402 | Vitamin K 3 | Diflunisal |

TABLE S1-continued

Molecules that regulate genes or gene products relevant to proline transport and metabolism.

| | | |
|---|---|---|
| alpha-Tocopherol | vorinostat | Sulpiride |
| Luteolin | Cyclosporine | valsartan |
| Genistein | phenacemide | 1-Methyl-3-isobutylxanthine |
| Ascorbic Acid | N,N'-diphenyl-4-phenylenediamine | 2-(4-morpholinyl)-8-phenyl-4H-1-benzopyran-4-one |
| Reserpine | Erythromycin | Pergolide |
| Streptomycin | Nitric Oxide | Lorazepam |
| Chlorpyrifos | lapatinib | Melphalan |
| efavirenz | atorvastatin | bortezomib |
| Enalapril | Dactinomycin | Fluorouracil |
| Lamivudine | Hydroxyurea | Isoproterenol |

K2. Molecules that down regulate SLC6A13:

| | | |
|---|---|---|
| Aroclors | ferric nitrilotriacetate | Ethionine |
| Aminosalicylic Acid | Methapyrilene | amineptin |
| tianeptine | carvedilol | Labetalol |
| Paclitaxel | Itraconazole | Yohimbine |
| desloratadine | sulconazole | Sotalol |
| Methiocarb | Amantadine | coumarin |
| Chloroquine | Colchicine | cyanoginosin LR |
| TO-901317 | Hexachlorobenzene | Doxepin |
| Omeprazole | tenidap | Methylcellulose |
| piperidolate | Monocrotaline | Estriol |
| beta-Naphthoflavone | Ethinyl Estradiol | Safrole |
| norethindrone acetate | Chloroform | lansoprazole |
| Bacitracin | Tinidazole | Fluoxetine |
| Zidovudine | Ketoconazole | Tacrolim us |
| Clomipramine | Isotretinoin | gibberellic acid |
| Etodolac | Sulfisoxazole | Granisetron |
| lobelanidine | Loratadine | Dicumarol |
| Citalopram | Cyproterone | Hypericum extract LI 160 |
| methylparaben | N-nitrosomorpholine | Nortriptyline |
| Clozapine | Trimethadione | Metronidazole |
| KCB-1 protein, recombinant | epidermal growth factor (1-45) | Ethisterone |
| meloxicam | 2-Acetylaminofluorene | sunitinib |
| Tetracycline | Fursultiamin | Carbenoxolone |
| Desipramine | Carbon Tetrachloride | N-acetylsphingosine |
| Miconazole | Naloxone | gefitinib |
| Amphetamine | Secobarbital | bromobenzene |
| valdecoxib | Bretylium Tosylate | Chlorpromazine |
| Atropine | nimesulide | Amitriptyline |
| Doxapram | Ifosfamide | Lithium Carbonate |
| Acebutolol | Khellin | Cinnarizine |
| Thioctic Acid | Diethylstilbestrol | piperacetazine |
| mebeverine | pralidoxime | Ethambutol |
| Mestranol | Clotrimazole | flubendazole |
| Methyltestosterone | Sarin | eticlopride |
| aristolochic acid I | Diethylnitrosamine | Fonofos |
| Mycotoxins | Fluphenazine | Guanfacine |
| oxolamine | Metformin | Stavudine |
| Teriparatide | apicidin | Stanozolol |
| Mephentermine | pantoprazole | Isoniazid |
| Deoxyglucose | naringin | Diazepam |
| Rifampin | 6-Mercaptopurine | crotamiton |
| norflurane | 4-octylphenol | Sirolimus |
| Sulbactam | Cytarabine | Ramipril |
| Bicuculline | Vinblastine | Nifedipine |
| Paroxetine | Chlortetracycline | sulfabenzamide |
| Allopurinol | Cortisone | 1,2-dithiol-3-thione |
| HC toxin | rabeprazole | Sertraline |
| harman | acetovanillone | Mebendazole |
| Melatonin | Danazol | Hexamethonium |
| letrozole | Choline | marimastat |
| Aflatoxin B1 | Cetylpyridinium | pristane |
| Chlormezanone | Carbamazepine | 2,3-dioxo-6-nitro-7-sulfamoylbenzo(f)quinoxaline |
| Mifepristone | Tamoxifen | Roxithromycin |
| 4-nonylphenol | DDT | dexamisole |
| Ajmaline | Promazine | Folic Acid |
| cineole | pioglitazone | Propylthiouracil |
| Phenobarbital | Bezafibrate | testosterone 17 beta-cypionate |
| Abscisic Acid | olanzapine | 4-biphenylamine |
| salicylamide | Phalloidine | Azithromycin |
| beta-cyclodextrin-benzaldehyde | Ethionamide | Clonazepam |

TABLE S1-continued

Molecules that regulate genes or gene products relevant to proline transport and metabolism.

| | | |
|---|---|---|
| Vancomycin | ferulic acid | Tolazamide |
| tetrahydrotriamcinolone | Cytochalasin B | Benzo(a)pyrene |
| Cyclophosphamide | Azauridine | amlexanox |
| Fluocinolone Acetonide | Haloperidol | temozolomide |
| Minocycline | nimetazepam | Norethindrone |
| sorafenib | nateglinide | Dihydrotestosterone |
| 2-dichlorobenzene | Tetrachlorodibenzodioxin | Fluconazole |
| Alpha-Amanitin | idebenone | Amoxicillin |
| Vitamin E | Gemfibrozil | Bromisovalum |
| ascorbate-2-phosphate | Catechin | tosufloxacin |
| Ampicillin | Nafenopin | Nitrazepam |
| Chlormadinone Acetate | anastrozole | Spectinomycin |
| Glipizide | Econazole | Clomiphene |
| Sulindac | Azathioprine | quetiapine |
| Dinitrofluorobenzene | Dimenhydrinate | Clonidine |
| Amrinone | Thioacetamide | Levobunolol |
| Cephaloridine | Vanadates | Neostigmine |
| quintozene | Enoxacin | bromodichloromethane |
| diflorasone diacetate | Altretamine | Phenacetin |
| Phenelzine | Amoxapine | Streptozocin |
| Procainamide | artemisinine | lomefloxacin |
| enterotoxin B, staphylococcal | direct black 3 | Oxazepam |
| Lead | estradiol 3-benzoate | alginic acid |
| Levonorgestrel | Phenol | Phenformin |
| mono-(2-ethylhexyl)phthalate | Chlorpheniramine | LBH589 |
| Methylnitrosourea | pirinixic acid | Ethacrynic Acid |
| Chloramphenicol | Saquinavir | versipelostatin |
| Calcitriol | imatinib | 6-bromoindirubin-3'-oxime |
| doxofylline | Bupropion | perfluorooctanoic acid |
| Diltiazem | Caffeine | Disulfiram |
| Zalcitabine | Nicotine | Hydroxyzine |
| celecoxib | Theophylline | tenofovir |
| Perphenazine | Shiga Toxin | Rolipram |
| Ticlopidine | | |
| L1. Molecules that upregulate SLC6A14: | | |
| infliximab | moroxydine | Diethylhexyl Phthalate |
| Progesterone | N-methylolacrylamide | quintozene |
| Calcium | Trichloroepoxypropane | naphthalenediimide |
| bisphenol A | Lithium Carbonate | naphthalan |
| 8-Bromo Cyclic Adenosine Monophosphate | Vincamine | Vitamin K 2 |
| Methylene Chloride | cidofovir | Pyrogens |
| Dimethylnitrosamine | pipenzolate | Bismuth |
| Practolol | dipropizine | Penicillin G |
| Ticlopidine | 4-hydroxyestradiol-17 beta | 8-(3-Chlorostyryl)-1,3,7-trimethylxanthine |
| Pivampicillin | Quinidine | Ethinyl Estradiol |
| Idoxuridine | Terbutaline | BW B70C |
| 4,5-dianilinophthalimide | Enterotoxins | Netilmicin |
| CD 437 | 1-Methyl-3-isobutylxanthine | Amrinone |
| Cefotetan | 4'-N-benzoylstaurosporine | N-Methylscopolamine |
| vanadium pentoxide | Pregnenolone | Poly I-C |
| Hydrochloric Acid | picrotoxinin | Ethynodiol Diacetate |
| fenbufen | Hymecromone | Tetracycline |
| Pyocyanine | Spectinomycin | Pentamidine |
| Ultraviolet Rays | Dibucaine | Cyclopenthiazide |
| Tetradecanoylphorbol Acetate | Bleomycin | irinotecan |
| mycophenolate mofetil | lobelanidine | Proscillaridin |
| letrozole | canadine | Metronidazole |
| benfluorex | Clobetasol | daidzein |
| Cytochalasin B | Antimycin A | vinclozolin |
| Lactic Acid | Estrogens | 4-methyl-N-(3-(4-methylimidazol-1-yl)-5-(trifluoromethyl)phenyl)-3-((4-pyridin-3-ylpyrimidin-2-yl)amino)benzamide |
| wortmannin | Flecainide | Dexamethasone |
| Minoxidil | decitabine | Folic Acid |
| Vehicle Emissions | Piperonyl Butoxide | Podophyllotoxin |
| Dantrolene | Zalcitabine | Dichlororibofuranosylbenzimidazole |
| blebbistatin | Ascorbic Acid | Phosgene |
| Bupropion | Finasteride | Insulin |

TABLE S1-continued

Molecules that regulate genes or gene products relevant to proline transport and metabolism.

| | | |
|---|---|---|
| U 0126 | Disopyramide | 4-nonylphenol |
| docetaxel | Epitestosterone | celecoxib |
| Particulate Matter | colforsin | acidocin CH5, *Lactobacillus acidophilus* |
| Tetrachlorodibenzodioxin | pralidoxime | quelamycin |
| 4-(5-benzo(1,3)dioxol-5-yl-4-pyridin-2-yl-1H-imidazol-2-yl)benzamide | Methapyrilene | Ribavirin |
| Dactinomycin | Carboplatin | |

L2. Molecules that downregulate SLC6A14:

| | | |
|---|---|---|
| 1-amino-2,4-dibromoanthraquinone | fulvestrant | trimethobenzamide |
| Fluocinonide | gefitinib | tetrafluoroethylene |
| 4-amino-6-hydrazino-7-beta-D-ribofuranosyl-7H-pyrrolo(2,3-d)-pyrimidine-5-carboxamide | iodoform | Norethynodrel |
| Dihydroergotamine | solasodine | Benzo(a)pyrene |
| Milrinone | Thyroxine | 4-acetylaminofluorene |
| Estradiol | Levonorgestrel | Dilazep |
| Curcumin | Genistein | tris(2,3-dibromopropyl)phosphate |
| Thiostrepton | verteporfin | 15-deoxy-delta(12, 14)-prostaglandin J2 |
| Corticosterone | withaferin A | Diethylstilbestrol |
| Azoxymethane | Reserpine | 2-methoxyestradiol |
| phthalylsulfathiazole | Oxytocin | Apigenin |
| Scopolamine Hydrobromide | medrysone | 4-biphenylamine |
| meropenem | Carbachol | Niridazole |
| Chloroquine | 4-hydroxytamoxifen | diindolylmethane |
| Diazinon | Ethisterone | Isradipine |
| Alcuronium | chlorinated dibenzofurans | Trimipramme |
| tribenoside | Oxyphenbutazone | tyrphostin AG 1478 |
| Luteolin | Furazolidone | Atovaquone |
| Halcinonide | salmeterol | ergocryptine |
| Bromocriptine | ebselen | Clioquinol |
| Sulfisoxazole | Promegestone | Am 580 |
| polidocanol | chloropyramine | Trimethoprim |
| fluticasone | Phenoxybenzamine | rottlerin |
| piperlonguminine | lansoprazole | mometasone furoate |
| hydrastine | flunisolide | Zimeldine |
| Amoxicillin | Equilin | Cotinine |
| everolimus | skimmianine | 17-(dimethylaminoethylamino)-17-demethoxygeldanamycin |
| harpagoside | bromperidol | Isosorbide |
| prednicarbate | rosiglitazone | Theobromine |
| Etidronic Acid | Flavoxate | Clofazimine |
| sapphyrin | LBH589 | Fludrocortisone |
| Gossypol | resveratrol | cephaelin |
| Felodipine | Malathion | Imipenem |
| 1-(5-Isoquinolinesulfonyl)-2-Methylpiperazine | Natamycin | imatinib |
| epitiostanol | zardaverine | Catechin |
| phenethyl isothiocyanate | Atenolol | securinine |
| 17-(allylamino)-17-demethoxygeldanamycin | 6-thioguanosine | Prenylamine |
| sanguinarine | Propidium | discretamine |
| Androsterone | Lindane | ciclopirox |
| Methylergonovine | dironyl | Betahistine |
| Budesonide | famprofazone | Ethacrynic Acid |
| Clonidine | tripterine | Metaraminol |
| acacetin | Dextran Sulfate | Quercetin |
| nifuroxazide | Astemizole | oltipraz |
| Dinitrofluorobenzene | Sulfamerazine | methylbenzethonium |
| Vancomycin | triptolide | Vitamin K 3 |
| Tolbutamide | buparvaquone | Cadmium |
| sulconazole | enzastaurin | Bucladesine |
| Betaxolol | Griseofulvin | Bepridil |
| cinchonine | geldanamycin | Azathioprine |
| Vitamin E | Sulfamethoxazole | sulforafan |
| Trifluoperazine | Paclitaxel | vanoxerine |
| monorden | Diclofenac | Doxorubicin |
| Tretinoin | parthenolide | Mefloquine |
| Tunicamycin | torsemide | Thapsigargin |
| Lithium | Promazine | monastrol |
| GW 3965 | Selenomethionine | Aflatoxin B1 |
| Primaquine | Hydrocortisone | Raloxifene |

TABLE S1-continued

Molecules that regulate genes or gene products relevant to proline transport and metabolism.

| | | |
|---|---|---|
| Mexiletine | dibenzazepine | Dipyrone |
| Dipyridamole | Freund's Adjuvant | Papaverine |
| 2-(4-morpholinyl)-8-phenyl-4H-1-benzopyran-4-one | Cyclosporine | Hydrogen Peroxide |
| trichostatin A | Valproic Acid | Triiodothyronine |
| 1-Methyl-4-phenyl-1,2,3,6-tetrahydropyridine | enterotoxin B, staphylococcal | Puromycin |
| Isotretinoin | Pyrazinamide | Cycloheximide |
| benzyloxycarbonylleucyl-leucyl-leucine aldehyde | Estriol | vorinostat |
| erlotinib | Testosterone | Nifedipine |
| Carbamazepine | dasatinib | Chlorpromazine |
| Amiodarone | Hemin | Ketoconazole |
| Fluphenazine | Vincristine | Omeprazole |
| Sirolimus | Cyclophosphamide | Simvastatin |
| Lovastatin | Tamoxifen | Acetaminophen |
| Thioacetamide | Ethanol | Cisplatin |

M1. Molecules that upregulate SLC6A15:

| | | |
|---|---|---|
| flavanone | PI103 | alginic acid |
| Ethylene Dibromide | Oxymetholone | Hydroxyzine |
| Azacitidine | Cefixime | Cymarine |
| 4-octylphenol | Dimethadione | Doxycycline |
| Megestrol Acetate | Alprazolam | nimesulide |
| Diflunisal | nifenazone | versipelostatin |
| Finasteride | Diethylstilbestrol | Miconazole |
| Calcium | temsirolimus | Idarubicin |
| Ethisterone | Mephenytoin | Valproic Acid |
| Chorionic Gonadotropin | edelfosine | Carboplatin |
| Diethylhexyl Phthalate | vanadyl sulfate | Bromisovalum |
| Hydrochloric Acid | Norethindrone | X-Rays |
| Econazole | Chlorambucil | leflunomide |
| Simvastatin | Trichloroepoxypropane | Chlorpromazine |
| Ascorbic Acid | cefepime | Plicamycin |
| 2-(1H-indazol-4-yl)-6-(4-methanesulfonylpiperazin-1-ylmethyl)-4-morpholin-4-ylthieno(3,2-d)pyrimidine | LBH589 | Ibuprofen |
| Caerulein | Ethamsylate | Deoxyglucose |
| quintozene | pioglitazone | Pargyline |
| flumequine | Clopenthixol | gefitinib |
| Lactic Acid | amprenavir | N-methylolacrylamide |
| Rifampin | Enterotoxins | clemizole |
| Ivermectin | Acetylmuramyl-Alanyl-Isoglutamine | Nadolol |
| Cytokines | Clotrimazole | oxaliplatin |
| picotamide | Carbon Tetrachloride | Secobarbital |
| bromfenac | beta-cyclodextrin-benzaldehyde | Chloroquine |
| Rolitetracycline | Niacinamide | MRK 003 |
| Cytarabine | Equilin | Glycocholic Acid |
| Cyclopenthiazide | suxibuzone | tranilast |
| Metform in | Isocarboxazid | Hydrocortisone |
| ovalicin | vinclozolin | Ethylene Glycol |
| Sulindac | dexamisole | Hexestrol |
| Aztreonam | Epirizole | Practolol |
| tetrahydrotriamcinolone | furaltadon | Carbamazepine |
| Nafronyl | 3-hydroxyacetanilide | Butyric Acid |
| vorinostat | naftopidil | flunisolide |
| Sirolimus | Clofibrate | bromobenzene |
| Ultraviolet Rays | Acetylcysteine | Methylene Chloride |
| atorvastatin | 2-m ethoxyestradiol | Zidovudine |
| Cholecalciferol | Guanfacine | gatifloxacin |
| bortezomib | Puromycin | repaglinide |
| 6-Mercaptopurine | phthalylsulfathiazole | Mifepristone |
| Spectinomycin | candesartan | olanzapine |
| beta-glycerophosphoric acid | Ondansetron | Dimenhydrinate |
| Kainic Acid | Acepromazine | N-nitrosomorpholine |
| Bezafibrate | Tunicamycin | Carbachol |
| Deoxycholic Acid | rimexolone | Tobramycin |
| Mesalamine | Acetohexamide | Ethosuximide |
| Fluorometholone | Piroxicam | Diazepam |
| Cyclosporine | Heparin | Naloxone |
| Propafenone | Aphidicolin | Bacitracin |
| isoascorbic acid | Glyburide | cyclonite |
| Baclofen | Methyl Methanesulfonate | Amoxapine |
| Gliclazide | Dicumarol | Hydralazine |
| Cromolyn Sodium | Clomipramine | Amphetamine |

TABLE S1-continued

Molecules that regulate genes or gene products relevant to proline transport and metabolism.

| | | |
|---|---|---|
| naphthalan | vinorelbine | sodium arsenite |
| Amikacin | Formaldehyde | oxcarbazepine |
| Insulin | Levonorgestrel | Amiloride |
| Follicle Stimulating Hormone | Nitrendipine | Phenacetin |
| Asbestos | scriptaid | Particulate Matter |
| cerivastatin | 4-methyl-N-(3-(4-methylimidazol-1-yl)-5-(trifluoromethyl)phenyl)-3-((4-pyridin-3-ylpyrimidin-2-yl)amino)benzamide | sulconazole |
| quetiapine | celecoxib | Thalidomide |
| Trenbolone Acetate, (17beta)-isomer | Alpha-Amanitin | Perhexiline |
| Sulfisoxazole | 2-Acetylaminofluorene | Camptothecin |
| Zalcitabine | Ergocalciferols | Methylcholanthrene |
| Dantrolene | Nortriptyline | Fenofibrate |
| Griseofulvin | Amiodarone | Sparteine |
| Iproniazid | fomepizole | Ethinyl Estradiol |
| torsemide | Luteinizing | Hormone Citalopram |
| Lithium | Indomethacin | Methyldopa |
| Hydrochlorothiazide | Clofibric Acid | Lovastatin |
| Progesterone | zomepirac | Fluorouracil |
| Oxymetazoline | Bupropion | meloxicam |
| pralidoxime | Danazol | Calcitriol |
| Clozapine | Dactinomycin | Ketoconazole |
| Colchicine | Hydroxyurea | Ticlopidine |
| Azathioprine | Chlorpropamide | Bithionol |
| Tacrolimus | Azithromycin | Tetradecanoylphorbol Acetate |
| Vitamin K 3 | Isoniazid | Gemfibrozil |
| Atropine | Methapyrilene | Dimethylformamide |
| Terbutaline | Isoproterenol | |

M2. Molecules that downregulate SLC6A15:

| | | |
|---|---|---|
| tianeptine | Rotenone | polidocanol |
| Enalapril | 3-deazaneplanocin | Hydrogel |
| Ranitidine | geldanamycin | Botulinum Toxins |
| Antimycin A | 1-ethyl-2-benzimidazolinone | epoxomicin |
| Mitomycin | Corticosterone | Estriol |
| lactacystin | Tretinoin | U 0126 |
| Vitamin A | 4-(4-fluorophenyl)-2-(4-hydroxyphenyl)-5-(4-pyridyl)imidazole | Gonadotropins |
| Amphotericin B | Thioguanine | Fluoxetine |
| fasudil | decitabine | Gentamicins |
| trichostatin A | Estradiol | 1-amino-2,4-dibromoanthraquinone |
| temozolomide | Pyrazinamide | Cadmium |
| Promegestone | Chlorpyrifos | clopidogrel |
| Ouabain | mycophenolate mofetil | Diethylnitrosamine |
| Timolol | bisphenol A | Ceftriaxone |
| 25-hydroxycholesterol | Genistein | Tubocurarine |
| alpha-Amino-3-hydroxy-5-methyl-4-isoxazolepropionic Acid | Doxorubicin | Etoposide |
| Ifosfamide | Poly I-C | Sumatriptan |
| 4-(5-benzo(1,3)dioxol-5-yl-4-pyridin-2-yl-1H-imidazol-2-yl)benzamide | cyanopindolol | bafilomycin A |
| Ketamine | Paclitaxel | Sarin |
| Sotalol | Procarbazine | Atrazine |
| harman | Procainamide | Dexamethasone |
| lacidipine | n-hexanal | SB 203580 |
| Phenylephrine | Chitosan | Quercetin |
| 17-(allylamino)-17-demethoxygeldanamycin | Propranolol | lead tetraacetate |
| 2-(4-morpholinyl)-8-phenyl-4H-1-benzopyran-4-one | Streptomycin | Cisplatin |
| efavirenz | Lidocaine | cidofovir |
| Carbimazole | sildenafil | Acrolein |
| Acyclovir | enterotoxin B, staphylococcal | Y 27632 |
| Losartan | Lead | Loratadine |

TABLE S1-continued

Molecules that regulate genes or gene products relevant to proline transport and metabolism.

| | | |
|---|---|---|
| blebbistatin | Bleomycin | 4-hydroxytamoxifen |
| Dimethyl Sulfoxide | sulforafan | ciprofibrate |
| Vecuronium Bromide | N-Methyl-3,4-methylenedioxyamphetamine | linalool |
| fulvestrant | Immunotoxins | Lamivudine |
| Oxazepam | sodium selenate | 1-Methyl-3-isobutylxanthine |
| famciclovir | Folic Acid | Pyrogens |
| Anti-Retroviral Agents | Diphenhydramine | triptolide |
| Deferoxamine | Metribolone | sanguinarine |
| Triiodothyronine | Monocrotaline | gabapentin |
| Phenobarbital | Tranylcypromine | erlotinib |
| Captopril | Phenytoin | Ozone |
| Daunorubicin | Ethanol | Penicillamine |
| docetaxel | Tetrachlorodibenzodioxin | imatinib |
| Cyclophosphamide | Benzo(a)pyrene | Thapsigargin |
| cobaltous chloride | infliximab | rituximab |
| rosiglitazone | Dihydrotestosterone | Methotrexate |
| Nicotine | Forskolin | Epirubicin |
| Levodopa | Choline | |

N1. Molecules that upregulate SLC6A17:

| | | |
|---|---|---|
| alpha-Amino-3-hydroxy-5-methyl-4-isoxazolepropionic Acid | Deoxycholic Acid | alpha-Tocopherol |
| gamma-Tocopherol | 2-tert-butylhydroquinone | Enterotoxins |
| Dactinomycin | Tretinoin | Polychlorinated Biphenyls |
| trichostatin A | BCG Vaccine | LBH589 |
| Dichlororibofuranosylbenzimidazole | Hydrocortisone | 8-aminohexylamino cAMP |
| cobaltous chloride | Oxazepam | buparvaquone |
| Bicuculline | vinclozolin | SEW2871 |
| Epitestosterone | Lithium Chloride | AICA ribonucleotide |
| Cholecalciferol | enzastaurin | Bupropion |
| SU 5402 | Immunoglobulins, Intravenous | Diethylhexyl Phthalate |
| pirinixic acid | Plicamycin | Bucladesine |
| Insulin | Vincristine | 1-Methyl-3-isobutylxanthine |
| Methylene Chloride | Ethanol | Hydroxyurea |
| Oxyquinoline | Cycloheximide | Fluoxetine |
| Hydrogen Peroxide | decitabine | Growth Hormone |
| Cyclosporine | R 848 | Deferoxamine |
| vorinostat | Methimazole | Quercetin |
| Nifedipine | Cisplatin | Testosterone |
| Acetaminophen | Doxorubicin | Hemin |
| Phenobarbital | | |

N2. Molecules that down regulate SLC6A17:

| | | |
|---|---|---|
| Tranylcypromine | fasudil | Ouabain |
| 4-hydroxy-2-nonenal | Phorbol Esters | Forskolin |
| Pyrazinamide | Ethambutol | Tetrahydrocannabinol |
| Rifampin | imiquimod | Lithium |
| Staurosporine | Isoniazid | Zinc |
| monastrol | HC toxin | lactacystin |
| N-Methylaspartate | Dimethyl Sulfoxide | Pentachlorophenol |
| Coumaphos | Clodronic Acid | 4-biphenylamine |
| SB 203580 | Levodopa | 1-(5-Isoquinolinesulfonyl)-2-Methylpiperazine |
| Methamphetamine | Hydroxyzine | blebbistatin |
| Bleomycin | quintozene | bis(tri-n-butyltin)oxide |
| 1,2-dilinolenoyl-3-(4-aminobutyryl)propane-1,2,3-triol | Camptothecin | scriptaid |
| phosphonoacetamide | Cefuroxime | Glycerol |
| Y 27632 | apicidin | Luteinizing Hormone |
| bromodichloromethane | Freund's Adjuvant | Niacinamide |
| naphthalene | Ultraviolet Rays | Immunotoxins |
| Mycophenolic Acid | Estradiol | resveratrol |
| Phytohemagglutinins | Fluorouracil | troglitazone |
| Captopril | Azoxymethane | Ozone |
| Estriol | Dexamethasone | Rotenone |
| gefitinib | CPG-oligonucleotide | quelamycin |
| pioglitazone | bisphenol A | rosiglitazone |
| Benzo(a)pyrene | Alpha-Amanitin | Methotrexate |
| Tamoxifen | Amiodarone | Cyclophosphamide |
| Etoposide | Paclitaxel | Tunicamycin |

TABLE S1-continued

Molecules that regulate genes or gene products relevant to proline transport and metabolism.

| | | |
|---|---|---|
| bortezomib | erlotinib | X-Rays |
| Tetradecanoylphorbol Acetate | Diethylstilbestrol | Carbon Tetrachloride |
| Progesterone | Valproic Acid | |

O1. Molecules that upregulate SLC6A19:

| | | |
|---|---|---|
| 4-hydroxy-2-nonenal | imatinib | pelargonic acid |
| neuropeptide Y (18-36) | Paclitaxel | Fenretinide |
| Carboplatin | Testosterone | lysophosphatidic acid |
| Tetrachlorodibenzodioxin | Platelet Activating Factor | Inosine Monophosphate |
| Nicotine | TO-901317 | 4'-N-benzoylstaurosporine |
| 5'-methylthioadenosine | fulvestrant | gefitinib |
| dihydroquinghaosu | piperaquine | Oxyquinoline |
| Doxorubicin | monastrol | sulforafan |
| 2-methoxyestradiol | SU 5402 | sangivamycin |
| Sodium Dodecyl Sulfate | decitabine | Nitric Oxide |
| Perhexiline | SC 514 | imiquimod |
| Immunoglobulin G | dibenzazepine | enzastaurin |
| Reserpine | Cisplatin | bicalutamide |
| testosterone 17 beta-cypionate | Cefuroxime | Dactinomycin |
| blebbistatin | Methylnitrosourea | vorinostat |
| Azacitidine | Estradiol | efavirenz |
| Alpha-Amanitin | Enterotoxins | geldanamycin |
| Mannitol | Ethanol | Tolbutamide |
| Vitamin E | 1-Methyl-3-isobutylxanthine | Metformin |
| Hydrogen Peroxide | Theophylline | trichostatin A |
| Lamivudine | Amphotericin B | 2-Acetylaminofluorene |
| BCG Vaccine | beta-glycerophosphoric acid | Dexamethasone |
| Phenobarbital | Diethylnitrosamine | Cyclosporine |
| Methapyrilene | Indomethacin | Colchicine |
| Benzo(a)pyrene | nimesulide | Gentamicins |
| Sirolimus | Fluorouracil | Doxycycline |
| X-Rays | Tretinoin | Acetaminophen |

O2. Molecules that downregulate SLC6A19:

| | | |
|---|---|---|
| Fonofos | beta-cyclodextrin-benzaldehyde | Parathion |
| cyclonite | motexafin gadolinium | 8-aminohexylamino cAMP |
| phorbolol myristate acetate | R 848 | Beclomethasone |
| Concanavalin A | alpha-Amino-3-hydroxy-5-methyl-4-isoxazolepropionic Acid | Folic Acid |
| Ionomyin | alitretinoin | Choline |
| Epitestosterone | Cholecalciferol | Ascorbic Acid |
| Tetradecanoylphorbol Acetate | shikonin | direct black 3 |
| Am 580 | Anti-Retroviral Agents | Deoxyglucose |
| sodium arsenite | Freund's Adjuvant | Brefeldin A |
| Palmitic Acid | aluminum sulfate | Poly I-C |
| Bicuculline | infliximab | Chloroquine |
| Dinitrofluorobenzene | pioglitazone | Cycloheximide |
| Phytohemagglutinins | Kainic Acid | CPG-oligonucleotide |
| Tamoxifen | Captopril | bisphenol A |
| Insulin | rituximab | Dihydrotestosterone |
| Methotrexate | Ribavirin | Carbon Tetrachloride |

P1. Molecules that upregulate SLC38A2:

| | | |
|---|---|---|
| 2-tert-butyl-9-fluoro-3,6-dihydro-7H-benz(h)imidazo(4,5-f)isoquinoline-7-one | apratoxin A | 1-hydroxycholecalciferol |
| Niacin | 2-Acetylaminofluorene | Zalcitabine |
| pyrvinium | eseroline | Clomipramine |
| | N,N'-diphenyl-4-phenylenediamine | Tranylcypromine |
| Ethionamide | Dichlorvos | closantel |
| motexafin gadolinium | Aspirin | methylparaben |
| Phenacetin | phenylhydrazine | methyl salicylate |
| Sotalol | salicylamide | Clarithromycin |
| ferulic acid | Caffeine | compactin |
| Chlorpromazine | Niclosamide | Nitrofurantoin |
| lactacystin | trovafloxacin | Bromhexine |
| ibufenac | Praziquantel | Rolipram |
| temafloxacin | Methazolamide | Fenbendazole |
| Shiga Toxin | Thioridazine | Mianserin |
| Cinnarizine | Carbamazepine | Theophylline |
| Ergocalciferols | Monensin | Cholecalciferol |
| Baclofen | chloropyramine | Gentian Violet |
| Foscarnet | vinylidene chloride | coumarin |
| Norepinephrine | Trimeprazine | Buthionine Sulfoximine |
| ipriflavone | | |

TABLE S1-continued

Molecules that regulate genes or gene products relevant to proline transport and metabolism.

| | | |
|---|---|---|
| Ticrynafen | zaleplon | Fluphenazine |
| Chloramphenicol | Acetaminophen | butenafine |
| Chlorhexidine | Doxepin | Aflatoxin B1 |
| piclamilast | tranilast | dimethisoquin |
| Megestrol | balsalazide | romidepsin |
| Yellow Fever Vaccine | Methanol | nateglinide |
| Sulindac | Digoxin | Methotrimeprazine |
| glimepiride | Nitrazepam | Prednisolone |
| Phosgene | bendazolic acid | Methocarbamol |
| Bisacodyl | cyanoginosin LR | Dimaprit |
| Disulfiram | Glutamic Acid | PI103 |
| Dimethylformamide | Cephalothin | methylbenzethonium |
| hydrazine | Strophanthidin | zileuton |
| Mefenamic Acid | alclometasone dipropionate | Methyltestosterone |
| profenamine | Vecuronium Bromide | troglitazone |
| Halcinonide | GW 3965 | Metronidazole |
| oxfendazole | wortmannin | Dequalinium |
| Lindane | Pemoline | Lasalocid |
| ONO 2235 | Cymarine | 1,3-dichloro-2-propanol |
| Stanozolol | Amantadine | Thioacetamide |
| amitraz | Morphine | Gossypol |
| cloperastine | Chlorambucil | Budesonide |
| Verapamil | Safrole | Fluocinolone Acetonide |
| Chloroform | Capsaicin | Amiodarone |
| Isoniazid | beta-cyclodextrin-benzaldehyde | bromfenac |
| Lithocholic Acid | Cyclophosphamide | Pizotyline |
| Clofibric Acid | methixene | Colchicine |
| Domperidone | Albendazole | Fluocinonide |
| U 54494A | lysophosphatidic acid | Zinc Oxide |
| benzamil | amlexanox | Bupropion |
| Trimipramine | CEP 14083 | Digitoxigenin |
| homochlorocyclizine | Diquat | Dicyclomine |
| Tolazamide | thioperamide | Estradiol |
| Methyl Methanesulfonate | Dimethylnitrosamine | Chlormadinone Acetate |
| Fludrocortisone | Amphetamine | Inosine Monophosphate |
| Proglumide | Altretamine | Methiothepin |
| systhane | Aldosterone | Chloroquine |
| Niacinamide | Naproxen | Desipramine |
| Proadifen | rimexolone | Lidoflazine |
| Pyrilamine | cetraxate | cerivastatin |
| Ibuprofen | Gentamicins | Deoxycholic Acid |
| Pyrazinamide | Minocycline | Azaperone |
| Methapyrilene | Tunicamycin | Amlodipine |
| CPG-oligonucleotide | Clomiphene | nebivolol |
| phenothiazine | Amoxicillin | hydroquinidine |
| estradiol 3-benzoate | Propafenone | Albuterol |
| amineptin | Folic Acid | Cyclosporine |
| Estriol | 2-(4-morpholinoanilino)-6-cyclohexylaminopurine | Tacrine |
| olanzapine | tetrandrine | Epirubicin |
| Enalapril | Dexamethasone | Neostigmine |
| Histidinol | Trihexyphenidyl | triadimefon |
| Pregnenolone | eperisone | irinotecan |
| piperacetazine | Indomethacin | Isoflurophate |
| Prenylamine | Spironolactone | Diethylnitrosamine |
| Fluvoxamine | Sirolimus | 3-hydroxyacetanilide |
| Mustard Gas | alpha-Amino-3-hydroxy-5-methyl-4-isoxazolepropionic Acid | MF59 oil emulsion |
| bisphenol A | Rifabutin | Fluspirilene |
| meloxicam | anastrozole | Proscillaridin |
| Berberine | N-acetylsphingosine | leflunomide |
| Roflumilast | Bepridil | Benzo(a)pyrene |
| Mesoridazine | Oxprenolol | letrozole |
| hydroquinone | halofuginone | flunisolide |
| ubiquinol | Aflatoxins | piperlonguminine |
| halofantrine | Ethyl Methanesulfonate | lanatoside C |
| Ethambutol | Protriptyline | bromobenzene |
| calmidazolium | Monocrotaline | Etodolac |
| Thiorphan | nimesulide | Triprolidine |
| acemetacin | Spiperone | Triiodothyronine |
| Prednisone | tenidap | Prochlorperazine |
| Melatonin | Methyldopa | cobaltous chloride |
| direct black 3 | Alprazolam | monobenzone |
| KCB-1 protein, recombinant | epidermal growth factor (1-45) | Ciprofloxacin |
| 2-dichlorobenzene | gefitinib | Triamterene |
| Trifluoperazine | Zidovudine | diflorasone diacetate |
| Choline | chlorcyclizine | Carmustine |
| Hydralazine | Finasteride | Thapsigargin |

TABLE S1-continued

Molecules that regulate genes or gene products relevant to proline transport and metabolism.

| | | |
|---|---|---|
| valsartan | medrysone | Beclomethasone |
| geraniol | Tetradecanoylphorbol Acetate | Itraconazole |
| Erythromycin | Imipramine | Fendiline |
| Lovastatin | Astern izole | Dihydrotestosterone |
| 4-acetylaminofluorene | Methylprednisolone | mometasone furoate |
| Puromycin Aminonucleoside | Ceftriaxone | venlafaxine |
| nickel chloride | Chlorprothixene | pantoprazole |
| TO-901317 | Proguanil | Phenylbutazone |
| Tranexamic Acid | Clemastine | pramoxine |
| Danazol | R 848 | Cisapride |
| Diclofenac | parbendazole | oxidized-L-alpha-1-palmitoyl-2-arachidonoyl-sn-glycero-3-phosphorylcholine |
| Pyrogens | Vanadates | lansoprazole |
| Azathioprine | Mycophenolic Acid | Ethylene Glycol |
| Nefopam | Norethynodrel | clemizole |
| tripterine | nisoxetine | Tamoxifen |
| Chlormezanone | Nitrofurazone | Mefloquine |
| eticlopride | Tetracycline | Omeprazole |
| vanoxerine | Thiethylperazine | marimastat |
| dibenzazepine | lingzhi | prednicarbate |
| Desoxycorticosterone | Oxyquinoline | Cyproheptadine |
| tetrahydrotriamcinolone | Hexetidine | 4-hydroxy-2-nonenal |
| bortezomib | Captopril | Promethazine |
| Diazinon | Iproniazid | pimethixene |
| Propranolol | Vinblastine | doxofylline |
| Brefeldin A | Hydroxyzine | asperflavin |
| ursolic acid | Enoxacin | Acetazolamide |
| Nocodazole | 1-Methyl-4-phenyl-1,2,3,6-tetrahydropyridine | Saquinavir |
| Ouabain | Metergoline | Sumatriptan |
| boldine | Stavudine | N-(2-cyclohexyloxy-4-nitrophenyl)methanesulfonamide |
| Pravastatin | Nystatin | chelidonine |
| Diazepam | N, N-dimethylarginine | Perphenazine |
| dasatinib | Pergolide | Podophyllotoxin |
| Orphenadrine | Haloperidol | Ketorolac |
| Palmitic Acid | Promazine | Dizocilpine Maleate |
| Tinidazole | sodium arsenite | Furosemide |
| Diphenhydramine | Loxapine | bafilomycin A |
| Maprotiline | Propylthiouracil | Isoproterenol |
| Clopenthixol | Methamphetamine | Perhexiline |
| 4-(5-benzo(1,3)dioxol-5-yl-4-pyridin-2-yl-1H-imidazol-2-yl)benzamide | rabeprazole | Oxymetazoline |
| Pimozide | 2-methoxyestradiol | Nafenopin |
| Thioguanine | 2-(4-morpholinyl)-8-phenyl-4H-1-benzopyran-4-one | Penicillamine |
| 6-Mercaptopurine | phenacemide | Labetalol |
| Loratadine | Nordihydroguaiaretic Acid | Ethacrynic Acid |
| Nicotine | Lobeline | Phenoxybenzamine |
| Mephentermine | candesartan | fluvastatin |
| acadesine | idebenone | 6-methoxy-2-naphthylacetic acid |
| Chitosan | Fluconazole | Meclizine |
| Citalopram | Ifosfamide | Acetylcysteine |
| desloratadine | Nevirapine | Nitric Oxide |
| fragment C, human serum albumin | Risperidone | resveratrol |
| Amiloride | Soman | benzyloxycarbonylleucyl-leucyl-leucine aldehyde |
| Chlorpyrifos | Puromycin | Quinidine |
| HI 6 | alpha-Tocopherol | Streptomycin |
| 2-(1H-indazol-4-yl)-6-(4-methanesulfonylpiperazin-1-ylmethyl)-4-morpholin-4-ylthieno(3,2-d)pyrimidine | Rifampin | carvedilol |
| Staurosporine | 1-Methyl-3-isobutylxanthine | Moxisylyte |
| lamotrigine | Ketoprofen | perfluorooctanoic acid |
| MRK 003 | Vitamin K 3 | Nifedipine |
| erlotinib | Aminoglutethimide | Phytohemagglutinins |
| Methotrexate | Fluorouracil | Diltiazem |
| Ribavirin | Clozapine | |
| P2. Molecules that downregulate SLC38A2: | | |
| ellipticine | Mitoxantrone | 4'-epidaunomycin |
| N(1)-methyl-2-lysergic acid diethylamide | midecamycin | triptolide |

TABLE S1-continued

Molecules that regulate genes or gene products relevant to proline transport and metabolism.

| | | |
|---|---|---|
| Echinomycin | Paraoxon | quelamycin |
| Busulfan | Dactinomycin | sapphyrin |
| Buformin | Deoxyglucose | Chlortetracycline |
| Phenformin | Papaverine | Alpha-Amanitin |
| Econazole | cephaelin | versipelostatin |
| Coumarins | perfosfamide | Aclarubicin |
| Polychlorinated Biphenyls | Diamide | Adenosine-5'-(N-ethylcarboxamide) |
| sesamin | Metformin | Terfenadine |
| Antazoline | Cyproterone Acetate | CpG ODN 2216 |
| iodoform | Butyric Acid | Deferoxamine |
| Nisoldipine | Cortisone | Cyclandelate |
| oltipraz | Emetine | tenofovir |
| flavopiridol | insulin-like growth factor I (57-70) | 8-aminohexylamino cAMP |
| Ketoconazole | Hycanthone | verteporfin |
| neuropeptide Y (18-36) | amprenavir | 1-(2-cyano-3,12-dioxooleana-1,9-dien-28-oyl) imidazole |
| Guanethidine | apicidin | Ultraviolet Rays |
| Methylcholanthrene | Dinoprostone | Sulpiride |
| Atovaquone | Ceftazidime | aluminum sulfate |
| Zinc Sulfate | dihydroquinghaosu | piperaquine |
| beta-Naphthoflavone | Methylnitronitrosoguanidine | Bezafibrate |
| Ganciclovir | Fenofibrate | Testosterone |
| tropisetron | pirinixic acid | Paclitaxel |
| trichostatin A | Triacetin | Secobarbital |
| vanadium pentoxide | Doxorubicin | Cantharidin |
| Apigenin | Mifepristone | rosiglitazone |
| Phenobarbital | anisindione | hydrastine |
| gatifloxacin | isoconazole | Lorazepam |
| Amoxapine | acidocin CHS, Lactobacillus acidophilus | Hemin |
| Tretinoin | Carotenoids | Grape Seed Proanthocyanidins |
| fasudil | Dimenhydrinate | fipexide |
| Immunoglobulin M | grepafloxacin | Oxazepam |
| Mebendazole | Trimethadione | blebbistatin |
| daboiatoxin | X-Rays | 3-nitropropionic acid |
| N-Methyl-3,4-methylenedioxyamphetamine | edelfosine | Metribolone |
| Piperonyl Butoxide | trilinolein | Flurbiprofen |
| Cycloheximide | cineole | Y 27632 |
| Camptothecin | Luteolin | gabapentin |
| Pentobarbital | Rotenone | Lidocaine |
| Hydrogen Peroxide | Natriuretic Peptide, C-Type | Azithromycin |
| Insulin | Nadolol | Ipratropium |
| rofecoxib | pioglitazone | 7,8-Dihydro-7,8-dihydroxybenzo(a)pyrene 9,10-oxide |
| senecionine | Paroxetine | Ethionine |
| Clonazepam | Ethisterone | Poly I-C |
| Miconazole | shikonin | Dehydrocholic Acid |
| Flunarizine | Tacrolimus | imatinib |
| Valproic Acid | naphthalene | Benzalkonium Compounds |
| Azacitidine | valdecoxib | atorvastatin |
| Clofibrate | bis(tri-n-butyltin)oxide | Genistein |
| calycanthine | ethaverine | lacidipine |
| alginic acid | Doxapram | 4-nonylphenol |
| decitabine | Platelet Activating Factor | Timolol |
| Chlordiazepoxide | Glyburide | Ranitidine |
| vorinostat | 2,2'-(hydroxynitrosohydrazono)bis-ethanamine | Dichlororibofuranosylbenzimidazole |
| 4-(4-fluorophenyl)-2-(4-hydroxyphenyl)-5-(4-pyridyl)imidazole | Clotrimazole | Dobutamine |
| Benserazide | 4-methyl-N-(3-(4-methylimidazol-1-yl)-5-(trifluoromethyl)phenyl)-3-((4-pyridin-3-ylpyrimidin-2-yl)amino)benzamide | Amitriptyline |
| Dimethyl Sulfoxide | Nitroarginine | Malathion |
| Metaproterenol | Dacarbazine | Sarin |
| Acepromazine | acacetin | Tiapamil Hydrochloride |
| discretamine | Concanavalin A | Droperidol |

TABLE S1-continued

Molecules that regulate genes or gene products relevant to proline transport and metabolism.

| | | |
|---|---|---|
| 3-deazaneplanocin | Benperidol | Quinacrine |
| Digitoxin | Neomycin | LBH589 |
| procyanidin | Zimeldine | 8-Bromo Cyclic Adenosine Monophosphate |
| Quercetin | Atropine | U 0126 |
| dexchlorpheniramine | 2,2'-Dipyridyl | Simvastatin |
| Plicamycin | Ticlopidine | HC toxin |
| sildenafil | 1-(5-Isoquinolinesulfonyl)-2-Methylpiperazine | Famotidine |
| ochratoxin A | Vitamin E | Calcitriol |
| Phenylephrine | oxybutynin | Mitomycin |
| Lomustine | Terazosin | Ethylnitrosourea |
| Azauridine | Cytarabine | salmeterol |
| efavirenz | scriptaid | Clonidine |
| Gemfibrozil | Ascorbic Acid | SU 5402 |
| 17-(allylamino)-17-demethoxygeldanamycin | SB 203580 | Vincristine |
| Clindamycin | Pregnenolone Carbonitrile | Anisomycin |
| Losartan | Lamivudine | Ionomyin |
| Ramipril | Ofloxacin | Kainic Acid |
| NG-Nitroarginine Methyl Ester | Atenolol | gemcitabine |
| Hydroxyurea | geldanamycin | Terbutaline |
| Levodopa | sorafenib | Probucol |
| Melphalan | Tocainide | |
| Q1. Molecules that upregulate SLC38A4: | | |
| 2-methoxyestradiol | 4-acetylaminofluorene | Captopril |
| N-(2-cyclohexyloxy-4-nitrophenyl)methanesulfonamide | Hydrocortisone | Sulfaguanidine |
| ascorbate-2-phosphate | Isoniazid | 6-bromoindirubin-3'-oxime |
| Ascorbic Acid | Rifampin | Ethylene Glycol |
| Trichloroepoxypropane | SEW2871 | sparfloxacin |
| Mitomycin | troglitazone | N-Methylaspartate |
| Penicillamine | Clarithromycin | 8-aminohexylamino cAMP |
| vinclozolin | Dihydrotestosterone | Ozone |
| Nitrendipine | lapatinib | Sulfisoxazole |
| Ergocalciferols | Zalcitabine | Sirolimus |
| Dexamethasone | Calcium | Cetylpyridinium |
| Mannitol | Dextran Sulfate | Aflatoxin B1 |
| Ibuprofen | Benzethonium | Theophylline |
| 4-nonylphenol | aluminum sulfate | ibufenac |
| benoxaprofen | Rifabutin | Ciprofloxacin |
| meloxicam | Nimodipine | temsirolimus |
| methyl salicylate | Azoxymethane | cidofovir |
| cryptoxanthin | U 0126 | hydrazine |
| lead tetraacetate | torsemide | Gentian Violet |
| Lomustine | Tryptophan | Valproic Acid |
| boldine | trovafloxacin | Probenecid |
| Aspirin | flavopiridol | Dimethylnitrosamine |
| Doxorubicin | 4'-N-benzoylstaurosporine | Procarbazine |
| amprenavir | pristane | tosufloxacin |
| butenafine | 5-fluorouridine | Fluocinolone Acetonide |
| arsenic acid | Busulfan | Amphotericin B |
| rofecoxib | Hydralazine | phenethyl isothiocyanate |
| Atenolol | 2-tert-butylhydroquinone | Diethylhexyl Phthalate |
| Ethylestrenol | Niacin | Choline |
| cilostazol | vinorelbine | Epirubicin |
| chloroxylenol | Thioguanine | Chlorambucil |
| Chorionic Gonadotropin | ferric nitrilotriacetate | Physostigmine |
| Diethylnitrosamine | Indomethacin | Bithionol |
| Camptothecin | Caffeine | Nafenopin |
| Tiapamil Hydrochloride | Sparteine | Citalopram |
| Forskolin | diphenidol | Gentamicins |
| pramoxine | Oxyquinoline | Roxithromycin |
| Didanosine | Fenofibrate | Betamethasone |
| Octopamine | valsartan | Phenacetin |
| 1-Methyl-3-isobutylxanthine | LPS 9 | gefitinib |
| diloxanide furoate | estradiol 3-benzoate | Daunorubicin |
| sildenafil | Itraconazole | Acetazolamide |
| arsenic trioxide | Nortriptyline | Digitoxin |
| efavirenz | Clofibrate | 3,3',4',5-tetrachlorosalicylanilide |
| Chlorpromazine | Felodipine | ebastine |
| Gonadotropins | Mexiletine | ifenprodil |
| Phosgene | Carbimazole | Zidovudine |
| Sulfadiazine | Monocrotaline | Diethylstilbestrol |
| Etomidate | coumarin | Clomiphene |
| Methylcholanthrene | Ouabain | Bezafibrate |

TABLE S1-continued

Molecules that regulate genes or gene products relevant to proline transport and metabolism.

| | | |
|---|---|---|
| harmol | Dexfenfluramine | Rolipram |
| sorafenib | Tolazamide | Meclofenoxate |
| Heparin | Promazine | lomefloxacin |
| Acyclovir | Amoxicillin | wortmannin |
| 4-octylphenol | Dimethylformamide | Chloramphenicol |
| Mercuric Chloride | Methyldopa | Lamivudine |
| fluvastatin | Vitamin K 3 | Levonorgestrel |
| Ketoconazole | zileuton | glimepiride |
| phenothiazine | Vincristine | methyleugenol |
| Thalidomide | Fluoxetine | Simvastatin |
| zomepirac | Cefuroxime | flubendazole |
| N-nitrosomorpholine | Progesterone | Melatonin |
| Altretamine | dihydroquinghaosu | piperaquine |
| Phenytoin | 1,2,3-trichloropropane | Lithocholic Acid |
| Levodopa | Mefenamic Acid | nabumetone |
| tranilast | idebenone | Etoposide |
| Aclarubicin | Neomycin | Methotrexate |
| 1-(5-lsoquinolinesulfonyl)-2-Methylpiperazine | Chlormezanone | buflomedil |
| Moxisylyte | artemether | Cocaine |
| Bupropion | SU 5402 | monastrol |
| Sotalol | Pyrazinamide | Methyl Methanesulfonate |
| Dicyclomine | Clomipramine | Trimethadione |
| Doxycycline | acidocin CH5, Lactobacillus acidophilus | Dichlorvos |
| acemetacin | Nystatin | dexibuprofen |
| Dinitrofluorobenzene | Nevirapine | Stanozolol |
| 2-Acetylaminofluorene | Ethambutol | Dactinomycin |
| Naproxen | Terbutaline | Naloxone |
| Fluconazole | Fluorouracil | Amoxapine |
| Ultraviolet Rays | Sulfadoxine | Tocainide |
| Lactic Acid | 6-Mercaptopurine | Stavudine |
| Ribavirin | erlotinib | Deoxyglucose |
| Spironolactone | R 848 | Norethindrone |
| olanzapine | Atropine | |
| Q2. Molecules that downregulate SLC38A4: | | |
| bicalutamide | apicidin | Tolbutamide |
| 1-amino-2,4-dibromoanthraquinone | scriptaid | 17-(allylamino)-17-demethoxygeldanamycin |
| Go 6976 | LBH589 | cobaltous chloride |
| vorinostat | Chitosan | Cycloheximide |
| Clonidine | Tetanus Toxin | HC toxin |
| Cholera Toxin | DDT | 2,4-diaminotoluene |
| Diazinon | Colchicine | 8-Bromo Cyclic Adenosine Monophosphate |
| infliximab | senecionine | triadimefon |
| Risperidone | Hexachlorobenzene | Okadaic Acid |
| Sulindac | Omeprazole | Tubocurarine |
| Lindane | GW 501516 | Simazine |
| trichostatin A | Ethylnitrosourea | Cyclosporine |
| Coumaphos | Thapsigargin | Danazol |
| Tretinoin | pioglitazone | trilinolein |
| quintozene | Insulin | cetraxate |
| rabeprazole | 25-hydroxycholesterol | 4'-epidaunomycin |
| Sulpiride | Cyclophosphamide | Carmustine |
| Propylthiouracil | Nisoldipine | Glycerol |
| Noscapine | Lead | Tetradecanoylphorbol Acetate |
| Cardiotoxins | ovalicin | Medroxyprogesterone Acetate |
| testosterone 17 beta-cypionate | Norepinephrine | Tinidazole |
| Azathioprine | hexachlorobutadiene | mono-(2-ethylhexyl)phthalate |
| Plicamycin | Disopyramide | Ranitidine |
| Labetalol | Perhexiline | ranolazine |
| Eugenol | Alpha-Amanitin | Benzbromarone |
| famciclovir | beta-Naphthoflavone | Bromocriptine |
| Benzo(a)pyrene | cathelicidin antimicrobial peptide | rosiglitazone |
| Vecuronium Bromide | Hexachlorophene | Papaverine |
| trichlorofluoromethane | (melle-4)cyclosporin | Cisplatin |
| clopidogrel | ipriflavone | bendazolic acid |
| Beclomethasone | doxofylline | Diclofenac |
| Erythromycin | Flutamide | Nifedipine |
| cortisone acetate | Phenobarbital | atorvastatin |
| Bleomycin | Tunicamycin | geraniol |
| Pyrogens | Promethazine | Etidronic Acid |
| Tacrine | crotamiton | Caerulein |

TABLE S1-continued

Molecules that regulate genes or gene products relevant to proline transport and metabolism.

| | | |
|---|---|---|
| Dipyrone | celecoxib | Primidone |
| vanadium pentoxide | sodium selenate | sodium arsenite |
| Cyproterone Acetate | Ethionine | Terazosin |
| Bromhexine | Acetaminophen | Sulbactam |
| Miconazole | Malathion | Ticlopidine |
| Phenol | Tetrachlorodibenzodioxin | Cadmium |
| nitrosobenzylmethylamine | Carbamazepine | Estradiol |
| terbinafine | Paclitaxel | Haloperidol |
| Aminoglutethimide | Mestranol | Vinblastine |
| Methyltestosterone | Palmitic Acid | Carbon Tetrachloride |
| Ketorolac | Fenbendazole | Aminosalicylic Acid |
| ciprofibrate | Lovastatin | Chlormadinone Acetate |
| Cholecalciferol | Tetracaine | genipin |
| lead acetate | sulforafan | Nitrofurantoin |
| Dantrolene | ferulic acid | Methapyrilene |
| Tamoxifen | sulconazole | Clotrimazole |
| quetiapine | Isoproterenol | Idarubicin |
| Hydroxyzine | Ethinyl Estradiol | Dimenhydrinate |
| Azacitidine | Nizatidine | Clonazepam |
| Procaine | bromfenac | Pyocyanine |
| artemisinine | anastrozole | nimesulide |
| Isotretinoin | Tetracycline | Particulate Matter |
| decitabine | heliotrine | Furosemide |
| Cyproheptadine | MF59 oil emulsion | Bacitracin |
| Finasteride | Vitamin E | Salicylic Acid |
| Ethanol | Fluphenazine | Acrolein |
| Loratadine | Netilmicin | AICA ribonucleotide |
| acadesine | lansoprazole | Hydrogen Peroxide |
| Gemfibrozil | Cytarabine | Melphalan |
| Mitoxantrone | Streptomycin | compactin |
| Diazepam | Y 27632 | pantoprazole |
| Quercetin | Lithium | Chlorzoxazone |
| Mifepristone | carvedilol | Deoxycholic Acid |
| SB 203580 | 1,2-dilinolenoyl-3-(4-aminobutyryl)propane-1,2,3-triol | bromobenzene |
| Acarbose | fulvestrant | Doxapram |
| Metform in | Piperonyl Butoxide | leflunomide |
| Sulfadimethoxine | Poly I-C | irinotecan |
| 3-hydroxyacetanilide | acyline | bisphenol A |
| Ticrynafen | Dobutamine | Kainic Acid |
| 2-(4-morpholinyl)-8-phenyl-4H-1-benzopyran-4-one | Nitrofurazone | Imipramine |
| Minoxidil | norethindrone acetate | Calcitriol |
| Tranylcypromine | Chloroform | NG-Nitroarginine Methyl Ester |
| Lorazepam | Methimazole | Amiodarone |
| Chloroquine | Diltiazem | Doxepin |
| Sertraline | Amlodipine | Dinoprostone |
| Estriol | Ifosfamide | Amantadine |
| benzyloxycarbonylleucyl-leucyl-leucine aldehyde | 2-dichlorobenzene | Genistein |
| Carboplatin | pralidoxime | imatinib |
| Thioacetamide | Enalapril | Amitriptyline |
| R1. Molecules that upregulate SLC6A7: | | |
| Canavanine | Lithium | sodium arsenite |
| Theobromine | amprenavir | aceclofenac |
| Digitoxin | Nomifensine | diindolylmethane |
| Ribostamycin | telenzepine | nabumetone |
| Nitrendipine | N-Methyl-3,4-methylenedioxyamphetamine | Hydroxyzine |
| valsartan | Dimethylformamide | tetrahydrotriamcinolone |
| Sulindac | Glycopyrrolate | Clopamide |
| Capsaicin | Trichloroacetic Acid | Secobarbital |
| Pentobarbital | Nadolol | Aminophylline |
| Mitomycin | Aminopyrine | sildenafil |
| triptolide | Ketoprofen | trovafloxacin |
| 4-octylphenol | alverine | Simvastatin |
| Diflunisal | Cefmetazole | Ouabain |
| Chlorambucil | Hesperidin | Bisacodyl |
| phenethyl isothiocyanate | cephalonium | lead acetate |
| Clofibrate | Salicylates | moxonidine |
| Ticrynafen | Ibuprofen | Dyphylline |

TABLE S1-continued

Molecules that regulate genes or gene products relevant to proline transport and metabolism.

| | | |
|---|---|---|
| tranilast | Erythromycin Ethylsuccinate | Bithionol |
| Progesterone | Digoxin | Sparteine |
| buflomedil | Methacycline | esculetin |
| olanzapine | Amantadine | 4-(N-methyl-N-nitrosamino)-1-(3-pyridyl)-1-butanone |
| Lovastatin | Clarithromycin | carcinine |
| oxybutynin | benazepril | Mexiletine |
| benoxaprofen | Probucol | Azathioprine |
| Gliclazide | Foscarnet | Rifabutin |
| Metoprolol | Methyldopa | Finasteride |
| Norethindrone | amylocaine | Hydrocortisone |
| Hydrochlorothiazide | Econazole | Megestrol Acetate |
| Diethylstilbestrol | leflunomide | Sulfadoxine |
| Ethamsylate | nimesulide | bromperidol |
| Clomiphene | Podophyllotoxin | Chlordiazepoxide |
| Citric Acid | Mifepristone | Didanosine |
| Canrenoate Potassium | Chlorpromazine | Clonidine |
| 4-methyl-N-(3-(4-methylimidazol-1-yl)-5-(trifluoromethyl)phenyl)-3-((4-pyridin-3-ylpyrimidin-2-yl)amino)benzamide | Flurbiprofen | Stavudine |
| gabapentin | temafloxacin | Ethisterone |
| tenidap | compactin | Procainamide |
| Chloroquine | Ranitidine | Aconitine |
| Fluconazole | famciclovir | Sulfameter |
| ibufenac | Amlodipine | Tetracaine |
| diphenidol | vinylidene chloride | Ethanol |
| Valproic Acid | flunisolide | clinafloxacin |
| Theophylline | Pantothenic Acid | sulforafan |
| Fursultiamin | Cisapride | tracazolate |
| 2-chloropyrazine | Meptazinol | verteporfin |
| 4'-N-benzoylstaurosporine | eperisone | atorvastatin |
| estradiol 3-benzoate | Acetaminophen | tropisetron |
| gibberellic acid | oxolamine | Etoposide |
| Propidium | phenothiazine | Tropicamide |
| Nafenopin | Carbon Tetrachloride | Nimodipine |
| Noscapine | Amitriptyline | pramoxine |
| Clomipramine | Roxarsone | pantoprazole |
| Tetracycline | Thiamphenicol | Ondansetron |
| Dicyclomine | anastrozole | oltipraz |
| Tetanus Toxin | Tiapamil Hydrochloride | Miconazole |
| Fluocinolone Acetonide | acacetin | heliotrine |
| oxfendazole | Hydroxyurea | wortmannin |
| Paroxetine | bisphenol A | dexibuprofen |
| Etidronic Acid | Nortriptyline | Droperidol |
| Ergocalciferols | pioglitazone | Lamivudine |
| Metolazone | Physostigmine | Betaxolol |
| Metoclopramide | Raloxifene | mycophenolate mofetil |
| marimastat | Cyclosporine | Cholera Toxin |
| Dexfenfluramine | Cisplatin | candesartan |
| Y 27632 | Flupenthixol | Chlorpheniramine |
| Phenobarbital | Doxazosin | TO-901317 |
| Immunoglobulin M | Chlortetracycline | Kainic Acid |
| Sulpiride | Estradiol | phenacemide |
| Minoxidil | ochratoxin A | Luteolin |
| Cimetidine | Cholecalciferol | Netilmicin |
| Lithium Chloride | Methimazole | Trifluoperazine |
| Bacitracin | Amiloride | Prazosin |
| Fluphenazine | Saquinavir | Colchicine |
| gefitinib | Itraconazole | Flavoxate |
| Vincamine | vanoxerine | Triacetin |
| Pemoline | N,N'-diphenyl-4-phenylenediamine | Gentamicins |
| oxcarbazepine | Losartan | rabeprazole |
| Azithromycin | Clobetasol | Clonazepam |
| Thioacetamide | nateglinide | Asbestos |
| Warfarin | Amiodarone | valdecoxib |
| Altretamine | Ramipril | N-nitrosomorpholine |
| lamotrigine | rituximab | zomepirac |
| Furosemide | Hydralazine | Puromycin |
| pirinixic acid | Paclitaxel | bromfenac |
| Diethylhexyl Phthalate | Aflatoxin B1 | Dexamethasone |
| Ketoconazole | Vinblastine | Thioguanine |
| Methylprednisolone | U 0126 | Calcitriol |

TABLE S1-continued

Molecules that regulate genes or gene products relevant to proline transport and metabolism.

| | | |
|---|---|---|
| bromobenzene | Ethinyl Estradiol | irinotecan |
| Haloperidol | Alpha-Amanitin | Dactinomycin |
| Vincristine | Cycloheximide | isoascorbic acid |
| fluvastatin | Tetradecanoylphorbol Acetate | |
| R2. Molecules that downregulate SLC6A7: | | |
| Nisoldipine | Ethylene Glycol | Nevirapine |
| Promethazine | Benzocaine | PK 11195 |
| solasodine | Hexachlorophene | Penicillin G Benzathine |
| Alprazolam | Atenolol | graveoline |
| Ciprofloxacin | lomefloxacin | Mebendazole |
| Nitrofurantoin | Cyproterone | Sulfinpyrazone |
| Cefaclor | flubendazole | Melatonin |
| Urethane | N-Methylaspartate | 3,3',4',5-tetrachlorosalicylanilide |
| Ifosfamide | zopiclone | Aminoglutethimide |
| lead tetraacetate | Glipizide | Oxymetazoline |
| Clofibric Acid | sparfloxacin | Chromium |
| balsalazide | Gentian Violet | Etiocholanolone |
| minaprine | Mesna | Penicillamine |
| Thioctic Acid | Trimethadione | Promazine |
| Omeprazole | citiolone | Hexetidine |
| Indomethacin | ipriflavone | alpha-Amino-3-hydroxy-5-methyl-4-isoxazolepropionic Acid |
| Aspirin | methyl salicylate | fenbufen |
| Vecuronium Bromide | Benzethonium | levocabastine |
| Acetazolamide | closantel | glimepiride |
| chlorinated dibenzofurans | Succinylcholine | Busulfan |
| Niacin | Sulfamethoxazole | Clotrimazole |
| Carmustine | Fonofos | Procarbazine |
| Cefotaxime | Propylthiouracil | Primaquine |
| modafinil | Tramadol | Isoproterenol |
| sodium selenate | rofecoxib | resveratrol |
| Neomycin | Enterotoxins | artemether |
| Clofazimine | Acyclovir | Rifampin |
| Griseofulvin | Methyltestosterone | salicylamide |
| chloroxylenol | Pempidine | letrozole |
| celecoxib | 6-methoxy-2-naphthylacetic acid | Diethylnitrosamine |
| Ticlopidine | Bromisovalum | Atropine |
| Isoflurophate | torsemide | Isoniazid |
| dexchlorpheniramine | Loratadine | Carboplatin |
| Cromolyn Sodium | Ritonavir | Mannitol |
| Lomustine | Vitamin E | Sulfaphenazole |
| Tocainide | Iproniazid | Tetrachlorodibenzodioxin |
| Phenacetin | tazobactam | Cyclophosphamide |
| Terazosin | norethindrone acetate | 2-methoxyestradiol |
| abamectin | Azacitidine | meloxicam |
| geraniol | 2,3-dioxo-6-nitro-7-sulfamoylbenzo(f)quinoxaline | Soman |
| Debrisoquin | Verapamil | Methocarbamol |
| acemetacin | Amikacin | ubiquinol |
| Beclomethasone | oxiconazole | Biperiden |
| Doxorubicin | troglitazone | Kanamycin |
| Mefenamic Acid | ozagrel | enrofloxacin |
| 7-aminocephalosporanic acid | Fenofibrate | HI 6 |
| Chloroform | Aminosalicylic Acid | Cytarabine |
| SC 514 | Tubocurarine | nifuroxazide |
| Zidovudine | ONO 2235 | Praziquantel |
| Chlorzoxazone | Astemizole | Safrole |
| valacyclovir | Fluoxetine | Dipyridamole |
| Bezafibrate | 4-nonylphenol | Oxytetracycline |
| clopidogrel | lansoprazole | Bleomycin |
| venlafaxine | telmisartan | methylatropine |
| idebenone | Citalopram | Gossypol |
| Erythromycin | 1,5-naphthalenediamine | meropenem |
| Cinnarizine | diphemanil methylsulfate | Albendazole |
| phthalylsulfathiazole | Tranexamic Acid | Estriol |
| Cortisone | artemisinine | 1-hydroxycholecalciferol |
| tianeptine | ethotoin | Piperonyl Butoxide |
| Norfloxacin | Oxazepam | Riluzole |
| bromodichloromethane | Aztreonam | Nystatin |
| Ethambutol | 2,2'-(hydroxynitrosohydrazono)bis-ethanamine | Spironolactone |
| 4,4'-diaminodiphenylmethane | Sertraline | Naproxen |
| Azlocillin | gatifloxacin | imiquimod |
| Metronidazole | Labetalol | Diazepam |
| zaleplon | Nicotine | Daunorubicin |
| Azoxymethane | Vancomycin | Tranylcypromine |
| enzastaurin | Fludrocortisone | lactacystin |

TABLE S1-continued

Molecules that regulate genes or gene products relevant to proline transport and metabolism.

| | | |
|---|---|---|
| Maprotiline | Pilocarpine | Tacrine |
| Mitoxantrone | Cyproterone Acetate | parthenolide |
| Hydrogen Peroxide | Methylcholanthrene | Sirolimus |
| quelamycin | Pyrazinamide | Pyrogallol |
| Freund's Adjuvant | Poly I-C | Doxepin |
| Tamoxifen | Prochlorperazine | Piroxicam |
| Diphenhydramine | fomepizole | Mestranol |
| Tolbutamide | Tolazamide | Roxithromycin |
| Genistein | Triamterene | imatinib |
| Prednisone | Carbimazole | pralidoxime |
| Fluorouracil | Forskolin | 17-(allylamino)-17-demethoxygeldanamycin |
| Tretinoin | Thioridazine | Levodopa |
| Bupropion | CPG-oligonucleotide | Streptozocin |
| Imipramine | Ultraviolet Rays | Melphalan |
| rosiglitazone | beta-Naphthoflavone | quintozene |
| Methotrexate | Caffeine | Epirubicin |
| 4-(5-benzo(1,3)dioxol-5-yl-4-pyridin-2-yl-1H-imidazol-2-yl)benzamide | Diclofenac | |

S1. Molecules that upregulate DTNBP1:

| | | |
|---|---|---|
| SC 514 | PK 11195 | Paraoxon |
| Go 6976 | decitabine | X-Rays |
| Emetine | Prostaglandins E | Azacitidine |
| Paclitaxel | Dinoprostone | norflurane |
| benzyloxycarbonylleucyl-leucyl-leucine aldehyde | emtricitabine | tetrafluoroethylene |
| shogaol | procyanidin | Promegestone |
| Cytochalasin D | temsirolimus | Moxisylyte |
| Mianserin | iodoform | Ethanol |
| Levodopa | Carcinogens | Immunoglobulin M |
| (melle-4)cyclosporin | gatifloxacin | tenofovir |
| Staurosporine | Antibodies, Monoclonal | sapphyrin |
| Ethionine | bortezomib | enrofloxacin |
| Ecdysterone | lenalidomide | Sodium Dodecyl Sulfate |
| 2-(1H-indazol-4-yl)-6-(4-methanesulfonylpiperazin-1-ylmethyl)-4-morpholin-4-ylthieno(3,2-d)pyrimidine | epoxomicin | Estradiol |
| Hemin | Azithromycin | Buspirone |
| Carboplatin | motexafin gadolinium | BCG Vaccine |
| monastrol | Isoproterenol | Disopyramide |
| Inosine Monophosphate | Cytochalasin B | Antimycin A |
| Ajmaline | Sulpiride | Amitriptyline |
| 1,3-dichlorobenzene | systhane | ascorbate-2-phosphate |
| vorinostat | 8-((4-chlorophenyl)thio)cyclic-3',5-AMP | Ethionamide |
| Spironolactone | Nifedipine | Tetrachlorodibenzodioxin |
| Poly I-C | Immunoglobulin G | Methamphetamine |
| mycophenolate mofetil | Daunorubicin | Tretinoin |
| Doxepin | Piperonyl Butoxide | dasatinib |
| acidocin CH5, *Lactobacillus acidophilus* | GW 3965 | 4-(5-benzo(1,3)dioxol-5-yl-4-pyridin-2-yl-1H-imidazol-2-yl)benzamide |
| gefitinib | CPG-oligonucleotide | erlotinib |
| U 0126 | everolimus | peginterferon alfa-2a |
| rituximab | rosiglitazone | cerivastatin |
| letrozole | atorvastatin | benziodarone |
| troglitazone | gemcitabine | bicalutamide |
| norethindrone acetate | HI 6 | nimesulide |
| withaferin A | lead acetate | methylatropine |
| arsenic trioxide | geldanamycin | Enalapril |
| NG-Nitroarginine Methyl Ester | Bleomycin | Triiodothyronine |
| Chitosan | Cortisone | Methylprednisolone |
| Fluocinolone Acetonide | Danazol | Norethindrone |
| Cyclosporine | Imipramine | Carbamazepine |
| Methotrexate | Genistein | Quercetin |
| Aflatoxin B1 | Rolipram | Propylthiouracil |
| Phenobarbital | Tunicamycin | Hydralazine |
| Paroxetine | Flunarizine | Ranitidine |
| Benzbromarone | Clonidine | Reserpine |
| Quinidine | Tolbutamide | Chlorpropamide |
| Acetylcysteine | Pyrogallol | Sarin |
| Nitrofurantoin | Haloperidol | Ifosfamide |
| Minocycline | Doxycycline | Idarubicin |
| Sulindac | Thapsigargin | Amantadine |

TABLE S1-continued

Molecules that regulate genes or gene products relevant to proline transport and metabolism.

| | | |
|---|---|---|
| Isotretinoin | Diethylhexyl Phthalate | Ascorbic Acid |
| Azoxymethane | Methapyrilene | Metformin |
| Flutamide | Atenolol | Cadmium |

S2. Molecules that downregulate DTNBP1:

| | | |
|---|---|---|
| N (1)-methyl-2-lysergic acid diethylamide | lysophosphatidic acid | triptolide |
| Nickel | Diquat | Terbutaline |
| alpha-Amino-3-hydroxy-5-methyl-4-isoxazolepropionic Acid | Nerve Growth Factors | Propanil |
| ubiquinol | Melphalan | bis(tri-n-butyltin)oxide |
| Aphidicolin | 2-amino-1-methyl-6-phenylimidazo(4,5-b)pyridine | Acetylmuramyl-Alanyl-Isoglutamine |
| CEP 14083 | Topotecan | 4-acetylaminofluorene |
| Triazolam | coumarin | Ethambutol |
| Camptothecin | Ceftriaxone | Theophylline |
| R 848 | indole-3-carbinol | Platelet Activating Factor |
| 8-aminohexylamino cAMP | trichostatin A | Alpha-Amanitin |
| 4-hydroxytamoxifen | Pentachlorophenol | 7,8-Dihydro-7,8-dihydroxybenzo(a)pyrene 9,10-oxide |
| 1-(5-Isoquinolinesulfonyl)-2-Methylpiperazine | Cisplatin | Zinc Oxide |
| n-hexanal | Dihydrotestosterone | Ibuprofen |
| sangivamycin | Acrolein | Dactinomycin |
| sulforafan | naphthalan | Growth Hormone |
| Doxorubicin | 4-biphenylamine | cobaltous chloride |
| Cytokines | shikonin | Curcumin |
| Colchicine | cidofovir | Sirolimus |
| Tacrine | Estrogens | 8-Bromo Cyclic Adenosine Monophosphate |
| bevacizumab | Cholera Toxin | Acetaminophen |
| Phosphorylcholine | 3-deazaneplanocin | Phenacetin |
| Dichlororibofuranosylbenzimidazole | Potassium Dichromate | Plicamycin |
| quintozene | CpG ODN 2216 | 4-amino-6-hydrazino-7-beta-D-ribofuranosyl-7H-pyrrolo(2,3-d)-pyrimidine-5-carboxamide |
| fasudil | penciclovir | Benzo(a)pyrene |
| Dantrolene | Vincristine | ferric nitrilotriacetate |
| Chorionic Gonadotropin | Testosterone | phenethyl isothiocyanate |
| Hydrogel | Insulin | Acetazolamide |
| N-nitrosomorpholine | Pyrazinamide | Isoniazid |
| Caffeine | Ultraviolet Rays | Methyltestosterone |
| Cephapirin | SB 203580 | Lithium |
| Brefeldin A | N-methylpyrrolidone | Rifampin |
| 1,2-dilinolenoyl-3-(4-am inobutyryl)propane-1,2,3-triol | Vehicle Emissions Acetate | Tetradecanoylphorbol |
| imatinib | Dexamethasone | Penicillamine |
| Vancomycin | Methylene Chloride | Deferoxamine |
| lapatinib | dibenzazepine | sunitinib |
| Roflumilast | 17-(allylamino)-17-demethoxygeldanamycin | infliximab |
| lactacystin | fluvastatin | phosphonoacetamide |
| 2,3-dioxo-6-nitro-7-sulfamoylbenzo(f)quinoxaline | pioglitazone | resveratrol |
| irinotecan | 4-nonylphenol | terbinafine |
| bromobenzene | enterotoxin B, staphylococcal | phenothiazine |
| beta-glycerophosphoric acid | AICA ribonucleotide | oxaliplatin |
| pralidoxime | ochratoxin A | bromodichloromethane |
| closantel | quelamycin | sodium arsenite |
| testosterone 17 beta-cypionate | bisphenol A | crotamiton |
| Pyrogens | Cardiotoxins | Anti-Retroviral Agents |
| Ribavirin | Immunoglobulins, Intravenous | Antigen-Antibody Complex |
| N-Methylaspartate | Ionomyin | Dinoprost |
| Medroxyprogesterone Acetate | Progesterone | Prednisolone |
| Cyproterone Acetate | Chlormadinone | Acetate Ergocalciferols |
| Ciprofloxacin | Oxyquinoline | Indomethacin |
| Luteolin | beta-Naphthoflavone | Diazepam |
| Cycloheximide | Hydroxyzine | Fluconazole |
| Miconazole | Econazole | Monocrotaline |
| Azathioprine | Chlormezanone | Omeprazole |
| Fluphenazine | Chlorpromazine | Mitomycin |

TABLE S1-continued

Molecules that regulate genes or gene products relevant to proline transport and metabolism.

| | | |
|---|---|---|
| Bithionol | Diethylnitrosamine | Cyclophosphamide |
| Chlorambucil | Chloroform | Carbon Tetrachloride |
| Vitamin K 3 | Tetracycline | Epirubicin |
| Raloxifene | Tamoxifen | Diethylstilbestrol |
| Lactic Acid | Diclofenac | Puromycin Aminonucleoside |
| Aspirin | Valproic Acid | Disulfiram |
| Mycophenolic Acid | Fenofibrate | Clofibrate |
| Bezafibrate | Atropine | Tranylcypromine |
| Methyldopa | Guanethidine | Sulfisoxazole |
| Thioacetamide | 2-Acetylaminofluorene | Formaldehyde |
| Glycerol | Lead | Hydrogen Peroxide |
| T1. Molecules that upregulate NDN: | | |
| neuropeptide Y (18-36) | perfosfamide | decitabine |
| naphthalene | norflurane | dibenzazepine |
| trichostatin A | Papaverine | Cytochalasin D |
| tyloxapol | Methionine Sulfoximine | mycophenolate mofetil |
| Okadaic Acid | Parathyroid Hormone | beta-cyclodextrin-benzaldehyde |
| Pivampicillin | pelargonic acid | Nocodazole |
| Clodronic Acid | lonidamine | Tryptophan |
| trichlorofluoromethane | Botulinum Toxins, Type A | fazarabine |
| Edrophonium | acodazole | Tranylcypromine |
| Dibucaine | Riboflavin | Tetanus Toxin |
| Norepinephrine | Tretinoin | Ergocalciferols |
| velnacrine | diindolylmethane | tetrahydrozoline |
| Mianserin | 2,4-diaminotoluene | amylocaine |
| 1-(2-cyano-3,12-dioxooleana-1,9-dien-28-oyl) imidazole | tris(2,3-dibromopropyl)phosphate | tetrafluoroethylene |
| Puromycin Aminonucleoside | telenzepine | Isoproterenol |
| Betazole | midecamycin | Cholera Toxin |
| N-Methylscopolamine | Rolitetracycline | temsirolimus |
| Triprolidine | Fursultiamin | CPG-oligonucleotide |
| Talampicillin | Triflupromazine | LPS 9 |
| 1-amino-2,4-dibromoanthraquinone | Glycerol | dironyl |
| Isoxsuprine | Vitamin B 12 | hydrocotarnine |
| Estrone | Khellin | Dextran Sulfate |
| Cardiotoxins | solasodine | Doxorubicin |
| Sirolimus | oltipraz | iodoform |
| 2-methoxyestradiol | letrozole | Dimethyl Sulfoxide |
| dasatinib | Hydrogen Peroxide | Epirubicin |
| sertaconazole | Bupropion | gram me |
| Pregnenolone | Amitriptyline | 1-ethyl-2-benzimidazolinone |
| Cinnarizine | delsoline | Spiramycin |
| MF59 oil emulsion | Triamterene | Lynestrenol |
| ferric nitrilotriacetate | Cyclophosphamide | Bisoprolol |
| sulforafan | fenbufen | Tacrine |
| Propidium | efavirenz | sunitinib |
| phenethyl isothiocyanate | docetaxel | Roxarsone |
| 17-(dimethylaminoethylamino)-17-demethoxygeldanamycin | Vitamin E | Azacitidine |
| Albuterol | Calcitriol | Imipramine |
| Rifampin | aluminum sulfate | Heparin |
| Sulfamerazine | Bacitracin | resveratrol |
| acemetacin | bis(tri-n-butyltin)oxide | heliotrine |
| Ethambutol | cinchonine | acidocin CH5, *Lactobacillus acidophilus* |
| Diethylhexyl Phthalate | Atropine | Diazinon |
| N-methylpyrrolidone | Lamivudine | Allopurinol |
| Dapsone | Nicotine | fulvestrant |
| phosphonoacetamide | Cytokines | Paclitaxel |
| Amoxapine | Progesterone | Allantoin |
| Fenbendazole | GW 3965 | Mifepristone |
| Dimethylnitrosamine | Betahistine | Flavoxate |
| Fenoprofen | fluticasone | lapatinib |
| Androsterone | Cisplatin | Hydralazine |
| diflorasone diacetate | Alpha-Amanitin | Ethanol |
| Acetaminophen | Galantamine | N-nitrosomorpholine |
| gemcitabine | sulconazole | Pergolide |
| 2-(4-morpholinyl)-8-phenyl-4H-1-benzopyran-4-one | Propylthiouracil | Sulfadiazine |
| Pregnenolone Carbonitrile | Methimazole | Dactinomycin |
| Tetracycline | aristolochic acid I | Isotretinoin |
| Inosine Monophosphate | Doxycycline | Fluorouracil |

TABLE S1-continued

Molecules that regulate genes or gene products relevant to proline transport and metabolism.

| | | |
|---|---|---|
| Ultraviolet Rays | gefitinib | Dinoprostone |
| Norethindrone | Cytarabine | Carboplatin |
| Etoposide | Sulindac | Raloxifene |
| Tamoxifen | Metformin | |

T2. Molecules that upregulate NDN:

| | | |
|---|---|---|
| scriptaid | apicidin | X-Rays |
| shikonin | Cefoperazone | Natriuretic Peptide, C-Type |
| quintozene | Methylene Chloride | monophosphoryl lipid A |
| Pindolol | 2,2'-Dipyridyl | 2,4-Dinitrophenol |
| Enterotoxins | Ethylene Oxide | naphthalan |
| vanadium pentoxide | Estrogens, Conjugated (USP) | vorinostat |
| ranolazine | Emodin | TO-901317 |
| 4,4'-diaminodiphenylmethane | Pyrazinamide | Etidronic Acid |
| Piperonyl Butoxide | N-Methylaspartate | Anti-Retroviral Agents |
| Cymarine | Fusidic Acid | Ozone |
| Ethylene Dibromide | enterotoxin B, staphylococcal | VX |
| Butyric Acid | Fonofos | Deoxycholic Acid |
| testosterone 17 beta-cypionate | Rotenone | 1,2,3-trichloropropane |
| Thiethylperazine | Ampicillin | Shiga Toxin |
| Trichloroepoxypropane | 1-Methyl-3-isobutylxanthine | Parathion |
| chlorinated dibenzofurans | isoconazole | ceforanide |
| Phenobarbital | Immunoglobulins, Intravenous | Abscisic Acid |
| Fluocinolone Acetonide | alpha-Amino-3-hydroxy-5-methyl-4-isoxazolepropionic Acid | Methylnitrosourea |
| Phosgene | direct black 3 | perfluorooctane sulfonic acid |
| iturelix | Dexfenfluramine | Hydrocortisone |
| beta-glycerophosphoric acid | infliximab | lactacystin |
| valdecoxib | rosiglitazone | Creatine |
| Ranitidine | Risperidone | 1-Methyl-4-phenyl-1,2,3,6-tetrahydropyridine |
| Benzo(a)pyrene | benzyloxycarbonylleucyl-leucyl-leucine aldehyde | everolimus |
| Acrolein | Terfenadine | R848 |
| ubiquinol | Thapsigargin | Insulin |
| Chitosan | Metolazone | temozolomide |
| Chorionic Gonadotropin | Azoxymethane | Phytohemagglutinins |
| Isoniazid | cyclobenzaprine | Cyproterone Acetate |
| 4-biphenylamine | Bleomycin | Y 27632 |
| 6-methoxy-2-naphthylacetic acid | Paroxetine | Calcium |
| Dexamethasone | Ascorbic Acid | 4-O-methyl-12-O-tetradecanoylphorbol 13-acetate |
| halofuginone | Testosterone | Hydrochloric Acid |
| Cyproheptadine | Enalapril | Ouabain |
| Urethane | Chlorpropamide | Gonadotropins |
| Moclobemide | Diethylstilbestrol | linezolid |
| Dinitrofluorobenzene | Vehicle Emissions | Corticosterone |
| LBH589 | dexchlorpheniramine | Valproic Acid |
| mono-(2-ethylhexyl)phthalate | imatinib | Lithium |
| Pyrogens | 4-dichlorobenzene | alginic acid |
| Medroxyprogesterone Acetate | Carbamazepine | Deoxyglucose |
| Benzethonium | Cefuroxime | Lactic Acid |
| 4-hydroxy-2-nonenal | Mitoxantrone | isoascorbic acid |
| Captopril | Propofol | Estradiol |
| Tolbutamide | Tetrachlorodibenzodioxin | U 0126 |
| Methylprednisolone | Phenacetin | Loratadine |
| tenofovir | Dinoprost | Forskolin |
| Quercetin | Tetradecanoylphorbol Acetate | glimepiride |
| 4-(5-benzo(1,3)dioxol-5-yl-4-pyridin-2-yl-1H-imidazol-2-yl)benzamide | Vancomycin | Cycloheximide |
| Azauridine | Caffeine | Methyl Methanesulfonate |
| Tunicamycin | Monocrotaline | Fluoxetine |
| Chlormadinone Acetate | Metronidazole | Betamethasone |
| Ethinyl Estradiol | Methotrexate | Bucladesine |
| Ethionine | Folic Acid | atorvastatin |
| Amiodarone | sodium arsenite | hydrazine |
| Prednisolone | Genistein | Lovastatin |
| Trimethadione | gatifloxacin | Diazepam |
| bortezomib | Fenofibrate | Nitrofurantoin |
| Diethylnitrosamine | Neomycin | BCG Vaccine |
| Ethionamide | fluvastatin | pioglitazone |
| troglitazone | leflunomide | bisphenol A |
| Poly I-C | Ionomyin | Epitestosterone |
| Cyclosporine | Indomethacin | Miconazole |
| Vincristine | Colchicine | Chlorpromazine |

TABLE S1-continued

Molecules that regulate genes or gene products relevant to proline transport and metabolism.

| | | |
|---|---|---|
| Azithromycin | Carbon Tetrachloride | Ibuprofen |
| Diclofenac | Gemfibrozil | Bezafibrate |
| Thioacetamide | | |

U1. Molecules that upregulate TP53:

| | | |
|---|---|---|
| sangivamycin | 4-amino-6-hydrazino-7-beta-D-ribofuranosyl-7H-pyrrolo(2,3-d)-pyrimidine-5-carboxamide | Curcumin |
| pirlindole | Paclitaxel | Piroxicam |
| Ethionine | Mannitol | versipelostatin |
| Caerulein | 2-Acetylaminofluorene | Ethylene Oxide |
| Dimethylnitrosamine | Acetylmuramyl-Alanyl-Isoglutamine | sapphyrin |
| Foscarnet | Sulfisoxazole | Dicloxacillin |
| 4-(N-methyl-N-nitrosamino)-1-(3-pyridyl)-1-butanone | Cefmetazole | Diclofenac |
| isoxicam | Go 6976 | thiocolchicoside |
| Oxytocin | Plicamycin | tranilast |
| alphaxalone | Moricizine | Fluorouracil |
| 1-hydroxycholecalciferol | 1-Methyl-4-phenyl-1,2,3,6-tetrahydropyridine | Diethylhexyl Phthalate |
| Idoxuridine | Mitomycin | hexachlorobutadiene |
| Viomycin | phenoclor | Gentamicins |
| benoxaprofen | Zalcitabine | Isoniazid |
| Estradiol | lead tetraacetate | Midodrine |
| Pyrazinamide | naphthalene | Nickel |
| Spironolactone | Amiodarone | Emetine |
| Ethynodiol Diacetate | Phenobarbital | Oxyquinoline |
| Thioacetamide | bisphenol A | PI103 |
| flumequine | estradiol 3-benzoate | Methylene Chloride |
| Vecuronium Bromide | apratoxin A | Phytohemagglutinins |
| Benzo(a)pyrene | glycitein | lornoxicam |
| motexafin gadolinium | Benzethonium | Y 27632 |
| Yellow Fever Vaccine | fasudil | Netilmicin |
| flavanone | Nifedipine | Histidinol |
| (melle-4)cyclosporin | Ethambutol | Naproxen |
| Ketorolac | eseroline | testosterone 17 beta-cypionate |
| Megestrol Acetate | Acrolein | hydrastine |
| pipenzolate | Methylcholanthrene | Aristolochic Acids |
| Cyclosporine | Diethylnitrosamine | Furosemide |
| Methimazole | Nordefrin | aceclofenac |
| Oxytetracycline | Sulfaphenazole | phenacemide |
| Aconitine | Ethionamide | Methyldopa |
| Molsidomine | Botulinum Toxins | Orotic Acid |
| 1,3-dichlorobenzene | Malathion | phenothiazine |
| daidzein | Cephapirin | temafloxacin |
| artemisinine | Botulinum Toxins, Type A | Tunicamycin |
| piclamilast | Didanosine | Roflumilast |
| Epitestosterone | Soman | Metformin |
| Cefoxitin | Nom ifensine | hexachloroethane |
| sulfathiazole | 4-octylphenol | Methotrexate |
| deferiprone | Mebendazole | quintozene |
| Nitrofurazone | Dihydrotestosterone | sodium arsenite |
| Sulfadoxine | Betamethasone | ethamivan |
| monophosphoryl lipid A | Lomustine | erlotinib |
| Enalapril | Ranitidine | Clotrimazole |
| triptolide | Rifampin | Bupropion |
| Acetylcysteine | lactacystin | direct black 3 |
| HI 6 | nateglinide | 1,5-naphthalenediamine |
| tris(2,3-dibromopropyl)phosphate | Quinpirole | sildenafil |
| Captopril | Vitamin E | nimesulide |
| lead acetate | Ribostamycin | sodium selenate |
| Methapyrilene | Disulfiram | Tetradecanoylphorbol Acetate |
| Monocrotaline | Tryptophan | Forskolin |
| Mifepristone | Risperidone | Ganciclovir |
| polidocanol | Remoxipride | beta-cyclodextrin-benzaldehyde |
| N-Ac-CHAVC-NH2 | Abscisic Acid | isopyrin |
| Metribolone | 6-azathymine | Azacitidine |
| benazepril | Bethanechol | Famotidine |
| Vancomycin | diisopropyl methylphosphonate | Ethylene Dibromide |
| Fluspirilene | atorvastatin | iodoform |
| 7,8-Dihydro-7,8-dihydroxybenzo(a)pyrene 9,10-oxide | Oxyphenisatin Acetate | 1-amino-2,4-dibromoanthraquinone |
| Ionidamine | Pinacidil | methylatropine |
| Estriol | Melphalan | cephaelin |

TABLE S1-continued

Molecules that regulate genes or gene products relevant to proline transport and metabolism.

| | | |
|---|---|---|
| Pirenzepine | Altretamine | beta-Naphthoflavone |
| alpha-Amino-3-hydroxy-5-methyl-4-isoxazolepropionic Acid | Cadmium | Mesna |
| Bithionol | Ibuprofen | Nafronyl |
| Tolazoline | Sotalol | Muromonab-CD3 |
| Calcitriol | amitraz | Amphotericin B |
| Cholecalciferol | Sulbactam | Insulin |
| Beclomethasone | Cardiotoxins | Azlocillin |
| SU 5416 | Selenomethionine | oxcarbazepine |
| Kanamycin | Lithium | Etodolac |
| 1,2,3-trichloropropane | Mephenytoin | Clarithromycin |
| Carboplatin | Chlorpromazine | Enoxacin |
| Azithromycin | modafinil | Cyproterone Acetate |
| hydroxytamoxifen | Moxalactam | Ciprofloxacin |
| Milrinone | Miconazole | rituximab |
| Ethinyl Estradiol | Aminosalicylic Acid | 6-Mercaptopurine |
| Freund's Adjuvant | CpG ODN 2216 | Methyltestosterone |
| Cyclophosphamide | Busulfan | nabumetone |
| Harmaline | Diflunisal | Lincomycin |
| Azathioprine | Cyclopenthiazide | Stavudine |
| N, N'-diphenyl-4-phenylenediamine | Rolipram | Phenylalanine |
| ONO 2235 | celecoxib | 4-hydroxy-2-nonenal |
| Sulindac | lamotrigine | Ketoprofen |
| Indomethacin | Digoxin | Cytarabine |
| Baclofen | fluvastatin | cilostazol |
| Nordihydroguaiaretic Acid | Amphetamine | Penicillamine |
| Nystatin | temozolomide | dibenzazepine |
| linezolid | lacidipine | flavopiridol |
| acadesine | olanzapine | Hydroxyurea |
| Nevirapine | Chlorpyrifos | Acetazolamide |
| Streptomycin | Niacin | ciprofibrate |
| Flupenthixol | Econazole | Allopurinol |
| 17-(allylamino)-17-demethoxygeldanamycin | Amlodipine | 2,2'-Dipyridyl |
| Nicotine | Nitrendipine | Neomycin |
| edelfosine | Mycophenolic Acid | Fluphenazine |
| Sumatriptan | canadine | Edrophonium |
| acetovanillone | Doxazosin | Domperidone |
| Atropine | N-Methylaspartate | Fluconazole |
| Lovastatin | mono-(2-ethylhexyl)phthalate | U 0126 |
| Dexfenfluramine | alpha-Tocopherol | Methazolamide |
| Ketoconazole | desloratadine | Aphidicolin |
| Quercetin | Citalopram | Nadolol |
| Podophyllotoxin | Perhexiline | leflunomide |
| ferulic acid | lansoprazole | MRK 003 |
| pirinixic acid | Omeprazole | Papaverine |
| Vinblastine | Kainic Acid | Luteolin |
| 4-(5-benzo(1,3)dioxol-5-yl-4-pyridin-2-yl-1H-imidazol-2-yl)benzamide | Lisinopril | Staurosporine |
| Nimodipine | NG-Nitroarginine Methyl Ester | tenofovir |
| Finasteride | Levodopa | Paroxetine |
| carvedilol | Aminoglutethimide | Terbutaline |
| Imipramine | Clonazepam | Pregnenolone Carbonitrile |
| anastrozole | pralidoxime | |
| U2. Molecules that downregulate TP53: | | |
| Cycloserine | monastrol | JM 3100 |
| nilutamide | Aclarubicin | 1-(5-Isoquinolinesulfonyl)-2-Methylpiperazine |
| blebbistatin | Vincristine | LBH589 |
| geldanamycin | N-benzyladenine | tridihexethyl |
| Dimethyl Sulfoxide | cyanoginosin LR | buflomedil |
| 4-acetylaminofluorene | trichostatin A | apicidin |
| Coumaphos | Cefotiam | PK 11195 |
| Prilocaine | HC toxin | Biotin |
| scriptaid | Butyric Acid | Deoxycholic Acid |
| Piracetam | 4,4'-diam inodiphenylmethane | Immunoglobulin M |
| Histamine | decitabine | Suppressor Factors, Immunologic |
| Doxycycline | Amikacin | Primaquine |
| bafilomycin A | Debrisoquin | 7-aminocephalosporanic acid |
| DDT | phenylhydrazine | Etiocholanolone |
| Simazine | 4-biphenylamine | Asbestos |
| Mycotoxins | 3-deazaneplanocin | 8-aminohexylamino cAMP |

TABLE S1-continued

Molecules that regulate genes or gene products relevant to proline transport and metabolism.

| | | |
|---|---|---|
| 9-(2-hydroxy-3-nonyl)adenine | Chlordiazepoxide | Theophylline |
| anisindione | Reserpine | geraniol |
| Bromhexine | Dobutamine | 2-(4-morpholinoanilino)-6-cyclohexylaminopurine |
| Piperonyl Butoxide | kavain | abamectin |
| pimethixene | bromodichloromethane | Sirolimus |
| halofuginone | Probucol | Clorgyline |
| Vitamin B 12 | Tetanus Toxin | ochratoxin A |
| Procainamide | diphenidol | cidofovir |
| compactin | Growth Hormone | Promegestone |
| Antibodies, Monoclonal | Bismuth | Ofloxacin |
| Eugenol | Ergocalciferols | Citric Acid |
| 1-ethyl-2-benzimidazolinone | N-Methyl-3,4-methylenedioxyamphetamine | Doxapram |
| Sparteine | adiphenine | Aflatoxin B1 |
| Valproic Acid | Sulfamonomethoxine | Cholera Toxin |
| Amoxapine | Cycloheximide | Acetaminophen |
| cineole | Phenol | Doxorubicin |
| Hydrocortisone | quelamycin | doxofylline |
| Sodium Dodecyl Sulfate | vinclozolin | Antimycin A |
| Lamivudine | Nitric Oxide | Fluoxetine |
| Ethacrynic Acid | Flavoxate | Guanethidine |
| Dactinomycin | Lindane | vorinostat |
| Zinc Oxide | Triacetin | Methylnitrosourea |
| clinafloxacin | rifapentine | CPG-oligonucleotide |
| phensuximide | Disopyramide | benfluorex |
| Methoxsalen | Flufenamic Acid | Fusaric Acid |
| Carcinogens | irinotecan | 4-dichlorobenzene |
| Tacrine | Chlorpropamide | Tetracycline |
| Anti-Retroviral Agents | Azaperone | eburnamonine |
| methiazole | Cam ptothecin | Carbimazole |
| Buspirone | aluminum sulfate | Erythromycin |
| vinylidene chloride | Diltiazem | tosufloxacin |
| rauwolscine-OHPC | Buform in | pioglitazone |
| temsirolimus | Chloroquine | Colchicine |
| Ethyl Methanesulfonate | Lidocaine | Prochlorperazine |
| Nitrofurantoin | Etidronic Acid | Caffeine |
| Terazosin | Prednisolone | Dexamethasone |
| Moxisylyte | Amiloride | dexamisole |
| Alprazolam | Medroxyprogesterone | Daunorubicin |
| Fenbendazole | Deoxyglucose | methyl salicylate |
| Zidovudine | Ticlopidine | Fluocinolone Acetonide |
| enzastaurin | Procaine | Chlorambucil |
| oxybenzone | Lactic Acid | 1,1,1-trichloroethane |
| Diazinon | Flunarizine | Genistein |
| interferon alfa-2b | Pyrilamine | Clomipramine |
| romidepsin | oxiconazole | Clofibric Acid |
| 4-methyl-N-(3-(4-methylimidazol-1-yl)-5-(trifluoromethyl)phenyl)-3-((4-pyridin-3-ylpyrimidin-2-yl)amino)benzamide | meloxicam | Clemastine |
| Haloperidol | bis(tri-n-butyltin)oxide | Dothiepin |
| Metoprolol | shogaol | Aminocaproic Acids |
| 8-Bromo Cyclic Adenosine Monophosphate | n-hexanal | Clofibrate |
| Chlorpheniramine | Etoposide | hexylcaine |
| Dantrolene | Methylprednisolone | resveratrol |
| Alpha-Amanitin | epoxomicin | colforsin |
| Ascorbic Acid | Folic Acid | Safrole |
| loxoprofen | Dimethylformamide | securinine |
| letrozole | ranolazine | adalimumab |
| X-Rays | Atenolol | Clonidine |
| naringin | Verapamil | Phenacetin |
| vinpocetine | gabapentin | Topotecan |
| Dipyridamole | Nifurtimox | Pergolide |
| Losartan | Alendronate | Gemfibrozil |
| Promazine | tianeptine | Hexachlorophene |
| Loratadine | bortezomib | 1,10-phenanthroline |
| Oxymetazoline | candesartan | Azaguanine |
| Inosine Monophosphate | pantoprazole | Granisetron |
| Pentolinium Tartrate | efavirenz | Ifosfamide |
| Methyl Methanesulfonate | sorafenib | Doxepin |
| cerivastatin | 2-(4-morpholinyl)-8-phenyl-4H-1-benzopyran-4-one | Phenylephrine |
| Propidium | Mesoridazine | ebselen |
| Aspirin | Dichlororibofuranosylbenzimidazole | Deferoxamine |
| VX | Gallamine Triethiodide | Isoflurophate |
| Clozapine | imatinib | Norepinephrine |
| Nocodazole | Metergoline | Rotenone |
| tropisetron | Simvastatin | Mianserin |
| ebastine | Sarin | Sulpiride |

TABLE S1-continued

Molecules that regulate genes or gene products relevant to proline transport and metabolism.

| | | |
|---|---|---|
| Propranolol | Gabexate | Thioridazine |
| Clindamycin | 3,3',4',5-tetrachlorosalicylanilide | Indinavir |
| Dimenhydrinate | 1-Methyl-3-isobutylxanthine | Ribavirin |
| Brefeldin A | Pravastatin | zaleplon |
| Dicumarol | valdecoxib | Terfenadine |
| Phenelzine | Timolol | Melatonin |
| Carmustine | fragment C, human serum albumin | Diazepam |
| Chloramphenicol | Nitrazepam | Shiga Toxin |
| Isoproterenol | 2-methoxyestradiol | Amitriptyline |
| Fluvoxamine | phosphonoacetamide | isoascorbic acid |
| clopidogrel | 2,3-dioxo-6-nitro-7-sulfamoylbenzo(f)quinoxaline | Albendazole |
| Labetalol | Maprotiline | Choline |
| Trihexyphenidyl | zileuton | Propylthiouracil |
| rofecoxib | venlafaxine | Ionomyin |
| SU 5402 | Tocainide | Ramipril |
| Bezafibrate | Flurbiprofen | oxybutynin |
| dasatinib | gemcitabine | gefitinib |
| Tranylcypromine | Sertraline | Thioguanine |
| Vitamin K 3 | Promethazine | |
| V1. Molecules that upregulate PPAR-γ: | | |
| rosiglitazone | 1,5-naphthalenediamine | 2-(4-morpholinyl)-8-phenyl-4H-1-benzopyran-4-one |
| N, N'-diphenyl-4-phenylenediamine | Dimaprit | Lithocholic Acid |
| Ethylestrenol | Tolazamide | benphothiamine |
| 1,3-dichlorobenzene | compactin | artemether |
| Spironolactone | Brom hexine | amineptin |
| eperisone | Halcinonide | 5-fluorouridine |
| Erythromycin | Chlorzoxazone | Cinnarizine |
| Mycotoxins | Tretinoin | Azaguanine |
| Clioquinol | acemetacin | artemisinine |
| geraniol | Carbamazepine | Am 580 |
| ONO 2235 | Tinidazole | Isosorbide |
| Praziquantel | nateglinide | Niacinamide |
| GW 3965 | SU 5416 | Dipyridamole |
| trimethylcolchicinic acid | 3,3,4,5-tetrachlorosalicylanilide | Staurosporine |
| Danazol | Stavudine | Pyrazinamide |
| Tropicamide | Curcumin | Raloxifene |
| 4-acetylaminofluorene | Pentolinium Tartrate | Colchicine |
| Dipyrone | zileuton | ipriflavone |
| Methyltestosterone | salicylamide | Thioridazine |
| Warfarin | diphenidol | Metoclopramide |
| 1-Methyl-3-isobutylxanthine | Hemin | Atractyloside |
| nabumetone | 9-(2-hydroxy-3-nonyl)adenine | Apomorphine |
| Monensin | Nisoldipine | Buthionine Sulfoximine |
| cetraxate | 4,5-dianilinophthalimide | Prochlorperazine |
| Hydralazine | Oxyquinoline | Loperamide |
| Propylthiouracil | N-acetylsphingosine | daboiatoxin |
| anisindione | ponasterone A | Citric Acid |
| Alprazolam | Estriol | pantoprazole |
| Phytohemagglutinins | diisopropyl methylphosphonate | Isocarboxazid |
| Clomipramine | dibenzazepine | Ticrynafen |
| norethindrone acetate | Granisetron | Lithium Carbonate |
| Sulfaphenazole | cyclazosin | Triacetin |
| Amoxapine | 3-nitropropionic acid | Mestranol |
| Ofloxacin | Bupropion | hydrazine |
| Penicillin G | Ifosfamide | Floxuridine |
| Tranexamic Acid | Bendroflumethiazide | idebenone |
| Mianserin | flavanone | Malathion |
| Neomycin | Aminosalicylic Acid | tosufloxacin |
| 4-(4-fluorophenyl)-2-(4-hydroxyphenyl)-5-(4-pyridyl)imidazole | Cyproterone Acetate | Ciprofloxacin |
| benoxaprofen | dexchlorpheniramine | Fludrocortisone |
| Methapyrilene | Guaifenesin | Flurandrenolone |
| Fluocinonide | trichlorofluoromethane | Terazosin |
| Histamine | 6-methoxy-2-naphthylacetic acid | Concanavalin A |
| Metformin | Ticlopidine | amitraz |
| Primidone | Idarubicin | lansoprazole |
| epigallocatechin gallate | desloratadine | Lasalocid |
| Flavoxate | doxifluridine | zopiclone |
| Sertraline | Clonazepam | Dimenhydrinate |
| Cyclosporine | Tacrolimus | Clotrimazole |
| Sulfisoxazole | bisphenol A | Cytochalasin D |
| mycophenolate mofetil | Albuterol | lactacystin |
| Triamterene | Nitrazepam | Glycine |
| Carboplatin | Vincamine | Omeprazole |
| Gossypol | Amlodipine | Nitrofurazone |

TABLE S1-continued

Molecules that regulate genes or gene products relevant to proline transport and metabolism.

| | | |
|---|---|---|
| 8-Bromo Cyclic Adenosine Monophosphate | 4-(5-benzo(1,3)dioxol-5-yl-4-pyridin-2-yl-1H-imidazol-2-yl)benzamide | romidepsin |
| Hexachlorophene | oxfendazole | gabapentin |
| Insulin | Promazine | Dinitrofluorobenzene |
| resveratrol | Acetazolamide | quetiapine |
| beta-1,3-glucan | Metribolone | Neostigmine |
| Merbromin | neuropeptide Y (18-36) | Chlorthalidone |
| Paraquat | Methimazole | Epinephrine |
| methyl salicylate | flunisolide | Bezafibrate |
| doxofylline | Aspirin | glimepiride |
| 2-Acetylaminofluorene | 1,1,1-trichloroethane | 2-(4-morpholinoanilino)-6-cyclohexylaminopurine |
| Milrinone | Ganciclovir | Gemfibrozil |
| Phenylephrine | phorbolol myristate acetate | Glipizide |
| Mefenamic Acid | Chlormezanone | leflunomide |
| Oxymetholone | abamectin | Metronidazole |
| Chlordiazepoxide | terbinafine | Triiodothyronine |
| Tamoxifen | 1-hydroxycholecalciferol | Immunotoxins |
| rabeprazole | Cadmium | cyanoginosin LR |
| Minoxidil | oxaliplatin | Budesonide |
| Fluoxetine | Safrole | lamotrigine |
| Nafcillin | Endotoxins | Epirubicin |
| Sotalol | Terfenadine | sodium arsenite |
| Trifluoperazine | Benzo(a)pyrene | MK 0591 |
| diflorasone diacetate | Diethylhexyl Phthalate | Oxymetazoline |
| Ritonavir | decitabine | Griseofulvin |
| clopidogrel | Bretylium Tosylate | 6-Mercaptopurine |
| loxoprofen | Etidronic Acid | Aflatoxins |
| CD 437 | 4-dichlorobenzene | Rifabutin |
| Nafenopin | vanoxerine | 4,4'-diaminodiphenylmethane |
| Bleomycin | Daunorubicin | Phenobarbital |
| 4-nonylphenol | Carbimazole | olmesartan |
| flubendazole | Losartan | sildenafil |
| salsolidine | blebbistatin | Methotrimeprazine |
| Calcitriol | ibufenac | Rolipram |
| iturelix | Folic Acid | Loratadine |
| Tiapamil Hydrochloride | candesartan | Desipramine |
| Norepinephrine | bromobenzene | Cholecalciferol |
| parbendazole | Ethionamide | venlafaxine |
| 8-((4-chlorophenyl)thio)cyclic-3',5-AMP | Tolazoline | bromperidol |
| Cefoxitin | Aflatoxin B1 | Timolol |
| Anisomycin | Labetalol | Phalloidine |
| Ethacrynic Acid | trovafloxacin | Amantadine |
| Bromisovalum | bephenium hydroxynaphthoate | Protriptyline |
| Camptothecin | valdecoxib | Doxapram |
| Clemastine | Doxepin | Diethylnitrosamine |
| Procarbazine | tranilast | Gallamine Triethiodide |
| sulconazole | letrozole | diloxanide furoate |
| Phosphorylcholine | Phenacetin | marimastat |
| Clenbuterol | Lorazepam | Sulfachlorpyridazine |
| fomepizole | Amanitins | Streptozocin |
| Aminoglutethimide | Escin | Cromolyn Sodium |
| phenethyl isothiocyanate | Ketoprofen | Cefoperazone |
| Thioacetamide | Cobalt | trilinolein |
| 1-(5-Isoquinolinesulfonyl)-2-Methylpiperazine | Penicillamine | lapatinib |
| Isoniazid | rofecoxib | Quinacrine |
| bafilomycin A | Clonidine | Trihexyphenidyl |
| 4'-N-benzoylstaurosporine | Tetracycline | Triazolam |
| Quercetin | Flunarizine | Clozapine |
| Betazole | Fluspirilene | Sulpiride |
| Nordihydroguaiaretic Acid | oltipraz | celecoxib |
| Cyclophosphamide | Clofibric Acid | SB 203580 |
| Atenolol | Diazepam | Catechin |
| benzamil | Dihydroergotamine | Perhexiline |
| Propranolol | cephaelin | Y 27632 |
| Alprostadil | Deoxyglucose | Nizatidine |
| Cycloserine | Alprenolol | Metaproterenol |
| Captopril | Vincristine | wortmannin |
| Nortriptyline | imatinib | Clarithromycin |
| Choline | Famotidine | Rotenone |
| Carbachol | Vidarabine | Nocodazole |
| Phenelzine | Moxisylyte | gemcitabine |
| Paroxetine | Cocaine | Verapamil |
| Ionomycin | Deferoxamine | Haloperidol |
| olanzapine | Ramipril | Levodopa |
| Melatonin | Emetine | Podophyllotoxin |
| Maprotiline | Azacitidine | Amitriptyline |
| Nitric Oxide | Thapsigargin | Nevirapine |

TABLE S1-continued

Molecules that regulate genes or gene products relevant to proline transport and metabolism.

| | | |
|---|---|---|
| U 0126 | Dichlorvos | Allopurinol |
| Ascorbic Acid | triptolide | Atropine |
| Perphenazine | ochratoxin A | Ribavirin |
| Vitamin K 3 | Kainic Acid | Gentamicins |
| Chitosan | | |
| V2. Molecules that downregulate PPAR-γ: | | |
| troglitazone | pioglitazone | tomatidine |
| ebastine | N-Methylaspartate | Diphenhydramine |
| nifuroxazide | Betaxolol | imazalil |
| Prostaglandins E | titanium dioxide | Benzethonium |
| chloroxylenol | Mycophenolic Acid | Hydrogel |
| oxiconazole | 8-(3-Chlorostyryl)-1,3,7-trimethylxanthine | 15-deoxy-delta(12,14)-prostaglandin J2 |
| Thiostrepton | Methylcholanthrene | Dinoprostone |
| Ibuprofen | lycorine | Gentian Violet |
| 1,2,3-trichloropropane | Itraconazole | Isoproterenol |
| Etodolac | Ketoconazole | Acetylmuramyl-Alanyl-Isoglutamine |
| Sulindac | Zidovudine | Hydrocortisone |
| pramoxine | Vinblastine | telmisartan |
| Estradiol | Fenoprofen | Adenosine-5'-(N-ethylcarboxamide) |
| Phenoxybenzamine | Isotretinoin | Fluocinolone Acetonide |
| Droperidol | atorvastatin | Foscarnet |
| Topotecan | arsenic trioxide | MRK 003 |
| Hemicholinium 3 | Ethylnitrosourea | Immunoglobulins, Intravenous |
| Acetaminophen | Valproic Acid | Methylnitrosourea |
| BCG Vaccine | carvedilol | Primaquine |
| Chlorhexidine | Chlorambucil | Ketorolac |
| gliquidone | Ceftazidime | ranolazine |
| Apazone | withaferin A | Dexamethasone |
| Finasteride | Thioguanine | Methyldopa |
| Cholera Toxin | Coumarins | 4-hydroxytamoxifen |
| Ethylene Glycol | Antigen-Antibody Complex | zardaverine |
| Nitrendipine | Methotrexate | Chorionic Gonadotropin |
| Dichlororibofuranosylbenzimidazole | Cetylpyridinium | Growth Hormone |
| Nystatin | Cortisone | Indomethacin |
| Carbon Tetrachloride | Chlorpromazine | Methoxsalen |
| fazarabine | Ambroxol | Busulfan |
| Fluconazole | Cytarabine | Digoxin |
| infliximab | lornoxicam | Diclofenac |
| cinchonine | Enoxacin | Naproxen |
| Monocrotaline | monobenzone | Remoxipride |
| Lovastatin | nimesulide | Cefuroxime |
| Ultraviolet Rays | Dobutamine | 4-octylphenol |
| riddelliine | fluvastatin | Pyrilamine |
| indole-3-carbinol | Dinoprost | monophosphoryl lipid A |
| sapphyrin | Roflumilast | Albendazole |
| Baclofen | Norethindrone | benazepril |
| phenothiazine | irbesartan | Azithromycin |
| cerivastatin | phosphonoacetamide | Disulfiram |
| Tocainide | marinobufagenin | Vanadates |
| Tetrachlorodibenzodioxin | Dexfenfluramine | Betamethasone |
| tenidap | sparfloxacin | Poly I-C |
| 4-(N-methyl-N-nitrosamino)-1-(3-pyridyl)-1-butanone | Mebendazole | 3,3',5-triiodothyroacetic acid |
| Debrisoquin | Strophanthidin | senecionine |
| Ethinyl Estradiol | lanatoside C | Ethoxyquin |
| Fluphenazine | meloxicam | Hydroxyurea |
| shikonin | Diflunisal | alginic acid |
| Glafenine | Zalcitabine | Palmitic Acid |
| Prednisone | Simvastatin | 2-(1H-indazol-4-yl)-6-(4-methanesulfonylpiperazin-1-ylmethyl)-4-morpholin-4-ylthieno(3,2-d)pyrimidine |
| sunitinib | erlotinib | Azathioprine |
| Fenoterol | Mifepristone | geldanamycin |
| Hyaluronic Acid | Gonadotropins | Trimetazidine |
| Cimetidine | Tetrahydrocannabinol | Pravastatin |
| 1,10-phenanthroline | trichostatin A | lomefloxacin |
| beta-Naphthoflavone | Econazole | Estrogens |
| piperlonguminine | Ergocalciferols | tracazolate |
| Doxorubicin | Bisacodyl | Lamivudine |
| glycidol | Forskolin | acidocin CH5, *Lactobacillus acidophilus* |
| NSC 652287 | Cisplatin | pepstatin |
| Spiperone | Tryptophan | Kanamycin |

TABLE S1-continued

Molecules that regulate genes or gene products relevant to proline transport and metabolism.

| | | |
|---|---|---|
| vorinostat | valsartan | Lithium |
| hydroquinone | Streptomycin | 17-(allylamino)-17-demethoxygeldanamycin |
| sodium selenate | Amiodarone | Dicumarol |
| Carmustine | Metoprolol | acadesine |
| Genistein | gefitinib | Tubocurarine |
| Papaverine | Methyl Methanesulfonate | Physostigmine |
| Clofibrate | Doxazosin | Risperidone |
| Ranitidine | apicidin | Citalopram |
| fasudil | 4-methyl-N-(3-(4-methylimidazol-1-yl)-5-(trifluoromethyl)phenyl)-3-((4-pyridin-3-ylpyrimidin-2-yl)amino)benzamide | Betahistine |
| ellipticine | Miconazole | Digitoxin |
| Diltiazem | Thiethylperazine | Chlorpyrifos |
| Furazolidone | LBH589 | diphenylpyraline |
| dasatinib | Dactinomycin | Puromycin |
| Furosemide | Promethazine | Lomustine |
| hesperetin | Mitomycin | Pyrogallol |
| Altretamine | linezolid | N-Methyl-3,4-methylenedioxyamphetamine |
| Tranylcypromine | Vitamin E | monorden |
| Ouabain | Paclitaxel | Caffeine |
| isoascorbic acid | ciprofibrate | Netilmicin |
| Azauridine | Nimodipine | pirinixic acid |
| Chloramphenicol | lysophosphatidic acid | Enalapril |
| mono-(2-ethylhexyl)phthalate | Dicyclomine | Cycloheximide |
| Imipramine | Buspirone | Alpha-Amanitin |
| Theophylline | Probucol | pralidoxime |
| Fluorouracil | irinotecan | sorafenib |
| bortezomib | | |

W1. Molecules that upregulate TMEM27:

| | | |
|---|---|---|
| Mitomycin | resveratrol | cidofovir |
| NG-Nitroarginine Methyl Ester | Neomycin | Neostigmine |
| Lorazepam | flubendazole | Methocarbamol |
| Methylnitrosourea | hydrazine | Fenbendazole |
| fluvastatin | Cetylpyridinium | geraniol |
| PK 11195 | Promazine | Cymarine |
| Oxytetracycline | PI103 | testosterone 17 beta-cypionate |
| atorvastatin | Mycophenolic Acid | Famotidine |
| norethindrone acetate | salicylamide | diphenidol |
| Nitrendipine | Enterobactin | Clomipramine |
| Poly I-C | Doxorubicin | closantel |
| artemisinine | ipriflavone | Bromisovalum |
| nateglinide | Daunorubicin | Clotrimazole |
| Alprazolam | Verapamil | oxcarbazepine |
| pralidoxime | Galantamine | balsalazide |
| Nizatidine | sulfathiazole | Diazepam |
| benazepril | Moclobemide | 3-hydroxyacetanilide |
| Testosterone | Labetalol | Flunarizine |
| Baclofen | Ethinyl Estradiol | Tramadol |
| Cisplatin | Piracetam | 4,4'-diaminodiphenylmethane |
| Tranexamic Acid | Diethylstilbestrol | Aflatoxin B1 |
| gabapentin | Methimazole | Benzo(a)pyrene |
| Hemin | Paroxetine | Clofibrate |
| olanzapine | oxybutynin | Zinc Oxide |
| 6-Mercaptopurine | Aclarubicin | Pentoxifylline |
| Finasteride | Clofibric Acid | 2-(1H-indazol-4-yl)-6-(4-methanesulfonylpiperazin-1-ylmethyl)-4-morpholin-4-ylthieno(3,2-d)pyrimidine |
| Prazosin | Stanozolol | Cimetidine |
| Busulfan | nimesulide | Simvastatin |
| Metoprolol | Secobarbital | Benzalkonium Compounds |
| Tamoxifen | Mifepristone | Amlodipine |
| Sulindac | anastrozole | Sotalol |
| Propranolol | Chloroform | Clemastine |
| Clarithromycin | Amitriptyline | quetiapine |
| geldanamycin | Prednisolone | Thiabendazole |
| moxonidine | cerivastatin | valsartan |
| Captopril | Alpha-Amanitin | Procaine |
| Spironolactone | motexafin gadolinium | Itraconazole |
| Miconazole | Econazole | Cytokines |
| leflunomide | Dimethyl Sulfoxide | erlotinib |
| Calcium | Acetaminophen | Hydroxyurea |
| Etoposide | Ethylene Glycol | Bezafibrate |

TABLE S1-continued

Molecules that regulate genes or gene products relevant to proline transport and metabolism.

| | | |
|---|---|---|
| Clobetasol | Indomethacin | Diethylhexyl Phthalate |
| Clonidine | Methotrexate | Enterotoxins |
| 2-amino-1-methyl-6-phenylimidazo(4,5-b)pyridine | Mercuric Chloride | Glycine |
| Ketoconazole | Sumatriptan | Aspirin |
| Pemoline | Chlorambucil | Fenoprofen |
| Equilin | Cyproheptadine | dibenzazepine |
| Lovastatin | Griseofulvin | Diclofenac |
| Cyclosporine | decitabine | Zinc |
| zomepirac | Carmustine | aceclofenac |
| Chlormadinone Acetate | Ibuprofen | Aminocaproic Acids |
| meloxicam | Fluphenazine | Ergocalciferols |
| Clomiphene | ochratoxin A | dexibuprofen |
| Roxarsone | Chloramphenicol | Norethindrone |
| Ribavirin | withaferin A | Diflunisal |
| Ritonavir | Azacitidine | Sulfadimethoxine |
| enrofloxacin | Fenofibrate | monastrol |
| trichostatin A | vinylidene chloride | blebbistatin |
| Doxycycline | Vincristine | Naproxen |
| Dantrolene | Ethanol | Ramipril |
| Piroxicam | Carbamazepine | Tretinoin |
| Bromhexine | 17-(allylamino)-17-demethoxygeldanamycin | fulvestrant |
| Gemfibrozil | Carboplatin | Hydrochloric Acid |
| candesartan | Soman | Dinoprost |
| Cycloheximide | Netilmicin | Folic Acid |
| HI 6 | Sirolimus | Dimethylformamide |
| zileuton | Hydrochlorothiazide | bevacizumab |
| methylatropine | Tetracycline | pantoprazole |
| lapatinib | Quercetin | Thapsigargin |
| rofecoxib | Carbon Tetrachloride | oxaliplatin |
| Rotenone | valdecoxib | Azathioprine |
| Nicotine | Tacrine | Lactic Acid |
| Epirubicin | vorinostat | bortezomib |
| quelamycin | Fluconazole | Penicillamine |
| U 0126 | Progesterone | infliximab |
| Acetazolamide | Isotretinoin | Risperidone |
| Chlorpromazine | 4-(5-benzo(1,3)dioxol-5-yl-4-pyridin-2-yl-1H-imidazol-2-yl)benzamide | X-Rays |
| Bleomycin | | |
| W2. Molecules that downregulate TMEM27: | | |
| oxfendazole | Oxyquinoline | Estriol |
| meropenem | chloroxylenol | Cyproterone Acetate |
| sorafenib | cyclonite | Nystatin |
| Trichloroacetic Acid | Aztreonam | pramoxine |
| Atropine | daidzein | Gentamicins |
| Menthol | Am 580 | bromodichloromethane |
| Melphalan | Fonofos | Promegestone |
| bisphenol A | Acyclovir | Bacitracin |
| sulconazole | Noscapine | Estradiol |
| Allopurinol | gefitinib | Lead |
| VX | Acetylmuramyl-Alanyl-Isoglutamine | chlorinated dibenzofurans |
| Valproic Acid | famciclovir | Fluocinolone Acetonide |
| lead acetate | 4'-N-benzoylstaurosporine | 2-dichlorobenzene |
| Genistein | Diethylnitrosamine | Aphidicolin |
| hydroquinone | beta-cyclodextrin-benzaldehyde | sodium arsenite |
| SU 5402 | shikonin | Paclitaxel |
| Cephaloridine | tianeptine | compactin |
| CPG-oligonucleotide | 1,2,3-trichloropropane | 3-deazaneplanocin |
| fragment C, human serum albumin | Pravastatin | Theophylline |
| Ifosfamide | Acetylcysteine | enzastaurin |
| linalool | Thioguanine | triadimefon |
| gatifloxacin | oxaprozin | penciclovir |
| Dexamethasone | Ouabain | Perhexiline |
| Chorionic Gonadotropin | Vancomycin | lead tetraacetate |
| Metribolone | Trichloroethylene | trovafloxacin |
| Benzethonium | pioglitazone | Insulin |
| 4-nonylphenol | Flurbiprofen | Colchicine |
| Fluoxetine | Cam ptothecin | Cadmium |
| Cyclophosphamide | sulforafan | Monocrotaline |
| Papaverine | Danazol | Luteinizing Hormone |
| Trimethadione | Omeprazole | Fluorouracil |
| Medroxyprogesterone Acetate | Isoniazid | Disopyramide |
| aristolochic acid I | Ultraviolet Rays | Dihydrotestosterone |
| Flutamide | Methylprednisolone | rosiglitazone |

TABLE S1-continued

Molecules that regulate genes or gene products relevant to proline transport and metabolism.

| | | |
|---|---|---|
| Triiodothyronine | Bithionol | Caffeine |
| Amiodarone | Rifampin | Phenacetin |
| Tetradecanoylphorbol Acetate | Phenobarbital | Tetrachlorodibenzodioxin |

X1. Molecules that upregulate ACE2:

| | | |
|---|---|---|
| Oxytetracycline | Ethylene Dibromide | erlotinib |
| Calcium | diperodon | N-methylolacrylamide |
| Y 27632 | Fursultiamin | hydroxyachillin |
| Sulfisoxazole | Bendroflumethiazide | Terbutaline |
| Aflatoxins | Trichlormethiazide | quintozene |
| althiazide | naphthalan | Pyrogens |
| Poly I-C | acetylleucine | epitiostanol |
| 2-(4-morpholinoanilino)-6-cyclohexylaminopurine | Cytarabine | Colistin |
| 2-dichlorobenzene | Cytochalasin D | cidofovir |
| Trichloroepoxypropane | Pregnenolone | Demeclocycline |
| apratoxin A | Sulfamethazine | Humic Substances |
| Piperacillin | 4-dichlorobenzene | Dequalinium |
| Cefmetazole | ethaverine | SC 514 |
| fosfosal | vinpocetine | carbetapentane |
| Ozone | canadine | diphemanil methylsulfate |
| 1,2-dilinolenoyl-3-(4-aminobutyryl)propane-1,2,3-triol | Doxorubicin | Reserpine |
| 4-hydroxy-2-nonenal | Cinoxacin | cinchonine |
| Testosterone | Methylene Chloride | bromobenzene |
| Captopril | N-nitrosomorpholine | tyloxapol |
| Ethambutol | oxybutynin | Ipratropium |
| sertaconazole | Isoflurane | Tetradecanoylphorbol Acetate |
| Tranylcypromine | Monocrotaline | solasodine |
| Oxytocin | Cefotaxime | citiolone |
| flunisolide | Tamoxifen | Propidium |
| Amrinone | Ethanol | gefitinib |
| Biotin | Daunorubicin | Sulfamethoxypyridazine |
| Thioacetamide | Gossypol | monobenzone |
| carcinine | Ribavirin | Roxithromycin |
| bevacizumab | Phentolamine | Lobeline |
| Bromocriptine | wortmannin | Flunarizine |
| vorinostat | medrysone | 16-ketoestradiol |
| Ampicillin | Dextran Sulfate | dexibuprofen |
| Clobetasol | Mitomycin | Alpha-Amanitin |
| Tretinoin | Sulfamethoxazole | Paroxetine |
| aluminum sulfate | oxidized-L-alpha-1-palmitoyl-2-arachidonoyl-sn-glycero-3-phosphorylcholine | Dehydroepiandrosterone |
| vinclozolin | triptolide | decitabine |
| Dexamethasone | peginterferon alfa-2a | Epitestosterone |
| 4-hydroxytamoxifen | Nitrofurantoin | Cholecalciferol |
| blebbistatin | trichostatin A | Azacitidine |
| Diquat | Procainamide | Forskolin |
| Cyclophosphamide | 1-Methyl-4-phenyl-1,2,3,6-tetrahydropyridine | torsemide |
| mycophenolate mofetil | Hydroxyzine | Aflatoxin B1 |
| Mycophenolic Acid | Oxyquinoline | Hydralazine |
| LBH589 | Hemin | pralidoxime |
| Mebendazole | Cephalothin | celecoxib |
| Hydrochloric Acid | fulvestrant | docetaxel |
| pioglitazone | Enalapril | Chitosan |
| Rifampin | Carbamazepine | Dactinomycin |
| Genistein | Diazepam | Nifedipine |
| Cycloheximide | Lactic Acid | Diethylhexyl Phthalate |
| Bezafibrate | Atropine | Promethazine |
| Metformin | Formaldehyde | Isoproterenol |
| Asbestos | | |

X2. Molecules that downregulate ACE2:

| | | |
|---|---|---|
| sunitinib | polidocanol | VX |
| sorafenib | ubiquinol | Dichlorvos |
| naphthalene | 2-methoxyestradiol | Azoxymethane |
| Ganciclovir | shikonin | 1,5-naphthalenediamine |
| 6-bromoindirubin-3'-oxime | 1-amino-2,4-dibromoanthraquinone | Tacrolimus |
| Benzalkonium Compounds | Hydrogel | Niacinamide |
| Bleomycin | ferric nitrilotriacetate | Malathion |
| Shiga Toxin | Folic Acid | tris(2,3-dibromopropyl)phosphate |
| Lead | bromodichloromethane | Clodronic Acid |
| Furosemide | heliotrine | Quercetin |
| enrofloxacin | perfluorooctane sulfonic acid | Choline |
| Norfloxacin | valdecoxib | Lindane |
| testosterone 17 beta-cypionate | Allopurinol | DDT |

TABLE S1-continued

Molecules that regulate genes or gene products relevant to proline transport and metabolism.

| | | |
|---|---|---|
| Tetrachloroethylene | Ultraviolet Rays | Cadmium |
| Acrolein | lead tetraacetate | 4'-N-benzoylstaurosporine |
| Cyclosporine | imatinib | Propylthiouracil |
| Sulindac | SB 203580 | versipelostatin |
| Dihydrotestosterone | Diazinon | Cisplatin |
| sulmazole | Methapyrilene | Eugenol |
| Terfenadine | Enterotoxins | Diethylstilbestrol |
| Fluocinolone Acetonide | R 848 | Methimazole |
| enterotoxin B, staphylococcal | Theophylline | Netilmicin |
| aristolochic acid I | cyclonite | Flurbiprofen |
| chlorinated dibenzofurans | SU 5402 | infliximab |
| Estradiol | Tacrine | oxaprozin |
| Bromisovalum | Ethylnitrosourea | Papaverine |
| Tetrachlorodibenzodioxin | Dinitrofluorobenzene | Deoxyglucose |
| Prednisolone | Capsaicin | Sirolimus |
| Praziquantel | Acetaminophen | fluvastatin |
| atorvastatin | Phosgene | Fluoxetine |
| CPG-oligonucleotide | Bacitracin | 4-(4-fluorophenyl)-2-(4-hydroxyphenyl)-5-(4-pyridyl)imidazole |
| Ethionine | Paclitaxel | rosiglitazone |
| U 0126 | trovafloxacin | Valproic Acid |
| Carboplatin | lapatinib | Isotretinoin |
| Azathioprine | Epirubicin | Naproxen |
| leflunomide | Lovastatin | bicalutamide |
| Isoniazid | Particulate Matter | Methotrexate |
| 17-(allylamino)-17-demethoxygeldanamycin | Colchicine | Vinblastine |
| Insulin | X-Rays | 2-(4-morpholinyl)-8-phenyl-4H-1-benzopyran-4-one |
| irinotecan | oxaliplatin | bisphenol A |
| arsenic trioxide | Cardiotoxins | Progesterone |
| Hydrocortisone | Cortisone | Danazol |
| Mifepristone | 1-Methyl-3-isobutylxanthine | Risperidone |
| Phenobarbital | Trimethadione | Omeprazole |
| Ifosfamide | Chlorambucil | Benzo(a)pyrene |
| Etoposide | Doxycycline | Diclofenac |
| Gemfibrozil | Hydrogen Peroxide | |

Y1. Molecules that upregulate PPAR-a:

| | | |
|---|---|---|
| Fenofibrate | N-Ac-CHAVC-NH2 | ferulic acid |
| ibufenac | Teicoplanin | 1-hydroxycholecalciferol |
| N, N'-diphenyl-4-phenylenediamine | eperisone | tranilast |
| temafloxacin | cetraxate | bromfenac |
| Ciprofloxacin | Fludrocortisone | sparfloxacin |
| Zalcitabine | Sotalol | amitraz |
| benoxaprofen | Amlodipine | Dipyrone |
| piclamilast | trovafloxacin | 1,1,1-trichloroethane |
| oxfendazole | Safrole | Acetylcysteine |
| Nafenopin | Butyric Acid | Rifabutin |
| rabeprazole | Spironolactone | Ketorolac |
| sodium arsenite | 1-(2-cyano-3,12-dioxooleana-1,9-dien-28-oyl)imidazole | methylparaben |
| Ethylestrenol | Cinnarizine | methyl salicylate |
| Sulindac | Ibuprofen | zomepirac |
| Erythromycin Ethylsuccinate | Cefsulodin | ONO 2235 |
| pantoprazole | Lomustine | Bromisovalum |
| Citric Acid | ipriflavone | Melatonin |
| phenylhydrazine | anastrozole | Omeprazole |
| Busulfan | zileuton | 2-Acetylaminofluorene |
| Roflumilast | beta-Naphthoflavone | Bupropion |
| hydrazine | sulfathiazole | troglitazone |
| Ergocalciferols | Sulfaphenazole | bromodichloromethane |
| Disulfiram | Azathioprine | geraniol |
| rosiglitazone | Carbamazepine | Rolipram |
| Cetylpyridinium | Perhexiline | Ethanol |
| Tacrine | Stanozolol | Amiodarone |
| Fenbendazole | Thioguanine | phenothiazine |
| Raloxifene | Erythromycin | Methylcholanthrene |
| Diethylnitrosamine | 2-nitrofluorene | flubendazole |
| bisphenol A | Ticrynafen | Methyldopa |
| Digoxin | Auranofin | zopiclone |
| sildenafil | balsalazide | Praziquantel |
| Diclofenac | Clomipramine | Propanil |
| pioglitazone | rofecoxib | Promethazine |
| Amantadine | lead acetate | Acetaminophen |
| Clofibric Acid | Pravastatin | Epitestosterone |
| Norethindrone | harman | Phenacetin |

TABLE S1-continued

Molecules that regulate genes or gene products relevant to proline transport and metabolism.

| | | |
|---|---|---|
| Nevirapine | Valproic Acid | Foscarnet |
| oxcarbazepine | deferiprone | Acetazolamide |
| Clonazepam | Neomycin | lead tetraacetate |
| imiquimod | Epirubicin | Niacinamide |
| Thiabendazole | erlotinib | Tocainide |
| zaleplon | 6-Mercaptopurine | Lovastatin |
| salicylamide | Mefenamic Acid | Ethylene Glycol |
| Aminoglutethimide | hexachloroethane | Alprazolam |
| Fluphenazine | 1,2-dilinolenoyl-3-(4-aminobutyryl)propane-1,2,3-triol | Clotrimazole |
| Clarithromycin | Indomethacin | Lidocaine |
| Methapyrilene | Griseofulvin | torsemide |
| Etoposide | 4,4'-diaminodiphenylmethane | Bithionol |
| nimesulide | Triacetin | Nisoldipine |
| Dexamethasone | Ketoconazole | 3-hydroxyacetanilide |
| terbinafine | Finasteride | Mifepristone |
| imatinib | Neostigmine | lamotrigine |
| MRK 003 | Citalopram | 4-biphenylamine |
| Oxymetazoline | Bezafibrate | Naproxen |
| Ofloxacin | gefitinib | Estradiol |
| Nifedipine | Sulfisoxazole | Trichloroethylene |
| fipronil | Albendazole | cryptoxanthin |
| Dimethylformamide | norethindrone acetate | Carmustine |
| Fluconazole | celecoxib | Dicloxacillin |
| Pyrogallol | Enoxacin | Bromhexine |
| Tolazamide | geldanamycin | Oxytetracycline |
| aluminum sulfate | Nitrofurantoin | Itraconazole |
| Aclarubicin | gamma-Tocopherol | Minoxidil |
| Chloroform | Choline | Caffeine |
| 4-nonylphenol | Simazine | Acyclovir |
| Streptomycin | compactin | Moxisylyte |
| tenofovir | Pyrazinamide | dexamisole |
| irinotecan | Ticlopidine | bicalutamide |
| Ivermectin | garcinol | Practolol |
| Econazole | Chlorpromazine | ovalicin |
| Gemfibrozil | closantel | Simvastatin |
| mosapride | Morphine | Sertraline |
| tosufloxacin | Gliclazide | Dexfenfluramine |
| Indinavir | Fenoprofen | trilinolein |
| fluvastatin | Curcumin | vinylidene chloride |
| Doxycycline | leflunomide | Menthol |
| diisopropyl methylphosphonate | diloxanide furoate | abamectin |
| Roxarsone | artemisinine | Staurosporine |
| Levamisole | bromobenzene | phenacemide |
| crotamiton | Metoclopramide | Propylthiouracil |
| Cytarabine | Mannitol | Miconazole |
| Gentamicins | Isoproterenol | 1-methyl-6-methoxy-dihydro-beta-carboline |
| Metronidazole | Diethylhexyl Phthalate | Pentoxifylline |
| Dichlorvos | Cefaclor | Tetrachlorodibenzodioxin |
| Benzocaine | dexchlorpheniramine | 4,5-dianilinophthalimide |
| Luteinizing Hormone | Niacin | Trichloroepoxypropane |
| ergocryptine | ponasterone A | diindolylmethane |
| ciprofibrate | Brefeldin A | Chlorambucil |
| Diazepam | Megestrol Acetate | Rolitetracycline |
| Carbon Tetrachloride | alpha-Tocopherol | Azithromycin |
| Quercetin | Thalidomide | Dimethylnitrosamine |
| Concanavalin A | Carbimazole | Trimethadione |
| Fluoxetine | Progesterone | Prednisone |
| nateglinide | fomepizole | Cobalt |
| Pemoline | Phenol | venlafaxine |
| Ketoprofen | dironyl | Chlorpyrifos |
| pimecrolimus | meloxicam | Cefuroxime |
| Nitrazepam | benziodarone | Lincomycin |
| acyline | valdecoxib | Cefotetan |
| 1,2,3-trichloropropane | 4-dichlorobenzene | Mexiletine |
| 17-(allylamino)-17-demethoxygeldanamycin | Ethambutol | Halothane |
| laudanosine | fazarabine | Cephalexin |
| Methylnitrosourea | Clofibrate | Am 580 |

TABLE S1-continued

Molecules that regulate genes or gene products relevant to proline transport and metabolism.

| | | |
|---|---|---|
| Aspirin | quetiapine | 2,4-diaminotoluene |
| bevacizumab | Mesna | Carboplatin |
| Eugenol | 2-(4-morpholinyl)-8-phenyl-4H-1-benzopyran-4-one | Hydroxyurea |
| 1-(5-Isoquinolinesulfonyl)-2-Methylpiperazine | bafilomycin A | Bisoprolol |
| N-(2-cyclohexyloxy-4-nitrophenyl)methanesulfonamide | Ritodrine | Ranitidine |
| atorvastatin | Dicyclomine | Levobunolol |
| Dipyridamole | Diazinon | Genistein |
| HC toxin | desloratadine | Puromycin |
| Labetalol | Zidovudine | scriptaid |
| 2-(1H-indazol-4-yl)-6-(4-methanesulfonylpiperazin-1-ylmethyl)-4-morpholin-4-ylthieno(3,2-d)pyrimidine | lansoprazole | Amitriptyline |
| Captopril | 2,2'-(hydroxynitrosohydrazono)bis-ethanamine | Doxepin |
| bromopride | vorinostat | gabapentin |
| CEP 14083 | Cimetidine | Enalapril |
| Diltiazem | Methyl Methanesulfonate | phenethyl isothiocyanate |
| chlorcyclizine | tenidap | Lam ivudine |
| hydroquinone | efavirenz | Isocarboxazid |
| Colchicine | 6-hydroxy-2,5,7,8-tetramethylchroman-2-carboxylic acid | Clindamycin |
| Carbachol | pirinixic acid | Diflunisal |
| Cisapride | Cyclophosphamide | Flurbiprofen |
| Pentobarbital | Bromocriptine | Rifampin |
| 8-Bromo Cyclic Adenosine Monophosphate | benzyloxycarbonylleucyl-leucyl-leucine aldehyde | Zimeldine |
| LBH589 | Norfloxacin | Lisinopril |
| Atovaquone | Iproniazid | Isoniazid |
| letrozole | N-acetylsphingosine | Promazine |
| Vidarabine | Heparin | 8-aminohexylamino cAMP |
| Propranolol | Flupenthixol | Fluorouracil |
| Droperidol | Amanitins | marimastat |
| Netilmicin | Cyproheptadine | Pergolide |
| 1-Methyl-4-phenyl-1,2,3,6-tetrahydropyridine | Ethionamide | apicidin |
| Losartan | Atropine | Mebendazole |
| Secobarbital | Saquinavir | Topotecan |
| Sulpiride | Azauridine | Clonidine |
| sorafenib | Oxyquinoline | Terbutaline |
| Hydrochlorothiazide | dasatinib | gemcitabine |
| Calcitriol | | |
| Y2. Molecules that downregulate PPAR-a: | | |
| Primidone | Trichloroacetic Acid | Proglumide |
| Tinidazole | tropisetron | Naloxone |
| Streptozocin | Capsaicin | artemether |
| Etodolac | Hexachlorophene | Ethisterone |
| Gentian Violet | bestatin | Phenobarbital |
| glimepiride | Tetracycline | vinorelbine |
| Okadaic Acid | Carotenoids | paricalcitol |
| Shiga Toxin | valacyclovir | Cortisone |
| isopyrin | versipelostatin | marinobufagenin |
| Altretamine | oxiconazole | Salicylic Acid |
| Ifosfamide | Cyproterone Acetate | Sulfamethoxazole |
| Cardiotoxins | Caerulein | Dextran Sulfate |
| fludarabine | senecionine | Methylcellulose |
| Amoxapine | idebenone | aceclofenac |
| Aminosalicylic Acid | Paclitaxel | Doxapram |
| Tunicamycin | arsenic trioxide | Cyclosporine |
| Methiocarb | Antipyrine | Phenformin |
| Benzethonium | olanzapine | anisindione |
| lacidipine | Heptachlor Epoxide | 3-deazaneplanocin |
| Nystatin | Phalloidine | 4-octylphenol |
| Buformin | pristane | n-hexanal |
| Rotenone | Aflatoxins | Lithium Carbonate |
| Ethylnitrosourea | Papaverine | sunitinib |
| decitabine | Chloroquine | blebbistatin |
| Dimenhydrinate | lomefloxacin | Piperonyl Butoxide |
| famciclovir | doxofylline | nimetazepam |
| Isotretinoin | Norepinephrine | shikonin |
| Stavudine | Methoxsalen | Plicamycin |
| Vinblastine | Kinetin | Clemastine |
| trichostatin A | Deoxyglucose | Cholecalciferol |
| Glycine | enterotoxin I, staphylococcal | Allopurinol |
| Tranexamic Acid | bamipine | Tacrolimus |
| MF59 oil emulsion | Azacitidine | cerivastatin |

TABLE S1-continued

Molecules that regulate genes or gene products relevant to proline transport and metabolism.

| | | |
|---|---|---|
| Tretinoin | 4-hydroxy-2-nonenal | beta-glycerophosphoric acid |
| Chlormadinone Acetate | Dihydrotestosterone | Mestranol |
| candesartan | Glycerol | Canavanine |
| benazepril | Vancomycin | Estriol |
| Furosemide | Phytohemagglutinins | Benzo(a)pyrene |
| Botulinum Toxins | Nadolol | Mitomycin |
| monastrol | Azoxymethane | Aminocaproic Acids |
| picotamide | Immunoglobulin M | polidocanol |
| Ondansetron | Methotrexate | Bacitracin |
| Insulin | procyanidin | loxoprofen |
| isoascorbic acid | Chlorhexidine | Antimycin A |
| Tetradecanoylphorbol Acetate | naphthalene | Lead |
| infliximab | Nimodipine | adalimumab |
| cineole | Theophylline | Bleomycin |
| buflomedil | Aflatoxin B1 | Mianserin |
| bis(tri-n-butyltin)oxide | Glipizide | cilostazol |
| Lorazepam | Vecuronium Bromide | carvedilol |
| Dimethyl Sulfoxide | Amiloride | Malathion |
| Ascorbic Acid | Vincristine | Tiapamil Hydrochloride |
| Ethionine | 4-amino-6-hydrazino-7-beta-D-ribofuranosyl-7H-pyrrolo(2,3-d)-pyrimidine-5-carboxamide | Buthionine Sulfoximine |
| valsartan | Echinomycin | Phenylephrine |
| Cycloheximide | Y 27632 | Reserpine |
| Isradipine | Digitoxin | Melphalan |
| cyanoginosin LR | Pregnenolone Carbonitrile | tenoxicam |
| SU 5402 | Penicillamine | Acarbose |
| Dactinomycin | fasudil | clopidogrel |
| Palmitic Acid | Paroxetine | U 0126 |
| Loratadine | Nitrendipine | Chlordiazepoxide |
| Prochlorperazine | SC 514 | Terfenadine |
| Nitric Oxide | Ritonavir | Gallamine Triethiodide |
| Emetine | Ramipril | Tubocurarine |
| Guanethidine | Verapamil | Prazosin |
| Luteolin | Buspirone | enzastaurin |
| Inosine Monophosphate | Diphenhydramine | Flunarizine |
| Camptothecin | resveratrol | Galantamine |
| Vitamin E | Haloperidol | Clozapine |
| Kainic Acid | SB 203580 | Atenolol |
| pralidoxime | Vitamin K 3 | Ionomyin |
| Deferoxamine | 4-(5-benzo(1,3)dioxol-5-yl-4-pyridin-2-yl-1H-imidazol-2-yl)benzamide | bortezomib |
| Nocodazole | | |

All patents, patent applications, and publications cited herein are incorporated herein by reference in their entirety as if recited in full herein.

The invention being thus described, it will be obvious that the same may be varied in many ways. Such variations are not to be regarded as a departure from the spirit and scope of the invention and all such modifications are intended to be included within the scope of the following claims.

CITED DOCUMENTS

1. Allen N C, et al. Systematic meta-analyses and field synopsis of genetic association studies in schizophrenia: the SzGene database. Nat Genet 2008; 40(7):827-34
2. Arnould A, Rochat L, Azouvi P, Van der Linden M. (2015) Apathetic symptom presentations in patients with severe traumatic brain injury: Assessment, heterogeneity and relationships with psychosocial functioning and caregivers' burden. Brain Inj. 29(13-14): 1597-603.
3. Baker K D, Skuse D H. Adolescents and young adults with 22q11 deletion syndrome: psychopathology in an at-risk group. Br J Psychiatry 2005; 186:115-20
4. Baxter C F, et al. High proline levels in the brains of mice as related to specific learning deficits. Pharmacol Biochem Behav 1985; 22(6):1053-9
5. Bender H U, et al. Functional consequences of PRODH missense mutations. Am J Hum Genet 2005; 76:409-20
6. Benoit M, Andrieu S, Lechowski L, Gillette-Guyonnet S, Robert P H, Vellas B; REAL-FR group. (2008) Apathy and depression in Alzheimer's disease are associated with functional deficit and psychotropic prescription. Int J Geriatr Psychiatry. 23(4):409-14.
7. Bilder R M, et al. The catechol-O-methyltransferase polymorphism: relations to the tonic-phasic dopamine hypothesis and neuropsychiatric phenotypes. Neuropsychopharmacology 2004; 29(11):1943-61
8. Blanchard J J, et al. Toward the next generation of negative symptom assessments: the collaboration to advance negative symptom assessment in schizophrenia. Schizophr Bull 2011; 37(2):291-9
9. Brodaty H, Connors M H, Xu J, Woodward M, Ames D. (2015) The course of neuropsychiatric symptoms in dementia: a 3-year longitudinal study. J Am Med Dir Assoc. 16(5):380-7.
10. Cattelani R, Roberti R, Lombardi F. (2008) Adverse effects of apathy and neurobehavioral deficits on the community integration of traumatic brain injury subjects. Eur J Phys Rehabil Med. September; 44(3):245-51.
11. Chen J, et al. Functional analysis of genetic variation in catechol-O-methyltransferase (COMT): effects on mRNA, protein, and enzyme activity in postmortem human brain. Am J Hum Genet 2004; 75(5):807-21
12. Clelland C L, et al. Evidence for association of hyperprolinemia with schizophrenia and a measure of clinical outcome. Schizophr Res 2011; 131(1-3):139-45

13. Clelland C L, et al. Evidence that COMT genotype and proline interact on negative-symptom outcomes in schizophrenia and bipolar disorder. Translational Psychiatry 2016. In press
14. Cohen S M, Nadler J V. Proline-induced inhibition of glutamate release in hippocampal area CA1. Brain Res 1997; 769:333-9
15. Cohen S M, Nadler J V. Proline-induced potentiation of glutamate transmission. Brain Res 1997; 761:271-82
16. Crabtree G W, et al. Cytosolic Accumulation of L-Proline Disrupts GABA-Ergic Transmission through GAD Blockade. Cell Rep 2016 Oct. 4; 17(2):570-582
17. de Jonghe J F, Goedhart A W, Ooms M E, Kat M G, Kalisvaart K J, van Ewijk W M, Ribbe M W. (2003) Negative symptoms in Alzheimer's disease: a confirmatory factor analysis. Int J Geriatr Psychiatry; 18(8):748-53.
18. Dingman W, Sporn M B. The penetration of proline and proline derivatives into brain. J Neurochem 1959; 4(2): 148-53
19. Drake R E, Mueser K T. Co-occurring alcohol use disorder and schizophrenia. Alcohol Research & Health 2002; 26(2): 99-102
20. Drew L J, et al. The 22q11.2 microdeletion: fifteen years of insights into the genetic and neural complexity of psychiatric disorders. Int J Dev Neurosci 2011; 29(3): 259-81
21. Efrom M L. Familial hyperprolinemia. Report of a second case, associated with congenital renal malformations, hereditary hematuria and mild mental retardation, with demonstration of an enzyme defect. N Engl J Med 1965; 272:1243-54
22. Fauth E B, Gibbons A. (2014) Which behavioral and psychological symptoms of dementia are the most problematic? Variability by prevalence, intensity, distress ratings, and associations with caregiver depressive symptoms. Int J Geriatr Psychiatry. 29(3):263-71.
23. Fernandez-Garcimartin H, et al. Is it possible to combine different psychotic symptom scales in bipolar disorder? Psychiatry Res 2014; 220(3):1090-3
24. Fine S E, et al. Autism spectrum disorders and symptoms in children with molecularly confirmed 22q11.2 deletion syndrome. J Autism Dev Disord 2005; 35(4):461-70
25. Forlenza O V, Loureiro J C, Pais M V, Stella F. (2017) Recent advances in the management of neuropsychiatric symptoms in dementia. Curr Opin Psychiatry. 2017 March; 30(2): 151-158.
26. Galynker I, Ieronimo C, Miner C, Rosenblum J, Vilkas N, Rosenthal R. (1997) Methylphenidate treatment of negative symptoms in patients with dementia. J Neuropsychiatry Clin Neurosci. 9(2):231-9. Review.
27. Galynker I I, Dutta E, Vilkas N, Ongseng F, Finestone H, Gallagher R, Serseni D, Rosenthal R N. (2000) Hypofrontality and negative symptoms in patients with dementia of Alzheimer type. Neuropsychiatry Neuropsychol Behav Neurol. 13(1):53-9.
28. Goghari V M, Sponheim S R. Differential association of the COMT Val158Met polymorphism with clinical phenotypes in schizophrenia and bipolar disorder. Schizophr Res 2008; 103(1-3):186-91
29. Gogos J A, et al. The gene encoding proline dehydrogenase modulates sensorimotor gating in mice. Nat Genet 1999; 21(4):434-9
30. Gothelf D, et al. Obsessive-compulsive disorder in patients with velocardiofacial (22q11 deletion) syndrome. Am J Med Genet B Neuropsychiatr Genet. 2004; 126B (1):99-105
31. Grainger D J, Aitken S. A microtitre format assay for proline in human serum or plasma. Clin Chim Acta. 2004; 343(1-2):1 13-8
32. Guillot C R, et al. COMT Associations with Disordered Gambling and Drinking Measures. J Gambl Stud. 2015 June; 31(2): 513-524
33. Hashimoto K, et al. Decreased serum levels of D-serine in patients with schizophrenia: evidence in support of the N-methyl-D-aspartate receptor hypofunction hypothesis of schizophrenia. Arch Gen Psychiatry 2003 June; 60(6): 572-6
34. Hwang T J, Masterman D L, Ortiz F, Fairbanks L A, Cummings J L. (2004) Mild cognitive impairment is associated with characteristic neuropsychiatric symptoms. Alzheimer Dis Assoc Disord. 18(1):17-21.
35. Inoue H, et al. Determination of total hydroxyproline and proline in human serum and urine by HPLC with fluorescence detection. Biol Pharm Bull. 1996; 19(2):163-6
36. Ismail Z, Smith E E, Geda Y, Sultzer D, Brodaty H, Smith G, AgUera-Ortiz L, Sweet R, Miller D, Lyketsos C G; ISTAART Neuropsychiatric Symptoms Professional Interest Area. (2016) Neuropsychiatric symptoms as early manifestations of emergent dementia: Provisional diagnostic criteria for mild behavioral impairment. Alzheimers Dement. February; 12(2): 195-202.
37. Jacquet H, et al. Hyperprolinemia is a risk factor for schizoaffective disorder. Mol Psychiatry 2005; 10(5):479-85
38. Jiménez-Jiménez F J, et al. Neurotransmitter amino acids in cerebrospinal fluid of patients with Alzheimer's disease. J Neural Transm (Vienna) 1998; 105(2-3):269-77
39. Joober R, et al. Catechol-O-methyltransferase Val-108/158-Met gene variants associated with performance on the Wisconsin Card Sorting Test. Arch Gen Psychiatry 2002; 59(7):662-3
40. Kane J, et al. Clozapine for the treatment-resistant schizophrenic. A double-blind comparison with chlorpromazine. Arch Gen Psychiatry 1988; 45(9):789-96
41. Karayiorgou M, et al. 22q11.2 microdeletions: linking DNA structural variation to brain dysfunction and schizophrenia. Nat Rev Neurosci 2010; 11:402-16
42. Karttunen K, Karppi P, Hiltunen A, Vanhanen M, Välimäki T, Martikainen J, Valtonen H, Sivenius J, Soininen H, Hartikainen S, Suhonen J, Pirttilä T. (2011) Neuropsychiatric symptoms and quality of life in patients with very mild and mild Alzheimer's disease. Int J Geriatr Psychiatry. 26(5):473-82.
43. Lachman H M, et al. Human catechol-O-methyltransferase pharmacogenetics: description of a functional polymorphism and its potential application to neuropsychiatric disorders. Pharmacogenetics 1996; 6(3):243-50
44. Landes A M, Sperry S D, Strauss M E. (2005) Prevalence of apathy, dysphoria, and depression in relation to dementia severity in Alzheimer's disease. J Neuropsychiatry Clin Neurosci. 17(3):342-9.
45. Le Boucher J, Charret C, Coudray-Lucas C, Giboudeau J, Cynober L. Amino acid determination in biological fluids by automated ion-exchange chromatography: performance of Hitachi L-8500A. Clin Chem. 1997; 43(8 Pt 1):1421-8
46. Lechowski L, Benoit M, Chassagne P, Vedel I, Tortrat D, Teillet L, Vellas B. (2009) Persistent apathy in Alzheimer's disease as an independent factor of rapid functional decline: the REAL longitudinal cohort study. Int J Geriatr Psychiatry. 24(4):341-6.
47. Leoutsakos J M, Forrester S N, Lyketsos C G, Smith G S. (2015) Latent Classes of Neuropsychiatric Symptoms in NACC Controls and Conversion to Mild Cognitive Impairment or Dementia. J Alzheimers Dis. 48(2):483-93. doi: 10.3233/JAD-150421.
48. Lewis D A, et al. Dopamine transporter immunoreactivity in monkey cerebral cortex: regional, laminar, and ultrastructural localization. J Comp Neurol 2001; 432(1): 119-36
49. Liang S, et al. Determination of proline in human serum by a robust LC-MS/MS method: application to identification of human metabolites as candidate biomarkers for esophageal cancer early detection and risk stratification. Biomed. Chromatogr. 2015, 29: 570-577
50. Lindenmayer J P, et al. Dimensions of psychosis in patients with bipolar mania as measured by the positive and negative syndrome scale. Psychopathology 2008; 41(4):264-70
51. Luykx J J, et al. D-amino acid aberrations in cerebrospinal fluid and plasma of smokers. Neuropsychopharmacology 2013 September; 38(10):2019-26
52. Luykx J J, et al. Genome-wide association study of NMDA receptor coagonists in human cerebrospinal fluid and plasma. Mol Psychiatry. 2015; doi: 10.1038/mp.2014.190
53. Lyketsos C G, Carrillo M C, Ryan J M, Khachaturian A S, Trzepacz P, Amatniek J, Cedarbaum J, Brashear R, Miller D S. (2011) Neuropsychiatric symptoms in Alzheimer's disease. Alzheimers Dement. 7(5):532-9.
54. Molina J A, Jiménez-Jiménez F J, Vargas C, Gómez P, de Bustos F, Orti-Pareja M, Tallón-Barranco A, Benito-León J, Arenas J, Enriquez-de-Salamanca R. (1998) Cerebrospinal fluid levels of non-neurotransmitter amino acids in patients with Alzheimer's disease. J Neural Transm (Vienna); 105(2-3):279-86.
55. Nadler J V. Sodium-dependent proline uptake in the rat hippocampal formation: association with ipsilateral-commissural projections of CA3 pyramidal cells. J Neurochem 1987; 49:1155-60
56. Negrón A E, Reichman W E. (2000) Risperidone in the treatment of patients with Alzheimer's disease with negative symptoms. Int Psychogeriatr. 12(4):527-36.
57. Nickolson V J. "On" and "off" responses of K+-induced synaptosomal proline release: involvement of the sodium pump. J Neurochem 1982; 38:289-92
58. Orešič, et al. Metabolome in schizophrenia and other psychotic disorders: a general population-based study. Genome Med 2011; 3(3):19
59. Paterlini M, et al. Transcriptional and behavioral interaction between 22q11.2 orthologs modulates schizophrenia-related phenotypes in mice. Nat Neurosci 2005; 8(11): 1586-94
60. Phang J M, et al. Disorders of proline and hydroxyproline metabolism, in Metabolic and molecular basis of inherited disease. New York, McGraw-Hill Press, 2001, pp 1821-1838
61. Pomara N, et al. Glutamate and other CSF amino acids in Alzheimer's disease. Am J Psychiatry 1992 February; 149(2):251-4
62. Pomara N, Singh R, Deptula D, Chou J C, Schwartz M B, LeWitt P A. (1992) Glutamate and other CSF amino acids in Alzheimer's disease. Am J Psychiatry. 149(2): 251-4.
63. Raux G, et al. Involvement of hyperprolinemia in cognitive and psychiatric features of the 22q11 deletion syndrome. Hum Mol Genet 2007; 16(1):83-91
64. Reichman W E, Coyne A C, Amirneni S, Molino B Jr, Egan S. (1996) Negative symptoms in Alzheimer's disease. Am J Psychiatry. 153(3):424-6.
65. Renick S E, et al. The mammalian brain high-affinity L-proline transporter is enriched preferentially in synaptic vesicles in a subpopulation of excitatory nerve terminals in rat forebrain. J Neurosci 1999; 19:21-33
66. Scholl-Bürgi S, et al. The relation of cerebrospinal fluid and plasma glycine levels in propionic acidaemia, a 'ketotic hyperglycinaemia'. J Inherit Metab Dis 2008 June; 31(3):395-8
67. Shifman S, et al. A highly significant association between a COMT haplotype and schizophrenia. Am J Hum Genet 2002; 71(6):1296-302
68. Shifman S, et al. COMT: a common susceptibility gene in bipolar disorder and schizophrenia. Am J Med Genet B Neuropsychiatr Genet 2004; 128B(1):61-4
69. Sonne S C, Brady K T. Bipolar Disorder and Alcoholism. NIAAA publication 2002 November; http://pubs-.niaaa.nih.gov/publications/arh26-2/103-108.htm
70. Starkstein S E, Pahissa J. (2014) Apathy following traumatic brain injury. Psychiatr Clin North Am. 37(1): 103-12. Review.
71. Stefan A, Mathé J F; SOFMER group. (2016) What are the disruptive symptoms of behavioral disorders after traumatic brain injury? A systematic review leading to recommendations for good practices. Ann Phys Rehabil Med. February; 59(1):5-17.
72. Tomiya M, et al. Alterations in serum amino acid concentrations in male and female schizophrenic patients. Clin Chim Acta 2007; 380(1-2):186-90
73. Trushina E, Dutta T, Persson X M, Mielke M M, Petersen R C. (2013) Identification of altered metabolic pathways in plasma and CSF in mild cognitive impairment and Alzheimer's disease using metabolomics. PLoS One. May 20; 8(5):e63644. doi: 10.1371/journal-.pone.0063644.
74. Tunbridge E M, et al. Catechol-o-methyltransferase, cognition, and psychosis: Val158Met and beyond. Biol Psychiatry 2006; 60:141-151
75. Van Dam D, Vermeiren Y, Dekker A D, Naudé P J, Deyn P P. (2016)Neuropsychiatric Disturbances in Alzheimer's Disease: What Have We Learned from Neuropathological Studies? Curr Alzheimer Res. 13(10):1145-64.
76. Vercelletto M, Martinez F, Lanier S, Magne C, Jaulin P, Bourin M. (2002) Negative symptoms, depression and Alzheimer's disease. Int J Geriatr Psychiatry. 17(4):383-7.
77. Vorstman J A, et al. Proline affects brain function in 22q11DS children with the low activity COMT 158 allele. Neuropsychopharmacology 2009; 34(3):739-46
78. Wu, G. Determination of proline by reversed-phase high-performance liquid chromatography with automated pre-column o-phthaldialdehyde derivatization. Journal of Chromatography A. Volume 641, Issue 1, 1993, Pages 168-175.
79. Yoneda Y, Roberts E. A new synaptosomal biosynthetic pathway of proline from ornithine and its negative feedback inhibition by proline. Brain Res 1982; 239:479-88
80. Zarchi 0, et al. Schizophrenia-like neurophysiological abnormalities in 22q11.2 deletion syndrome and their association to COMT and PRODH genotypes. J Psychiatr Res 2013; 47(11):1623-9

What is claimed is:

1. A method for treating or ameliorating the effects of schizophrenia in a subject in need thereof comprising:
   a) obtaining a biological sample from the subject;
   b) determining, in the biological sample, the presence or absence of a Val$^{158}$Met polymorphism in the COMT gene; and c) administering to the subject an effective amount of an agent that increases proline levels if the subject is determined from step b) to have a Val/Val genotype at codon 158; or d) administering to the subject an effective amount of an agent that decreases proline levels if the subject is determined from step b) to have a Val/Met or Met/Met genotype at codon 158, wherein the agent that increases proline levels is valproic acid (VPA) and the agent that decreases proline levels is vitamin D3.

2. The method of claim 1, further comprising determining a proline level in the subject and adjusting a treatment protocol for the subject based on the determined proline level.

3. The method of claim 1, wherein the subject is human.

4. The method of claim 1, wherein the Val$^{158}$Met polymorphism in the COMT gene is a rs4680 G>A single nucleotide polymorphism (SNP).

5. The method of claim 1, which reduces a negative symptom of schizophrenia.

6. The method of claim 5, wherein the negative symptom is selected from the group consisting of diminished emotional expression, avolition, impaired social functioning, alogia, apathy, anhedonia and combinations thereof.

7. The method of claim 5, which comprises decreasing a total Scale for Negative Symptoms (SANS) score, a Brief Psychiatric Rating Scale (BPRS) negative symptom sub-scale score, a Positive and Negative Syndrome Scale (PANSS) negative symptom sub-scale score, a Brief Negative Symptom Scale (BNSS) score, clinical assessment interview for negative symptoms, negative assessment, or other measures of negative symptoms in the subject.

8. The method of claim 1, wherein the biological sample is selected from the group consisting of a blood sample, a biopsy sample, a plasma sample, a saliva sample, a tissue sample, a serum sample, a tear sample, a sweat sample, a skin sample, a cell sample, a hair sample, an excretion sample, a waste sample, a bodily fluid sample, a nail sample, a cheek swab, a cheek cell sample, and a mucous sample.

9. A method for treating or ameliorating the effects of schizophrenia in a subject in need thereof comprising:

a) determining, using a biological sample of the subject, the presence or absence of a Val$^{158}$Met polymorphism in the COMT gene of the subject; and b) administering to the subject an effective amount of an agent that increases proline levels if the subject is determined from step a) to have a Val/Val genotype at codon 158; or c) administering to the subject an effective amount of an agent that decreases proline levels if the subject is determined from step a) to have a Val/Met or Met/Met genotype at codon 158, wherein the agent that increases proline levels is valproic acid (VPA) and the agent that decreases proline levels is vitamin D3.

10. The method of claim 9, further comprising determining a proline level in the subject and adjusting a treatment protocol for the subject based on the determined proline level.

* * * * *

UNITED STATES PATENT AND TRADEMARK OFFICE
CERTIFICATE OF CORRECTION

PATENT NO. : 11,041,207 B2
APPLICATION NO. : 15/977144
DATED : June 22, 2021
INVENTOR(S) : Catherine L. Clelland and James D. Clelland Page 1 of 1

It is certified that error appears in the above-identified patent and that said Letters Patent is hereby corrected as shown below:

In the Specification

In Column 1, please replace the paragraph following the heading "GOVERNMENT FUNDING" and immediately before the heading "FIELD OF THE INVENTION" with the following:
This invention was made with government support under RR024157, MH082331, MH100219, and MH070601 awarded by the National Institutes of Health. The government has certain rights in the invention.

Signed and Sealed this
Ninth Day of July, 2024

Katherine Kelly Vidal
*Director of the United States Patent and Trademark Office*